US007414124B2

(12) United States Patent
Fischer et al.

(10) Patent No.: US 7,414,124 B2
(45) Date of Patent: Aug. 19, 2008

(54) PROMOTER FOR EXPRESSION OF A HETEROLOGOUS POLYNUCLEOTIDE IN A FEMALE GAMETOPHYTE

(75) Inventors: Robert L. Fischer, El Cerrito, CA (US); Yeonhee Choi, Emeryville, CA (US); Mike Hannon, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/449,042

(22) Filed: Jun. 7, 2006

(65) Prior Publication Data

US 2006/0292687 A1 Dec. 28, 2006

Related U.S. Application Data

(63) Continuation of application No. 09/840,743, filed on Apr. 23, 2001, now Pat. No. 7,109,394, which is a continuation-in-part of application No. 09/553,690, filed on Apr. 21, 2000, now Pat. No. 6,476,296.

(51) Int. Cl.
*C12N 15/11* (2006.01)
*C12N 15/82* (2006.01)

(52) U.S. Cl. ...................................................... 536/24.1

(58) Field of Classification Search ....................... None
See application file for complete search history.

(56) References Cited

U.S. PATENT DOCUMENTS 6,476,296 B1 11/2002 Fischer et al.

OTHER PUBLICATIONS

Donald et al, 1990, EMBO J. 9:1717-1726.*
Chen et al, 2000, Sex. Plant Reprod. 13:85-94.*
Benfrey et al, 1990, Science 250:959-966.*
Kim et al, 1994, Plant Mol. Biol. 24:105-117.*
Izawa et al, 1993, J. Mol. Biol. 230:1131-1144.*
Genbank Accession No. AL069706., Oct. 1999.*
Akama, et al. "Efficient Transformation of *Arabidopsis thaliana*; Comparison of the Efficiencies with Various Organs, Plant Ecotypes and *Agrobacterium* Strains" *Plant Cell Reports* (1992) vol. 12, pp. 7-11.
Bevan, et al. GenBank Accession No. AL1602875, Mar. 31, 2000.
Bevan, et al. GenBank Accession No. AL162972, Apr. 3, 2000.
Bevan, et al. Accession No. T48452, *Protein Sequence Database* Apr. 20, 2000.
Bevan, et al. Accession No. T48453, *Protein Sequence Database* Apr. 20, 2000.
Bevan, et al. Accession No. T48454, *Protein Sequence Database* Apr. 20, 2000.
Bork, et al. Accession No. Y10157, Jul. 1, 1998.
Bult, et al. GenBank Accession No. Q58030, Nov. 1, 1997.
Rounsley, et al. GenBank Accession No. B60854, 1997.
Rounsley, et al. GenBank Accession No. B28303, 1997.
Scharer and Jiricny, "Recent Progress in the Biology, Chemistry and Structural Biology of DNA Glycosylases" *BioEssays* (2001) vol. 23, pp. 270-281.
Smith, et al. GenBank Accession No. AE000855 Nov. 15, 1997.
Smith, et al. Accession No. AE000666 Nov. 15, 1997.
White, et al. GenBank Accession No. AE002073 Nov. 22, 1999.
White, et al. Accession No. AE000513 Nov. 22, 1999.
Lazar, et al, 1988, Mol. Cell. Biol. 8:1247-1252.
Hill, et al., 1998, Biochem. Biophys Res. Comm. 244:573-577.
Lin, et al. May 1, 2000, Sptrembl Accession Nos. Q9SR66 and Q9SJQ6.
Bevan, et al. Jun. 1, 1998, GenBank Accession No. O49498.
Asada, et al. 2001, EMBL Accession No. Q94LX6.
Duggleby, 1997, Gene 190:245-249.
Roldan-Arjona, et al. 2000, Plant Mol. Biol. 44:43-52.
Choi et al., 2002, Cell 110:1-20.
Leyser et al. 1992, Devel. 116:397-403.
Thomas, et al., 2001, Plant J. 25:417-425.
Xiao et al., 2003, Devel. Cell 5:891-901.
Chuang et al, 2000, Proc. Natl. Acad. Sci. 97:4985-4990.

* cited by examiner

*Primary Examiner*—Anne R Kubelik
(74) *Attorney, Agent, or Firm*—Townsend and Townsend and Crew LLP

(57) ABSTRACT

This invention is directed to plant genetic engineering. In particular, it relates to, for example, modulating seed (and in particular endosperm, embryo and seed coat) development, flowering time, chromosomal DNA methylation and modulating transcription in plants.

3 Claims, No Drawings

PROMOTER FOR EXPRESSION OF A HETEROLOGOUS POLYNUCLEOTIDE IN A FEMALE GAMETOPHYTE

CROSS-REFERENCES TO RELATED APPLICATIONS

This application is a continuation of U.S. patent application Ser. No. 09/840,743, filed Apr. 23, 2001, now U.S. Pat. No. 7,109 394 which is a continuation-in-part of U.S. patent application Ser. No. 09/553,690, filed Apr. 21, 2000, now U.S. Pat. No. 6,476,296, each of which is incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant No. 97-35304-4941, awarded by the United States Department of Agriculture. The government has certain rights in this invention.

FIELD OF THE INVENTION

This invention is directed to plant genetic engineering. It relates to, for example, modulating seed (and in particular endosperm, embryo and seed coat) development, flowering time, chromosomal DNA methylation and modulating transcription in plants.

BACKGROUND OF THE INVENTION

A fundamental problem in biology is to understand how seed development. In flowering plants, the ovule generates the female gametophyte, which is composed of egg, central, synergid and antipodal cells (Reiser, et al., *Plant Cell,* 1291-1301 (1993)). All are haploid except the central cell which contains two daughter nuclei that fuse prior to fertilization. One sperm nucleus fertilizes the egg to form the zygote, whereas another sperm nucleus fuses with the diploid central cell nucleus to form the triploid endosperm nucleus (van Went, et al., *Embryology of Angiosperms*, pp. 273-318 (1984)). The two fertilization products undergo distinct patterns of development. In *Arabidopsis*, the embryo passes through a series of stages that have been defined morphologically as preglobular, globular, heart, cotyledon and maturation (Goldberg, R. B., et al., *Science* (1994) 266: 605-614; Mansfield, S. G., et al, *Arabidopsis: An Atlas of Morphology and Development*, pp. 367-383 (1994)). The primary endosperm nucleus undergoes a series of mitotic divisions to produce nuclei that migrate into the expanding central cell (Mansfield, S. G., et al., *Arab Inf Serv* 27: 53-64 (1990); Webb, M. C., et al., *Planta* 184:187-195 (1991)). Cytokinesis sequesters endosperm cytoplasm and nuclei into discrete cells (Mansfield, S. G., et al., *Arab Inf Serv* 27:65-72 (1990)) that produce storage proteins, starch, and lipids which support embryo growth (Lopes, M. A. et al., *Plant Cell* 5:1383-1399 (1993)). Fertilization also activates development of the integument cell layers of the ovule that become the seed coat, and induces the ovary to grow and form the fruit, or silique, in *Arabidopsis*.

Of particular interest are recent discoveries of genes that control seed, and in particular endosperm, development. For instance, *MEDEA* (*MEA*) (also known as *FIEI* (see, e.g., copending U.S. patent application Ser. No. 09/071,838) and F644 (see, e.g., Kiyosue T, et al. (1999) *Proc Natl Acad Sci USA* 96(7):4186-91) encodes an *Arabidopsis* SET domain polycomb protein that appears to play a role in endosperm development. Inheritance of a maternal loss-of-function mea allele results in embryo abortion and prolonged endosperm production, irrespective of the genotype of the paternal allele. Thus, only the maternal wild-type MEA allele is required for proper embryo, endosperm, and seed coat development (Kinoshita T, et al. (1999) *Plant Cell* 10:1945-52). These results reveal functions for plant polycomb proteins in the suppression of central cell proliferation and endosperm development (Kiyosue T, et al. supra).

Another gene product that controls seed development is FIE, also known as FIE3 (see, e.g., copending U.S. patent application Ser. No. 09/071,838). The FIE protein is a homolog of the WD motif-containing Polycomb proteins from Drosophila and mammals (Ohad, N. et al. *Plant Cell* 11(3):407-16 (1999)). In Drosophila, these proteins function as repressors of homeotic genes. Loss of function mutations in the FIE gene result in endosperm phenotypes that are identical to medea loss of function mutations. A female gametophyte with a loss-of-function allele of fie undergoes replication of the central cell nucleus and initiates endosperm development without fertilization. These results suggest that the FIE Polycomb protein functions to suppress a critical aspect of early plant reproduction, namely, endosperm development, until fertilization occurs. Moreover, hypomethylation of fie mutants leads to the development of differentiated endosperm. Vinkenoog et al., *Plant Cell* 12:2271-2282 (2000).

Control of the expression of genes that control egg and central cell differentiation, or those that control reproductive development, i.e. embryo, endosperm and seed coat, is useful in the production of plants with a range of desired traits. These and other advantages are provided by the present application.

SUMMARY OF THE INVENTION

This invention provides isolated nucleic acids comprising a polynucleotide sequence, or its complement, encoding a DMT polypeptide comprising an amino acid sequence with at least 70% sequence identity to at least one of the following consensus sequences:

This invention provides isolated nucleic acids comprising a polynucleotide sequence, or its complement, encoding a DMT polypeptide comprising an amino acid sequence with at least 70% sequence identity to at least one of the following consensus sequences:

DMT Domain A

KV<1>(I,l)D(D,p)(E,v)T<3>W<1>(L,v)L(M,I)(E,d) <0-2>D(K,e)<1>(K,t) <1>(K,a)(W,k)(W,l)<1>(E,k) ER<2>F<1>(G,t)R<1>(D,n)(S,l)FI(A,n)RM(H,r)<1>(V,l) QG (D,n)R<1>F<1>(P,q)WKGSVVDSV(I,v)GVFLTQN(V,t)D(H,y)(L,s)SS(S,n)A(F,y)M<1>(L,v)A (A,s)<1>FP (SEQ ID NO:71)

DMT Domain B

W(D,n)<1>(L,f)R<5>E<3-6>D(S,t)<1>(D,n)(Y,w) <3>R<10>I<2>RG(M,q) (N,f)<2>L(A,s)<1>RI<2-12>FL<3>V<2>(H,n)G<1>IDLEWLR<2>(P,d)(P,s)(D,h) <1>(A,v) K<1>(Y,f)LL(S,e)(I,f)<1>G(L,i)GLKS(V,a) ECVRLL<1>L(H,k)<2>AFPVDTNVGRI(A,c)VR (M,l)G (W,l)VPL(Q,e)PLP<2>(L,v)Q(L,m)H(L,q)L(E,f) <1>YP<1>(L,m)(E,d)(S,n)(I,v)QK (F,y)LWPRLCKL(D,p) Q<1>TLYELHY(Q,h)(L,m)ITFGK<0-2>FCTK<2>PNCNACPM(R,k)<0-2>EC (R,k)(H,y)(F,y)(A,s)SA<1>(A,v)<0-10>S(A,s)(R,k)<1>(A,l)L(P,e)<1>(P,t) (SEQ ID NO:72)

DMT Domain C.

P(I,l)(I,v)E(E,f)P<1>(S,t)P<2-5>E<0-15>(D,a)IE(D,e) <4-23>(I,v)p<1>I<1>(L,f)(N,d)<8-17>(S,a)<1>(A,d) LV<8>(I,l)P<2-5>(K,r)(L,m)K<4>LRTEH<1>V(Y,f) (E,v) LPD<1>H<1>(L,i)L(E,k)<1>(D,e)D(P,i)<2>YLL(A,s)IW (T,q)P(G,d)(E,g)<6-8>(P,s)<3>C<6-10>(M,l) C<4>C<2>C<3>(R,k)E<5>(V,f)RGT(L,i)L<0-22>(L,v) FADH<1>(S,t) (S,r)<2>PI<3>(R,t)<3>(W,k)<1>L<1>(R,k) R<4>G(T,s)(S,t)<2>(S,t)I(F,c)(R,k)(G,l)L <1>(T,v)<2>I<2> (C,n)F(W,q)<1>G(F,y)(V,l)C(V,l)R<1>F(E,d)<3>(R,g) <1>P(R,k)<1>L <2>(R,h)LH<2>(A,v)SK (SEQ ID NO:73)

In some embodiments, the nucleic acids of the invention do not encode a polypeptide at least 40% identical to SEQ ID NO:2, or alternatively at least 45%, 50%, 55%, 60%, 65%, 70%, 75%, 80%, 85%, 90%, 95%, 99% or 100% to SEQ ID NO:2. In some embodiments, the DMT polypeptide comprises an amino acid sequence 100% identical to the above-listed consensus sequences.

In some embodiments, the DMT polypeptides ar at least 45%,50%,55%,60%,65%,70%,75%,80%,85%,90%,95%,97%,98%,99% or 100% identical to DMT domains A, B and/or C.

In one aspect, the invention provides DMt polypeptides capable of exhibiting at least one of the following biological activities:

(a) glycosylase activity;

(b) demethylation of polynucleotides;

(c) DNA repair;

(d) wherein expression of the polypeptide in a plant modulates organ identity;

(e) wherein expression of the polypeptide in a plant modulates organ number;

(f) wherein expression of the polypeptide in a plant modulate meristem stem and/or activity;

(g) wherein enhanced expression of the polypeptide in a plant results in a delay in flowering time;

(h) wherein introduction of the polypeptide into a cell results in modulation of methylation of chromosomal DNA in the cell;

(i) wherein reduction of expression of the polypeptide in a plant results in modulation of endosperm development;

(j) wherein expression of the polypeptide in an *Arabidopsis* leaf results in modulation of expression of the MEDEA gene.

In some aspects, the polypeptide comprises either a (i) basic region;

(ii) nuclear localization signal;

(iii) leucine zipper;

(iv) helix-hairpin-helix structure;

(v) glycine-proline rich loop with a terminal aspartic acid or (vi) helix that is capable of binding DNA.

In one aspect, the invention provides methods of modulating in a plant one or more of the following:

(a) DNA repair;

(b) wherein expression of the polypeptide in a plant modulates organ identity;

(c) wherein expression of the polypeptide in a plant modulates organ number;

(d) wherein expression of the polypeptide in a plant modulate meristem stem and/or activity;

(e) wherein enhanced expression of the polypeptide in a plant results in a delay in flowering time;

(f) wherein introduction of the polypeptide into a cell results in modulation of methylation of chromosomal DNA in the cell;

(g) wherein reduction of expression of the polypeptide in a plant results in modulation of endosperm development;

(h) wherein expression of the polypeptide in an *Arabidopsis* leaf results in expression of the MEDEA gene, wherein the method comprises:

(a) introducing into a plant cell a nucleic acid of claim 1; and (b) generating conditions where the plant cell can transcribe the nucleic acid described above.

In some embodiments, the polypeptides comprise between 1500 and 2000 amino acids. In some aspects, the polypeptide has glycosylase activity. In some embodiments, introduction of the nucleic acid into a cell results in modulation of methylation of chromosomal DNA in the cell. In some embodiments, enhanced expression of the nucleic acids of the invention into a plant results in a delay in flowering time. In some embodiments, reduction of expression of a DMT polypeptide in a plant results in enhanced endosperm development. In addition, in some embodiments, expression of the nucleic acid of the invention in an *Arabidopsis* leaf results in expression of the MEDEA gene.

This invention provides isolated nucleic acids comprising a polynucleotide sequence, or its complement, encoding a DMT polypeptide exhibiting at least 60% sequence identity to SEQ ID NO:2 or exhibiting at least 70% sequence identity to at least one of DMT domain A, B, or C. For instance, the nucleic acid can encode the DMT polypeptide displayed in SEQ ID NO:2. In one aspect, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter is from a DMT gene. For example, the promoter can comprise a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation.

The invention also provides an isolated nucleic acid molecule comprising a polynucleotide sequence exhibiting at least 60% sequence identity to SEQ ID NO: 1.

The invention also provides an expression cassette comprising a promoter operably linked to a heterologous polynucleotide sequence, or complement thereof, encoding a DMT polypeptide exhibiting at least 60% sequence identity to SEQ ID NO:2. For instance, the nucleic acid can encode the DMT polypeptide displayed in SEQ ID NO:2. In some aspects, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter is from a DMT gene. For example, the promoter can comprise a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation.

The invention also provides an expression cassette for the expression of a heterologous polynucleotide in a plant cell. In some aspects, the expression cassette comprises a promoter polynucleotide at least 70% identical to SEQ ID NO:3 that is operably linked to a heterologous polynucleotide. In some aspects, the promoter comprises SEQ ID NO:3. In some aspects, the promoter further comprises a polynucleotide at least 70% identical to SEQ ID NO:4. For instance, in some embodiments, the promoter comprises SEQ ID NO:4. In some aspects, the promoter further comprises a polynucleotide at least 70% identical to SEQ ID NO:6. In some aspects, the promoter comprises SEQ ID NO:6.

The present invention also provides a host cell comprising an exogenous polynucleotide sequence comprising a polynucleotide sequence, or complement thereof, encoding a DMT polypeptide exhibiting at least 60% sequence identity to SEQ ID NO:2 or exhibiting at least 70% sequence identity to at least one of DMT domain A, B, or C. In some aspects of the invention, the nucleic acid further comprises a promoter operably linked to the polynucleotide sequence. In some aspects, the promoter is constitutive. In some aspects, the promoter comprises a polynucleotide at least 70% identical to SEQ ID NO:3. The promoter, for instance, can comprise SEQ ID NO:3. In some aspects, the promoter further comprises a polynucleotide at least 70% identical to SEQ ID NO:4. For instance, in some embodiments, the promoter comprises SEQ ID NO:4. In some aspects, the promoter is operably linked to the exogenous polynucleotide sequence in an antisense orientation.

The present invention also provides an isolated polypeptide comprising an amino acid sequence at least 60% identical to SEQ ID NO:2 or an amino acid sequence at least 70% sequence identical to at least one of DMT domain A, B, or C and capable of exhibiting at least one biological activity of the polypeptide displayed in SEQ ID NO:2, or fragment thereof. The present invention also provides for an antibody capable of binding such polypeptides.

The present invention also provides a method of introducing an isolated nucleic acid into a host cell comprising, (a) providing an isolated nucleic acid or its complement, encoding a DMT polypeptide exhibiting at least 60% sequence identity to SEQ ID NO:2 or exhibiting at least 70% sequence identity to at least one of DMT domain A, B, or C and (b) contacting the nucleic acid with the host cell under conditions that permit insertion of the nucleic acid into the host cell.

The present invention also provides a method of modulating transcription, comprising introducing into a host cell an expression cassette comprising a promoter operably linked to a heterologous DMT polynucleotide, the heterologous DMT polynucleotide encoding a DMT polypeptide at least 60% identical to SEQ ID NO:2 or at least 70% sequence identical to at least one of DMT domain A, B, or C, and detecting a host cell with modulated transcription. In some aspects of the invention, the heterologous DMT polynucleotide encodes SEQ ID NO:2. In some aspect, the polynucleotide sequence comprises SEQ ID NO:5 or SEQ ID NO:1. In some aspects, the expression cassette is introduced into a host cell by *Agrobacterium*. In some aspects, the expression cassette is introduced by a sexual cross. In some aspects of the method of the invention, modulating transcription results in the modulation of endosperm development in a plant. In some aspects, endosperm development is enhanced. In other aspects, endosperm development is decreased. In some aspects of the methods of the invention, the promoter is operably linked to the DMT polynucleotide in an antisense orientation.

The present invention also provides a method of detecting a nucleic acid in a sample, comprising (a) providing an isolated nucleic acid molecule comprising a polynucleotide sequence, or its complement, encoding a DMT polypeptide exhibiting at least 60% sequence identity to SEQ ID NO:2 or exhibiting at least 70% sequence identity to at least one of DMT domain A, B, or C, (b) contacting the isolated nucleic acid molecule with a sample under conditions that permit a comparison of the sequence of the isolated nucleic acid molecule with the sequence of DNA in the sample, and (c) analyzing the result of the comparison. In some aspects of the method, the isolated nucleic acid molecule and the sample are contacted under conditions that permit the formation of a duplex between complementary nucleic acid sequences.

The present invention also provides a transgenic plant cell or transgenic plant comprising a polynucleotide sequence, or its complement, encoding a DMT polypeptide exhibiting at least 60% sequence identity to SEQ ID NO:2 or exhibiting at least 70% sequence identity to at least one of DMT domain A, B, or C. For instance, the nucleic acid can encode the DMT polypeptide displayed in SEQ ID NO:2. In one aspect, the polynucleotide sequence comprises SEQ ID NO:5 or SEQ ID NO: 1. In some aspects of the invention, the nucleic acid further comprises a promoter operably linked to the polynucleotide. In some embodiments, the promoter is constitutive. In other embodiments, the promoter comprises a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation. The present invention also provides a plant that is regenerated from a plant cell as described above.

The present invention also provides an expression cassette for the expression of a heterologous polynucleotide in a plant cell, wherein the expression cassette comprises a promoter at least 70% identical to SEQ ID NO:3 and the promoter is operably linked to a heterologous polynucleotide. In some embodiments, the promoter comprises a polynucleotide at least 70% identical to SEQ ID NO:4 and/or SEQ ID NO:6. In some embodiments, the promoter specifically directs expression of the heterologous polynucleotide in a female gametophyte when the expression cassette is introduced into a plant.

DEFINITIONS

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of flowering plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like. "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a TO for the primary transgenic plant and TI for the first generation. The term "exogenous" as used herein is also intended to encompass inserting a naturally found element into a non-naturally found location.

The phrase "host cell" refers to a cell from any organism. Preferred host cells are derived from plants, bacteria, yeast, fungi, insects or other animals, including humans. Methods for introducing polynucleotide sequences into various types of host cells are well known in the art.

The "biological activity of a polypeptide" refers to any molecular activity or phenotype that is caused by the polypeptide. For example, the ability to transfer a phosphate to a substrate or the ability to bind a specific DNA sequence is a biological activity. One biological activity of DMT is glycosylase activity, i.e., cleavage of the nucleotide base from the nucleotide sugar). Another biological activity of DMT is to demethylate nucleotides (e.g., DMT has 5'-methylcytosine glycosylase activity). In addition, DMT has the ability to modulate endosperm production, as described herein, and to modulate flowering time in plants. For example, when DMT expression or DMT activity is increased in a plant, the flowering time of the plant is delayed. Moreover, expression of a DMT polypeptide in a plant tissue (e.g., a leaf) that does not typically express the MEDEA gene (Grossniklaus U, et al., *Science* 280(5362):446-50 (1998)) results in the expression of MEDEA.

Additional biological activities of DMT polypeptides include: nuclear localization (e.g., as localized by amino acids 43-78 of SEQ ID NO:2); the ability to modulate plant organ size and/or number; the ability to modulate meristem size and/or activity; and to perform DNA repair, including nucleotide methylation or demethylation and/orrepair and/or removal of mis-matched nucleotides from DNA.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

A "DMT nucleic acid" or "DMT polynucleotide sequence" of the invention is a subsequence or full length polynucleotide sequence of a gene which encodes a polypeptide involved in control of reproductive development and which, when the maternal allele is mutated or when DMT activity is reduced or eliminated in a maternal tissue or plant, allows for increased production of the endosperm and/or abortion of the embryo. In addition, overexpression of DMT in plants results in delayed time to flowering. Moreover, DMT is necessary and sufficient for expression of MEDEA in a plant cell. An exemplary nucleic acid of the invention is the *Arabidopsis* DMT sequence (SEQ ID NO:1). Additional DMT nucleic acid and amino acid sequences from a variety of plant species are also provided (e.g., SEQ ID NOs: 7-70). DMT polynucleotides are defined by their ability to hybridize under defined conditions to the exemplified nucleic acids or PCR products derived from them. A DMT polynucleotide is typically at least about 30-40 nucleotides to about 7000, usually less than about 10,000 nucleotides in length. More preferably, DMT polynucleotides contain a coding sequence of from about 100 to about 5500 nucleotides, often from about 500 to about 3600 nucleotides in length. A DMT polypeptide is typically at least 500 amino acids, typically at least 1000 amino acids, more typically at least 1500 amino acids. In some embodiments, a DMT polypeptide comprises fewer than 2000 amino acids, more typically fewer than 3000 amino acid and still more typically fewer than 5000 or 7500 amino acid in length.

As described below, DMT nucleic acid sequences encode polypeptides with substantial identity to at least one of following the consensus sequences:

DMT Domain A

KV<1>(I,l)D(D,p)(E,v)T<3>W<1>(L,v)L(M,l)(E,d)<0-2>D(K,e)<1>(K,t) <1>(K,a)(W,k)(W,l)<1>(E,k) ER<2>F<1>(G,t)R<1>(D,n)(S,l)FI(A,n)RM(H,r)<1>(V,l) QG (D,n)R<1>F<1>(P,q)WKGSVVDSV(I,v)GVFLTQN(V,t)D(H,y)(L,s)SS(S,n)A(F,y)M<1>(L,v)A (A,s)<1>FP (SEQ ID NO:71)

DMT Domain B

W(D,n)<1>(L,f)R<5>E<3-6>D(S,t)<1>(D,n)(Y,w) <3>R<10>I<2>RG(M,q) (N,f)<2>L(A,s)<1>RI<2-12>FL<3>V<2>(H,n)G<1>IDLEWLR<2>(P,d)(P,s)(D,h) <1>(A,v) K<1>(Y,f)LL(S,e)(I,f)<1>G(L,i)GLKS(V,a) ECVRLL<1>L(H,k)<2>AFPVDTNVGRI(A,c)VR (M,l)G (W,l)VPL(Q,e)PLP<2>(L,v)Q(L,m)H(L,q)L(E,f) <1>YP<1>(L,m)(E,d)(S,n)(I,v)QK (F,y)LWPRLCKL(D,p) Q<1>TLYELHY(Q,h)(L,m)ITFGK<0-2>FCTK<2>PNCNACPM(R,k)<0-2>EC (R,k)(H,y)(F,y)(A,s)SA<1>(A,v)<0-10>S(A,s)(R,k)<1>(A,l)L(P,e)<1>(P,t) (SEQ ID NO:72)

DMT Domain C.

P(I,l)(I,v)E(E,f)P<1>(S,t)P<2-5>E<0-15>(D,a)IE(D,e) <4-23>(I,v)P<1>I<1>(L,f)(N,d)<8-17>(S,a)<1>(A,d) LV<8>(I,l)P<2-5>(K,r)(L,m)K<4>LRTEH<1>V(Y,f) (E,v) LPD <1>H<1>(L,i)L(E,k)<1>(D,e)D(P,i)<2>YLL(A,s)IW (T,q)P(G,d)(E,g)<6-8>(P,s)<3>C<6-10>(M,l) C<4>C<2>C<3>(R,k)E<5>(V,f)RGT(L,i)L<0-22>(L.v) FADH<1>(S,t) (S,r)<2>PI<3>(R,t)<3>(W,k)<1>L<1>(R,k) R<4>G(T,s)(S,t)<2>(S,t)I(F,c)(R,k)(G,l)L <1>(T,v)<2>I<2> (C,n)F(W,q)<1>G(F,y)(V,l)C(V,l)R<l>F(E,d)<3>(R,g)<1>P (R,k)<1>L <2>(R,h)LH<2>(A,v)SK (SEQ ID NO:73)

In addition, the following consensus sequence spanning all three domains was identified:

<9-14>(T,q)(A,i)(S,k)(I,l)<3>(A,r)(S,k)<1>(G,m)<2>(S,r)(P,k)<2>(K,f)<2>(E,l)K <0-l>K<0-3>(P,r)<2>(P,r)<1>(K,r)(K,r)(G,d)(R,k)<1>(G,v)<1>(K,g)<3-5(P,s)(P,k) <3>(S,n)<1>(I,l)<0-2>(Q,d)<9>(P,q)<4>(K,a)(P,s)<14-16>(P,a)<4>L<0-10>D<1>(I,l) <0-4>(L,n)<12-46>(K,d)<2-7>(P,a)KV<1>(I,l)D(D,p)(E,v)T<3>W<1>(L,v)L(M,l)(E,d)<0-2>D(K,e)<1>(K,t)<1>(K,a)(W,k)(W,l)<1>(E,k)ER<2>F<1>(G,t)R<1>(D,n)(S,l)FI (A,n)RM(H,r)<1>(V,l)QG(D,n)R<1>F<1>(P,q)WKGSVVDSV(I,v)GVFLTQN(V,t)D(H,y)(L,s)SS( S,n)A(F,y)M<1>(L,v)A(A,s)<1>FP<0-16>(P,v)<6-15>(S,h)<3>(E,d)<10-24>(S,t)<1>(S,e)<6>(K,n)<8-55>(E,i)<8-9>(I,v)<1>(N,s)<1-4>(E,d)<1>(E,s<4>(Q,l)<0-11>(D,h) <1>(F,m)<5>(Q,n)<0-3>(G,e)<2>(G,d)S<1>(K,d)<7-11>(T,m)<2>(V,l)<3>(S,q)<6-10>(S,e)<2-3>(S,v)<19-25>(T,s)<16-28>(R,s)<2-6>(T,p)<5>(P,k)<10>(Q,e)<4>(D,s) <1-4>(S,r)<5>(D,p)<3>(N,d)<3>(P,y)<2>(F,s)<1>(R,k)<1>(G,s)<1>(S,a)(V,r)(P,e)<3>(T,s)<3-6>(I,l)<3>(P,e)<1>E<3-5>(L,q)<1>(G,c)<1>(S,h)(S,n)<1>(V,q)<1>(E,d)<3>T(Q,e) <1-2>(N,g)<3>(E,n)<20-30>(N,a)(P,g)<1-6>(S,l)<25-46>(Q,d)W(D,n)<1>(L,f)R<5>E<3-6>D(S,t)<1>(D,n)(Y,w)<3>R<10>I<2>RG(M,q)(N,f)<2>L(A,s)<1>RI<2-12>FL<3>V<2>(H,n)G<1>IDLEWLR<2>(P,d)(P,s)(D,h)<1>(A,v)K<1>(Y,f)LL(S,e)(I,f)<1>G(L,i)GLKS (V,a)ECVRLL<1>L(H,k)<2>AFPVDTNVGRI(A,c)VR(M,l)G(W,l)VPL(Q,e)PLP<2>(L,v)Q(L,m)H (L,q)L(E,f)<1>YP<1>(L,m)(E,d)(S,n)(I,v)QK(F,y)LWPRLCKL(D,p)Q<1>TLYELHY(Q,h) (L,m)ITFGK<0-2>FCTK<2>PNCNACPM(R,k)<0-2>EC(R,k)(H,y)(F,y)(A,s)SA<1>(A,v)<0-10>S(A,s)(R,k)<1>(A,l)L(P,e)<1>(P,t)(E,q)<7-16>P(I,l)(I,v)E(E,f)P<1>(S,t)P<2-5>E <0-15>(D,a)IE(D,e)<4-23>(I,v)P<1>I<1>(L,f)(N,d)<8-17>(S,a)<1>(A,d)LV<8>(I,l)P <2-5>(K,r)(L,m)K<4>LRTEH<1>V(Y,f)(E,v)LPD<1>H<1>(L,i)L(E,k)<1>(D,e)D(P,i)<2>YLL (A,s)IW(T,q)P(G,d)(E,g)<6-8>(P,s)<3>C<6-10>(M,l)C<4>C<2>C<3>(R,k)E<5>(V,f)RGT (L,i)L<0-22>(L,v)FADH<1>(S,t)(S,r)<2>PI<3>(R,t)<3>(W,k)<1>L<1>(R,k)R<4>G(T,s) (S,t)<2>(S,t)I(F,c)(R,k)(G,l)L<1>(T,v)<2>I<2>(C,n)F(W,q)<1>G(F,y)(V,l)C(V,l)R <1>F(E,d)<3>(R,g)<1>P(R,k)<1>L<2>(R,h)LH<2>(A,v)SK (SEQ ID NO:74)

DMT domain A corresponds to amino acid positions 697 through 796 of SEQ ID NO:2. DMT domain B corresponds to amino acid positions 1192 through 1404 of SEQ ID NO:2. DMT domain C corresponds to amino acid positions 1452 through 1722 of SEQ ID NO:2. The consensus sequence provides amino acid sequences by position using single letter amino acid abbreviations. Numbers in carrots ("<" or ">") refer to amino acid positions where there is no consensus and which therefore, can be any amino acid. Amino acid abbreviations in parentheses indicate alternative amino acids at the same position. Capitalized letters refer to predominant consensus amino acids and lower case letters refer to amino acids that are commonly found in DMT sequences, but are not predominant. Thus, it is a simple matter to identify whether any particular nucleic acid sequence is a DMT nucleic acid and/or encodes a DMT polypeptide.

The structure of full-length DMT polypeptides comprises the following domains and regions. These regions are generally described with reference to SEQ ID NO:2. First, as described above, domain B DMT polypeptides can comprise a bipartite nuclear localization signal (e.g., amino acid positions 43-60 and 61-78 in SEQ ID NO:2) comprised of basic amino acids. Amino acids 36-91 are homologous to human G/T mismatch-specific thymine DNA glycosylase (Genbank accession number AAC50540.1), which has 5-methylcytosine glycosylase activity (Zhu et al., *Nuc. Acids Res.* 28:4157-4165 (2000)). DMT polypeptides also contain a leucine zipper sequence (e.g., positions 1330-1351 of SEQ ID NO:2), that can be involved in protein-protein interactions as well as DNA binding. In addition, the amino portion of the DMT polypeptide (amino acids 43-78) is generally basic, similar to histone H1. Thus, without intending to limit the scope of the invention, it is believed this basic portion of DMT facilitates interactions with DNA and/or chromatic proteins.

In addition, amino acids 1-800 is related to the beta subunit of bacterial DNA-dependent RNA polymerases. Without intending to limit the scope of the invention, it is believed the RNA polymerase-like domain facilitates interaction of DMT with DNA.

Amino acids 1167-1368 is related to proteins in the HhH-GPD superfamily. Amino acids 1,271 to 1,304 correspond to the conserved HhH-GPD motif. The corresponding DMT sequence is DKAKDYLLSIRGLGLKSVECVRLLTLHNLAFPVD (SEQ ID NO:75). Secondary structure prediction (Jpred program) indicates that DMT has two alpha-helices (1,271-1,279 and 1,286 to 1,295) that correspond to the conserved alphaK and alphaL helices in the HhH-GPD motif of the crystallized hOGG1 DNA repair protein (Bruner et al *Nature* 403:859-866 (2000)). In between the two helices (1280 to 1285), is a hairpin with conserved glycines (G1282 and G1284). Amino acids 1286 to 1295 are related to the alphaL helix of hOGG 1, which contacts the DNA backbone (Bruner et al *Nature* 403:859-866 (2000). Thus, without intending to limit the scope of the invention, it is believed this region of DMT contacts the DNA. The catalytic lysine (K1286) and aspartic acid (D1304) residues are conserved in the HhH-GPD motif of DMT. Without intending to limit the scope of the invention, by analogy to hOGG1, K1286 is predicted to displace the modified base and to promote conjugate elimination of the 3'-phosphodiester bond. Without intending to limit the scope of the invention, by analogy to hOGG1, D1304 is believed to assist the reaction by transferring protons to and from K1286.

DMT nucleic acids are a new class of plant regulatory genes that encode polypeptides with sequence identity to members of the endonuclease III genes found in a diverse collection of organisms. Endonuclease III is implicated in various DNA repair reactions. Thus proteins related to endonuclease III are likely to have a chromosomal function. DMT (SEQ ID NO:1) is most related to endonuclease III from *Deinococcus radiodurans* Genbank Accession No. AE002073 (see, e.g., White, O. et al. *Science* 286:1571-1577 (1999)). DMT polypeptides have glycosylase activity (i.e., the capability to cleave the base portion of a nucleotide from the sugar portion). More particularly, DMT polypeptides have demethylase activity, and in more preferred embodiments, have 5-methylcytosine glycosylase activity. Demethylation activity can be assayed in vivo by expressing a candidate polypeptide in the nucleus of a cell and then assaying for a change in methylation of the cell's DNA. See, e.g., Vong, et al., *Science* 260:1926-1928 (1993). Changes in chromosomal methylation can be measured by comparing the ability of methylation sensitive and insensitive endonucleases to cleave DNA from a cell expressing a polypeptide suspected of having demethylase or methylase activity. Alternatively, bisulfate sequencing can be used to identify which base pairs are methylated in a DNA sequence. For a discussion of both methods, see Soppe et al., *Molec. Cell.* 6:791-802 (2000). In vitro assays to measure demethylase activity using labeled substrates are also known to those of skill in the art. See, e.g., Vhu et al., *Proc. Natl. Acad. Sci. USA* 97:5135-5139 (2000).

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term DMT nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "DMT nucleic acid". In addition, the term specifically includes those sequences substantially identical (determined as described below) with a DMT polynucleotide sequence disclosed here and that encode polypeptides that are either mutants of wild type DMT polypeptides or retain the function of the DMT polypeptide (e.g., resulting from conservative substitutions of amino acids in the DMT polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of I and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 40% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 95%, or 99% compared to a reference sequence using the programs described herein; preferably BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W). (see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 55° C., sometimes 60° C., and sometimes 65° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising DMT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C. and sometimes 65° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DETAILED DESCRIPTION

This invention provides molecular strategies for controlling plant development, including methylation of chromosomal DNA, endosperm development and flowering time.

Reproduction in flowering plants involves two fertilization events in the haploid female gametophyte. One sperm nucleus fertilizes the egg to form the embryo. A second sperm nucleus fertilizes the central cell to form the endosperm, a unique tissue that supports the growth of the embryo. Fertilization also activates maternal tissue differentiation, the ovule integuments form the seed coat and the ovary forms the fruit.

The present invention is based, at least in part, on the discovery of a set of female-gametophytic mutations and the subsequent cloning of the gene involved, termed DEMETER (DMT), formally known as A TROPOS (ATR). Two mutant alleles of DMT disclosed here were created using a T-DNA tag, thereby disrupting an exon of the gene. The dmt mutations affect endosperm production, allowing for increased endosperm development. Generally, the mutant dmt alleles are not transmitted by the female gametophyte. Inheritance of a mutant dmt allele by the female gametophyte usually results in embryo abortion and endosperm overproduction, even when the pollen bears the wild-type DMT allele.

In contrast, transmission of dmt mutant alleles through the male gametophyte (i.e., pollen) is ecotype-dependent in *Arabidopsis*. For instance, in some ecotypes (e.g., Columbia), transmission of dmt mutant alleles is less than 50%. However, in Landsberg erecta, transmission is almost normal.

DMT is a repressor of endosperm both before and after fertilization. DMT is both necessary and sufficient for MEDEA transcription. DMT is related to 5-methylcytosine glycosylases. DMT regulates transcription of specific target genes (i.e., MEA) by a demethylation mechanism. DMT is also required for maintaining the proper global pattern of methylation of chromosomal DNA in cells.

The isolated sequences prepared as described herein, can be used in a number of techniques, for example, to suppress or enhance endogenous DMT gene expression. Modulation of DMT gene expression or DMT activity in plants is particularly useful, for example, in producing embryo-less or embryo-reduced seed, seed with increased endosperm, as part of a system to generate seed, to modulate time to flowering, organ identity, size and/or number, meristem size or activity in plants, or to modulate methylation, and thus gene expression in plants. Another use is the expression of DMT polynucleotides in animal cells, for instance as a DNA repair enzyme useful in preventing the unnatural proliferation of cells (including cancer) due to chromosomal lesions. See, e.g., Bruner, et al., *Nature* 403:859 (2000).

As described in more detail below, reduction of expression of DMT in plants results in a number of diverse phenotypes. Without intending to limit the invention to particular embodiments, it is believed that some of the phenotypes that are generated in plants are epigenetic mutations, i.e., effects due to differences in the methylation state of the chromosome that result in altered gene expression. Thus, DMT provides a powerful tool to develop any number of plant lines with a variety of desired phenotypes.

Isolation of DMT Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of DMT nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are legated with vector DNA to form concatemers that can be packaged into the appropriate vector. To prepare a cDNA library, mRNA is isolated from the desired organ, such as ovules, and a cDNA library which contains the DMT gene transcript is prepared from the mRNA. Alternatively, cDNA may be prepared from mRNA extracted from other tissues in which DMT genes or homologs are expressed.

The cDNA or genomic library can then be screened using a probe based upon the sequence of a cloned DMT gene disclosed here. Probes may be used to hybridize with genomic DNA or cDNA sequences to isolate homologous genes in the same or different plant species. Alternatively, antibodies raised against a DMT polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the DMT genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), Academic Press, San Diego (1990).

Appropriate primers and probes for identifying DMT sequences from plant tissues are generated from comparisons of the sequences provided here with other related genes. For instance, DMT can be compared to the other endonuclease III genes, such as Genbank Accession No. AE002073. Using these techniques, one of skill can identify conserved regions in the nucleic acids disclosed here to prepare the appropriate primer and probe sequences. Primers that specifically hybridize to conserved regions in DMT genes can be used to amplify sequences from widely divergent plant species. Appropriate primers for amplification of the genomic region or cDNA of DMT include the following primers (SEQ ID NOS:76-119):

```
Xba-SKEN-7;     CCTCTAGAGGAATTGTCGGCAAAATCGAG

SKB-8;          GGAGAGACGGTTATTGTCAACC
```

-continued

| | |
|---|---|
| SKB-7; | AAAAGTCTACAAGGGAGAGAGAGT |
| SKB-5; | GTAGATGTACATACGTACC |
| SKEN-8; | GCATCCTCCAACAAGTAACAATCCACTC |
| SKB-6; | CACTGAGATTAATTCTTCAGACTCG |
| SKEN-3.5; | CTCAGGCGAGTCAATGCCGGAGAACAC |
| SKEN-3; | CGAGGGCTGATCCGGGGGATAGATATTTT |
| SKEN-2; | CCCCCGGATCAGCCCTCGAATTC |
| SKEN-1; | CCCCTGTCTACAAATTCACCACCTGG |
| SKEL-4; | CTGACCCAACTGCTTCTCTTC |
| skes1.5; | TCACCTGTTCTGAACAGACTGG |
| SKES-1.4; | CAGCAGACGAGTCCATAATGCTCTGC |
| SKES-2.4; | GGTTTGCCTTCCACGACCACC |
| SKES-1; | GGAAGCCACGCAAAGCTGCAACTCAGG |
| SKES-2.45; | GAGTTGCAGCTTTGCGTGGCTTCC |
| SKES2.5; | TTCAGACTCAGAGTCACCTTGC |
| SKES-2; | ACCAGCAGCCTTGCTTGGCC |
| SKES-3; | CATGCCAGAGAAGCAGGGCTCC |
| SKES3.5; | CGATGATACTGTCTCTTCGAGC |
| SKES-6; | CCTCCGCCTGCTCATGCCTCAG |
| SKEN-4; | GTCCATCAGGAGAACTTCTGTGTCAGGAT |
| SKES-4; | GGGAACAAGTGCACCATCTCC |
| SKEN-6; | GCTCTCATAGGGAACAAGTGCACCATCTC |
| SKES-5; | CGCTCGCATGCACCTGGTAC |
| SKB-1; | GGAGGGAATCGAGCAGCTAGAG |
| SKB-2; | GAGCAGCTAAGGGACTGTTCAAACTC |
| SKB-3; | CCAGGAATGGGATTGTCCGG |
| 3' RACE-2; | CTTGGACGGCGCTTGAGGAACC |
| 3' RACE-1; | GCCTACAAGCCAGTGGGATAG |
| cDNA-1; | GCCAAGGACTATCTCTTGAGC |
| SKB-4; | GGATGGACTCGAGCACTGGG |
| SKE2.2-4; | AGAGGAGAGTGCAGACACTTTG |
| cDNA-3; | GAGGACCCTGACGAGATCCCAAC |
| cDNA-9; | CCATGTGTTCCCGTAGAGTCATTCC |
| 2.2 + SKE-1; | ATGGAGCTCCAAGAAGGTGACATG |
| cDNA-5; | CAGAAGTGTGGAGGGAAAGCGTCTGGC |
| cDNA-4; | CCCTCAGACTGTTACACTCAGAAC |
| cDNA-2; | CCCGTTGAGCGGAAAACTTCCTCTCATGGC |
| cDNA-7; | GGAAAGGATTCGTATGTGTCCGTGG |
| SKEN-5; | GCAATGCGTTTGCTTTCTTCCAGTCATCT |

-continued

| | |
|---|---|
| cDNA-6; | GAGGAGAGCAGAGAAGCAATGCGTTTGC |
| cDNA-8; | GTTAGAGAGAAAATAAATAACCC |
| 2.2 + SKE-3; | CCGTAAACAACACCGGATACAC |

The amplification conditions are typically as follows. Reaction components: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per ml Taq polymerase. Program: 96 C for 3 min., 30 cycles of 96 C for 45 sec., 50 C for 60 sec., 72 for 60 sec, followed by 72 C for 5 min.

Standard nucleic acid hybridization techniques using the conditions disclosed above can then be used to identify full-length cDNA or genomic clones.

Alternatively, a number of methods for designing modifications of polynucleotide sequences are known to those of skill in the art. For example, oligonucleotide directed mutagenesis can be used to introduce site-specific mutations in a nucleic acid sequence of interest. Examples of such techniques are found in the references above and, e.g., in Reidhaar-Olson et al. *Science,* 241:53-57 (1988) and Ausubel et al. Similarly, gene shuffling (Stemmer *Proc. Natl. Acad. Sci. USA* 91:10747-10751(1994); Ostermeier et al. *Proc. Natl. Acad. Sci. USA,* 96: 3562-67(1999))) can be used to introduce variation into one or more DMT sequences or subsequences. For example, orthologous (between species) or homologous (within a species) DMT nucleic acids can be interchanged, combined or shuffled to produce novel variations within the scope of the invention.

Additionally, error prone PCR can also be used to introduce variation into a nucleic acid sequence. See, Leung et al. (1989) *Technique* 1:11-15 and Caldwell et al. (1992) *PCR Methods Applic.* 2:28-33.

Control of DMT Activity or Gene Expression

Since DMT genes are involved in controlling seed, in particular endosperm, development, inhibition of endogenous DMT activity or gene expression is useful in a number of contexts. For instance, reduction of DMT activity can be used for production of seed with enhanced endosperm. By reducing and/or eliminating DMT activity, plants with seed containing increased endosperm can be produced.

Alternatively, substantial inhibition of DMT activity can be used for production of fruit with small and/or degraded seed (referred to here as "seedless fruit") after fertilization. In many plants, particularly dicots, the endosperm is not persistent and eventually is degraded. Thus, in plants of the invention in which DMT activity is inhibited, embryo-less seed do not persist and seedless fruit are produced. For production of dicots with enhanced endosperm, the most beneficial effect may be to reduce, but not eliminate DMT activity. On the other hand, in monocots, which have persistent endosperm, it is advantageous to eliminate DMT activity.

Alternatively, plants of the invention can be used to prevent pre-harvest sprouting in seeds, especially those derived from cereals. In these plants, the endosperm persists and is the major component of the mature seed. Premature growth of embryos in stored grain causes release of degradative enzymes which digest starch and other components of the endosperm. Plants of the present invention are useful in addressing this problem because the seeds lack an embryo and thus will not germinate.

Moreover, as discussed herein, time to flowering and DNA methylation can also be modulated by modulating DMT activity in a cell. For example, DMT can be used to modulate the amount of methylated DNA in a cell. Indeed, since expression of many genes is dependent on their methylation state, modulation of DMT activity modulates gene expression in a cell. Examples of genes whose expression is modulated by DMT include MEDEA.

One of skill will recognize that a number of methods can be used to modulate DMT activity or gene expression. DMT activity can be modulated in the plant cell at the gene, transcriptional, posttranscriptional, translational, or posttranslational, levels. Techniques for modulating DMT activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Alternatively, homologous recombination can be used to induce targeted gene disruptions by specifically deleting or altering the DMT gene in vivo (see, generally, Grewal and Klar, *Genetics* 146: 1221-1238 (1997) and Xu et al., *Genes Dev.* 10:2411-2422 (1996)). Homologous recombination has been demonstrated in plants (Puchta et al., *Experientia* 50:277-284 (1994), Swoboda et al., *EMBO J* 13:484-489 (1994); Offringa et al., *Proc. Natl. Acad. Sci. USA* 90: 7346-7350 (1993); and Kempin et al. *Nature* 389:802-803 (1997)).

In applying homologous recombination technology to the genes of the invention, mutations in selected portions of a DMT gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91:4303-4307 (1994); and Vaulont et al. *Transgenic Res.* 4:247-255 (1995) are conveniently used to increase the efficiency of selecting for altered DMT gene expression in transgenic plants. The mutated gene will interact with the target wild-type gene in such a way that homologous recombination and targeted replacement of the wild-type gene will occur in transgenic plant cells, resulting in suppression of DMT activity.

Alternatively, oligonucleotides composed of a contiguous stretch of RNA and DNA residues in a duplex conformation with double hairpin caps on the ends can be used. The RNA/DNA sequence is designed to align with the sequence of the target DMT gene and to contain the desired nucleotide change. Introduction of the chimeric oligonucleotide on an extrachromosomal T-DNA plasmid results in efficient and specific DMT gene conversion directed by chimeric molecules in a small number of transformed plant cells. This method is described in Cole-Strauss et al. *Science* 273:1386-1389 (1996) and Yoon et al. *Proc. Natl. Acad. Sci. USA* 93:2071-2076 (1996).

Gene expression can be inactivated using recombinant DNA techniques by transforming plant cells with constructs comprising transposons or T-DNA sequences. DMT mutants prepared by these methods are identified according to standard techniques. For instance, mutants can be detected by PCR or by detecting the presence or absence of DMTmRNA, e.g., by Northern blots. Mutants can also be selected by assaying for development of endosperm in the absence of fertilization.

The isolated nucleic acid sequences prepared as described herein, can also be used in a number of techniques to control endogenous DMT gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci. (Limerick)* 105:125-149 (1995); Pantopoulos In Progress in Nucleic Acid Research and Molecular Biology, Vol.48. Cohn, W. E. and K. Moldave (Ed.). Academic Press, Inc.: San Diego, Calif., USA; London, England, UK. p. 181-238; Heiseret al. *Plant Sci.* (*Shannon*) 127:61-69 (1997)) and by preventing the accumulation of mRNA which encodes the protein of interest, (see, Baulcombe *Plant Mol. Bio.* 32:79-88 (1996); Prins and Goldbach *Arch. Virol.* 141:2259-2276 (1996); Metzlaffet al. *Cell* 88:845-854 (1997), Sheehy et al., *Proc. Nat. Acad. Sci. USA,* 85:8805-8809 (1988), and Hiatt et al., U.S. Pat. No. 4,801,340).

The nucleic acid segment to be introduced generally will be substantially identical to at least a portion of the endogenous DMT gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 7000 nucleotides is especially preferred.

A number of gene regions can be targeted to suppress DMT gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to DMT gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed. In one embodiment, transgenic plants are selected for DMT activity that is reduced but not eliminated.

Oligonucleotide-based triple-helix formation can be used to disrupt DMT gene expression. Triplex DNA can inhibit DNA transcription and replication, generate site-specific mutations, cleave DNA, and induce homologous recombination (see, e.g., Havre and Glazer *J. Virology* 67:7324-7331 (1993); Scanlon et al. *FASEB J.* 9:1288-1296 (1995); Giovannangeli et al. *Biochemistry* 35:10539-10548 (1996); Chan and Glazer *J. Mol. Medicine* (*Berlin*) 75:267-282 (1997)). Triple helix DNAs can be used to target the same sequences identified for antisense regulation.

Catalytic RNA molecules or ribozymes can also be used to inhibit expression of DMT genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum* nodiflorum mottle virus and subterranean clover mottle virus. The design and use of target RNA-specific ribozymes is described in Zhao and Pick *Nature* 365:448-451 (1993); Eastham and Ahlering *J. Urology* 156:1186-1188 (1996); Sokol and Murray *Transgenic Res.* 5:363-371 (1996); Sun et al. *Mol. Biotechnology* 7:241-251 (1997); and Haseloff et al. *Nature,* 334:585-591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol Bio.* 22:1067-1085 (1993); Flavell *Proc. Natl. Acad. Sci. USA* 91:3490-3496 (1994); Stam et al *Annals Bot.* 79:3-12 (1997); Napoli et al., *The Plant Cell* 2:279-289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

In a preferred embodiment, expression of a nucleic acid of interest can be suppressed by the simultaneous expression of both sense and antisense constructs (Waterhouse et al., *Proc. Natl. Acad. Sci. USA* 95:13959-13964 (1998). See also Tabara et al. *Science* 282:430-431 (1998).

Alternatively, DMT activity may be modulated by eliminating the proteins that are required for DMT cell-specific gene expression. Thus, expression of regulatory proteins and/or the sequences that control DMT gene expression can be modulated using the methods described here.

Another method is use of engineered tRNA suppression ofDMTmRNA translation. This method involves the use of suppressor tRNAs to transactivate target genes containing premature stop codons (see, Betzner et al. *Plant J.* 11:587-595 (1997); and Choisne et al. *Plant J.* 11:597-604 (1997). A plant line containing a constitutively expressed DMT gene that contains an amber stop codon is first created. Multiple lines of plants, each containing tRNA suppressor gene constructs under the direction of cell-type specific promoters are also generated. The tRNA gene construct is then crossed into the DMT line to activate DMT activity in a targeted manner. These tRNA suppressor lines could also be used to target the expression of any type of gene to the same cell or tissue types.

DMT proteins may form homogeneous or heterologous complexes in vivo. Thus, production of dominant-negative forms of DMT polypeptides that are defective in their abilities to bind to other proteins in the complex is a convenient means to inhibit endogenous DMT activity. This approach involves transformation of plants with constructs encoding mutant DMT polypeptides that form defective complexes and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831-845 (1996).

Another strategy to affect the ability of a DMT protein to interact with itself or with other proteins involves the use of antibodies specific to DMT. In this method cell-specific expression of DMT-specific Abs is used inactivate functional domains through antibody:antigen recognition (see, Hupp et al. *Cell* 83:237-245 (1995)).

After plants with reduced DMT activity are identified, a recombinant construct capable of expressing low levels of DMT in embryos can be introduced using the methods discussed below. In this fashion, the level of DMT activity can be regulated to produce preferred plant phenotypes. For example, a relatively weak promoter such as the ubiquitin promoter (see, e.g., Garbarino et al. *Plant Physiol.* 109(4):1371-8 (1995); Christensen et al *Transgenic Res.* 5(3):213-8 (1996); and Holtorf et al. *Plant. Mol. Biol.* 29(4):637-46 (1995)) is useful to produce plants with reduced levels of DMT activity or expression. Such plants are useful for producing, for instance, plants that produce seed with enhanced endosperm.

Use of Nucleic Acids of the Invention to Enhance DMT Gene Expression

Isolated sequences prepared as described herein can also be introduced into a plant cell, thereby modulating expression of a particular DMT nucleic acid to enhance or increase endogenous gene expression. For instance, without being bound to any theory, in light of DMT's relation to Exonuclease III and DNA glycosylases, applicants believe that DMT binds DNA or chromatin and acts to modulate transcription by modulating the methylation state of DNA. Enhanced expression can therefore be used to control plant morphology by controlling expression of genes under DMT's control, such as MEDEA, in desired tissues or cells. Enhanced expression can also be used, for instance, to increase vegetative growth by preventing the plant from setting seed. Where overexpression of a gene is desired, the desired gene from a different species may be used to decrease potential sense suppression effects.

Moreover, as discussed herein, time to flowering and DNA methylation can also be modulated by modulating DMT activity in a cell. For example, increased expression of DMT in a plant results in delayed time to flowering. Similarly, DMT can be used to modulate the amount of methylated DNA in a cell. Indeed, since expression of many genes is dependent on their methylation state, modulation of DMT activity modulates gene expression in a cell. Examples of genes whose expression is modulated by DMT include MEDEA.

One of skill will recognize that the polypeptides encoded by the genes of the invention, like other proteins, have different domains that perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of flowering plant species are well known and described in the technical and scientific literature. See, for example, Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPcl from maize (GenBank No. X15596, Martinez et al. *J. Mol. Biol* 208:551-565 (1989)), and Gpc2 from maize (GenBank No. U45855, Manjunath et al., *Plant Mol. Biol.* 33:97-112 (1997)).

Alternatively, the plant promoter may direct expression of the DMT nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include a promoter from the ovule-specific BEL1 gene described in Reiser et al. *Cell* 83:735-742 (1995) (GenBank No. U39944). Other suitable seed specific promoters are derived from the following genes: MAC1 from maize (Sheridan et al. *Genetics* 142: 1009-1020 (1996), Cat3 from maize (GenBank No. L05934, Abler et al. *Plant Mol. Biol.* 22:10131-1038 (1993), the gene encoding oleosin 18 kD from maize (GenBank No. J05212, Lee et al. *Plant Mol. Biol.* 26:1981-1987 (1994)), vivparous-1 from *Arabidopsis* (Genbank No. U93215), the gene encoding oleosin from *Arabidopsis* (Genbank No. Z17657), Atmycl from *Arabidopsis* (Urao et al. *Plant Mol. Biol.* 32:571-576 (1996), the 2s seed storage protein gene family from *Arabidopsis* (Conceicao et al. *Plant* 5:493-505 (1994)) the gene encoding oleosin 20 kD from *Brassica napus* (GenBank No. M63985), napA from *Brassica napus* (GenBank No. J02798, Josefsson et al. *JBL* 26:12196-1301 (1987), the napin gene family from *Brassica napus* (Sjodahl et al. *Planta* 197:264-271 (1995), the gene encoding the 2S storage protein from *Brassica napus* (Dasgupta et al. *Gene* 133:301-302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266-268 (1995)).

In addition, the promoter sequences from the DMT genes disclosed here can be used to drive expression of the DMT polynucleotides of the invention or heterologous sequences. The sequences of the promoters are identified below.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Promoter and Enhancer Nucleic Acids of the Invention

The present invention provides polynucleotides useful as promoters and enhancers. The invention also provides methods of targeting heterologous polypeptides to a female gametophyte of a plant, including, e.g., the polar nuclei, the eggs and synergids and central cells. Promoter polynucleotides of the invention include, for example, sequences and subsequences of the DMT 5' flanking DNA (SEQ ID NO:3), the 5' UTR region (SEQ ID NO:6) and the 3' flanking region (SEQ ID NO:4). In some embodiments, the promoter sequences are operably linked to the 5' end of the DMT coding region, which is in turn fused to a polynucleotide of interest, typically encoding a polypeptide. An exemplary promoter sequence includes the last 3424 nucleotides of SEQ ID NO:3 linked to the first 1478 nucleotides of SEQ ID NO:5. In some embodiments, a further 444 nucleotides (e.g., the first 444 nucleotides of the DMT coding region) are incorporated into the promoter. In some embodiments, the promoter sequences of the invention specifically direct expression of polynucleotides to the female gametophyte and does not direct expression in tissues following fertilization.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens*host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486(1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be-analyzed according to well known procedures to identify plants with the desired trait. If antisense or other techniques are used to control DMT gene expression, Northern blot analysis can be used to screen for desired plants. In addition, the presence of fertilization independent reproductive development can be detected. Plants can be screened, for instance, for the ability to form embryo-less seed, form seed that abort after fertilization, or set fruit in the absence of fertilization. These procedures will depend, part on the particular plant species being used, but will be carried out according to methods well known to those of skill.

DMT Mutations, Fragments And Fusions

As discussed above, DMT polynucleotides and polypeptides are not limited to the sequences disclosed herein. Those of skill in the art that conservative amino acid substitutions, as well as amino acid additions or deletions may not result in any change in biological activity. Moreover, sequence variants with at least one modulated biological activity of DMT are also contemplated. For example, at least one DMT activity can be increased or decreased by introduction of single or multiple amino acid changes from the sequences disclosed herein. Those of skill in the art will recognize that conservative amino acid substitutions in important functional domains are typically useful in generating more active DMT polypeptides. Conversely, non-conservative substitutions of amino acid residues in functional domains, such as the HhH region of DMT (e.g., amino acids 1271-1304 of SEQ ID NO:2) are likely to disrupt at least one biological activity such as DNA binding. In some embodiments, the fragments of the invention consist of about 100, 200, 300 400, 500, 600, 700, 800, 900, or 1000 amino acids.

Alternatively, fragments of the sequences disclosed herein are contemplated. In some preferred embodiments, the polypeptide fragments have at least one biological activity of DMT. For example, amino acid sequences comprising DMT domain B represent polypeptide fragments with glycosylase or demethylase activity. In some embodiments, a fragment comprising amino acids 1167-1404, 1192-1404, 1192-1368 or 1167-1368 of SEQ ID NO:2 have glycosylase activity.

Mutations, fragments and fusions are also useful as dominant negative mutations. For instance, different regions of the DMT protein are responsible for different biological activities. Thus, mutation or deletion of one functional domain can eliminate one but not all activities. For example, mutation or deletion of the DNA binding domain may result in proteins that interact with proteins necessary for DMT function, effectively titrating out those proteins and preventing an active DMT protein from acting. Similarly, DMT fragments comprising the DNA binding portion of the protein with an inactive enzymatic domain or lacking an enzymatic domain are also useful as dominant negative mutants by competing with active DMT polypeptides for DNA binding sites. As described herein, domains of DMT that can be modulated include: the leucine zipper, nuclear localization sequence, HhH domain, the aspartic acid of the GPD domain, as well a DMT domains A, B or C. Without intending to limit the scope of the invention, based on the data provided herein, DMT has glycosylase and demethylase activity and is a DNA repair enzyme.

Targeting the Polypeptides of the Invention to Chromosomal Regions

Without intending to limit the scope of the invention, based on the data provided herein, it is believed that DMT has glycosylase and/or demethylase activity and is a DNA repair enzyme. DNA methylation plays an important role in the repression of gene transcription during animal development including embryogenesis, myogenesis and blood cell development. Methylated DNA is recognized by MeCP2 which intum represses gene transcription by recruiting the Sin3 repressor complex that contains catalytically active histone deacetylase (Jones et al. *Nature Genetics* 19(2):187-191 (1998)). Histone H3 and H4 deacetylation contributes to the formation of transcriptionally inactive chromatin. Thus, DMT can be used for the purpose of modulating the activity of target genes through chromatin architecture in animal cells as well as plant cells. For example, in some embodiments, DMT is used to catalytically remove 5-MeC from target gene DNA in several ways: e.g., (1) by fusing DMT to a sequence specific DNA binding protein, or (2) by fusing DMT to a subunit of the target repressor complex such as MeCP2 or Sin3. When combined with cell, tissue, or developmentally specific promoters DMT can be used to modulate specific sets of target genes.

In addition, reactive oxygen species, partially reduced species that are produced as intermediates of aerobic respiration, are powerful oxidizing agents that escape the mitochondria and attach vial cellular components. Ionizing radiation and other agents that generate free radicals also produce reactive oxygen species that can attack the genome and cause lesions that are thought to have a key role in in causing cancer and ageing. For example, 7,8-dihydro-8-oxoguanine (oxoG) is a very deleterious adduct generated by oxidation of the guanine base in DNA. The oxoG protein can pair with either cytosine or adenine during DNA replication. Thus, oxoG residues in DNA give rise to G/C to T/A transfusion mutations. These transversions are common somatic mutations found in human cancers. HhH-GPD enzymes, such as those described herein, represent a defense against oxoG by catalysing the expulsion of the oxoG. Thus, in some embodiments, enhanced DMT activity is a method to reduce the incidence of mutations in animal cells. Also, DMT can be used to catalytically remove oxoG from a target gene by fusing DMT to a sequence specific DNA binding protein. When combined with a cell, tissue, or developmentally specific promoters DMT can be used to modulate repair of target genes.

As described above, the polypeptides of the invention can be targeted to chromosomal regions of interest by linking the polypeptides of the invention, including fragments with demethylase activity, to a DNA-binding domain that binds a target sequence. For example, it is known that an enzyme that methylates DNA (Dam methylase) can be targeted to specific sites in the genome (B. V. Steensel and S. Henikoff, *Nature Biotechnology* 18:424-428 (2000)). Specifically, the methylase was tethered to the DNA-binding domain of GAL4. When recombinant GAL4-methylase protein was expressed in transgenic Drosophila, targeted methylation occurred in a region of a few kilobases surrounding the GAL4 DNA binding sequence. In a analogous fashion, DMT, or a portion of DMT that has biological activity (e.g., a portion containing the HhH-GpD motif amino acids such as 1167 to 1368 of SEQ ID NO:2), can be tethered (e.g., as a translational fusion or chemically linked) to proteins that interact at specific sites in the genome. As a result, specific targeted regions of the genome are hypomethylated by DMT. As discussed above, typically hypomethylation promotes transcription of genes (S. E. Jacobsen, *Current Biology* 9, 617 (1999). The invention provides compositions and methods for methylation of a desired area of the chromosome by targeting DMT to those regions. Thus, these embodiments provide additional ways to activate transcription of a desired gene in a targeted chromosomal region.

The following Examples are offered by way of illustration, not limitation.

EXAMPLE

Example 1

This example shows the characterization of dmt mutant plants and the isolation of DMT.

*Arabidopsis* plants were transformed by infiltrating them with *Agrobacterium*containing the SK115 T-DNA vector (generously provided by D. Weigel (Salk Institute, La Jolla, Calif.)). T1 seeds were harvested. The SK115 vector has the bialaphos resistance (BAR) gene that allowed us to directly select transgenic plants in soil after spraying with the commercially available herbicide, Basta. Siliques from approximately 5,000 Basta resistant plants were opened, and those displaying approximately 50% seed abortion were identified.

Two lines, B13 and B33, were identified for further characterization. Genetic analysis of the mutants revealed that the dmt mutants were female sterile. Male fertility, however, depended on the genetic background of the mutant alleles. For instance, in the Columbia background, transmission of the dmt mutation is less than 50%. However, in the Landsberg erecta background, transmission through the male was almost normal.

Molecular analysis confirmed that the two mutations were allelic. For example, both the B13 and B33 alleles carry the SK115 T-DNA within a DMT exon, confirming that disruption of the DMT gene resulted in the observed B13 and B33 phenotypes.

5'- and 3'-RACE were used to delineate the 5'- and 3'-ends of the cDNA, respectively. 5'-RACE was carried out using reagents and protocols provided by 5' RACE System for Rapid Amplification of cDNA Ends, Version 2.0, GIBCO BRL, LIFE TECHNOLOGIES, Grand Island, N.Y. and Marathon cDNA Amplification Kit, Clontech, Palo Alto, Calif. Final gene specific 5'-RACE primers were SKES-4 (GGGAACAAGTGCACCATCTCC; SEQ ID NO:97) and SKES3.5 (CGATGATACTGTCTCTTCGAGC; SEQ ID NO:95). 3'-RACE was carried out using reagents and protocols provided by Marathon cDNA Amplification Kit, Clontech, Palo Alto. Final gene-specific 3' end was obtained from cDNA library screening.

The nucleotide sequence of the genomic copy of DMT was also determined (SEQ ID NO:1). The 5'-end of the DMT RNA is located at position 3,425 of SEQ ID NO:1. The position of the 3'-end of the DMT RNA is at position 12,504 of SEQ ID NO:1. The position of the ATG translation initiation codon is at position 4,903 of SEQ ID NO:1. The position of the TAA translation termination codon is at position 12,321 of SEQ ID NO:1.

A portion of the DMT polynucleotide sequence, including the first exon, is encompassed by the bacterial artificial chromosome (BAC) clone T9J15TRB. For example, sequences 3820-4299, 4319-4558, 4546-5025 and 9320-9777 of SEQ ID NO:1 were previously determined using the BAC clone as a template. Moreover, a separate independently sequenced region (Bork, C. et al *Gene* 28:147-153 (1998)) also overlaps the DMT sequence at positions 11,087 to 12,785 of SEQ ID NO:1.

The predicted DMT protein has 1,729 amino acids. This sequence was compared to known protein sequences using BLAST and revealed homology to several Endonuclease III proteins. The highest homology was to the Endonuclease III protein from *Deinococcus radiodurans*, Genbank Accession No. AE002073 (see, e.g., White, O. et al. *Science* 286:1571-1577 (1999)). Other DMT motifs include two consecutive nuclear localization signals at positions 43-60 and 61-78 and a leucine zipper at positions 1330-1351.

Example 2

This example provides further evidence that mutant phenotypes are caused by loss-of-function mutations.

A new allele, dmt-3, was obtained. The dmt-3 allele was caused by insertion of the simple pD991 T-DNA vector (M. R. Sussman, et al., *Plant Physiol.* 124:1465 (2000)) into the 2nd exon of the DMT gene. In contrast, the previous two alleles, dmt-1 and dmt-2, were caused by insertion of the activation T-DNA vector, SKI015 vector. The mutant phenotypes generated by all three dmt alleles are the same. Because pD991 does not have activation sequences, it suggests that all three mutant alleles are loss-of-function alleles. Consistent with this conclusion, seed abortion can be rescued with a transgene with 3,373 base pairs of 5'-DMT flanking sequences plus 1,478 base pairs of 5-'UTR ligated to a cDNA encoding the full-length DMT polypeptide (i.e., DMTp::DMT). Thus, dmt/DMT heterozygous plants that are hemizygous for the DMTp::DMT transgene displayed 25% seed abortion. Control dmt/DMT plants displayed 50% seed abortion.

Example 3

This example shows that DMT is necessary and sufficient for MEA gene expression.

As discussed above, when fertilization of dmt/dmt homozygous mutant flowers was prevented, fertilization-independent endosperm development was observed. This is very similar to when fertilization of mutant mea flowers is prevented. Thus, before fertilization, both DMT and MEA, a polycomb protein (T. Kiyosue et al., *Proc. Natl. Acad. Sci. USA* 96:4186 (1999)), prevent the central cell of the female gametophyte from forming an endosperm. This is consistent with DMT being a positive regulator of MEDEA (MEA).

As further evidence of this relationship, MEA RNA accumulates in immature floral (IF) buds and open flowers (OF). However, in dmt/dmt mutant plants there was no detectable MEA RNA. Thus, DMT is necessary for MEA gene expression.

In addition, we have generated plants with a transgene, CaMV::DMT, designed to overexpress DMT. The full-length DMTcDNA was ligated to the constitutive cauliflower mosaic virus promoter, CaMV (S. G. Rogers, H. J. Klee, R. B. Horsch, R. T. Fraley, *Meth Enzymol* 153:253 (1987)). In control wild type plants, the DMT and MEA genes were not significantly expressed in the leaf. However, in 35S::DMT plants, both DMT and MEA RNA level increased significantly. This shows that DMT is sufficient to induce MEA gene expression in the leaf.

Example 4

This example shows that DMT is a member of the HhH-GPD superfamily of DNA repair enzymes.

A BLAST search, followed by a conserved domain search, revealed that DMT is highly related to the HhH-GPD superfamily of base excision DNA repair proteins (i.e., score of 70.1, E-value of $8e^{-13}$). This family contains a diverse range of structurally related DNA repair proteins. The superfamily is called the HhH-GPD family after its hallmark helix-hairpin-helix and Gly/Pro rich loop followed by a conserved aspartate (S. D. Bruner, et al., *Nature* 403:859 (2000)). This includes endonuclease III (EC:4.9.99.18), 8-oxoguanine DNA glycosylases (i.e., yeast OGGI), the thymine DNA glycosylase of methyl-CPG binding protein MBD4 (B. Hendrich, et al., *Nature* 401:301 (1999)), and DNA-3-methyladenine glycosylase 11 (EC:3.2.2.21). The predicted amino acid sequence of DMT contains many of the conserved amino acids of this superfamily.

The hallmark of the superfamily of base-excision DNA repair proteins is a helix-hairpin-helix structural element followed by a Gly/Pro-rich loop and a conserved aspartic acid (i.e., HhH-GPD motif). The DMT polypeptide is 1,729 amino acids in length. Amino acids 1,271 to 1,304 correspond to the conserved HhH-GPD motif. The DMT sequence is DKAKDYLLSIRGLGLKSVECVRLLTLHNLAFPVD (SEQ ID NO:75). The catalytic lysine (K1286) and aspartic acid (DI304) residues are conserved in the HhH-GPD motif of DMT. Secondary structure prediction (Jpred program) indicates that DMT has two alpha-helices (amino acids 1,271-1,279 and 1,286 to 1,295) that correspond to the conserved alphaK and alphaL helices in the HhH-GPD motif of the crystallized hOGGI DNA repair protein (Bruner et al *Nature* 403:859-866 (2000)).

The *Arabidopsis* DMT coding sequences were also used to identify homologous sequences in both public and proprietary databases using both the BLAST and PSI-BLAST computer algorithms. This analysis revealed amino acid sequences from several plant species, including wheat, maize, rice, soybean and *Arabidopsis* (SEQ ID NOS:8, 9, 11, 12, 14, 15, 17, 18, 20, 22, 24, 25, 27 and 29). Based on these sequences, the following consensus sequences for DMT were determined:

DMT Domain A

KV<1>(I,l)D(D,p)(E,v)T<3>W<1>(L,v)L(M,l)(E,d)<0-2>D(K,e)<1>(K,t) <1>(K,a)(W,k)(W,l)<1>(E,k) ER<2>F<1>(G,t)R<1>(D,n)(S,l)FI(A,n)RM(H,r)<1>(V,l) QG (D,n)R<1>F<1>(P,q)WKGSVVDSV(I,v)GVFLTQN(V,t)D(H,y)(L,s)SS(S,n)A(F,y)M<1>(L,v)A (A,s)<1>FP (SEQ ID NO:71)

DMT Domain B

W(D,n)<1>(L,f)R<5>E<3-6>D(S,t)<1>(D,n)(Y,w) <3>R<10>I<2>RG(M,q) (N,f)<2>L(A,s)<1>RI<2-12>FL<3>V<2>(H,n)G<1>IDLEWLR<2>(P,d)(P,s)(D,h) <1>(A,v) K<1>(Y,f)LL(S,e)(I,f)<1>G(L,i)GLKS(V,a) ECVRLL<1>L(H,k)<2>AFPVDTNVGRI(A,c)VR (M,l)G (W,l)VPL(Q,e)PLP<2>(L,v)Q(L,m)H(L,q)L(E,f) <1>YP<1>(L,m)(E,d)(S,n)(I,v)QK (F,y)LWPRLCKL(D,p) Q<1>TLYELHY(Q,h)(L,m)ITFGK<0-

2>FCTK<2>PNCNACPM(R,k)<0-2>EC (R,k)(H,y)(F,y)(A, s)SA<1>(A,v)<0-10>S(A,s)(R,k)<1>(A,l)L(P,e)<1>(P,t) (SEQ ID NO:72)

DMT Domain C.

P(I,l)(I,v)E(E,f)P<1>(S,t)P<2-5>E<0-15>(D,a)IE(D,e) <4-23>(I,v)P<1>I<1>(L,f)(N,d)<8-17>(S,a)<1>(A,d) LV<8>(I,l)P<2-5>(K,r)(L,m)K<4>LRTEH<1>V(Y,f) (E,v) LPD <1>H<1>(L,i)L(E,k)<1>(D,e)D(P,i)<2>YLL(A,s)IW (T,q)P(G,d)(E,g)<6-8>(P,s)<3>C<6-10>(M,l) C<4>C<2>C<3>(R,k)E<5>(V,f)RGT(L,i)L<0-22>(L,v) FADH<1>(S,t) (S,r)<2>PI<3>(R,t)<3>(W,k)<1>L<1>(R,k) R<4>G(T,s)(S,t)<2>(S,t)I(F,c)(R,k)(G,l)L <1>(T,v)<2>I<2> (C,n)F(W,q)<1>G(F,y)(V,l)C(V,l)R<1>F(E,d)<3>(R,g) <1>P(R,k)<1>L <2>(R,h)LH<2>(A,v)SK (SEQ ID NO:73)

The first consensus sequence listed above corresponds to amino acid positions 586 through 937 of SEQ ID NO:2. The second consensus sequence listed above corresponds to amino acid positions 1117 through 1722 of SEQ ID NO:2. The consensus sequence provides amino acid sequences by position using single letter amino acid abbreviations. Numbers in carrots ("<" or ">") refer to amino acid positions where there is no consensus and which therefore, can be any amino acid. Amino acid abbreviations in parentheses indicate alternative amino acids at the same position. Capitalized letters refer to predominant consensus amino acids and lower case letters refer to amino acids that are commonly found in DMT sequences, but are not predominant.

Example 5

This example demonstrates the relationship between DNA repair and demethylation.

For many years, attention was focused on the ability of DNA glycosylases to repair DNA. For example, glycosylases are involved in the repair of G/T mismatched bases by depurinating the thymidine base moiety. Recently it was shown that avian (B. Zhu et al., *Proc. Natl. Acad. Sci. USA* 97:5135 (2000)) and mammalian (B. Zhu et al., *Nucl. Acid Res.* 28:4157 (2000)). G/T mismatch DNA glycosylases also have 5-methylcytosine-DNA glycosylase activity. That is, these enzymes are demethylases that remove 5-methylcytosine that is later replaced by cytosine. Without intending to limit the scope of the invention, it is believed that as a member of this superfamily, DMT is a demethylase (i.e., 5-methylcytosine glycosylase).

The methylation (i.e., amount of 5-methylcytosine) state of a gene can have a profound effect on its expression. In general, hypomethylation is associated with elevated gene expression, whereas hypermethylation is associated with decreased gene expression (S. E. Jacobsen, *Current Biology* 9:617 (1999)). Thus, it is likely that DMT activates MEA gene expression by reducing its level of methylation.

Mutations in the DDM1 gene in *Arabidopsis* reduce by 70% the overall genome cytosine methylation (E. J. Finnegan, et al., *Proc. Natl. Acad. Sci. USA* 93:8449 (1996); M. J. Ronemus, et al., *Science* 273:654 (1996)). Such plants develop a number of phenotypic abnormalities including floral phenotypes (T. Kakutani, et al., *Proc. Natl. Acad. Sci. USA* 93:12406 (1996)). Similarly, phenotypic abnormalities have been observed developing in dmt/dmt homozygous plants that affect petal number, floral organ fusion, and floral organ identity. Moreover, independent CaMV::DMT transgenic lines that overexpress DMT frequently are late-flowering. This is particularly interesting because late flowering of ddml plants was shown to be due to hypomethylation of the FWA gene (W. J. J. Soppe et al., *Mol Cell* 6:791 (2000)). Thus, without intending to limit the scope of the invention, it is believed that both ddml loss-of-function mutations and overexpression of DMT (i.e., CaMV::DMT) may result in genome hypomethylation.

Example 6

This example demonstrates targeting gene expression to the female gametophyte using a DMT promoter sequence.

DMT RNA accumulates in many plant organs such as immature flowers, mature flowers, open flowers, stems and to a lesser extent, leaves. To understand the spatial and temporal regulation of DMT RNA accumulation, the expression of the DMT promoter fused to reporter genes was analyzed. We fused 2,282 base pairs of5'-DMT sequences, the full-length 5'-UTR (1,478 base pairs), 444 base pairs of DMT coding sequences that contain a nuclear localization signal to two reporter genes, the green fluorescent protein (GFP; (Y. Niwa, et al., *Plant J.* 18:455 (1999))) and β-glucuronidase (GUS; (R. A. Jefferson, T. A. Kavanagh, M. V. Bevan, *EMBO J.* 6:3901 (1987))). Reporter gene expression was observed in the developing female gametophyte, in the polar nuclei before they fuse, in the egg and synergids, and in the central cell. Expression was not detected after fertilization. Thus, this promoter is useful for targeting gene expression to the female gametophyte.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An expression cassette for the expression of a heterologous polynucleotide in a plant cell, wherein the expression cassette comprises a promoter comprising SEQ ID NO:6, and the promoter is operably linked to a heterologous polynucleotide.

2. The expression cassette of claim 1, wherein the expression cassette further comprises SEQ ID NO:3.

3. The expression cassette of claim 1, wherein the expression cassette further comprises SEQ ID NO:4.

* * * * *

SEQUENCE LISTING

```
<160> NUMBER OF SEQ ID NOS: 119

<210> SEQ ID NO 1
<211> LENGTH: 12785
<212> TYPE: DNA
<213> ORGANISM: Arabidopsis thaliana
<220> FEATURE:
<223> OTHER INFORMATION: DEMETER (DMT) genomic sequence

<400> SEQUENCE: 1

aagcttaaag ctaccaacat cgaatttagt aaaagaccca tgatttgaaa ttggaattgt      60
```

-continued

```
cggcaaaatc gagaagatat agagccgaca cgggaacagt gaaaaccaca aagcgcgtaa    120
gaatgaaaca gtgggagaag gaagagagaa tcttaccgat cattcgaggg aaaagatggg    180
aatcagagaa aaatctggaa aaaaagaaat taagagaaag agagagaaga aagtgaggag    240
gaagatgcag tgaagactgc tatagccaca tcccacatgg tgtgatgaga gagagagaga    300
gagaggttaa agcagcaaat tgtggagaga taaagagaga gagagactga gcgagtcaag    360
ttcgtcgtcg tgtttaaaag aaagaatcct atatttgcct ttttctttac tactttattt    420
tcagactatt tgcttatttt gcctcaaact tttttgattg tcacttttcg atcctaaagt    480
gtttgacaat ttacctgcct ttttctccaa gaaaaatcag aacagaccac agcaaattta    540
tgtattttct attaaaaaag aaagaaagaa ttcatattac ttatagaatt aaaagctaag    600
cagttgaaaa cgtgaaagca gaatttctaa aaaaaatagt aaactgctac aaacttattt    660
atgtgtatat aacatatcta taaagaaact caaatatatg ataaatcatt ttaacaaaat    720
ttctatgaaa ttataataaa aaaagtcact tttgacactt aaaaggttga caataaccgt    780
ctctccaaaa aaaaatcaaa acatttataa tttctaaaac tatggtgtaa ttttgctgaa    840
atcaaaaaga aaagaaggat ttctatatca taagtttcat tattgtatca aactttcaaa    900
tttcatgtaa tttgaaagga aaaaaattaa gatataatgt tgtttttgtt tcttatgtta    960
cattttcatg gaatatatat tcataacaaa aaatgtattt taatatgatg agagattacc   1020
atccaaaagg tcgaacttat ataaaacaag ttaataacta aacaatacat gtgatcacaa   1080
tcaatgacag ttttgatctt aaaatagaaa tgattgagca aacctcaaaa atgtcttctt   1140
aggatcacaa aatctttcct ttagcttatt aaagccggga gttcaactct ctctcccttg   1200
tagacttttt gttttcaaat ctttttcttt caaaaaatca ataattagtt aatgggcata   1260
atatttggtt ttaattaagt ccatagattt tttaggacca tctctaatca cgacaaatat   1320
cctaaattgt aacacattta aaacttaaaa gtattgcatt cacaatcctt aaaatatata   1380
tatatatata tatatatata tatatatata tatatgaaag ttatatagaa acgataactc   1440
cttactcaac aattagccca aaaaaacatc cataatgcat ttaaactagg aattttaaca   1500
aactcaaata ggttggtagt taaaaaaaaa caaatagtag atgtacatac gtacctttaa   1560
aaatatatac tcatatcgaa agttttaaat tttgcgaaat taaatacatt tatctatcaa   1620
ttaaaataca tttaataatg cataattctg taatatctat ctttaatttc catatagaac   1680
caaaacaaaa taaacatatc aaatagtttt aacttaacaa aaacgttagg gaaaagttga   1740
cctaactagc ttgattgacg ttgaacttgt caatgcgaaa gcgatatttc caatatatac   1800
tacatgtagt attatttata tggaagtttc taaaaaggtg ttgagtggat tgttacttgt   1860
tggaggatgc tattttttcc ttcttgccat aatattttac gagtatggga taactacata   1920
ctcatgatta tgaaacgctc actttatttg aaaaacctcc taatacacca aatatgtcac   1980
tagattccaa aacgtagacc aattgtatct aatctcaaat tctcaatcaa agtattaatt   2040
taccgatggt aagaaaagtt aaccgatata attatcaaaa gaaagaataa gtcaacagat   2100
tcttaatctc tttattttgg tatatgaaca tttgtacaaa aatctcaaaa gatatgtaac   2160
tgtttaaaat ataaattcac tgagattaat tcttcagact cgtgttagct ataataatgt   2220
caagagttct tcttgtttca aggaaaaacc ttaaagatat gtatattttc tgtaattatg   2280
atgatataat ttgctattca ttgtcacaaa cattacttta aaaaatcgta ttttcattac   2340
tacaatgttg actaagaaca aaaatacatt gattattgat atatcgtcaa ctgaattttc   2400
ttccgaggga tataattctc aaacatagca agaatctcat aataatgttt cgtgactacc   2460
```

-continued

```
tttagacgaa atttttttaa gattcgtaac gtgacttatg gtctcttgct gtgggggtca   2520
atgcgaataa atctaaatgt atgggagtca aataaaatac caagaaaaat aaaggagcag   2580
cacccaataa actatatggg accagaaatc ctttcattgg tttaaaatag gattatcccg   2640
aaagatgaag gactaaattg aaactgattg ggggtaggaa gagatccgtc acaatcatta   2700
atggcttcca cgcggaaact tgtcgtttat acaatttcat taactttcgg gtcgggttta   2760
tattccaaat gggtcaaata atattagttt aatacactaa cggagtaatt aattggtgac   2820
tacaatttta tcagtttggt gcaattagaa acgaacatag tcgtaaaata cgagttcggt   2880
gttatacctt tatttacgtt aaaaaaatac gagaattttg tgtcaaattt caaattaatt   2940
tcatgaatat atggaaatta ttagatactc tagcgaaaat agtgattatg agcgttttac   3000
aaaaatacga ttttagcatt gaacttcctt tatgtaattc ggtcaaatgt tggcatgaag   3060
aagcaagttt gcaacattaa atttcattta aaaatcgtgt tgacatactt taaaatctaa   3120
atataggaag aagaccaaaa cattaaattt agtaagattc taatgaacat tttataagtta  3180
taacttataa ccaacaaaag ttgggtttag cgttgttgct ttatctgaaa acttgcaaac   3240
taaaccattt taataggact aatgacaatt aacaacaaaa tacacttaag caacaacgtc   3300
ctcgtgaata taatttgggc ctcaggccca tattgctaac gccaactgat atttcacttt   3360
attccttctt catctcacca cactctctct ctatctctat ctctaacggc atagctgact   3420
cagtgttctc cggcattgac tcgcctgaga atcagaaagc ttagatcggt gagcttttag   3480
ctccatttc tgtttattta catattattt cctttttttc tctctccctt ttttatctgg   3540
aatttgttct gctaaatttt ccagctgtta cattttccga tcacgagaag aatcactggg   3600
tttttatgtt aatcaataca tgttcctgtt ttctgatcat aaatctcagc tattaacacc   3660
tgattttgat tctgcgtaat aaaaaacctct gatttgcttt tatcttcact ttccccataa  3720
acattgctta ctttattcgc tcttctttta ccgtttccag ctaaaaaatt cttcgctatt   3780
caatgtgttt ctcgttttgt tgatgagaaa aatatctgac aaaaaatcat ttattgcatt   3840
ttatggtgca gattcttagt taatgtcgcc ttctctaacc aagtcagatt aaaaaggagt   3900
gttcgtccat gttgctttgt tttggtgttt ggagagagtt ttcggagagt taggtgagtg   3960
ttatttgggg tgaggtagtg ataaggtttg aagggggagt gattcatcaa gtgtgttatg   4020
aattcgaggg ctgatccggg ggatagatat tttcgagttc ctttggagaa tcaaactcaa   4080
caagagttca tgggttcttg gattccattt acacccaaaa aacctagatc aagtctgatg   4140
gtagatgaga gagtgataaa ccaggatcta aatgggtttc caggtggtga atttgtagac   4200
aggggattct gcaacactgg tgtggatcat aatggggttt ttgatcatgg tgctcatcag   4260
ggcgttacca acttaagtat gatgatcaat agcttagcgg gatcacatgc acaagcttgg   4320
agtaatagtg agagagatct tttgggcagg agtgaggtga cttctccttt agcaccagtt   4380
atcagaaaca ccaccggtaa tgtagagccg gtcaatggaa attttacttc agatgtgggt   4440
atggtaaatg gtcctttcac ccagagtggc acttctcaag ctggctataa tgagtttgaa   4500
ttggatgact tgttgaatcc tgatcagatg cccttctcct tcacaagctt gctgagtggt   4560
ggggatagct tattcaaggt tcgtcaatgt gagtgatcaa atctattttc agtttttttt   4620
tttccctttc ttccgttctt gcagtactta gagtagaaca tgaattagaa tatcttaaga   4680
aagtcatggt tttgaacaga tggacctcca gcgtgtaaca agcctcttta caatttgaat   4740
tcaccaatta gaagagaagc agttgggtca gtctgtgaaa gttcgtttca atatgtaccg   4800
```

-continued

```
tcaacgccca gtctgttcag aacaggtgaa aagactggat tccttgaaca gatagttaca   4860
actactggac atgaaatccc agagccgaaa tctgacaaaa gtatgcagag cattatggac   4920
tcgtctgctg ttaatgcgac ggaagctact gaacaaaatg atggcagcag acaagatgtt   4980
ctggagttcg accttaacaa aactcctcag cagaaaccct ccaaaaggaa aaggaagttc   5040
atgcccaagg tggtcgtgga aggcaaacct aaaagaaagc cacgcaaacc tgcagaactt   5100
cccaaagtgg tcgtggaagg caaacctaaa aggaagccac gcaaagctgc aactcaggaa   5160
aaagtgaaat ctaaagaaac cgggagtgcc aaaaagaaaa atttgaaaga atcagcaact   5220
aaaaagccag ccaatgttgg agatatgagc aacaaaagcc ctgaagtcac actcaaaagt   5280
tgcagaaaag ctttgaattt tgacttggag aatcctggag atgcgaggca aggtgactct   5340
gagtctgaaa ttgtccagaa cagtagtggc gcaaactcgt tttctgagat cagagatgcc   5400
attggtggaa ctaatggtag tttcctggat tcagtgtcac aaatagacaa gaccaatgga   5460
ttgggggcta tgaaccagcc acttgaagtg tcaatgggaa accagccaga taaactatct   5520
acaggagcga aactggccag agaccaacaa cctgatttat tgactagaaa ccagcaatgc   5580
cagttcccag tggcaaccca gaacacccag ttcccaatgg aaaaccaaca agcttggctt   5640
cagatgaaaa accaacttat tggctttcca tttggtaacc agcaacctcg catgaccata   5700
agaaaccagc agccttgctt ggccatgggt aatcaacaac ctatgtatct gataggaact   5760
ccacggcctg cattagtaag tggaaaccag caactaggag gtccccaagg aaacaagcgg   5820
cctatatttt tgaatcacca gacttgttta cctgctggaa atcagctata tggatcacct   5880
acagacatgc atcaacttgt tatgtcaacc ggagggcaac aacatggact actgataaaa   5940
aaccagcaac ctggatcatt aataagaggc cagcagcctt gcgtaccttt gattgaccag   6000
caacctgcaa ctccaaaagg ttttactcac ttgaatcaga tggtagctac cagcatgtca   6060
tcgcctgggc ttcgacctca ttctcagtca caagttccta caacatatct acatgtggaa   6120
tctgtttcca ggattttgaa tgggactaca ggtacatgcc agagaagcag ggctcctgca   6180
tacgattctt tacagcaaga tatccatcaa ggaaataagt acatactttc tcatgagata   6240
tccaatggta atgggtgcaa gaaagcgtta cctcaaaact cttctctgcc aactccaatt   6300
atggctaaac ttgaggaagc caggggctcg aagagacagt atcatcgtgc aatgggacag   6360
acggaaaagc atgatctaaa cttagctcaa cagattgctc aatcacaaga tgtggagaga   6420
cataacagca gcacgtgtgt ggaatattta gatgctgcaa agaaaacgaa aatccagaaa   6480
gtagtccaag aaaatttgca tggcatgcca cctgaggtta tagaaatcga ggatgatcca   6540
actgatgggg caagaaaagg taaaaatact gccagcatca gtaaaggtgc atctaaagga   6600
aactcgtctc cagttaaaaa gacagcagaa aaggagaaat gtattgtccc aaaaacgcct   6660
gcaaaaaagg gtcgagcagg tagaaaaaaa tcagtacctc cgcctgctca tgcctcagag   6720
atccagcttt ggcaacctac tcctccaaag acacctttat caagaagcaa gcctaaagga   6780
aaagggagaa agtccataca agattcagga aaagcaagag gtaactaatg tattctacaa   6840
tctctgtgat ataattttga gattttagta actgatgtgt ccaaaccagc tccttatcac   6900
tgttggtgcg ttgtataggt ccatcaggag aacttctgtg tcaggattct attgcggaaa   6960
taatttacag gatgcaaaat ctgtatctag gagacaaaga aagagaacaa gagcaaaatg   7020
caatggtctt gtacaaagga gatggtgcac ttgttcccta tgagagcaag aagcgaaaac   7080
caagacccaa agttgacatt gacgatgaaa caactcgcat atggaactta ctgatgggga   7140
aaggagatga aaaagaaggg gatgaagaga aggataaaaa gaaagagaag tggtgggaag   7200
```

-continued

```
aagaaagaag agtcttccga ggaagggctg attccttcat cgctcgcatg cacctggtac   7260
aaggtgaaga tccacttctc ttctcaactc catttttatt cacacaaatt agtagaatac   7320
tcaaaaatga tgttttgttt gcaaaatttt aaaattcact agttaaccat gtcaaataat   7380
attcataatg catcttgtga agaacaggtg tgcatttatg gtgacagctg aatggtttat   7440
gtgcctatta tttcttttac tgctatagat gaccaattga acttaaacgt ttacaggaga   7500
tagacgtttt tcgccatgga agggatcggt ggttgattcg gtcattggag ttttccttac   7560
acagaatgtc tcggatcacc tttcaaggta tatgagttgc cttaataaat tgagttccaa   7620
aacatagaaa ttaacccatg gtggttttac aatgcagctc tgcgttcatg tctctagctg   7680
ctcgattccc tccaaaatta agcagcagcc gagaagatga aaggaatgtt agaagcgtag   7740
ttgttgaaga tccagaagga tgcattctga acttaaatga aattccttcg tggcaggaaa   7800
aggttcaaca tccatctgac atggaagttt ctggggttga tagtggatca aaagagcagc   7860
taagggactg ttcaaactct ggaattgaaa gatttaattt cttagagaag agtattcaaa   7920
atttagaaga ggaagtatta tcatcacaag attcttttga tccggcgata tttcagtcgt   7980
gtgggagagt tggatcctgt tcatgttcca aatcagacgc agagtttcct acaaccaggt   8040
gtgaaacaaa aactgtcagt ggaacatcac aatcagtgca aactgggagc ccaaacttgt   8100
ctgatgaaat ttgtcttcaa gggaatgaga gaccgcatct atatgaagga tctggtgatg   8160
ttcagaaaca agaaactaca aatgtcgctc agaagaaacc tgatcttgaa aaaacaatga   8220
attggaaaga ctctgtctgt tttggtcagc caagaaatga tactaattgg caaacaactc   8280
cttccagcag ctatgagcag tgtgcgactc gacagccaca tgtactagac atagaggatt   8340
ttggaatgca gggtgaaggc cttggttatt cttggatgtc catctcacca agagttgaca   8400
gagtaaagaa caaaaatgta ccacgcaggt tttcagaca aggtggaagt gttccaagag   8460
aattcacagg tcagatcata ccatcaacgc ctcatgaatt accaggaatg ggattgtccg   8520
gttcctcaag cgccgtccaa gaacaccagg acgataccca acataatcaa caagatgaga   8580
tgaataaagc atcccattta caaaaaacat ttttggatct gctcaactcc tctgaagaat   8640
gccttacaag acagtccagt accaaacaga acatcacgga tggctgtcta ccgagagata   8700
gaactgctga agacgtggtt gatccgctca gtaacaattc aagcttacag aacatattgg   8760
tcgaatcaaa ttccagcaat aaagagcaga cggcagttga atacaaggag acaaatgcca   8820
ctattttacg agagatgaaa gggacgcttg ctgatgggaa aaagcctaca agccagtggg   8880
atagtctcag aaaagatgtg gaggggaatg aagggagaca ggaacgaaac aaaaacaata   8940
tggattccat agactatgaa gcaataagac gtgctagtat cagcgagatt tctgaggcta   9000
tcaaggaaag agggatgaat aacatgttgg ccgtacgaat taaggtaaat ctactaattt   9060
cagttgagac cctcatcaaa tctgtcagaa ggcttgaaca tcagtaaatt atgtaaccat   9120
atttacaaca ttgcaggatt tcctagaacg gatagttaaa gatcatggtg gtatcgacct   9180
tgaatggttg agagaatctc ctcctgataa agccaagtgg gtaaatcaca tttttagtga   9240
ctgcaacact agcacgatcg atttactcaa caattacgtc aaactgagta ttaacaagtt   9300
gctcatgaac atttcacagg gactatctct tgagcataag aggtctgggt ttgaaaagtg   9360
ttgaatgcgt gcgactctta acactccaca atcttgcttt ccctgtgagt cagactattc   9420
cattatctac taaaaactta gaataactcc ggctaactaa gctggaactt gtattgatga   9480
tatgaaggtt gacacgaatg ttggaaggat agcagttagg atgggatggg tgcctctaca   9540
```

-continued

```
acccctacct gaatcacttc agttacacct cctggagctg taagtttctt tttgtttgtc   9600
atctaaacaa cgaaattttt atgcaagtca taaccatgct gtgttttcac agatacccag   9660
tgctcgagtc catccaaaaa tttctttggc caagactttg caaactcgat caacgaacac   9720
tgtatgctca taaactctaa caaatcatct gtctgaaaaa ccaatatttc tttggtagaa   9780
ttctattgtc attactcatt actaacagcg aaattaatta acgttctttt tcttactcag   9840
gtatgaatta cactaccaac tgattacgtt tggaaaggta ttattgctct aagctttgaa   9900
tttatcatat ggtaatttca agcattgtag gcacctgatc aattatgtgt ctaaatcatg   9960
tgaattcatg tcaggtattt tgcacaaaga gtagaccaaa ttgtaatgca tgtccaatga  10020
gaggagagtg cagacacttt gccagtgctt atgctaggta agcaagcttt catgtactta  10080
tatgcaataa ttaaagataa aatttaggat tatgggtaag ttacaaaaaa ttaggctcag  10140
tttcatggta gctagctgga aatagtatta caagaacaac ataaagatca aagacagaat  10200
catggatcca tatgcactat cattttagct cttgtaatcc atacatgaac actatatgcc  10260
aaagtaggga tttcaaatat gagattcgat gactgatgcc attgtaacag tgcaagactt  10320
gctttaccgg caccagagga gaggagctta acaagtgcaa ctattccggt ccctcccgag  10380
tcctatcctc ctgtagccat cccgatgata gaactacctc ttccgttgga gaaatcccta  10440
gcaagtggag caccatcgaa tagagaaaac tgtgaaccaa taattgaaga gccggcctcg  10500
cccgggcaag agtgcactga aataaccgag agtgatattg aagatgctta ctacaatgag  10560
gaccctgacg agatcccaac aataaaactc aacattgaac agtttggaat gactctacgg  10620
gaacacatgg aaagaaacat ggagctccaa gaaggtgaca tgtccaaggc tttggttgct  10680
ttgcatccaa caactacttc tattccaact cccaaactaa agaacattag ccgtctcagg  10740
acagagcacc aagtgtaagc taatatctcc tcctatattt tatcttccat ataaattttg  10800
gggaaaaaat cgctctccat ctggttttag aacatgcggg tcagccaggg ttatggcatt  10860
tttatatatt tcaccgatcg gcccgagctg gctctggttg actcgtatgc caccctgcat  10920
tgaacaaacc agtaggagac aagcaagcaa aacgttttaa gataaggtct atggtaaaat  10980
gacaaggtaa ctgataaatg tgtcgtctat ttgcaggtac gagctcccag attcacatcg  11040
tctccttgat ggtgtaagtc aatttttaac tctctctata ctcgagttgt ttcacttgag  11100
caacactgtt taaaagtcct catttgataa aataacagat ggataaaaga gaaccagatg  11160
atccaagtcc ttatctctta gctatatgga caccaggtga gaataaaact gcaatgtttc  11220
attcatgtgt ctacagtatc aaagaaagta cagctagagc taaaaagcat ttgaaataga  11280
gtcggttaaa tatgaaagtt tgaatctgta aatgaaagcc ggaacgtagc attggtggat  11340
gttatatgta aattagtttt tgagattggt ctaatgtagt tgtttgactg ccaggtgaaa  11400
cagcgaattc ggcacaaccg cctgaacaga agtgtggagg gaaagcgtct ggcaaaatgt  11460
gctttgacga gacttgttct gagtgtaaca gtctgaggga agcaaactca cagacagttc  11520
gaggaactct tctggtgaga ttatcttgat cttttgtgtt gctcatgaaa aggagaagtg  11580
agaatacaag tttgctaata tcatttttttc gtcattcaca gataccttgt cggactgcca  11640
tgagaggaag ttttccgctc aacgggacat atttccaagt caacgaggtt agatgaaata  11700
aaactcaaac agacagacga aacattattt ctgtttagtg ttggttcttt atcctccttg  11760
ccatttttta tcttgcagtt atttgcagac cacgagtcca gtctcaaacc catcgatgtt  11820
cctagagatt ggatatggga tctcccaaga aggactgttt acttcggaac atcagtaaca  11880
tcaatattca gaggtaaaaa cattcgtaat agagttagtt aatcaaatgt ccaaaacaca  11940
```

-continued

```
agaaagcttc accgtccaat acacaagaaa gcttcacctt ctctttgcca aaaaagatct  12000
tagaatgttt tgctgaattt gtgcaggtct ttcaacggag cagatacagt tctgcttttg  12060
gaaaggtaaa cgttaacttt cgacccagag aaatccggaa aatctattgc tttgttctga  12120
tcaatacgtt aaacatatac acacacactt tacacttagg accaatactg ttctgatctg  12180
tgatagaaac tggtaaacat ctaacaatta tgattgcagg attcgtatgt gtccgtggat  12240
tcgaacagaa gacaagagca ccgcgtccat taatggcaag gttgcatttt cctgcgagca  12300
aattgaagaa caacaaaacc taaagatgac tggaagaaag caaacgcatt gcttctctgc  12360
tctcctctat ttaaagccag gaaaagtccc atttagacat aataacagga atccaaatag  12420
gctattttct ctttctttct tatttcattc atagagcaga agcgacacaa aaaagttttt  12480
tgggttattt attttctctc taacaaattt gtagcgtttt gggtcttttt ctggctgtca  12540
ctagcgtggc aaatccaatg tccgcgcaca cttaggcgca ttgtcaataa attctccggc  12600
caccggagtg ttacgatctt ttccaacggc ggctaatgcg atatttccgg taacacatat  12660
tccttattct atgttggttt tgtgtacggc gtgggcctta ctagacaatg atcatcaata  12720
aaactaacac aaagttgaat gctacaaagt agaaagtgaa gaaaaaataa tatagacatt  12780
gccga                                                               12785
```

<210> SEQ ID NO 2
<211> LENGTH: 1729
<212> TYPE: PRT
<213> ORGANISM: Arabidopsis thaliana
<220> FEATURE:
<223> OTHER INFORMATION: DEMETER (DMT)

<400> SEQUENCE: 2

```
Met Gln Ser Ile Met Asp Ser Ser Ala Val Asn Ala Thr Glu Ala Thr
  1               5                  10                  15

Glu Gln Asn Asp Gly Ser Arg Gln Asp Val Leu Glu Phe Asp Leu Asn
             20                  25                  30

Lys Thr Pro Gln Gln Lys Pro Ser Lys Arg Lys Arg Lys Phe Met Pro
         35                  40                  45

Lys Val Val Val Glu Gly Lys Pro Lys Arg Lys Pro Arg Lys Pro Ala
     50                  55                  60

Glu Leu Pro Lys Val Val Val Glu Gly Lys Pro Lys Arg Lys Pro Arg
 65                  70                  75                  80

Lys Ala Ala Thr Gln Glu Lys Val Lys Ser Lys Glu Thr Gly Ser Ala
                 85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
    130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190

Pro Leu Glu Val Ser Met Gly Asn Gln Pro Asp Lys Leu Ser Thr Gly
        195                 200                 205
```

-continued

```
Ala Lys Leu Ala Arg Asp Gln Gln Pro Asp Leu Leu Thr Arg Asn Gln
    210                 215                 220

Gln Cys Gln Phe Pro Val Ala Thr Gln Asn Thr Gln Phe Pro Met Glu
225                 230                 235                 240

Asn Gln Gln Ala Trp Leu Gln Met Lys Asn Gln Leu Ile Gly Phe Pro
                245                 250                 255

Phe Gly Asn Gln Gln Pro Arg Met Thr Ile Arg Asn Gln Gln Pro Cys
            260                 265                 270

Leu Ala Met Gly Asn Gln Gln Pro Met Tyr Leu Ile Gly Thr Pro Arg
        275                 280                 285

Pro Ala Leu Val Ser Gly Asn Gln Gln Leu Gly Gly Pro Gln Gly Asn
    290                 295                 300

Lys Arg Pro Ile Phe Leu Asn His Gln Thr Cys Leu Pro Ala Gly Asn
305                 310                 315                 320

Gln Leu Tyr Gly Ser Pro Thr Asp Met His Gln Leu Val Met Ser Thr
                325                 330                 335

Gly Gly Gln Gln His Gly Leu Leu Ile Lys Asn Gln Gln Pro Gly Ser
            340                 345                 350

Leu Ile Arg Gly Gln Gln Pro Cys Val Pro Leu Ile Asp Gln Gln Pro
        355                 360                 365

Ala Thr Pro Lys Gly Phe Thr His Leu Asn Gln Met Val Ala Thr Ser
    370                 375                 380

Met Ser Ser Pro Gly Leu Arg Pro His Ser Gln Ser Gln Val Pro Thr
385                 390                 395                 400

Thr Tyr Leu His Val Glu Ser Val Ser Arg Ile Leu Asn Gly Thr Thr
                405                 410                 415

Gly Thr Cys Gln Arg Ser Arg Ala Pro Ala Tyr Asp Ser Leu Gln Gln
            420                 425                 430

Asp Ile His Gln Gly Asn Lys Tyr Ile Leu Ser His Glu Ile Ser Asn
        435                 440                 445

Gly Asn Gly Cys Lys Lys Ala Leu Pro Gln Asn Ser Ser Leu Pro Thr
    450                 455                 460

Pro Ile Met Ala Lys Leu Glu Glu Ala Arg Gly Ser Lys Arg Gln Tyr
465                 470                 475                 480

His Arg Ala Met Gly Gln Thr Glu Lys His Asp Leu Asn Leu Ala Gln
                485                 490                 495

Gln Ile Ala Gln Ser Gln Asp Val Glu Arg His Asn Ser Ser Thr Cys
            500                 505                 510

Val Glu Tyr Leu Asp Ala Ala Lys Lys Thr Lys Ile Gln Lys Val Val
        515                 520                 525

Gln Glu Asn Leu His Gly Met Pro Pro Glu Val Ile Glu Ile Glu Asp
    530                 535                 540

Asp Pro Thr Asp Gly Ala Arg Lys Gly Lys Asn Thr Ala Ser Ile Ser
545                 550                 555                 560

Lys Gly Ala Ser Lys Gly Asn Ser Ser Pro Val Lys Lys Thr Ala Glu
                565                 570                 575

Lys Glu Lys Cys Ile Val Pro Lys Thr Pro Ala Lys Lys Gly Arg Ala
            580                 585                 590

Gly Arg Lys Lys Ser Val Pro Pro Pro Ala His Ala Ser Glu Ile Gln
        595                 600                 605

Leu Trp Gln Pro Thr Pro Pro Lys Thr Pro Leu Ser Arg Ser Lys Pro
    610                 615                 620
```

-continued

```
Lys Gly Lys Gly Arg Lys Ser Ile Gln Asp Ser Gly Lys Ala Arg Gly
625                 630                 635                 640

Pro Ser Gly Glu Leu Leu Cys Gln Asp Ser Ile Ala Glu Ile Ile Tyr
                645                 650                 655

Arg Met Gln Asn Leu Tyr Leu Gly Asp Lys Glu Arg Glu Gln Glu Gln
            660                 665                 670

Asn Ala Met Val Leu Tyr Lys Gly Asp Gly Ala Leu Val Pro Tyr Glu
        675                 680                 685

Ser Lys Lys Arg Lys Pro Arg Pro Lys Val Asp Ile Asp Asp Glu Thr
    690                 695                 700

Thr Arg Ile Trp Asn Leu Leu Met Gly Lys Gly Asp Glu Lys Glu Gly
705                 710                 715                 720

Asp Glu Glu Lys Asp Lys Lys Lys Glu Lys Trp Trp Glu Glu Glu Arg
                725                 730                 735

Arg Val Phe Arg Gly Arg Ala Asp Ser Phe Ile Ala Arg Met His Leu
            740                 745                 750

Val Gln Gly Asp Arg Arg Phe Ser Pro Trp Lys Gly Ser Val Val Asp
        755                 760                 765

Ser Val Ile Gly Val Phe Leu Thr Gln Asn Val Ser Asp His Leu Ser
    770                 775                 780

Ser Ser Ala Phe Met Ser Leu Ala Ala Arg Phe Pro Pro Lys Leu Ser
785                 790                 795                 800

Ser Ser Arg Glu Asp Glu Arg Asn Val Arg Ser Val Val Val Glu Asp
                805                 810                 815

Pro Glu Gly Cys Ile Leu Asn Leu Asn Glu Ile Pro Ser Trp Gln Glu
            820                 825                 830

Lys Val Gln His Pro Ser Asp Met Glu Val Ser Gly Val Asp Ser Gly
        835                 840                 845

Ser Lys Glu Gln Leu Arg Asp Cys Ser Asn Ser Gly Ile Glu Arg Phe
    850                 855                 860

Asn Phe Leu Glu Lys Ser Ile Gln Asn Leu Glu Glu Glu Val Leu Ser
865                 870                 875                 880

Ser Gln Asp Ser Phe Asp Pro Ala Ile Phe Gln Ser Cys Gly Arg Val
                885                 890                 895

Gly Ser Cys Ser Cys Ser Lys Ser Asp Ala Glu Phe Pro Thr Thr Arg
            900                 905                 910

Cys Glu Thr Lys Thr Val Ser Gly Thr Ser Gln Ser Val Gln Thr Gly
        915                 920                 925

Ser Pro Asn Leu Ser Asp Glu Ile Cys Leu Gln Gly Asn Glu Arg Pro
    930                 935                 940

His Leu Tyr Glu Gly Ser Gly Asp Val Gln Lys Gln Glu Thr Thr Asn
945                 950                 955                 960

Val Ala Gln Lys Lys Pro Asp Leu Glu Lys Thr Met Asn Trp Lys Asp
                965                 970                 975

Ser Val Cys Phe Gly Gln Pro Arg Asn Asp Thr Asn Trp Gln Thr Thr
            980                 985                 990

Pro Ser Ser Ser Tyr Glu Gln Cys Ala Thr Arg Gln Pro His Val Leu
        995                 1000                1005

Asp Ile Glu Asp Phe Gly Met Gln Gly Glu Gly Leu Gly Tyr Ser Trp
   1010                1015                1020

Met Ser Ile Ser Pro Arg Val Asp Arg Val Lys Asn Lys Asn Val Pro
1025                1030                1035                1040

Arg Arg Phe Phe Arg Gln Gly Gly Ser Val Pro Arg Glu Phe Thr Gly
```

-continued

```
                1045                1050                1055

Gln Ile Ile Pro Ser Thr Pro His Glu Leu Pro Gly Met Gly Leu Ser
            1060                1065                1070

Gly Ser Ser Ser Ala Val Gln Glu His Gln Asp Asp Thr Gln His Asn
        1075                1080                1085

Gln Gln Asp Glu Met Asn Lys Ala Ser His Leu Gln Lys Thr Phe Leu
    1090                1095                1100

Asp Leu Leu Asn Ser Ser Glu Glu Cys Leu Thr Arg Gln Ser Ser Thr
1105                1110                1115                1120

Lys Gln Asn Ile Thr Asp Gly Cys Leu Pro Arg Asp Arg Thr Ala Glu
                1125                1130                1135

Asp Val Val Asp Pro Leu Ser Asn Asn Ser Ser Leu Gln Asn Ile Leu
            1140                1145                1150

Val Glu Ser Asn Ser Ser Asn Lys Glu Gln Thr Ala Val Glu Tyr Lys
        1155                1160                1165

Glu Thr Asn Ala Thr Ile Leu Arg Glu Met Lys Gly Thr Leu Ala Asp
    1170                1175                1180

Gly Lys Lys Pro Thr Ser Gln Trp Asp Ser Leu Arg Lys Asp Val Glu
1185                1190                1195                1200

Gly Asn Glu Gly Arg Gln Glu Arg Asn Lys Asn Asn Met Asp Ser Ile
                1205                1210                1215

Asp Tyr Glu Ala Ile Arg Arg Ala Ser Ile Ser Glu Ile Ser Glu Ala
            1220                1225                1230

Ile Lys Glu Arg Gly Met Asn Asn Met Leu Ala Val Arg Ile Lys Asp
        1235                1240                1245

Phe Leu Glu Arg Ile Val Lys Asp His Gly Gly Ile Asp Leu Glu Trp
    1250                1255                1260

Leu Arg Glu Ser Pro Pro Asp Lys Ala Lys Asp Tyr Leu Leu Ser Ile
1265                1270                1275                1280

Arg Gly Leu Gly Leu Lys Ser Val Glu Cys Val Arg Leu Leu Thr Leu
                1285                1290                1295

His Asn Leu Ala Phe Pro Val Asp Thr Asn Val Gly Arg Ile Ala Val
            1300                1305                1310

Arg Met Gly Trp Val Pro Leu Gln Pro Leu Pro Glu Ser Leu Gln Leu
        1315                1320                1325

His Leu Leu Glu Leu Tyr Pro Val Leu Glu Ser Ile Gln Lys Phe Leu
    1330                1335                1340

Trp Pro Arg Leu Cys Lys Leu Asp Gln Arg Thr Leu Tyr Glu Leu His
1345                1350                1355                1360

Tyr Gln Leu Ile Thr Phe Gly Lys Val Phe Cys Thr Lys Ser Arg Pro
                1365                1370                1375

Asn Cys Asn Ala Cys Pro Met Arg Gly Glu Cys Arg His Phe Ala Ser
            1380                1385                1390

Ala Tyr Ala Ser Ala Arg Leu Ala Leu Pro Ala Pro Glu Glu Arg Ser
        1395                1400                1405

Leu Thr Ser Ala Thr Ile Pro Val Pro Pro Glu Ser Phe Pro Pro Val
    1410                1415                1420

Ala Ile Pro Met Ile Glu Leu Pro Leu Pro Leu Glu Lys Ser Leu Ala
1425                1430                1435                1440

Ser Gly Ala Pro Ser Asn Arg Glu Asn Cys Glu Pro Ile Ile Glu Glu
                1445                1450                1455

Pro Ala Ser Pro Gly Gln Glu Cys Thr Glu Ile Thr Glu Ser Asp Ile
            1460                1465                1470
```

-continued

```
Glu Asp Ala Tyr Tyr Asn Glu Asp Pro Asp Glu Ile Pro Thr Ile Lys
       1475                1480                1485

Leu Asn Ile Glu Gln Phe Gly Met Thr Leu Arg Glu His Met Glu Arg
   1490                1495                1500

Asn Met Glu Leu Gln Glu Gly Asp Met Ser Lys Ala Leu Val Ala Leu
1505                1510                1515                1520

His Pro Thr Thr Thr Ser Ile Pro Thr Pro Lys Leu Lys Asn Ile Ser
               1525                1530                1535

Arg Leu Arg Thr Glu His Gln Val Tyr Glu Leu Pro Asp Ser His Arg
           1540                1545                1550

Leu Leu Asp Gly Met Asp Lys Arg Glu Pro Asp Asp Pro Ser Pro Tyr
       1555                1560                1565

Leu Leu Ala Ile Trp Thr Pro Gly Glu Thr Ala Asn Ser Ala Gln Pro
   1570                1575                1580

Pro Glu Gln Lys Cys Gly Gly Lys Ala Ser Gly Lys Met Cys Phe Asp
1585                1590                1595                1600

Glu Thr Cys Ser Glu Cys Asn Ser Leu Arg Glu Ala Asn Ser Gln Thr
               1605                1610                1615

Val Arg Gly Thr Leu Leu Ile Pro Cys Arg Thr Ala Met Arg Gly Ser
           1620                1625                1630

Phe Pro Leu Asn Gly Thr Tyr Phe Gln Val Asn Glu Leu Phe Ala Asp
       1635                1640                1645

His Glu Ser Ser Leu Lys Pro Ile Asp Val Pro Arg Asp Trp Ile Trp
   1650                1655                1660

Asp Leu Pro Arg Arg Thr Val Tyr Phe Gly Thr Ser Val Thr Ser Ile
1665                1670                1675                1680

Phe Arg Gly Leu Ser Thr Glu Gln Ile Gln Phe Cys Phe Trp Lys Gly
               1685                1690                1695

Phe Val Cys Val Arg Gly Phe Glu Gln Lys Thr Arg Ala Pro Arg Pro
           1700                1705                1710

Leu Met Ala Arg Leu His Phe Pro Ala Ser Lys Leu Lys Asn Asn Lys
       1715                1720                1725

Thr


<210> SEQ ID NO 3
<211> LENGTH: 3424
<212> TYPE: DNA
<213> ORGANISM: Arabidopsis thaliana
<220> FEATURE:
<223> OTHER INFORMATION: DMT 5' flanking sequence

<400> SEQUENCE: 3

aagcttaaag ctaccaacat cgaatttagt aaaagaccca tgatttgaaa ttggaattgt      60

cggcaaaatc gagaagatat agagccgaca cgggaacagt gaaaaccaca aagcgcgtaa     120

gaatgaaaca gtgggagaag gaagagagaa tcttaccgat cattcgaggg aaaagatggg     180

aatcagagaa aaatctggaa aaaaagaaat taagagaaag agagagaaga aagtgaggag     240

gaagatgcag tgaagactgc tatagccaca tcccacatgg tgtgatgaga gagagagaga     300

gagaggttaa agcagcaaat tgtggagaga taaagagaga gagagactga gcgagtcaag     360

ttcgtcgtcg tgtttaaaag aaagaatcct atatttgcct ttttctttac tactttattt     420

tcagactatt tgcttatttt gcctcaaact tttttgattg tcacttttcg atcctaaagt     480

gtttgacaat ttacctgcct ttttctccaa gaaaaatcag aacagaccac agcaaattta     540
```

-continued

```
tgtattttct attaaaaaag aaagaaagaa ttcatattac ttatagaatt aaaagctaag    600
cagttgaaaa cgtgaaagca gaatttctaa aaaaaatagt aaactgctac aaacttattt    660
atgtgtatat aacatatcta taaagaaact caaatatatg ataaatcatt ttaacaaaat    720
ttctatgaaa ttataataaa aaaagtcact tttgacactt aaaaggttga caataaccgt    780
ctctccaaaa aaaaatcaaa acatttataa tttctaaaac tatggtgtaa ttttgctgaa    840
atcaaaaaga aaagaaggat ttctatatca taagtttcat tattgtatca aactttcaaa    900
tttcatgtaa tttgaaagga aaaaaattaa gatataatgt tgtttttgtt tcttatgtta    960
cattttcatg gaatatatat tcataacaaa aaatgtattt taatatgatg agagattacc   1020
atccaaaagg tcgaacttat ataaaacaag ttaataacta aacaatacat gtgatcacaa   1080
tcaatgacag ttttgatctt aaaatagaaa tgattgagca aacctcaaaa atgtcttctt   1140
aggatcacaa aatctttcct ttagcttatt aaagccggga gttcaactct ctctcccttg   1200
tagacttttt gttttcaaat ctttttcttt caaaaaatca ataattagtt aatgggcata   1260
atatttggtt ttaattaagt ccatagattt tttaggacca tctctaatca cgacaaatat   1320
cctaaattgt aacacattta aaacttaaaa gtattgcatt cacaatcctt aaaatatata   1380
tatatatata tatatatata tatatatata tatatgaaag ttatatagaa acgataactc   1440
cttactcaac aattagccca aaaaaacatc cataatgcat ttaaactagg aattttaaca   1500
aactcaaata ggttggtagt taaaaaaaaa caaatagtag atgtacatac gtacctttaa   1560
aaatatatac tcatatcgaa agttttaaat tttgcgaaat taaatacatt tatctatcaa   1620
ttaaaataca tttaataatg cataattctg taatatctat ctttaatttc catatagaac   1680
caaaacaaaa taaacatatc aaatagtttt aacttaacaa aaacgttagg gaaaagttga   1740
cctaactagc ttgattgacg ttgaacttgt caatgcgaaa gcgatatttc caatatatac   1800
tacatgtagt attatttata tggaagtttc taaaaaggtg ttgagtggat tgttacttgt   1860
tggaggatgc tattttttcc ttcttgccat aatattttac gagtatggga taactacata   1920
ctcatgatta tgaaacgctc actttatttg aaaaacctcc taatacacca aatatgtcac   1980
tagattccaa aacgtagacc aattgtatct aatctcaaat tctcaatcaa agtattaatt   2040
taccgatggt aagaaaagtt aaccgatata attatcaaaa gaaagaataa gtcaacagat   2100
tcttaatctc tttattttgg tatatgaaca tttgtacaaa aatctcaaaa gatatgtaac   2160
tgtttaaaat ataaattcac tgagattaat tcttcagact cgtgttagct ataataatgt   2220
caagagttct tcttgtttca aggaaaaacc ttaaagatat gtatattttc tgtaattatg   2280
atgatataat ttgctattca ttgtcacaaa cattacttta aaaaatcgta ttttcattac   2340
tacaatgttg actaagaaca aaaatacatt gattattgat atatcgtcaa ctgaattttc   2400
ttccgaggga tataattctc aaacatagca agaatctcat aataatgttt cgtgactacc   2460
tttagacgaa attttttaa gattcgtaac gtgacttatg gtctcttgct gtgggggtca   2520
atgcgaataa atctaaatgt atgggagtca aataaaatac caagaaaaat aaaggagcag   2580
cacccaataa actatatggg accagaaatc ctttcattgg tttaaaatag gattatcccg   2640
aaagatgaag gactaaattg aaactgattg ggggtaggaa gagatccgtc acaatcatta   2700
atggcttcca cgcggaaact tgtcgtttat acaatttcat taactttcgg gtcgggttta   2760
tattccaaat gggtcaaata atattagttt aatacactaa cggagtaatt aattggtgac   2820
tacaatttta tcagtttggt gcaattagaa acgaacatag tcgtaaaata cgagttcggt   2880
gttatacctt tatttacgtt aaaaaaatac gagaattttg tgtcaaattt caaattaatt   2940
```

-continued

```
tcatgaatat atggaaatta ttagatactc tagcgaaaat agtgattatg agcgttttac   3000

aaaaatacga ttttagcatt gaacttcctt tatgtaattc ggtcaaatgt tggcatgaag   3060

aagcaagttt gcaacattaa atttcattta aaaatcgtgt tgacatactt taaaatctaa   3120

atataggaag aagaccaaaa cattaaattt agtaagattc taatgaacat ttataagtta   3180

taacttataa ccaacaaaag ttgggtttag cgttgttgct ttatctgaaa acttgcaaac   3240

taaaccattt taataggact aatgacaatt aacaacaaaa tacacttaag caacaacgtc   3300

ctcgtgaata taatttgggc ctcaggccca tattgctaac gccaactgat atttcacttt   3360

attccttctt catctcacca cactctctct ctatctctat ctctaacggc atagctgact   3420

cagt                                                                3424
```

```
<210> SEQ ID NO 4
<211> LENGTH: 205
<212> TYPE: DNA
<213> ORGANISM: Arabidopsis thaliana
<220> FEATURE:
<223> OTHER INFORMATION: DMT 3' flanking sequence

<400> SEQUENCE: 4

agatgactgg aagaaagcaa acgcattgct tctctgctct cctctattta aagccaggaa     60

aagtcccatt tagacataat aacaggaatc caaataggct attttctctt tctttcttat    120

ttcattcata gagcagaagc gacacaaaaa agtttttttgg gttatttatt ttctctctaa    180

caaaaaaaaa aaaaaaaaac tcgag                                          205
```

```
<210> SEQ ID NO 5
<211> LENGTH: 6873
<212> TYPE: DNA
<213> ORGANISM: Arabidopsis thaliana
<220> FEATURE:
<223> OTHER INFORMATION: DMT cDNA

<400> SEQUENCE: 5

gttctccggc attgactcgc ctgagaatca gaaagcttag atcggtgagc ttttagctcc     60

attttctgtt tatttacata ttatttcctt tttttctctc tcccttttttt atctggaatt    120

tgttctgcta aattttccag ctgttacatt ttccgatcac gagaagaatc actgggtttt    180

tatgttaatc aatacatgtt cctgttttct gatcataaat ctcagctatt aacacctgat    240

tttgattctg cgtaataaaa acctctgatt tgcttttatc ttcactttcc ccataaacat    300

tgcttacttt attcgctctt cttttaccgt ttccagctaa aaaattcttc gctattcaat    360

gtgtttctcg ttttgttgat gagaaaaata tctgacaaaa aatcatttat tgcattttat    420

ggtgcagatt cttagttaat gtcgccttct ctaaccaagt cagattaaaa aggagtgttc    480

gtccatgttg ctttgttttg gtgtttggag agagttttcg gagagttagg tgagtgttat    540

ttggggtgag gtagtgataa ggtttgaagg gggagtgatt catcaagtgt gttatgaatt    600

cgagggctga tccgggggat agatattttc gagttccttt ggagaatcaa actcaacaag    660

agttcatggg ttcttggatt ccatttacac ccaaaaaacc tagatcaagt ctgatggtag    720

atgagagagt gataaaccag gatctaaatg ggtttccagg tggtgaattt gtagacaggg    780

gattctgcaa cactggtgtg gatcataatg gggtttttga tcatggtgct catcagggcg    840

ttaccaactt aagtatgatg atcaatagct tagcgggatc acatgcacaa gcttggagta    900

atagtgagag agatcttttg ggcaggagtg aggtgacttc tcctttagca ccagttatca    960
```

-continued

```
gaaacaccac cggtaatgta gagccggtca atggaaattt tacttcagat gtgggtatgg   1020
taaatggtcc tttcacccag agtggcactt ctcaagctgg ctataatgag tttgaattgg   1080
atgacttgtt gaatcctgat cagatgccct tctccttcac aagcttgctg agtggtgggg   1140
atagcttatt caaggttcgt caatgtgagt gatcaaatct attttcagtt ttttttttc    1200
cctttcttcc gttcttgcag tacttagagt agaacatgaa ttagaatatc ttaagaaagt   1260
catggttttg aacagatgga cctccagcgt gtaacaagcc tctttacaat ttgaattcac   1320
caattagaag agaagcagtt gggtcagtct gtgaaagttc gtttcaatat gtaccgtcaa   1380
cgcccagtct gttcagaaca ggtgaaaaga ctggattcct tgaacagata gttacaacta   1440
ctggacatga aatcccagag ccgaaatctg acaaaagtat gcagagcatt atggactcgt   1500
ctgctgttaa tgcgacggaa gctactgaac aaaatgatgg cagcagacaa gatgttctgg   1560
agttcgacct taacaaaact cctcagcaga aaccctccaa aaggaaaagg aagttcatgc   1620
ccaaggtggt cgtggaaggc aaacctaaaa gaaagccacg caaacctgca gaacttccca   1680
aagtggtcgt ggaaggcaaa cctaaaagga agccacgcaa agctgcaact caggaaaaag   1740
tgaaatctaa agaaaccggg agtgccaaaa agaaaaattt gaaagaatca gcaactaaaa   1800
agccagccaa tgttggagat atgagcaaca aaagccctga agtcacactc aaaagttgca   1860
gaaaagcttt gaattttgac ttggagaatc ctggagatgc gaggcaaggt gactctgagt   1920
ctgaaattgt ccagaacagt agtggcgcaa actcgttttc tgagatcaga gatgccattg   1980
gtggaactaa tggtagtttc ctggattcag tgtcacaaat agacaagacc aatggattgg   2040
gggctatgaa ccagccactt gaagtgtcaa tgggaaacca gccagataaa ctatctacag   2100
gagcgaaact ggccagagac caacaacctg atttattgac tagaaaccag caatgccagt   2160
tcccagtggc aacccagaac acccagttcc caatggaaaa ccaacaagct tggcttcaga   2220
tgaaaaacca acttattggc tttccatttg gtaaccagca acctcgcatg accataagaa   2280
accagcagcc ttgcttggcc atgggtaatc aacaacctat gtatctgata ggaactccac   2340
ggcctgcatt agtaagtgga aaccagcaac taggaggtcc ccaaggaaac aagcggccta   2400
tatttttgaa tcaccagact tgtttacctg ctggaaatca gctatatgga tcacctacag   2460
acatgcatca acttgttatg tcaaccggag ggcaacaaca tggactactg ataaaaaacc   2520
agcaacctgg atcattaata agaggccagc agccttgcgt acctttgatt gaccagcaac   2580
ctgcaactcc aaaaggtttt actcacttga atcagatggt agctaccagc atgtcatcgc   2640
ctgggcttcg acctcattct cagtcacaag ttcctacaac atatctacat gtggaatctg   2700
tttccaggat tttgaatggg actacaggta catgccagag aagcagggct cctgcatacg   2760
attctttaca gcaagatatc catcaaggaa ataagtacat actttctcat gagatatcca   2820
atggtaatgg gtgcaagaaa gcgttacctc aaaactcttc tctgccaact ccaattatgg   2880
ctaaacttga ggaagccagg ggctcgaaga gacagtatca tcgtgcaatg ggacagacgg   2940
aaaagcatga tctaaactta gctcaacaga ttgctcaatc acaagatgtg gagagacata   3000
acagcagcac gtgtgtggaa tatttagatg ctgcaaagaa aacgaaaatc cagaaagtag   3060
tccaagaaaa tttgcatggc atgccacctg aggttataga aatcgaggat gatccaactg   3120
atggggcaag aaaaggtaaa aatactgcca gcatcagtaa aggtgcatct aaaggaaact   3180
cgtctccagt taaaaagaca gcagaaaagg agaaatgtat tgtcccaaaa acgcctgcaa   3240
aaaagggtcg agcaggtaga aaaaaatcag tacctccgcc tgctcatgcc tcagagatcc   3300
agctttggca acctactcct ccaaagacac ctttatcaag aagcaagcct aaaggaaaag   3360
```

-continued

```
ggagaaagtc catacaagat tcaggaaaag caagaggtcc atcaggagaa cttctgtgtc   3420
aggattctat tgcggaaata atttacagga tgcaaaatct gtatctagga gacaaagaaa   3480
gagaacaaga gcaaaatgca atggtcttgt acaaaggaga tggtgcactt gttccctatg   3540
agagcaagaa gcgaaaacca agacccaaag ttgacattga cgatgaaaca actcgcatat   3600
ggaacttact gatggggaaa ggagatgaaa aagaagggga tgaagagaag gataaaaaga   3660
aagagaagtg gtgggaagaa gaaagaagag tcttccgagg aagggctgat tccttcatcg   3720
ctcgcatgca cctggtacaa ggagatagac gtttttcgcc atggaaggga tcggtggttg   3780
attcggtcat tggagttttc cttacacaga atgtctcgga tcacctttca agctctgcgt   3840
tcatgtctct agctgctcga ttccctccaa aattaagcag cagccgagaa gatgaaagga   3900
atgttagaag cgtagttgtt gaagatccag aaggatgcat tctgaactta aatgaaattc   3960
cttcgtggca ggaaaaggtt caacatccat ctgacatgga agtttctggg gttgatagtg   4020
gatcaaaaga gcagctaagg gactgttcaa actctggaat tgaaagattt aatttcttag   4080
agaagagtat tcaaaattta gaagaggaag tattatcatc acaagattct tttgatccgg   4140
cgatatttca gtcgtgtggg agagttggat cctgttcatg ttccaaatca gacgcagagt   4200
ttcctacaac caggtgtgaa acaaaaactg tcagtggaac atcacaatca gtgcaaactg   4260
ggagcccaaa cttgtctgat gaaatttgtc ttcaagggaa tgagagaccg catctatatg   4320
aaggatctgg tgatgttcag aaacaagaaa ctacaaatgt cgctcagaag aaacctgatc   4380
ttgaaaaaac aatgaattgg aaagactctg tctgttttgg tcagccaaga aatgatacta   4440
attggcaaac aactccttcc agcagctatg agcagtgtgc gactcgacag ccacatgtac   4500
tagacataga ggattttgga atgcaaggtg aaggccttgg ttattcttgg atgtccatct   4560
caccaagagt tgacagagta aagaacaaaa atgtaccacg caggtttttc agacaaggtg   4620
gaagtgttcc aagagaattc acaggtcaga tcataccatc aacgcctcat gaattaccag   4680
gaatgggatt gtccggttcc tcaagcgccg tccaagaaca ccaggacgat acccaacata   4740
atcaacaaga tgagatgaat aaagcatccc atttacaaaa aacatttttg gatctgctca   4800
actcctctga agaatgcctt acaagacagt ccagtaccaa acagaacatc acggatggct   4860
gtctaccgag agatagaact gctgaagacg tggttgatcc gctcagtaac aattcaagct   4920
tacagaacat attggtcgaa tcaaattcca gcaataaaga gcagacggca gttgaataca   4980
aggagacaaa tgccactatt ttacgagaga tgaaagggac gcttgctgat gggaaaaagc   5040
ctacaagcca gtgggatagt ctcagaaaag atgtggaggg gaatgaaggg agacaggaac   5100
gaaacaaaaa caatatggat tccatagact atgaagcaat aagacgtgct agtatcagcg   5160
agatttctga ggctatcaag gaaagaggga tgaataacat gttggccgta cgaattaagg   5220
atttcctaga acggatagtt aaagatcatg gtggtatcga ccttgaatgg ttgagagaat   5280
ctcctcctga taaagccaag gactatctct tgagcataag aggtctgggt ttgaaaagtg   5340
ttgaatgcgt gcgactctta acactccaca atcttgcttt ccctgttgac acgaatgttg   5400
gaaggatagc agttaggatg ggatgggtgc ctctacaacc cctacctgaa tcacttcagt   5460
tacacctcct ggagctatac ccagtgctcg agtccatcca aaaatttctt tggccaagac   5520
tttgcaaact cgatcaacga acactgtatg aattacacta ccaactgatt acgtttggaa   5580
aggtattttg cacaaagagt agaccaaatt gtaatgcatg tccaatgaga ggagagtgca   5640
gacactttgc cagtgcttat gctagtgcaa gacttgcttt accggcacca gaggagagga   5700
```

-continued

```
gcttaacaag tgcaactatt ccggtccctc ccgagtcctt tcctcctgta gccatcccga   5760

tgatagaact acctcttccg ttggagaaat ccctagcaag tggagcacca tcgaatagag   5820

aaaactgtga accaataatt gaagagccgg cctcgcccgg gcaagagtgc actgaaataa   5880

ccgagagtga tattgaagat gcttactaca atgaggaccc tgacgagatc ccaacaataa   5940

aactcaacat tgaacagttt ggaatgactc tacgggaaca catggaaaga aacatggagc   6000

tccaagaagg tgacatgtcc aaggctttgg ttgctttgca tccaacaact acttctattc   6060

caactcccaa actaaagaac attagccgtc tcaggacaga gcaccaagtg tacgagctcc   6120

cagattcaca tcgtctcctt gatggtatgg ataaaagaga accagatgat ccaagtcctt   6180

atctcttagc tatatggaca ccaggtgaaa cagcgaattc ggcacaaccg cctgaacaga   6240

agtgtggagg gaaagcgtct ggcaaaatgt gctttgacga gacttgttct gagtgtaaca   6300

gtctgaggga agcaaactca cagacagttc gaggaactct tctgatacct tgtcggactg   6360

ccatgagagg aagttttccg ctcaacggga catatttcca agtcaacgag ttatttgcag   6420

accacgagtc cagtctcaaa cccatcgatg ttcctagaga ttggatatgg gatctcccaa   6480

gaaggactgt ttacttcgga acatcagtaa catcaatatt cagaggtctt tcaacggagc   6540

agatacagtt ctgcttttgg aaaggattcg tatgtgtccg tggattcgaa cagaagacaa   6600

gagcaccgcg tccattaatg gcaaggttgc atttcctgc gagcaaattg aagaacaaca   6660

aaacctaaag atgactggaa gaaagcaaac gcattgcttc tctgctctcc tctatttaaa   6720

gccaggaaaa gtcccattta gacataataa caggaatcca aataggctat tttctctttc   6780

tttcttattt cattcataga gcagaagcga cacaaaaaag ttttttgggt tatttatttt   6840

ctctctaaca aaaaaaaaaa aaaaaaactc gag                                6873
```

<210> SEQ ID NO 6
<211> LENGTH: 1478
<212> TYPE: DNA
<213> ORGANISM: Arabidopsis thaliana
<220> FEATURE:
<223> OTHER INFORMATION: DMT 5' untranslated region

<400> SEQUENCE: 6

```
gttctccggc attgactcgc ctgagaatca gaaagcttag atcggtgagc ttttagctcc     60

atttctgtt tatttacata ttatttcctt tttttctctc tcccttttt atctggaatt     120

tgttctgcta aattttccag ctgttacatt ttccgatcac gagaagaatc actgggtttt    180

tatgttaatc aatacatgtt cctgttttct gatcataaat ctcagctatt aacacctgat    240

tttgattctg cgtaataaaa acctctgatt tgcttttatc ttcactttcc ccataaacat    300

tgcttacttt attcgctctt cttttaccgt ttccagctaa aaaattcttc gctattcaat    360

gtgtttctcg ttttgttgat gagaaaaata tctgacaaaa aatcatttat tgcattttat    420

ggtgcagatt cttagttaat gtcgccttct ctaaccaagt cagattaaaa aggagtgttc    480

gtccatgttg ctttgttttg gtgtttggag agagttttcg gagagttagg tgagtgttat    540

ttggggtgag gtagtgataa ggtttgaagg gggagtgatt catcaagtgt gttatgaatt    600

cgagggctga tccgggggat agatattttc gagttccttt ggagaatcaa actcaacaag    660

agttcatggg ttcttggatt ccatttacac ccaaaaaacc tagatcaagt ctgatggtag    720

atgagagagt gataaaccag gatctaaatg ggtttccagg tggtgaattt gtagacaggg    780

gattctgcaa cactggtgtg gatcataatg ggtttttga tcatggtgct catcagggcg     840

ttaccaactt aagtatgatg atcaatagct tagcgggatc acatgcacaa gcttggagta    900
```

-continued atagtgagag agatcttttg ggcaggagtg aggtgacttc tcctttagca ccagttatca 960
gaaacaccac cggtaatgta gagccggtca atggaaattt tacttcagat gtgggtatgg 1020
taaatggtcc tttcacccag agtggcactt ctcaagctgg ctataatgag tttgaattgg 1080
atgacttgtt gaatcctgat cagatgccct tctccttcac aagcttgctg agtggtgggg 1140
atagcttatt caaggttcgt caatgtgagt gatcaaatct attttcagtt ttttttttc 1200 cctttcttcc gttcttgcag tacttagagt agaacatgaa ttagaatatc ttaagaaagt 1260
catggttttg aacagatgga cctccagcgt gtaacaagcc tctttacaat ttgaattcac 1320
caattagaag agaagcagtt gggtcagtct gtgaaagttc gtttcaatat gtaccgtcaa 1380
cgcccagtct gttcagaaca ggtgaaaaga ctggattcct tgaacagata gttacaacta 1440
ctggacatga aatcccagag ccgaaatctg acaaaagt 1478

<210> SEQ ID NO 7
<211> LENGTH: 10620
<212> TYPE: DNA
<213> ORGANISM: Arabidopsis thaliana
<220> FEATURE:
<223> OTHER INFORMATION: DMT1 (1DMT5) gene sequence from BAC T32M21

<400> SEQUENCE: 7
tcactagatt ccaaaacgta gaccaattgt atctaatctc aaattctcaa tcaaagtatt 60
aatttaccga tggtaagaaa agttaaccga tataattatc aaaagaaaga ataagtcaac 120
agattcttaa tctctttatt ttggtatatg aacatttgta caaaaatctc aaaagatatg 180
taactgttta aaatataaat tcactgagat taattcttca gactcgtgtt agctataata 240
atgtcaagag ttcttcttgt ttcaaggaaa aaccttaaag atatgtatat tttctgtaat 300
tatgatgata taatttgcta ttcattgtca caaacattac tttaaaaaat cgtattttca 360
ttactacaat gttgactaag aacaaaaata cattgattat tgatatatcg tcaactgaat 420
tttcttccga gggatataat tctcaaacat agcaagaatc tcataataat gtttcgtgac 480
tacctttaga cgaaattttt ttaagattcg taacgtgact tatggtctct tgctgtgggg 540
gtcaatgcga ataaatctaa atgtatggga gtcaaataaa ataccaagaa aaataaagga 600
gcagcaccca ataaactata tgggaccaga aatcctttca ttggtttaaa ataggattat 660
cccgaaagat gaaggactaa attgaaactg attgggggta ggaagagatc cgtcacaatc 720
attaatggct tccacgcgga aacttgtcgt ttatacaatt tcattaactt tcgggtcggg 780
tttatattcc aaatgggtca aataatatta gtttaataca ctaacggagt aattaattgg 840
tgactacaat tttatcagtt tggtgcaatt agaaacgaac atagtcgtaa aatacgagtt 900
cggtgttata cctttattta cgttaaaaaa atacgagaat tttgtgtcaa atttcaaatt 960
aatttcatga atatatggaa attattagat actctagcga aaatagtgat tatgagcgtt 1020
ttacaaaaat acgattttag cattgaactt cctttatgta attcggtcaa atgttggcat 1080
gaagaagcaa gtttgcaaca ttaaatttca tttaaaaatc gtgttgacat actttaaaat 1140
ctaaatatag gaagaagacc aaaacattaa atttagtaag attctaatga acatttataa 1200
gttataactt ataaccaaca aaagttgggt ttagcgttgt tgctttatct gaaaacttgc 1260
aaactaaacc attttaatag gactaatgac aattaacaac aaaatacact taagcaacaa 1320
cgtcctcgtg aatataattt gggcctcagg cccatattgc taacgccaac tgatatttca 1380
ctttattcct tcttcatctc accacactct ctctctatct ctatctctaa cggcatagct 1440

-continued

```
gactcagtgt tctccggcat tgactcgcct gagaatcaga aagcttagat cggtgagctt   1500

ttagctccat tttctgttta tttacatatt atttcctttt tttctctctc cctttttttat   1560

ctggaatttg ttctgctaaa ttttccagct gttacatttt ccgatcacga gaagaatcac   1620

tgggttttta tgttaatcaa tacatgttcc tgttttctga tcataaatct cagctattaa   1680

cacctgattt tgattctgcg taataaaaac ctctgatttg cttttatctt cactttcccc   1740

ataaacattg cttactttat tcgctcttct tttaccgttt ccagctaaaa aattcttcgc   1800

tattcaatgt gtttctcgtt ttgttgatga gaaaaatatc tgacaaaaaa tcatttattg   1860

cattttatgg tgcagattct tagttaatgt cgccttctct aaccaagtca gattaaaaag   1920

gagtgttcgt ccatgttgct ttgttttggt gtttggagag agttttcgga gagttaggtg   1980

agtgttattt ggggtgaggt agtgataagg tttgaagggg gagtgattca tcaagtgtgt   2040

tatgaattcg agggctgatc cgggggatag atattttcga gttcctttgg agaatcaaac   2100

tcaacaagag ttcatgggtt cttggattcc atttacaccc aaaaaaccta gatcaagtct   2160

gatggtagat gagagagtga taaaccagga tctaaatggg tttccaggtg gtgaatttgt   2220

agacagggga ttctgcaaca ctggtgtgga tcataatggg gtttttgatc atggtgctca   2280

tcagggcgtt accaacttaa gtatgatgat caatagctta gcgggatcac atgcacaagc   2340

ttggagtaat agtgagagag atcttttggg caggagtgag gtgacttctc ctttagcacc   2400

agttatcaga aacaccaccg gtaatgtaga gccggtcaat ggaaatttta cttcagatgt   2460

gggtatggta aatggtcctt tcacccagag tggcacttct caagctggct ataatgagtt   2520

tgaattggat gacttgttga atcctgatca gatgcccttc tccttcacaa gcttgctgag   2580

tggtggggat agcttattca aggttcgtca atgtgagtga tcaaatctat tttcagtttt   2640

ttttttcccc tttcttccgt tcttgcagta cttagagtag aacatgaatt agaatatctt   2700

aagaaagtca tggttttgaa cagatggacc tccagcgtgt aacaagcctc tttacaattt   2760

gaattcacca attagaagag aagcagttgg gtcagtctgt gaaagttcgt ttcaatatgt   2820

accgtcaacg cccagtctgt tcagaacagg tgaaaagact ggattccttg aacagatagt   2880

tacaactact ggacatgaaa tcccagagcc gaaatctgac aaaagtatgc agagcattat   2940

ggactcgtct gctgttaatg cgacggaagc tactgaacaa aatgatggca gcagacaaga   3000

tgttctggag ttcgacctta acaaaactcc tcagcagaaa ccctccaaaa ggaaaaggaa   3060

gttcatgccc aaggtggtcg tggaaggcaa acctaaaaga aagccacgca aacctgcaga   3120

acttcccaaa gtggtcgtgg aaggcaaacc taaaaggaag ccacgcaaag ctgcaactca   3180

ggaaaaagtg aaatctaaag aaaccgggag tgccaaaaag aaaaatttga aagaatcagc   3240

aactaaaaag ccagccaatg ttggagatat gagcaacaaa agccctgaag tcacactcaa   3300

aagttgcaga aaagctttga attttgactt ggagaatcct ggagatgcga ggcaaggtga   3360

ctctgagtct gaaattgtcc agaacagtag tggcgcaaac tcgttttctg agatcagaga   3420

tgccattggt ggaactaatg gtagtttcct ggattcagtg tcacaaatag acaagaccaa   3480

tggattgggg gctatgaacc agccacttga agtgtcaatg ggaaaccagc cagataaact   3540

atctacagga gcgaaactgg ccagagacca acaacctgat ttattgacta gaaaccagca   3600

atgccagttc ccagtggcaa cccagaacac ccagttccca atggaaaacc aacaagcttg   3660

gcttcagatg aaaaaccaac ttattggctt tccatttggt aaccagcaac ctcgcatgac   3720

cataagaaac cagcagcctt gcttggccat gggtaatcaa caacctatgt atctgatagg   3780

aactccacgg cctgcattag taagtggaaa ccagcaacta ggaggtcccc aaggaaacaa   3840
```

-continued

```
gcggcctata tttttgaatc accagacttg tttacctgct ggaaatcagc tatatggatc   3900
acctacagac atgcatcaac ttgttatgtc aaccggaggg caacaacatg gactactgat   3960
aaaaaaccag caacctggat cattaataag aggccagcag ccttgcgtac ctttgattga   4020
ccagcaacct gcaactccaa aaggttttac tcacttgaat cagatggtag ctaccagcat   4080
gtcatcgcct gggcttcgac ctcattctca gtcacaagtt cctacaacat atctacatgt   4140
ggaatctgtt tccaggattt tgaatgggac tacaggtaca tgccagagaa gcagggctcc   4200
tgcatacgat tctttacagc aagatatcca tcaaggaaat aagtacatac tttctcatga   4260
gatatccaat ggtaatgggt gcaagaaagc gttacctcaa aactcttctc tgccaactcc   4320
aattatggct aaacttgagg aagccagggg ctcgaagaga cagtatcatc gtgcaatggg   4380
acagacggaa aagcatgatc taaacttagc tcaacagatt gctcaatcac aagatgtgga   4440
gagacataac agcagcacgt gtgtggaata tttagatgct gcaaagaaaa cgaaaatcca   4500
gaaagtagtc caagaaaatt tgcatggcat gccacctgag gttatagaaa tcgaggatga   4560
tccaactgat ggggcaagaa aaggtaaaaa tactgccagc atcagtaaag gtgcatctaa   4620
aggaaactcg tctccagtta aaaagacagc agaaaaggag aaatgtattg tcccaaaaac   4680
gcctgcaaaa aagggtcgag caggtagaaa aaaatcagta cctccgcctg ctcatgcctc   4740
agagatccag ctttggcaac ctactcctcc aaagacacct ttatcaagaa gcaagcctaa   4800
aggaaaaggg agaaagtcca tacaagattc aggaaaagca agaggtaact aatgtattct   4860
acaatctctg tgatataatt ttgagatttt agtaactgat gtgtccaaac cagctcctta   4920
tcactgttgg tgcgttgtat aggtccatca ggagaacttc tgtgtcagga ttctattgcg   4980
gaaataattt acaggatgca aaatctgtat ctaggagaca aagaaagaga acaagagcaa   5040
aatgcaatgg tcttgtacaa aggagatggt gcacttgttc cctatgagag caagaagcga   5100
aaaccaagac ccaaagttga cattgacgat gaaacaactc gcatatggaa cttactgatg   5160
gggaaaggag atgaaaaaga aggggatgaa gagaaggata aaaagaaaga gaagtggtgg   5220
gaagaagaaa gaagagtctt ccgaggaagg gctgattcct tcatcgctcg catgcacctg   5280
gtacaaggtg aagatccact tctcttctca actccatttt tattcacaca aattagtaga   5340
atactcaaaa atgatgtttt gtttgcaaaa ttttaaaatt cactagttaa ccatgtcaaa   5400
taatattcat aatgcatctt gtgaagaaca ggtgtgcatt tatggtgaca gctgaatggt   5460
ttatgtgcct attatttctt ttactgctat agatgaccaa ttgaacttaa acgtttacag   5520
gagatagacg tttttcgcca tggaagggat cggtggttga ttcggtcatt ggagttttcc   5580
ttacacagaa tgtctcggat cacctttcaa ggtatatgag ttgccttaat aaattgagtt   5640
ccaaaacata gaaattaacc catggtggtt ttacaatgca gctctgcgtt catgtctcta   5700
gctgctcgat tccctccaaa attaagcagc agccgagaag atgaaaggaa tgttagaagc   5760
gtagttgttg aagatccaga aggatgcatt ctgaacttaa atgaaattcc ttcgtggcag   5820
gaaaaggttc aacatccatc tgacatggaa gtttctgggg ttgatagtgg atcaaaagag   5880
cagctaaggg actgttcaaa ctctggaatt gaaagattta atttcttaga gaagagtatt   5940
caaaatttag aagaggaagt attatcatca caagattctt ttgatccggc gatatttcag   6000
tcgtgtggga gagttggatc ctgttcatgt tccaaatcag acgcagagtt tcctacaacc   6060
aggtgtgaaa caaaaactgt cagtggaaca tcacaatcag tgcaaactgg gagcccaaac   6120
ttgtctgatg aaatttgtct tcaagggaat gagagaccgc atctatatga aggatctggt   6180
```

-continued

```
gatgttcaga aacaagaaac tacaaatgtc gctcagaaga aacctgatct tgaaaaaaca   6240
atgaattgga aagactctgt ctgttttggt cagccaagaa atgatactaa ttggcaaaca   6300
actccttcca gcagctatga gcagtgtgcg actcgacagc cacatgtact agacatagag   6360
gattttggaa tgcaaggtga aggccttggt tattcttgga tgtccatctc accaagagtt   6420
gacagagtaa agaacaaaaa tgtaccacgc aggtttttca gacaaggtgg aagtgttcca   6480
agagaattca caggtcagat cataccatca acgcctcatg aattaccagg aatgggattg   6540
tccggttcct caagcgccgt ccaagaacac caggacgata cccaacataa tcaacaagat   6600
gagatgaata aagcatccca tttacaaaaa acatttttgg atctgctcaa ctcctctgaa   6660
gaatgcctta caagacagtc cagtaccaaa cagaacatca cggatggctg tctaccgaga   6720
gatagaactg ctgaagacgt ggttgatccg ctcagtaaca attcaagctt acagaacata   6780
ttggtcgaat caaattccag caataaagag cagacggcag ttgaatacaa ggagacaaat   6840
gccactattt tacgagagat gaaagggacg cttgctgatg ggaaaaagcc tacaagccag   6900
tgggatagtc tcagaaaaga tgtggagggg aatgaaggga gacaggaacg aaacaaaaac   6960
aatatggatt ccatagacta tgaagcaata agacgtgcta gtatcagcga gatttctgag   7020
gctatcaagg aaagagggat gaataacatg ttggccgtac gaattaaggt aaatctacta   7080
atttcagttg agaccctcat caaatctgtc agaaggcttg aacatcagta aattatgtaa   7140
ccatatttac aacattgcag gatttcctag aacggatagt taaagatcat ggtggtatcg   7200
accttgaatg gttgagagaa tctcctcctg ataaagccaa gtgggtaaat cacattttta   7260
gtgactgcaa cactagcacg atcgatttac tcaacaatta cgtcaaactg agtattaaca   7320
agttgctcat gaacatttca cagggactat ctcttgagca taagaggtct gggtttgaaa   7380
agtgttgaat gcgtgcgact cttaacactc cacaatcttg ctttccctgt gagtcagact   7440
attccattat ctactaaaaa cttagaataa ctccggctaa ctaagctgga acttgtattg   7500
atgatatgaa ggttgacacg aatgttggaa ggatagcagt taggatggga tgggtgcctc   7560
tacaacccct acctgaatca cttcagttac acctcctgga gctgtaagtt tctttttgtt   7620
tgtcatctaa acaacgaaat ttttatgcaa gtcataacca tgctgtgttt tcacagatac   7680
ccagtgctcg agtccatcca aaaatttctt tggccaagac tttgcaaact cgatcaacga   7740
acactgtatg ctcataaact ctaacaaatc atctgtctga aaaaccaata tttctttggt   7800
agaattctat tgtcattact cattactaac agcgaaatta attaacgttc tttttcttac   7860
tcaggtatga attacactac caactgatta cgtttggaaa ggtattattg ctctaagctt   7920
tgaatttatc atatggtaat ttcaagcatt gtaggcacct gatcaattat gtgtctaaat   7980
catgtgaatt catgtcaggt attttgcaca aagagtagac caaattgtaa tgcatgtcca   8040
atgagaggag agtgcagaca ctttgccagt gcttatgcta ggtaagcaag ctttcatgta   8100
cttatatgca ataattaaag ataaaattta ggattatggg taagtaacaa aaaattaggc   8160
tcagtttcat ggtagctagc tggaaatagt attacaagaa caacataaag atcaaagaca   8220
gaatcatgga tccatatgca ctatcatttt agctcttgta atccatacat gaacactata   8280
tgccaaagta gggatttcaa atatgagatt cgatgactga tgccattgta acagtgcaag   8340
acttgcttta ccggcaccag aggagaggag cttaacaagt gcaactattc cggtccctcc   8400
cgagtcctat cctcctgtag ccatcccgat gatagaacta cctcttccgt tggagaaatc   8460
cctagcaagt ggagcaccat cgaatagaga aaactgtgaa ccaataattg aagagccggc   8520
ctcgcccggg caagagtgca ctgaaataac cgagagtgat attgaagatg cttactacaa   8580
```

-continued

```
tgaggaccct gacgagatcc caacaataaa actcaacatt gaacagtttg gaatgactct   8640
acgggaacac atggaaagaa acatggagct ccaagaaggt gacatgtcca aggctttggt   8700
tgctttgcat ccaacaacta cttctattcc aactcccaaa ctaaagaaca ttagccgtct   8760
caggacagag caccaagtgt aagctaatat ctcctcctat attttatctt ccatataaat   8820
tttggggaaa aaatcgctct ccatctggtt ttagaacatg cgggtcagcc agggttatgg   8880
catttttata tatttcaccg atcggcccga gctggctctg gttgactcgt atgccaccct   8940
gcattgaaca aaccagtagg agacaagcaa gcaaaacgtt ttaagataag gtctatggta   9000
aaatgacaag gtaactgata aatgtgtcgt ctatttgcag gtacgagctc ccagattcac   9060
atcgtctcct tgatggtgta agtcaatttt taactctctc tatactcgag ttgtttcact   9120
tgagcaacac tgtttaaaag tcctcatttg ataaaataac agatggataa aagagaacca   9180
gatgatccaa gtccttatct cttagctata tggacaccag gtgagaataa aactgcaatg   9240
tttcattcat gtgtctacag tatcaaagaa agtacagcta gagctaaaaa gcatttgaaa   9300
tagagtcggt taaatatgaa agtttgaatc tgtaaatgaa agccggaacg tagcattggt   9360
ggatgttata tgtaaattag tttttgagat tggtctaatg tagttgtttg actgccaggt   9420
gaaacagcga attcggcaca accgcctgaa cagaagtgtg gagggaaagc gtctggcaaa   9480
atgtgctttg acgagacttg ttctgagtgt aacagtctga gggaagcaaa ctcacagaca   9540
gttcgaggaa ctcttctggt gagattatct tgatcttttg tgttgctcat gaaaaggaga   9600
agtgagaata caagtttgct aatatcattt tttcgtcatt cacagatacc ttgtcggact   9660
gccatgagag gaagttttcc gctcaacggg acatatttcc aagtcaacga ggttagatga   9720
aataaaactc aaacagacag acgaaacatt atttctgttt agtgttggtt ctttatcctc   9780
cttgccattt tttatcttgc agttatttgc agaccacgag tccagtctca aacccatcga   9840
tgttcctaga gattggatat gggatctccc aagaaggact gtttacttcg gaacatcagt   9900
aacatcaata ttcagaggta aaaacattcg taatagagtt agttaatcaa atgtccaaaa   9960
cacaagaaag cttcaccgtc caatacacaa gaaagcttca ccttctcttt gccaaaaaag  10020
atcttagaat gttttgctga atttgtgcag gtctttcaac ggagcagata cagttctgct  10080
tttggaaagg taaacgttaa ctttcgaccc agagaaatcc ggaaaatcta ttgctttgtt  10140
ctgatcaata cgttaaacat atacacacac actttacact taggaccaat actgttctga  10200
tctgtgatag aaactggtaa acatctaaca attatgattg caggattcgt atgtgtccgt  10260
ggattcgaac agaagacaag agcaccgcgt ccattaatgg caaggttgca ttttcctgcg  10320
agcaaattga agaacaacaa aacctaaaga tgactggaag aaagcaaacg cattgcttct  10380
ctgctctcct ctatttaaag ccaggaaaag tcccatttag acataataac aggaatccaa  10440
ataggctatt ttctctttct ttcttatttc attcatagag cagaagcgac acaaaaaagt  10500
tttttgggtt atttattttc tctctaacaa atttgtagcg ttttgggtct ttttctggct  10560
gtcactagcg tggcaaatcc aatgtctgcg cacacttagg cgcattgtca ataaaatttc  10620
```

<210> SEQ ID NO 8
<211> LENGTH: 1413
<212> TYPE: PRT
<213> ORGANISM: Arabidopsis thaliana
<220> FEATURE:
<223> OTHER INFORMATION: DMT2 (1DMT2)

<400> SEQUENCE: 8

-continued

```
Met Glu Lys Gln Arg Arg Glu Glu Ser Ser Phe Gln Gln Pro Pro Trp
  1               5                  10                  15

Ile Pro Gln Thr Pro Met Lys Pro Phe Ser Pro Ile Cys Pro Tyr Thr
             20                  25                  30

Val Glu Asp Gln Tyr His Ser Ser Gln Leu Glu Glu Arg Arg Phe Val
         35                  40                  45

Gly Asn Lys Asp Met Ser Gly Leu Asp His Leu Ser Phe Gly Asp Leu
     50                  55                  60

Leu Ala Leu Ala Asn Thr Ala Ser Leu Ile Phe Ser Gly Gln Thr Pro
 65                  70                  75                  80

Ile Pro Thr Arg Asn Thr Glu Val Met Gln Lys Gly Thr Glu Glu Val
                 85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
    290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
    370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
```

-continued

```
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
    450                 455                 460

Asp Glu Leu Trp Lys Arg Arg Asn Ser Ile Glu Thr Ile Ser Glu Leu
465                 470                 475                 480

Leu Arg Leu Leu Asp Ile Asn Arg Glu His Ser Glu Thr Ala Leu Val
                485                 490                 495

Pro Tyr Thr Met Asn Ser Gln Ile Val Leu Phe Gly Gly Gly Ala Gly
            500                 505                 510

Ala Ile Val Pro Val Thr Pro Val Lys Lys Pro Arg Pro Arg Pro Lys
        515                 520                 525

Val Asp Leu Asp Asp Glu Thr Asp Arg Val Trp Lys Leu Leu Leu Glu
    530                 535                 540

Asn Ile Asn Ser Glu Gly Val Asp Gly Ser Asp Glu Gln Lys Ala Lys
545                 550                 555                 560

Trp Trp Glu Glu Glu Arg Asn Val Phe Arg Gly Arg Ala Asp Ser Phe
                565                 570                 575

Ile Ala Arg Met His Leu Val Gln Gly Asp Arg Arg Phe Thr Pro Trp
            580                 585                 590

Lys Gly Ser Val Val Asp Ser Val Val Gly Val Phe Leu Thr Gln Asn
        595                 600                 605

Val Ser Asp His Leu Ser Ser Ser Ala Phe Met Ser Leu Ala Ser Gln
    610                 615                 620

Phe Pro Val Pro Phe Val Pro Ser Ser Asn Phe Asp Ala Gly Thr Ser
625                 630                 635                 640

Ser Met Pro Ser Ile Gln Ile Thr Tyr Leu Asp Ser Glu Glu Thr Met
                645                 650                 655

Ser Ser Pro Pro Asp His Asn His Ser Ser Val Thr Leu Lys Asn Thr
            660                 665                 670

Gln Pro Asp Glu Glu Lys Asp Tyr Val Pro Ser Asn Glu Thr Ser Arg
        675                 680                 685

Ser Ser Ser Glu Ile Ala Ile Ser Ala His Glu Ser Val Asp Lys Thr
    690                 695                 700

Thr Asp Ser Lys Glu Tyr Val Asp Ser Asp Arg Lys Gly Ser Ser Val
705                 710                 715                 720

Glu Val Asp Lys Thr Asp Glu Lys Cys Arg Val Leu Asn Leu Phe Pro
                725                 730                 735

Ser Glu Asp Ser Ala Leu Thr Cys Gln His Ser Met Val Ser Asp Ala
            740                 745                 750

Pro Gln Asn Thr Glu Arg Ala Gly Ser Ser Ser Glu Ile Asp Leu Glu
        755                 760                 765

Gly Glu Tyr Arg Thr Ser Phe Met Lys Leu Leu Gln Gly Val Gln Val
    770                 775                 780

Ser Leu Glu Asp Ser Asn Gln Val Ser Pro Asn Met Ser Pro Gly Asp
785                 790                 795                 800

Cys Ser Ser Glu Ile Lys Gly Phe Gln Ser Met Lys Glu Pro Thr Lys
                805                 810                 815

Ser Ser Val Asp Ser Ser Glu Pro Gly Cys Cys Ser Gln Gln Asp Gly
            820                 825                 830

Asp Val Leu Ser Cys Gln Lys Pro Thr Leu Lys Glu Lys Gly Lys Lys
        835                 840                 845
```

-continued

```
Val Leu Lys Glu Glu Lys Lys Ala Phe Asp Trp Asp Cys Leu Arg Arg
    850                 855                 860

Glu Ala Gln Ala Arg Ala Gly Ile Arg Glu Lys Thr Arg Ser Thr Met
865                 870                 875                 880

Asp Thr Val Asp Trp Lys Ala Ile Arg Ala Ala Asp Val Lys Glu Val
                885                 890                 895

Ala Glu Thr Ile Lys Ser Arg Gly Met Asn His Lys Leu Ala Glu Arg
            900                 905                 910

Ile Gln Tyr Leu Thr Leu Asn Met Lys Ile Met Gln Gly Phe Leu Asp
        915                 920                 925

Arg Leu Val Asn Asp His Gly Ser Ile Asp Leu Glu Trp Leu Arg Asp
    930                 935                 940

Val Pro Pro Asp Lys Ala Lys Glu Tyr Leu Leu Ser Phe Asn Gly Leu
945                 950                 955                 960

Gly Leu Lys Ser Val Glu Cys Val Arg Leu Leu Thr Leu His His Leu
                965                 970                 975

Ala Phe Pro Val Asp Thr Asn Val Gly Arg Ile Ala Val Arg Leu Gly
            980                 985                 990

Trp Val Pro Leu Gln Pro Leu Pro Glu Ser Leu Gln Leu His Leu Leu
        995                 1000                1005

Glu Met Tyr Pro Met Leu Glu Ser Ile Gln Lys Tyr Leu Trp Pro Arg
   1010                1015                1020

Leu Cys Lys Leu Asp Gln Lys Thr Leu Tyr Glu Leu His Tyr Gln Met
1025               1030                1035                1040

Ile Thr Phe Gly Lys Val Phe Cys Thr Lys Ser Lys Pro Asn Cys Asn
               1045                1050                1055

Ala Cys Pro Met Lys Gly Glu Cys Arg His Phe Ala Ser Ala Phe Ala
           1060                1065                1070

Arg Lys Phe Ser Asn Ile His Leu Phe Tyr Ser Ala Arg Leu Ala Leu
       1075                1080                1085

Pro Ser Thr Glu Lys Gly Met Gly Thr Pro Asp Lys Asn Pro Leu Pro
   1090                1095                1100

Leu His Leu Pro Glu Pro Phe Gln Arg Glu Gln Gly Ser Glu Val Val
1105               1110                1115                1120

Gln His Ser Glu Pro Ala Lys Lys Val Thr Cys Cys Glu Pro Ile Ile
               1125                1130                1135

Glu Glu Pro Ala Ser Pro Glu Pro Glu Thr Ala Glu Val Ser Ile Ala
           1140                1145                1150

Asp Ile Glu Glu Ala Phe Phe Glu Asp Pro Glu Glu Ile Pro Thr Ile
       1155                1160                1165

Arg Leu Asn Met Asp Ala Phe Thr Ser Asn Leu Lys Lys Ile Met Glu
   1170                1175                1180

His Asn Lys Glu Leu Gln Asp Gly Asn Met Ser Ser Ala Leu Val Ala
1185               1190                1195                1200

Leu Thr Ala Glu Thr Ala Ser Leu Pro Met Pro Lys Leu Lys Asn Ile
               1205                1210                1215

Ser Gln Leu Arg Thr Glu His Arg Val Tyr Glu Leu Pro Asp Glu His
           1220                1225                1230

Pro Leu Leu Ala Gln Leu Glu Lys Arg Glu Pro Asp Asp Pro Cys Ser
       1235                1240                1245

Tyr Leu Leu Ala Ile Trp Thr Pro Gly Glu Thr Ala Asp Ser Ile Gln
   1250                1255                1260
```

-continued

```
Pro Ser Val Ser Thr Cys Ile Phe Gln Ala Asn Gly Met Leu Cys Asp
1265                1270                1275                1280

Glu Glu Thr Cys Phe Ser Cys Asn Ser Ile Lys Glu Thr Arg Ser Gln
                1285                1290                1295

Ile Val Arg Gly Thr Ile Leu Ile Pro Cys Arg Thr Ala Met Arg Gly
            1300                1305                1310

Ser Phe Pro Leu Asn Gly Thr Tyr Phe Gln Val Asn Glu Val Phe Ala
        1315                1320                1325

Asp His Ala Ser Ser Leu Asn Pro Ile Asn Val Pro Arg Glu Leu Ile
    1330                1335                1340

Trp Glu Leu Pro Arg Arg Thr Val Tyr Phe Gly Thr Ser Val Pro Thr
1345                1350                1355                1360

Ile Phe Lys Gly Leu Ser Thr Glu Lys Ile Gln Ala Cys Phe Trp Lys
                1365                1370                1375

Gly Tyr Val Cys Val Arg Gly Phe Asp Arg Lys Thr Arg Gly Pro Lys
            1380                1385                1390

Pro Leu Ile Ala Arg Leu His Phe Pro Ala Ser Lys Leu Lys Gly Gln
        1395                1400                1405

Gln Ala Asn Leu Ala
    1410


<210> SEQ ID NO 9
<211> LENGTH: 480
<212> TYPE: PRT
<213> ORGANISM: Arabidopsis thaliana
<220> FEATURE:
<223> OTHER INFORMATION: DMT2 (1DMT2) novel amino terminus

<400> SEQUENCE: 9

Met Glu Lys Gln Arg Arg Glu Glu Ser Ser Phe Gln Gln Pro Pro Trp
  1               5                  10                  15

Ile Pro Gln Thr Pro Met Lys Pro Phe Ser Pro Ile Cys Pro Tyr Thr
             20                  25                  30

Val Glu Asp Gln Tyr His Ser Ser Gln Leu Glu Glu Arg Arg Phe Val
         35                  40                  45

Gly Asn Lys Asp Met Ser Gly Leu Asp His Leu Ser Phe Gly Asp Leu
     50                  55                  60

Leu Ala Leu Ala Asn Thr Ala Ser Leu Ile Phe Ser Gly Gln Thr Pro
 65                  70                  75                  80

Ile Pro Thr Arg Asn Thr Glu Val Met Gln Lys Gly Thr Glu Glu Val
                 85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205
```

-continued

```
Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
    290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
    370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
    450                 455                 460

Asp Glu Leu Trp Lys Arg Arg Asn Ser Ile Glu Thr Ile Ser Glu Leu
465                 470                 475                 480
```

<210> SEQ ID NO 10
<211> LENGTH: 8880
<212> TYPE: DNA
<213> ORGANISM: Arabidopsis thaliana
<220> FEATURE:
<223> OTHER INFORMATION: DMT2 (1DMT2) sequence from BAC F1011

<400> SEQUENCE: 10

```
tcgctgagcc tgggtttctt catcggacct ggatctctgg atctatcaaa cggtctacga      60

ggattctcca ttccaaagaa ctatacaata caagaggtac gcaaataatg ccctaaatta     120

aacctaatcg gcaaaaatcg attgcagtga caacaaatcc tcgttagagg ggaattcaga     180

gcattacaac aatcagtaac cctaagttac aatctaaaaa ttgagatgca taacgcgatt     240

ctgcgaagaa gacggagaag atagaaggaa tgcttcgaat tcggcaaaaa tgtcagagag     300

tttggacaat ctccgatcaa ttagggttgt gaattgggga ttttatggag acgagacaaa     360

aaaaagttga agatcggagc tggttccaaa aatatttagg cccatttaat gacccacatt     420

ccatgtataa taggcccatc atctaatatt tgacaacaat agaattcttt ggtccggttg     480

aactatctga tttaaaccaa gttaagtgag atcctccaca tatcgaacca gatcttgatt     540
```

-continued

```
caggtaacca aaagctaacc gtaaattcag atataaacca aacgaaggga acagagagtt    600
tacacagcta cgggtctgtt ttttgtgaca agtgtttgat acaaatttaa gacgaaacta    660
aaatgggatt tagaaacctt gtacaactct aggactgtta actttacgtt ttcactttct    720
tacattaact agattggaac agtgtgctct ctcactctta accataagct tgtatttgtt    780
tgcttgccaa cggattaggc gaggttagct tgttgtccct tcagtttgct cgccgggaag    840
tgcaatcttg caatcaaagg cttcggtccc ctcgtctttc gatcaaatcc acgtacacat    900
acgtacccta cataaatatca aaagataagt tatgtttcag aacaagaaga aactgcttaa    960
tacaaaatgt acctttccaa aagcaagcct gtatcttctc agttgataaa cctgagaaaa   1020
atagagctca agtggttaga acaactttct tttatataaa caatcgcatc acaatccaat   1080
aaagaaaatc ttatacottt gaatatcgta ggaacagagg taccaaaata gaccgttctt   1140
cgaggtaatt cccatatcaa ttcccttggg acattgattg ggtttaggct ggatgcatga   1200
tccgcaaaca cctgtatcaa tagaatacat cacaagtttc aatgcaaata attaaaatga   1260
aagagttgga gttattggag ttcaagtctt acctcattta cttgaaagta cgttccattt   1320
agaggaaaac taccccctcat cgctgttcta caaggaatct gtacaattta caacatatta   1380
atctgtagaa aacataagtg tagtaagccg cataaggaga ttgatgcaac tacttaccaa   1440
aattgtccct ctcacaattt gagatctagt ctccttgatg ctgttgcagg agaaacaagt   1500
ctcctcgtca caaagcatac catttgcttg gaatatgcac gtactaacag acggttgaat   1560
agaatcagcc gtctcacctg ttgaataaca catcgattaa agataccgat ttgatttcat   1620
gattaaaaga tatgcaaatc attaaattac ctggcgtcca tatagcaagc aaataagaac   1680
atggatcatc aggttctctc ttttccaact gccacaagaa atcacaaaca gctagtcaga   1740
ttttacaata tagacagcac tctatacggc atgtgtcctt atccagttag ctcacatacc   1800
tgagctagaa gaggatgctc gtctggaagt tcgtaactgc aagatacggg aaaagaaaca   1860
agttatggca tagcctgtaa ttattgggaa gtttgtctgc tttccaactt acgagttcat   1920
gcttggtcaa tcacttaaat attctactct gttcaagctt taataatttt gaaaaatgtg   1980
tttctgattt catttttaac ctaagaacga agaaaaacag agaaaaatgg attcttacac   2040
tcggtgttct gtccttaact ggctgatatt cttgagctta ggcattggaa gagaagcagt   2100
ttcagcagta agtgcaacta aagcgctgga catgtttccg tcttgaagtt ccttgttgtg   2160
ttccattatc ttcttcaagt tactggtaaa tgcatccatg tttagcctga tggtaggaat   2220
ttcttctgga tcctcaaaaa acgcctcctc tatgtcagct attgatactt ctgcggtttc   2280
tggctccggt gaagcaggct cttcgatgat tggttcacaa catgtgacct tttttgctgg   2340
ttctgagtgc tgtactactt cagacccttg ctctctctgg aatggctctg gcaggtgtag   2400
aggcaaaggg tttttatcag gtgtccccat acctttctct gtacttggta aagcaagcct   2460
tgcactgtaa aacaaatgaa tgttactaaa ttttctgtaa tgatgattca gagcttcgtt   2520
tagatacaga ccaattctca tttaactggg ttatatttta acaaggactt tcctcataga   2580
gtcatagtgg tactaaaggt ttaagagaac atgttgtagc accttgcaaa cgcactggca   2640
aaatgtctgc attctccttt catcggacat gcattgcaat taggtttgct ctttgtgcaa   2700
aagacctgat acaataatca agcagattac aaacctcatc atgtgagctg attttgacat   2760
acgtatatat gtatttcttt aatacatacc tttccaaaag taatcatctg gtagtgcaac   2820
tcatacctgt gagataatag ggtattaaac taatgaataa gtgtattaga ctgaggcatg   2880
aaaaaaaaaa agttagtgat aaacatcatt cttacaatgt tttttggtcg agtttgcaga   2940
```

-continued

```
gacggggcca aagatacttt tgaatagatt caagcatagg atacctagac aaaccaaacc   3000
tcagatgtat taagtaacaa attacaattt ccaagtagga ccattttgaa aagtgcttac   3060
atttccagaa gatgcaactg aagtgactct gggagcggct gaaggggcac ccatccaagt   3120
ctgacggcta tgcgcccaac atttgtatca acctgtcaat aaattaagtt catgcatcat   3180
ataattcact ttttataggg acagaaacaa aagtttgatc cttgcttact ggaaaggcaa   3240
gatggtgaag tgttagaagc cgcacacact ccacactttt cagtcccaat ccgttaaagc   3300
tcagaagata ttctctgcag ggttttgtaa tatacgagag tacataattc attattaagt   3360
cactaaaact gccaaagtag taatctttgt ataggttaat aaagaagaaa taaaatgctt   3420
cgtctttcaa acttactttg ctttatctgg tggaacatct ctcaaccatt caagatcgat   3480
acttccatgg tcatttacca gtcgatcaag gaagccctgc atgattttca tgttcagagt   3540
caaatactta aaatgaatgt tatcacgaaa tttagccact aaatttttac ctgtatacgt   3600
tctgcaagtt tatggttcat cccgcgactc ttgattgttt cagcaacttc cttaacatct   3660
gctgctcgta ttgccttcca atccacggtg tccattgtac ttcttgtttt ttctctaatt   3720
cctgctctag cttgggcttc tcttcttaaa caatcccagt caaacgcttt tttttcctcc   3780
ttcaaaacct ttttcccttt ttcttttaag gtaggtttct gacaactcaa aacatcccca   3840
tcttgctgag agcaacaacc aggttcacta ctatcaacag aggattttgt gggctctttc   3900
attgactgga aacccttaat ttctgagcta caatcacccg gagacatatt tggtgatact   3960
tgattggaat cttctagaga gacttgtacc ccctgtagga gcttcataaa ggaagtacga   4020
tactctcctt ctaagtcgat ctctgagctt gatcctgctc tctctgtatt ttgaggagca   4080
tcagacacca tcgaatgttg acatgtaagt gcagaatctt cagatggaaa caggttcagg   4140
acacgacact tctcatccgt cttatcaacc tctacacttg agccttttcg atctgaatca   4200
acatactcct ttgaatccgt ggttttgtca actgattcat gggctgagat ggcaatctca   4260
ctactgcttc tggaggtttc attgctaggt acataatcct tctcctcatc aggctgtgta   4320
tttttcaaag taacagaact gtgattgtga tcgggtgggc ttgacatcgt ttcctctgag   4380
tccaagtacg ttatttgaat agaaggcatc gagcttgttc cagcgtcaaa gttactgctc   4440
ggtacaaaag ggacagggaa ctgggaagcc aacgacatga aagccgaact acaaggagta   4500
aaaaacatca aagcaagtta gttttgtgac tttttgctgt cttggattta gtttgacata   4560
gaattatgta agagcttgta ccttgagaga tggtctgaaa cattttgagt gagaaatact   4620
ccaacaacag aatccacgac ggatcccttc caaggcgtaa aacgtcgatc ccctgttaga   4680
aaccaaagac cataacaaga agcagtagct gagacatact aattgaaacc atgtggttag   4740
aacagaaaca cataaaagga caagtgtggt gtataacctt gtacaaggtg catccttgca   4800
ataaatgagt cagctcgtcc tcgaaacaca ttacgttctt cctcccacca tttcgccttc   4860
tgctcgtctg atccgtcaac accttcgcta ttaatattct ccaatagcag tttccacact   4920
ctgtctgtct catcgtctag atcaaccttt ggtcgtgggc gtggtttttt aacaggagtt   4980
acaggcacaa ttgctccagc gccaccacca aagagtacaa tctggctatt cattgtgtaa   5040
ggaacgagag cagtttcaga atgctccctg ttgatgtcta atagacgcaa tagctcactg   5100
attgtttcga tcgagttacg tcgtttccaa agttcatctg gagaaagacc tgcaggaatc   5160
aaacatcatc attatcaaga aatagtctgc atttaacaga ttcaaaaaaa caaagaaata   5220
tagttctgta tctattcatt accagtaaat gaaggtggaa aacggcaaag attcggaaga   5280
```

-continued

```
agatttttct gtttggtttg tgatttctca gacttggttg gcttcttttt gctcacagtc   5340
acccgcgtat caacaagaat cttattattt tgctgtggct tgctacaata tcctgaggtt   5400
aaatgctcag gaacttccac aagtttattc attgaagaca aattccggaa tcgagcatgg   5460
cctgttgttt tcttcttgat cggcgtgtct atcttatccg agagaacatt tagctcagac   5520
tcttgccttc cttgaaagat accttctcgt ctttcttcaa cggttaggac tctattagca   5580
ctgagctgag atgtggaact gtagcacgta gcgtgaaagg cagaaacata attgtgctgt   5640
tgtccagaga atactttgct gcaaatggca tcatatctca tccctccctg ttgcaagttt   5700
ggggaataca accaatgcat tttctggtag tcacattgct catcatactg aatccctgat   5760
agattcatgt cgcaacaagt tggtccttgt cttctctttg cagcttgcgc catcgaaata   5820
tcgacttctt ctagattact gccatttttc tttggttgaa ctccctttct tttaccttgg   5880
ctgcgctttc tcttgggcgt gctaggagcc gaaagaaggc aatcttttaa ctcttgattc   5940
ccagaatcta actgcttctc ttgaagagct gattccatct cacctgcttc tctaatgtca   6000
ccgttggtct ggttttctcc attttcggct tcaaaatcca agactcgtct acagagcctc   6060
ttaggacgag ttgaagtttc aacagctgct gatgattcaa ccggagtagc gtcttgatcc   6120
ttactgactt caaccttctt ccgcacatat ttcctctttg gtgttttgct ttcttgacca   6180
tcggtgacaa cagacttcct cggagctcgt ggtttaggct ccctcttggg tttagcttct   6240
ctacgaacct ttggccgatg cttcttcctc ttaggttttt caggagtctt gaggatctgt   6300
tcagcaacat tgttactcac tgagctcaaa ctctccactt cttcagtacc tttttgcata   6360
acctctgtgt ttcctacatt gagaatcaca tctttctcag tccaactcaa acagaatcaa   6420
aatttgacaa agcgatttca tttctcatga gaccagaatc aaaatcccct cttacttgta   6480
ggtattggag tctgaccaga gaatatgagg gatgcagtgt tagctagagc aagcaaatcc   6540
ccaaaagaca agtgatcaag accactcata tccttgttcc caacaaatct cctgcatgca   6600
tcaatacctt acttaaccaa ttacccatca ctactctttg aaatttctca actttagaac   6660
aaaaaagcac aaaccttttcc tccaattgac tgctatgata ttgatcctcc accgtgtatg   6720
ggcagatcgg tgaaaatggc ttcatgggtg tctgaggaat ccatggaggt tgttgaaagc   6780
tgctttcttc tctcctctgt ttctccattt ctgactctat ttttactttt cttcactctt   6840
acttaaatca gaaccatttg agaaaaagct tggaactttc tattttttcc actgcaaaaa   6900
gttcaataat ttcttcaata aaagagatca ccaatttttt ttaaaaatca cgattttata   6960
aaatgatcag atccactttt ttctggggtt ttagagaaag agagatctcc ggaagtcatt   7020
gattttgggt gagtggcgac atgaacgatt aatccgttcg ttaggtgaaa gagagacttt   7080
ttagattcac aacaaaatgt aaaaaaaagt aagaaaaaaa caaaattcat taccagtaga   7140
atcaatggtt atggtggtga tggagagagt tagttcggtg gtagctatga gaggataaga   7200
tcactgatgc ttcgtttctt ctcttggaat cgatgaagtt aaagagtaat atagaaaaag   7260
ctttttggc ctaacgtata aagaagagga tataacatgt gttgttgtgt gtttcactat   7320
ttttcataac cgtttgttta tgtagggcga aagttcgttt ggttggcggg aaaagtttta   7380
cggaatttta ttttaaaaat aatgattctt ttctacaaaa tctcctagac tatgggaaag   7440
atgatttaaa aagttaataa tattgtcgtt gttatcgtca tcgtcatcat cgtcttttct   7500
gttatctttt tctctttaaa atttcgtatt ttttctcgtt tacgtaacta tttaaaatta   7560
tatgaactaa ctaattttat aattaataga aattataaaa taatcttaat tttgctttag   7620
atataaaata attagaactt tatttataaa tttatcatca aattatgatt taaacaaata   7680
```

-continued

```
acatgttatg taatccacgt ttataatttt gatcaataat atattatttt gctaattttt   7740

acgtaatctc ataaatttac acgttttcgt ttacatatgc agaagttaaa tgattcgttt   7800

tagaattatt attttccact gatatgggag ctagtgtagt agagtgatta ttaggctagt   7860

tgcccaacga gtctttcgtt tttgatcatt ccaaatgttt tagtctagta cgataggagt   7920

caaaatactg caccatatgt gtgaaactgt gaatgtgtgt gaaaaaaaga gtaattagtg   7980

tgctaacctt tgatttcctg tcatgcaaga aaccttcaaa gagacgtaca tgagaaatga   8040

gtattgtaaa tcatttattt catggacttg gttggaatct tagtgaatcg ttgttgtcaa   8100

tcttaacaac ttgttggatt ggttatgagc ctatgactta tgacttatga gtgagtcaat   8160

ggtggtcata acctaatgat tgggttatga gcaaagaaat ttggaatttg taaaaaaaaa   8220

aaaaaaaatc aagagctttt ttgtgtggac atatctatcc tagaaactga gacgaataat   8280

agtggataaa aagttgggaa cggattattc gaatgtttaa aactattatt gaaaacaata   8340

caactaaata tggtacaaaa gtaaacgaat tcgtatagct aaacctaatt caaattacga   8400

agctaatcca tacttggatc ctaaacgctt ttacttttac ttacggtttc tttttcaaaa   8460

aagtttttac aaatttgggt ttgtcttatg aagattatgg cagaagagac tgatcaaaag   8520

tgaatgccta attcggttta atccattcaa gtttatctta aacaatgaaa ctgaccatga   8580

aagtgaattc aaagaccaaa tcaaagaaaa attaaactga tttagttgta atattggtat   8640

tgaattaaac tataaataga aataaccaaa catataacca caaaagaaga ctatttatat   8700

aaatatatga gttggaagtc atttttggac tattatataa gatctaatta tcacacgacg   8760

tgtggatgta tggttagcag agttgtgttc agagagttcg ataaagccat cactccaaac   8820

atacaaaata tccatacatt gatccaccaa tataaccggc tgtgtgccaa gcaaagtgaa   8880
```

```
<210> SEQ ID NO 11
<211> LENGTH: 1332
<212> TYPE: PRT
<213> ORGANISM: Arabidopsis thaliana
<220> FEATURE:
<223> OTHER INFORMATION: DMT3 (1DMT3)

<400> SEQUENCE: 11

Met Glu Val Glu Gly Glu Val Arg Glu Lys Glu Ala Arg Val Lys Gly
1               5                   10                  15

Arg Gln Pro Glu Thr Glu Val Leu His Gly Leu Pro Gln Glu Gln Ser
            20                  25                  30

Ile Phe Asn Asn Met Gln His Asn His Gln Pro Asp Ser Asp Arg Arg
        35                  40                  45

Arg Leu Ser Leu Glu Asn Leu Pro Gly Leu Tyr Asn Met Ser Cys Thr
    50                  55                  60

Gln Leu Leu Ala Leu Ala Asn Ala Thr Val Ala Thr Gly Ser Ser Ile
65                  70                  75                  80

Gly Ala Ser Ser Ser Ser Leu Ser Ser Gln His Pro Thr Asp Ser Trp
                85                  90                  95

Ile Asn Ser Trp Lys Met Asp Ser Asn Pro Trp Thr Leu Ser Lys Met
            100                 105                 110

Gln Lys Gln Gln Tyr Asp Val Ser Thr Pro Gln Lys Phe Leu Cys Asp
        115                 120                 125

Leu Asn Leu Thr Pro Glu Glu Leu Val Ser Thr Ser Thr Gln Arg Thr
    130                 135                 140

Glu Pro Glu Ser Pro Gln Ile Thr Leu Lys Thr Pro Gly Lys Ser Leu
```

-continued

```
145                 150                 155                 160

Ser Glu Thr Asp His Glu Pro His Asp Arg Ile Lys Lys Ser Val Leu
                165                 170                 175

Gly Thr Gly Ser Pro Ala Ala Val Lys Lys Arg Lys Ile Ala Arg Asn
            180                 185                 190

Asp Glu Lys Ser Gln Leu Glu Thr Pro Thr Leu Lys Arg Lys Lys Ile
        195                 200                 205

Arg Pro Lys Val Val Arg Glu Gly Lys Thr Lys Lys Ala Ser Ser Lys
    210                 215                 220

Ala Gly Ile Lys Lys Ser Ser Ile Ala Ala Thr Ala Thr Lys Thr Ser
225                 230                 235                 240

Glu Glu Ser Asn Tyr Val Arg Pro Lys Arg Leu Thr Arg Arg Ser Ile
                245                 250                 255

Arg Phe Asp Phe Asp Leu Gln Glu Glu Asp Glu Glu Phe Cys Gly Ile
            260                 265                 270

Asp Phe Thr Ser Ala Gly His Val Glu Gly Ser Ser Gly Glu Glu Asn
        275                 280                 285

Leu Thr Asp Thr Thr Leu Gly Met Phe Gly His Val Pro Lys Gly Arg
    290                 295                 300

Arg Gly Gln Arg Arg Ser Asn Gly Phe Lys Lys Thr Asp Asn Asp Cys
305                 310                 315                 320

Leu Ser Ser Met Leu Ser Leu Val Asn Thr Gly Pro Gly Ser Phe Met
                325                 330                 335

Glu Ser Glu Glu Asp Arg Pro Ser Asp Ser Gln Ile Ser Leu Gly Arg
            340                 345                 350

Gln Arg Ser Ile Met Ala Thr Arg Pro Arg Asn Phe Arg Ser Leu Lys
        355                 360                 365

Lys Leu Leu Gln Arg Ile Ile Pro Ser Lys Arg Asp Arg Lys Gly Cys
    370                 375                 380

Lys Leu Pro Arg Gly Leu Pro Lys Leu Thr Val Ala Ser Lys Leu Gln
385                 390                 395                 400

Leu Lys Val Phe Arg Lys Lys Arg Ser Gln Arg Asn Arg Val Ala Ser
                405                 410                 415

Gln Phe Asn Ala Arg Ile Leu Asp Leu Gln Trp Arg Arg Gln Asn Pro
            420                 425                 430

Thr Gly Thr Ser Leu Ala Asp Ile Trp Glu Arg Ser Leu Thr Ile Asp
        435                 440                 445

Ala Ile Thr Lys Leu Phe Glu Glu Leu Asp Ile Asn Lys Glu Gly Leu
    450                 455                 460

Cys Leu Pro His Asn Arg Glu Thr Ala Leu Ile Leu Tyr Lys Lys Ser
465                 470                 475                 480

Tyr Glu Glu Gln Lys Ala Ile Val Lys Tyr Ser Lys Lys Gln Lys Pro
                485                 490                 495

Lys Val Gln Leu Asp Pro Glu Thr Ser Arg Val Trp Lys Leu Leu Met
            500                 505                 510

Ser Ser Ile Asp Cys Asp Gly Val Asp Gly Ser Asp Glu Glu Lys Arg
        515                 520                 525

Lys Trp Trp Glu Glu Glu Arg Asn Met Phe His Gly Arg Ala Asn Ser
    530                 535                 540

Phe Ile Ala Arg Met Arg Val Val Gln Gly Asn Arg Thr Phe Ser Pro
545                 550                 555                 560

Trp Lys Gly Ser Val Val Asp Ser Val Val Gly Val Phe Leu Thr Gln
                565                 570                 575
```

-continued

```
Asn Val Ala Asp His Ser Ser Ser Ser Ala Tyr Met Asp Leu Ala Ala
            580                 585                 590

Glu Phe Pro Val Glu Trp Asn Phe Asn Lys Gly Ser Cys His Glu Glu
        595                 600                 605

Trp Gly Ser Ser Val Thr Gln Glu Thr Ile Leu Asn Leu Asp Pro Arg
    610                 615                 620

Thr Gly Val Ser Thr Pro Arg Ile Arg Asn Pro Thr Arg Val Ile Ile
625                 630                 635                 640

Glu Glu Ile Asp Asp Asp Glu Asn Asp Ile Asp Ala Val Cys Ser Gln
                645                 650                 655

Glu Ser Ser Lys Thr Ser Asp Ser Ser Ile Thr Ser Ala Asp Gln Ser
            660                 665                 670

Lys Thr Met Leu Leu Asp Pro Phe Asn Thr Val Leu Met Asn Glu Gln
        675                 680                 685

Val Asp Ser Gln Met Val Lys Gly Lys Gly His Ile Pro Tyr Thr Asp
    690                 695                 700

Asp Leu Asn Asp Leu Ser Gln Gly Ile Ser Met Val Ser Ser Ala Ser
705                 710                 715                 720

Thr His Cys Glu Leu Asn Leu Asn Glu Val Pro Pro Glu Val Glu Leu
                725                 730                 735

Cys Ser His Gln Gln Asp Pro Glu Ser Thr Ile Gln Thr Gln Asp Gln
            740                 745                 750

Gln Glu Ser Thr Arg Thr Glu Asp Val Lys Lys Asn Arg Lys Lys Pro
        755                 760                 765

Thr Thr Ser Lys Pro Lys Lys Lys Ser Lys Glu Ser Ala Lys Ser Thr
    770                 775                 780

Gln Lys Lys Ser Val Asp Trp Asp Ser Leu Arg Lys Glu Ala Glu Ser
785                 790                 795                 800

Gly Gly Arg Lys Arg Glu Arg Thr Glu Arg Thr Met Asp Thr Val Asp
                805                 810                 815

Trp Asp Ala Leu Arg Cys Thr Asp Val His Lys Ile Ala Asn Ile Ile
            820                 825                 830

Ile Lys Arg Gly Met Asn Asn Met Leu Ala Glu Arg Ile Lys Ala Phe
        835                 840                 845

Leu Asn Arg Leu Val Lys Lys His Gly Ser Ile Asp Leu Glu Trp Leu
    850                 855                 860

Arg Asp Val Pro Pro Asp Lys Ala Lys Glu Tyr Leu Leu Ser Ile Asn
865                 870                 875                 880

Gly Leu Gly Leu Lys Ser Val Glu Cys Val Arg Leu Leu Ser Leu His
                885                 890                 895

Gln Ile Ala Phe Pro Val Asp Thr Asn Val Gly Arg Ile Ala Val Arg
            900                 905                 910

Leu Gly Trp Val Pro Leu Gln Pro Leu Pro Asp Glu Leu Gln Met His
        915                 920                 925

Leu Leu Glu Leu Tyr Pro Val Leu Glu Ser Val Gln Lys Tyr Leu Trp
    930                 935                 940

Pro Arg Leu Cys Lys Leu Asp Gln Lys Thr Leu Tyr Glu Leu His Tyr
945                 950                 955                 960

His Met Ile Thr Phe Gly Lys Val Phe Cys Thr Lys Val Lys Pro Asn
                965                 970                 975

Cys Asn Ala Cys Pro Met Lys Ala Glu Cys Arg His Tyr Ser Ser Ala
            980                 985                 990
```

-continued

Arg Ala Ser Ala Arg Leu Ala Leu Pro Glu Pro Glu Glu Ser Asp Arg
995 1000 1005

Thr Ser Val Met Ile His Glu Arg Arg Ser Lys Arg Lys Pro Val Val
1010 1015 1020

Val Asn Phe Arg Pro Ser Leu Phe Leu Tyr Gln Glu Lys Glu Gln Glu
1025 1030 1035 1040

Ala Gln Arg Ser Gln Asn Cys Glu Pro Ile Ile Glu Glu Pro Ala Ser
1045 1050 1055

Pro Glu Pro Glu Tyr Ile Glu His Asp Ile Glu Asp Tyr Pro Arg Asp
1060 1065 1070

Lys Asn Asn Val Gly Thr Ser Glu Asp Pro Trp Glu Asn Lys Asp Val
1075 1080 1085

Ile Pro Thr Ile Ile Leu Asn Lys Glu Ala Gly Thr Ser His Asp Leu
1090 1095 1100

Val Val Asn Lys Glu Ala Gly Thr Ser His Asp Leu Val Val Leu Ser
1105 1110 1115 1120

Thr Tyr Ala Ala Ala Ile Pro Arg Arg Lys Leu Lys Ile Lys Glu Lys
1125 1130 1135

Leu Arg Thr Glu His His Val Phe Glu Leu Pro Asp His His Ser Ile
1140 1145 1150

Leu Glu Gly Phe Glu Arg Arg Glu Ala Glu Asp Ile Val Pro Tyr Leu
1155 1160 1165

Leu Ala Ile Trp Thr Pro Gly Glu Thr Val Asn Ser Ile Gln Pro Pro
1170 1175 1180

Lys Gln Arg Cys Ala Leu Phe Glu Ser Asn Asn Thr Leu Cys Asn Glu
1185 1190 1195 1200

Asn Lys Cys Phe Gln Cys Asn Lys Thr Arg Glu Glu Glu Ser Gln Thr
1205 1210 1215

Val Arg Gly Thr Ile Leu Ile Pro Cys Arg Thr Ala Met Arg Gly Gly
1220 1225 1230

Phe Pro Leu Asn Gly Thr Tyr Phe Gln Thr Asn Glu Val Phe Ala Asp
1235 1240 1245

His Asp Ser Ser Ile Asn Pro Ile Asp Val Pro Thr Glu Leu Ile Trp
1250 1255 1260

Asp Leu Lys Arg Arg Val Ala Tyr Leu Gly Ser Ser Val Ser Ser Ile
1265 1270 1275 1280

Cys Lys Gly Leu Ser Val Glu Ala Ile Lys Tyr Asn Phe Gln Glu Gly
1285 1290 1295

Tyr Val Cys Val Arg Gly Phe Asp Arg Glu Asn Arg Lys Pro Lys Ser
1300 1305 1310

Leu Val Lys Arg Leu His Cys Ser His Val Ala Ile Arg Thr Lys Glu
1315 1320 1325

Lys Thr Glu Glu
1330

<210> SEQ ID NO 12
<211> LENGTH: 375
<212> TYPE: PRT
<213> ORGANISM: Arabidopsis thaliana
<220> FEATURE:
<223> OTHER INFORMATION: DMT3 (1DMT3) novel amino terminus

<400> SEQUENCE: 12

Met Glu Val Glu Gly Glu Val Arg Glu Lys Glu Ala Arg Val Lys Gly
1 5 10 15

-continued

```
Arg Gln Pro Glu Thr Glu Val Leu His Gly Leu Pro Gln Glu Gln Ser
            20                  25                  30

Ile Phe Asn Asn Met Gln His Asn His Gln Pro Asp Ser Asp Arg Arg
        35                  40                  45

Arg Leu Ser Leu Glu Asn Leu Pro Gly Leu Tyr Asn Met Ser Cys Thr
    50                  55                  60

Gln Leu Leu Ala Leu Ala Asn Ala Thr Val Ala Thr Gly Ser Ser Ile
 65                  70                  75                  80

Gly Ala Ser Ser Ser Ser Leu Ser Ser Gln His Pro Thr Asp Ser Trp
                85                  90                  95

Ile Asn Ser Trp Lys Met Asp Ser Asn Pro Trp Thr Leu Ser Lys Met
            100                 105                 110

Gln Lys Gln Gln Tyr Asp Val Ser Thr Pro Gln Lys Phe Leu Cys Asp
        115                 120                 125

Leu Asn Leu Thr Pro Glu Glu Leu Val Ser Thr Ser Thr Gln Arg Thr
    130                 135                 140

Glu Pro Glu Ser Pro Gln Ile Thr Leu Lys Thr Pro Gly Lys Ser Leu
145                 150                 155                 160

Ser Glu Thr Asp His Glu Pro His Asp Arg Ile Lys Lys Ser Val Leu
                165                 170                 175

Gly Thr Gly Ser Pro Ala Ala Val Lys Lys Arg Lys Ile Ala Arg Asn
            180                 185                 190

Asp Glu Lys Ser Gln Leu Glu Thr Pro Thr Leu Lys Arg Lys Lys Ile
        195                 200                 205

Arg Pro Lys Val Val Arg Glu Gly Lys Thr Lys Lys Ala Ser Ser Lys
    210                 215                 220

Ala Gly Ile Lys Lys Ser Ser Ile Ala Ala Thr Ala Thr Lys Thr Ser
225                 230                 235                 240

Glu Glu Ser Asn Tyr Val Arg Pro Lys Arg Leu Thr Arg Arg Ser Ile
                245                 250                 255

Arg Phe Asp Phe Asp Leu Gln Glu Glu Asp Glu Glu Phe Cys Gly Ile
            260                 265                 270

Asp Phe Thr Ser Ala Gly His Val Glu Gly Ser Ser Gly Glu Glu Asn
        275                 280                 285

Leu Thr Asp Thr Thr Leu Gly Met Phe Gly His Val Pro Lys Gly Arg
    290                 295                 300

Arg Gly Gln Arg Arg Ser Asn Gly Phe Lys Lys Thr Asp Asn Asp Cys
305                 310                 315                 320

Leu Ser Ser Met Leu Ser Leu Val Asn Thr Gly Pro Gly Ser Phe Met
                325                 330                 335

Glu Ser Glu Glu Asp Arg Pro Ser Asp Ser Gln Ile Ser Leu Gly Arg
            340                 345                 350

Gln Arg Ser Ile Met Ala Thr Arg Pro Arg Asn Phe Arg Ser Leu Lys
        355                 360                 365

Lys Leu Leu Gln Arg Ile Ile
    370                 375
```

<210> SEQ ID NO 13
<211> LENGTH: 8760
<212> TYPE: DNA
<213> ORGANISM: Arabidopsis thaliana
<220> FEATURE:
<223> OTHER INFORMATION: DMT3 (1DMT3) sequence from BAC T22K18

<400> SEQUENCE: 13

-continued

```
aatcaagtac taatgcagat ttaagggggg tgtattgacg gcgttaaaac ggtttctcaa     60
cggaatcgta cgtagtcaca cgtgatttta ttgtttaccc cggattggtc atgcgttcct    120
tcttttccac ttgcgcggac cactcaatga cactctcttc ttttgtagca gtggcccgac    180
accagaatgc agcatttaat ctctcaaatt accattttgc tcctacctct tttacccctt    240
ttggtatttt gtgtcttttt tctttctatt tcgtgtgaaa aaggatctct tccttaatcg    300
tattatttct tccgatatct acttttattc tgttttctat ttttggtagg ttacatcttt    360
tttataaaga aaatatgagc taacacgaca ttagtgttgt taaccaaaga attggaaaaa    420
agttataaga gagataataa gattctctta cagagactca cttcagtgaa aaaggaagaa    480
gcaagtggtt cccttaaggg aaaaaaaagt cacgtacgtt catatacaac tttaatacgt    540
actgtgtaac tcaatagatc gtgcagtaat attcagtcgt attagtaaga aggaatttat    600
ttgctaagta aactcaagcc tccttttttct cttttttttc tttttagtaa aaattaggct    660
agtgtttttt ttgactcagc aacactctgc ttaaatttag gagtaatttg acctattcct    720
acgagtttct aagtgaattc tgttggggtc aaagaagcaa ctagttgaat tagtggaaaa    780
tcgtttcctt tctttacgca tagttcacgt tggacactca gtctcaatgc tttcacgttt    840
cacgtagcaa caacatatat tcatcagttt gtgatcgtgc catcgtggat aagttgcaat    900
tcagtgaaac tctgcaccac tttgtgcaat tatttggccg tctaatctat ttgtgagaat    960
tttacaatct aattgttcta ttatttcatt tacttgtcat caatttatta tatttgtagc   1020
caatgaacgt tgtaattaaa gaaccaaaat aaattaatat cttgaaattt gtaacagtca   1080
ctagaagctg atttcttatt aattgtatca ctaaagtatt attaaaaacg gttacaaatt   1140
atgataatta tatatttaat aaatttcgtg tgtcacattt cttttaaact acaattatga   1200
atatctaaaa ctcattcatg catatcttaa aatttgaatt caaaactttc ttatcttatc   1260
tttaggttct taattaacag tcactaaaaa tagtcaaagt tttgaagttt atgaaaaaag   1320
ataagagtat aattaatgga tacgcctcgt aacaaattct tgtaaagtat agataatata   1380
catttgttaa atatgacacg tgtttatttt ttttttaaat atgatcaaaa tatattttaa   1440
ctacctagat ggtatgtatg tctccaattt tgaataacaa gtcaattgtt attagaaatg   1500
tcataaatata aagaagggaa ttaaatttgc aaagaaaaag tgaaaaacaa aggatttgta   1560
ttttggagaa aattaaggac tggatttgca aaaacgaaaa agtaacttca tgtatattgt   1620
cttccttata gtctctataa actattatct caaattttgt ctggactctg aaactcacaa   1680
gacttgactc tggcttactt ggcttcatct ttttctctct ggtaatctct cctgcaactt   1740
caagctttca ttttcaaata aatgtaatca aatctgttat tttcactcaa gaactaattg   1800
agttctctat ccctttcaat tgaaattgac attaaaatga aaagattttg aggaggtttc   1860
acctaccaca accgaatcac ttctttctcc aaatattgtt tctttcagtg gccaagaatc   1920
acaatcaatt tttgtatctt ccacaggtaa attaattgtg attgaacaga gaagaggaca   1980
agtgatcttg gttcaaaaga aatggaagtg gaaggtgaag tgagagagaa agaagctagg   2040
gttaaaggga gacaaccaga gacagaagtt ctacatggtc tgccacaaga acagtcaata   2100
tttaataaca tgcaacacaa ccatcagcct gactcagaca ggttttgtga ctcaaccgaa   2160
tttactctgt tcttctcccg gaatttccat attttctggt gattctgttt tgttaaattc   2220
tgcaaaagga agaaaataaa tcaaacattt ttcacttctt caaaacatga gtaaatgcaa   2280
aaactgagat atgtaaacac acagcaattt tttgatgaac tggttttggc tgtgtgatct   2340
ttgtgtctat gcaattacgt tttagttatt ttctacttta taaggagaga tgttaactga   2400
```

-continued

```
aactgttatt gatcatacag gaggaggctt agtcttgaaa acttacctgg actatacaac   2460
atgtcttgta cacaactctt ggctctggcc aatgccacag tcgccacagg ttcatcaatt   2520
ggtgcatcat catcatcgtt aagctctcag catccaacgg attcttggat taatagctgg   2580
aagatggact ctaatccgtg gactttgagt aaaatgcaaa aacaacaatg tgagtaaaat   2640
ttgttcctga atttgtagga tcttttaaga gaaagtaagc gtttatgtgt agattaagtc   2700
agactgaaat cgattatctc ataataagtt ctcagtgatc tctcaaatca tgaattttat   2760
gtttacctga tatcaacttc ttgtcttggt gaaccacaga tgatgtgtca actccgcaga   2820
agtttctttg tgaccttaat cttacacctg aagagttggt gagcaccagt acgcaacgaa   2880
cagaacctga gtctcctcaa ataactttaa agacaccagg aaaaagtctg tctgaaactg   2940
atcatgagcc tcacgaccgt atcaagaagt ctgttcttgg aactggatct cctgcagcag   3000
taaagaaaag aaagatagca agaaatgatg agaaatctca gctggaaaca ccaacactaa   3060
agagaaaaaa gatcaggcca aaggttgtcc gtgaaggcaa aacaaaaaaa gcatcatcta   3120
aagcagggat taaaaaatcc tctattgctg ctactgctac taaaacttct gaagagagca   3180
attatgttcg gccaaaaaga ttaacgagaa gatctatacg attcgacttt gaccttcaag   3240
aagaagatga ggaattttgt ggaatcgatt tcacatcagc aggtcacgta gagggttctt   3300
caggtgaaga aaatctaacc gatacaacac tgggaatgtt tggtcacgtc ccaaagggaa   3360
gaagagggca aagaagatcc aatggcttta aaaaaaccga caatgattgc ctcagttcta   3420
tgttgtctct tgtcaatacc ggaccaggaa gtttcatgga atcagaagaa gatcgtccga   3480
gtgattcaca aatttctctg ggaagacaga gatccattat ggcaaccaga ccgcgtaact   3540
tccgatcgtt aaagaaactt ttacaaagga ttataccaag caaacgtgat agaaaaggat   3600
gtaagcttcc tcgtggactt ccgaagctta ccgtcgcatc caagttgcaa ctaaaagtgt   3660
ttagaaagaa gcggagtcaa agaaaccgtg tagcaagcca gttcaatgca aggatattgg   3720
acttgcagtg gcgacgccaa aatccaacag gtgataaaca cacaagcaac tttcatctat   3780
aatattttc ttagatttct atcttttgaa ttaatactag ttttacaaaa tgcaggtaca   3840
tcgctagctg atatatggga aagaagtttg actattgatg ctatcactaa gttgtttgaa   3900
gaattagaca tcaacaaaga gggtctttgc cttccacata atagagaaac tgcacttatt   3960
ctatacaaaa agtcgtatga agagcaaaag gcaatagtga agtatagcaa gaagcagaaa   4020
ccgaaagtac aattggatcc tgaaacgagt cgagtgtgga aactcttaat gtcaagtatc   4080
gactgtgacg gtgttgatgg atcagatgag gaaaaacgta aatggtggga agaggagagg   4140
aacatgttcc atggacgtgc aaactcgttc attgcgcgaa tgcgtgttgt ccaaggtatt   4200
atttattgct ttagttatga cattgttgtg tggctttata ccttagatct ttctttcttt   4260
ctttttgta tccaaagcaa catggtctta aatcaagctt atcactgcag gcaatagaac   4320
tttctcacct tggaaagggt cagtagtgga ttcagtagtg ggagttttcc taacccagaa   4380
tgtcgcagac cattcatcaa ggtatatgca ttcaagagat ttctaataag tagaagatat   4440
atgcaacaga gtggtttaga aattataact tgttcacttt tgcagttctg catatatgga   4500
tttagctgct gagtttcctg tcgagtggaa cttcaacaag ggatcatgtc atgaagagtg   4560
gggaagttca gtaactcaag aaacaatact gaatttggat ccaagaactg gagtttcaac   4620
tccaagaatt cgcaatccaa ctcgcgtcat catagaggag attgatgatg atgagaacga   4680
cattgatgct gtttgtagtc aggaatcctc taaaacaagt gacagttcca taacttctgc   4740
```

-continued

```
agaccaatca aaaacgatgc tgctggatcc atttaacaca gttttgatga acgagcaagt   4800

tgattcccaa atggtaaaag gcaaaggtca tataccatac acggatgatc ttaatgactt   4860

gtcccagggg atttcgatgg tctcatctgc ttctactcat tgtgagttga acctaaatga   4920

agtaccacct gaagtagagt tgtgcagcca tcaacaagac ccggagagta ccattcagac   4980

acaagaccag caagagagca caagaacgga ggatgtgaag aagaatagga aaaaaccaac   5040

tacctccaaa ccaaagaaaa agtcaaagga atcagcaaag agcacgcaaa agaaaagcgt   5100

tgactgggat agtttgagaa aggaagcaga aagtggtggc cgaaagagag agagaacaga   5160

aagaacaatg gacacagttg attgggatgc acttcgatgt acagacgtac acaagatcgc   5220

taatataatc atcaaacgag ggatgaacaa catgcttgcc gaaagaatca aggtttgact   5280

aatcacagtg ctatatatac ctcatttata cattctaaca aggtgaattt ttttgactct   5340

ggaaattgga caggccttct taaacagact agttaaaaaa catggaagca ttgacttaga   5400

gtggctaaga gatgttcctc ctgataaagc caagtaagaa aattatttac aaatcttgag   5460

attatatgta gcctctggtt aaagaatata tctcagtaaa tggaatcgat agtaattgag   5520

atacatataa atgagagata cttgatagtg actactaatg gttgcaggga gtatctacta   5580

agcataaacg gattaggatt gaagagtgtg gagtgtgtta gacttttgtc actacatcag   5640

attgcattcc ctgtaagtca atgaaggata ctgaatactc agaccctaat gaatgtggaa   5700

cagatacatt aatagttacg tatttttaca aatgcaggtt gacacgaatg tcggacgcat   5760

agctgtaaga ctaggatggg ttcccttaca gccattgccc gacgagctgc aaatgcatct   5820

tttagagttg taagaaaaaa aaattaaaga tcattcttca atcatgaaag ggaacatgag   5880

aaatttacag tagttccctt taattctatt caggtaccca gttctagagt cagttcaaaa   5940

gtacctctgg ccacgcctct gcaagcttga ccaaaaaacc ttgtaagtaa attacattag   6000

catcaaccat tactctagac ccttaaactt ctctaactaa ctctaactgt atcatacaat   6060

tctaggtacg agctgcatta ccacatgata acatttggaa aggtacctca aacaaatttc   6120

aagtgtttgt ggaatgaaaa catcttaaag tggcttttcc tattttgcag gtcttttgca   6180

caaaagtaaa acccaattgc aatgcatgtc caatgaaggc ggagtgtcga cattactcta   6240

gtgcacgtgc aaggttaaac cccacaaaat tctttgttat tgccattaac atgaaaaaaa   6300

aaacactagc ttaaagagaa agagatctgc tcaaaatagt cattttaatg gttgtatgtt   6360

ctaaatgctt gtgttatatc gcagcgcacg gcttgcttta ccagaaccag aggagagtga   6420

cagaacaagt gtaatgatcc atgagaggag atctaaacgc aagcctgttg tggttaattt   6480

tcgaccatcc ttatttcttt atcaagaaaa agagcaagaa gcacaaagat cccaaaactg   6540

tgaaccaatc attgaggaac cagcatcacc agaaccagag tatatagaac atgatattga   6600

agactatcct cgggacaaaa acaacgttgg aacatcagag gatccttggg aaaataagga   6660

cgtaattcct accatcatcc tcaacaagga agctggtaca tcacatgatt tggtggtcaa   6720

caaggaagct ggtacgtcac atgatttggt ggtactaagc acatatgcag cagcaatacc   6780

tagacgtaaa ctcaagatca aggaaaagct acgcacagag caccacgtgt gagttgccac   6840

tttcaatttt ttcttctatt ataccctaaa ccgtaaaatt tgagactttc ctcagcattt   6900

atctcatact aattctcttt tacagatttg agctccctga tcaccattcc attctagaag   6960

gggttagtaa ctcttgcaaa atgatttagc aagaattttt ctacttattc ccgccttaaa   7020

aactgtttga ttatcttttt ttacagtttg agaggcgaga agctgaggat atagtccctt   7080

acttgttagc catttggacg ccaggtaaga agaaataggc acacaataaa atctgattat   7140
```

-continued

```
gatttttctt ttcaagaata ccgctatatt tttacgagtt ttcatcctta gatgtatatg   7200

actaatgtct aacaagtgat tgtaatattt ttccatacca ggtgaaaccg tgaattccat   7260

tcaaccgcca aaacaaagat gtgctttatt tgaaagcaat aatacattat gcaacgaaaa   7320

caaatgtttt caatgcaaca agacacggga agaggaatca cagactgtac gaggaactat   7380

attggtaaga ttctggtgga caattttcaa gagaatatct ctaagtagaa atataaggaa   7440

ggtataaaaa tgactaattt gtttgttaac agataccttg cagaacagca atgagaggtg   7500

gattcccttt gaatggcaca tacttccaaa ctaatgaggt aattttccca aaaatgaatt   7560

taacttaaac aaatgatcaa aagcaacatt ctcgtcaaag ctcgatttgg actatacttg   7620

tgcaggtttt tgctgaccat gactctagca taaaccctat cgacgtccca acagaactga   7680

tatgggatct aaaaagaaga gtcgcatact taggatcctc tgtatcctcg atttgtaaag   7740

gtaaattttc aaaacaaaac tgtcgattta tgcatgtgtt tggatatata aatccaaggt   7800

cttgtctcaa tatgtttttc tcattttttt aggtttatca gtggaagcca taaaatacaa   7860

tttccaggaa ggtatgctaa tatgtcttac actgaaaaca cctttagtat caaacattga   7920

attcatgaaa agaacaaaca atagtatcaa aatcagtcac gatgtttttg ctttggcgat   7980

gtaagatgtt gataggaaag tatagaagat atagcttaag ttggttaata ctgtttttat   8040

agagctttga ggtggggttt gactagcatt gtaatatata tgcaggatat gtctgtgtaa   8100

ggggattcga cagggagaat cgtaagccaa agagtctagt gaaaagactg cattgttctc   8160

acgtagcaat cagaactaaa gagaagacag aggaatgaaa ccttccagat tgcattaaca   8220

tgttagacat atttgattca ttggtttagg gtttacatca ccaaggtcat agaggatctt   8280

agcttttcat taacttttaa attcatgcaa ctctttttag gtgtttcttt ttgttccttg   8340

ccatagtttt gggcaatgga tggatgttct ttgcaaactc aggtttttttg tagtcattaa   8400

cagaaatttg cagcactaat tcatctttcc tattatctat caaagctctc agtgtttctc   8460

cataacttga tgagatttag tcactctcaa gctaattcag tctggtccta atttcaatca   8520

gatttggtaa aggaacaact gcaattgcta agtacaaatc gatccagatt tcaaacaagt   8580

tccaggttta atccaaatca tcacattcaa tcaaagacca aactagaatt caaaacatat   8640

aatctctgat tcagattcaa gaaagacaaa gcatgagaca tcattctgca agttaaccaa   8700

ttccggttat tctcgaatcc tactgaatta agcatcaatc atctaaagga acttcataag   8760
```

<210> SEQ ID NO 14
<211> LENGTH: 1114
<212> TYPE: PRT
<213> ORGANISM: Arabidopsis thaliana
<220> FEATURE:
<223> OTHER INFORMATION: DMT4 (1DMT4)

<400> SEQUENCE: 14

```
Met Glu Phe Ser Ile Asp Arg Asp Lys Asn Leu Leu Met Val Val Pro
  1               5                  10                  15

Glu Thr Arg Ile Lys Thr Lys Gln Phe Glu Lys Val Tyr Val Arg Arg
             20                  25                  30

Lys Ser Ile Lys Leu Pro Gln Asn Ser Met Val His Asn Thr Leu Ile
         35                  40                  45

Lys Met Ala Arg Gln Arg Ile Gln Lys Ser Met Lys Glu Ser Val Met
     50                  55                  60

Asn Gln His Ile Phe Lys Asn Phe Asp Ser Tyr Leu Ser Val Ile Tyr
 65                  70                  75                  80
```

-continued

```
His Pro Cys Cys Phe Val Ile Asn Asn Ser Gln Thr Thr His Lys Lys
                85                  90                  95

Lys Glu Lys Lys Asn Ser Lys Glu Lys His Gly Ile Lys His Ser Glu
            100                 105                 110

Ser Glu His Leu Gln Asp Asp Ile Ser Gln Arg Val Thr Gly Lys Gly
        115                 120                 125

Arg Arg Arg Asn Ser Lys Gly Thr Pro Lys Lys Leu Arg Phe Asn Arg
    130                 135                 140

Pro Arg Ile Leu Glu Asp Gly Lys Lys Pro Arg Asn Pro Ala Thr Thr
145                 150                 155                 160

Arg Leu Arg Thr Ile Ser Asn Lys Arg Arg Lys Lys Asp Ile Asp Ser
                165                 170                 175

Glu Asp Glu Val Ile Pro Glu Leu Ala Thr Pro Thr Lys Glu Ser Phe
            180                 185                 190

Pro Lys Arg Arg Lys Asn Glu Lys Ile Lys Arg Ser Val Ala Arg Thr
        195                 200                 205

Leu Asn Phe Lys Gln Glu Ile Val Leu Ser Cys Leu Glu Phe Asp Lys
    210                 215                 220

Ile Cys Gly Pro Ile Phe Pro Arg Gly Lys Lys Arg Thr Thr Thr Arg
225                 230                 235                 240

Arg Arg Tyr Asp Phe Leu Cys Phe Leu Leu Pro Met Pro Val Trp Lys
                245                 250                 255

Lys Gln Ser Arg Arg Ser Lys Arg Arg Lys Asn Met Val Arg Trp Ala
            260                 265                 270

Arg Ile Ala Ser Ser Ser Lys Leu Leu Glu Glu Thr Leu Pro Leu Ile
        275                 280                 285

Val Ser His Pro Thr Ile Asn Gly Gln Ala Asp Ala Ser Leu His Ile
    290                 295                 300

Asp Asp Thr Leu Val Arg His Val Val Ser Lys Gln Thr Lys Lys Ser
305                 310                 315                 320

Ala Asn Asn Val Ile Glu His Leu Asn Arg Gln Ile Thr Tyr Gln Lys
                325                 330                 335

Asp His Gly Leu Ser Ser Leu Ala Asp Val Pro Leu His Ile Glu Asp
            340                 345                 350

Thr Leu Ile Lys Ser Ala Ser Ser Val Leu Ser Glu Arg Pro Ile Lys
        355                 360                 365

Lys Thr Lys Asp Ile Ala Lys Leu Ile Lys Asp Met Gly Arg Leu Lys
    370                 375                 380

Ile Asn Lys Lys Val Thr Thr Met Ile Lys Ala Asp Lys Lys Leu Val
385                 390                 395                 400

Thr Ala Lys Val Asn Leu Asp Pro Glu Thr Ile Lys Glu Trp Asp Val
                405                 410                 415

Leu Met Val Asn Asp Ser Pro Ser Arg Ser Tyr Asp Asp Lys Glu Thr
            420                 425                 430

Glu Ala Lys Trp Lys Lys Glu Arg Glu Ile Phe Gln Thr Arg Ile Asp
        435                 440                 445

Leu Phe Ile Asn Arg Met His Arg Leu Gln Gly Asn Arg Lys Phe Lys
    450                 455                 460

Gln Trp Lys Gly Ser Val Val Asp Ser Val Val Gly Val Phe Leu Thr
465                 470                 475                 480

Gln Asn Thr Thr Asp Tyr Leu Ser Ser Asn Ala Phe Met Ser Val Ala
                485                 490                 495
```

-continued

```
Ala Lys Phe Pro Val Asp Ala Arg Glu Gly Leu Ser Tyr Tyr Ile Glu
            500                 505                 510

Glu Pro Gln Asp Ala Lys Ser Ser Glu Cys Ile Ile Leu Ser Asp Glu
        515                 520                 525

Ser Ile Ser Lys Val Glu Asp His Glu Asn Thr Ala Lys Arg Lys Asn
    530                 535                 540

Glu Lys Thr Gly Ile Ile Glu Asp Glu Ile Val Asp Trp Asn Asn Leu
545                 550                 555                 560

Arg Arg Met Tyr Thr Lys Glu Gly Ser Arg Pro Glu Met His Met Asp
                565                 570                 575

Ser Val Asn Trp Ser Asp Val Arg Leu Ser Gly Gln Asn Val Leu Glu
            580                 585                 590

Thr Thr Ile Lys Lys Arg Gly Gln Phe Arg Ile Leu Ser Glu Arg Ile
        595                 600                 605

Leu Lys Phe Leu Asn Asp Glu Val Asn Gln Asn Gly Asn Ile Asp Leu
    610                 615                 620

Glu Trp Leu Arg Asn Ala Pro Ser His Leu Val Lys Arg Tyr Leu Leu
625                 630                 635                 640

Glu Ile Glu Gly Ile Gly Leu Lys Ser Ala Glu Cys Val Arg Leu Leu
                645                 650                 655

Gly Leu Lys His His Ala Phe Pro Val Asp Thr Asn Val Gly Arg Ile
            660                 665                 670

Ala Val Arg Leu Gly Leu Val Pro Leu Glu Pro Leu Pro Asn Gly Val
        675                 680                 685

Gln Met His Gln Leu Phe Glu Tyr Pro Ser Met Asp Ser Ile Gln Lys
    690                 695                 700

Tyr Leu Trp Pro Arg Leu Cys Lys Leu Pro Gln Glu Thr Leu Tyr Glu
705                 710                 715                 720

Leu His Tyr Gln Met Ile Thr Phe Gly Lys Val Phe Cys Thr Lys Thr
                725                 730                 735

Ile Pro Asn Cys Asn Ala Cys Pro Met Lys Ser Glu Cys Lys Tyr Phe
            740                 745                 750

Ala Ser Ala Tyr Val Ser Ser Lys Val Leu Leu Glu Ser Pro Glu Glu
        755                 760                 765

Lys Met His Glu Pro Asn Thr Phe Met Asn Ala His Ser Gln Asp Val
    770                 775                 780

Ala Val Asp Met Thr Ser Asn Ile Asn Leu Val Glu Glu Cys Val Ser
785                 790                 795                 800

Ser Gly Cys Ser Asp Gln Ala Ile Cys Tyr Lys Pro Leu Val Glu Phe
                805                 810                 815

Pro Ser Ser Pro Arg Ala Glu Ile Pro Glu Ser Thr Asp Ile Glu Asp
            820                 825                 830

Val Pro Phe Met Asn Leu Tyr Gln Ser Tyr Ala Ser Val Pro Lys Ile
        835                 840                 845

Asp Phe Asp Leu Asp Ala Leu Lys Lys Ser Val Glu Asp Ala Leu Val
    850                 855                 860

Ile Ser Gly Arg Met Ser Ser Ser Asp Glu Glu Ile Ser Lys Ala Leu
865                 870                 875                 880

Val Ile Pro Thr Pro Glu Asn Ala Cys Ile Pro Ile Lys Pro Pro Arg
                885                 890                 895

Lys Met Lys Tyr Tyr Asn Arg Leu Arg Thr Glu His Val Val Tyr Val
            900                 905                 910

Leu Pro Asp Asn His Glu Leu Leu His Asp Phe Glu Arg Arg Lys Leu
```

-continued

```
        915                 920                 925

Asp Asp Pro Ser Pro Tyr Leu Leu Ala Ile Trp Gln Pro Gly Glu Thr
    930                 935                 940

Ser Ser Ser Phe Val Pro Pro Lys Lys Lys Cys Ser Ser Asp Gly Ser
945                 950                 955                 960

Lys Leu Cys Lys Ile Lys Asn Cys Ser Tyr Cys Trp Thr Ile Arg Glu
                965                 970                 975

Gln Asn Ser Asn Ile Phe Arg Gly Thr Ile Leu Val Phe Ala Asp His
            980                 985                 990

Glu Thr Ser Leu Asn Pro Ile Val Phe Arg Arg Glu Leu Cys Lys Gly
        995                1000                1005

Leu Glu Lys Arg Ala Leu Tyr Cys Gly Ser Thr Val Thr Ser Ile Phe
   1010                1015                1020

Lys Leu Leu Asp Thr Arg Arg Ile Glu Leu Cys Phe Trp Thr Gly Phe
1025                1030                1035                1040

Leu Cys Leu Arg Ala Phe Asp Arg Lys Gln Arg Asp Pro Lys Glu Leu
               1045                1050                1055

Val Arg Arg Leu His Thr Pro Pro Asp Glu Arg Gly Pro Asn Gly Phe
           1060                1065                1070

His Ile Val Val Val Asp Glu Lys Glu Glu Ser Pro Arg Val Gly Leu
       1075                1080                1085

Met Val Met Pro Gly Phe Trp Ile Gly Gly Ser Val Ile Gln Asn Arg
   1090                1095                1100

Val Tyr Val Ser Gly Val Lys Val Leu Glu
1105                1110


<210> SEQ ID NO 15
<211> LENGTH: 372
<212> TYPE: PRT
<213> ORGANISM: Arabidopsis thaliana
<220> FEATURE:
<223> OTHER INFORMATION: DMT4 (1DMT4) novel amino terminus

<400> SEQUENCE: 15

Met Glu Phe Ser Ile Asp Arg Asp Lys Asn Leu Leu Met Val Val Pro
  1               5                  10                  15

Glu Thr Arg Ile Lys Thr Lys Gln Phe Glu Lys Val Tyr Val Arg Arg
             20                  25                  30

Lys Ser Ile Lys Leu Pro Gln Asn Ser Met Val His Asn Thr Leu Ile
         35                  40                  45

Lys Met Ala Arg Gln Arg Ile Gln Lys Ser Met Lys Glu Ser Val Met
     50                  55                  60

Asn Gln His Ile Phe Lys Asn Phe Asp Ser Tyr Leu Ser Val Ile Tyr
 65                  70                  75                  80

His Pro Cys Cys Phe Val Ile Asn Asn Ser Gln Thr Thr His Lys Lys
                 85                  90                  95

Lys Glu Lys Lys Asn Ser Lys Glu Lys His Gly Ile Lys His Ser Glu
            100                 105                 110

Ser Glu His Leu Gln Asp Asp Ile Ser Gln Arg Val Thr Gly Lys Gly
        115                 120                 125

Arg Arg Arg Asn Ser Lys Gly Thr Pro Lys Lys Leu Arg Phe Asn Arg
    130                 135                 140

Pro Arg Ile Leu Glu Asp Gly Lys Lys Pro Arg Asn Pro Ala Thr Thr
145                 150                 155                 160

Arg Leu Arg Thr Ile Ser Asn Lys Arg Arg Lys Lys Asp Ile Asp Ser
```

-continued

```
                165                 170                 175

Glu Asp Glu Val Ile Pro Glu Leu Ala Thr Pro Thr Lys Glu Ser Phe
            180                 185                 190

Pro Lys Arg Arg Lys Asn Glu Lys Ile Lys Arg Ser Val Ala Arg Thr
        195                 200                 205

Leu Asn Phe Lys Gln Glu Ile Val Leu Ser Cys Leu Glu Phe Asp Lys
    210                 215                 220

Ile Cys Gly Pro Ile Phe Pro Arg Gly Lys Lys Arg Thr Thr Thr Arg
225                 230                 235                 240

Arg Arg Tyr Asp Phe Leu Cys Phe Leu Leu Pro Met Pro Val Trp Lys
                245                 250                 255

Lys Gln Ser Arg Arg Ser Lys Arg Arg Lys Asn Met Val Arg Trp Ala
            260                 265                 270

Arg Ile Ala Ser Ser Ser Lys Leu Leu Glu Glu Thr Leu Pro Leu Ile
        275                 280                 285

Val Ser His Pro Thr Ile Asn Gly Gln Ala Asp Ala Ser Leu His Ile
    290                 295                 300

Asp Asp Thr Leu Val Arg His Val Val Ser Lys Gln Thr Lys Lys Ser
305                 310                 315                 320

Ala Asn Asn Val Ile Glu His Leu Asn Arg Gln Ile Thr Tyr Gln Lys
                325                 330                 335

Asp His Gly Leu Ser Ser Leu Ala Asp Val Pro Leu His Ile Glu Asp
            340                 345                 350

Thr Leu Ile Lys Ser Ala Ser Ser Val Leu Ser Glu Arg Pro Ile Lys
        355                 360                 365

Lys Thr Lys Asp
    370


<210> SEQ ID NO 16
<211> LENGTH: 8580
<212> TYPE: DNA
<213> ORGANISM: Arabidopsis thaliana

<400> SEQUENCE: 16

gctatggatg tcaacagaga gaattacgaa ttgggtttac cgatcattga gaaagccggc      60

gttgctcaca agatcgactt cagggaaggc cctgctcttc ccgttcttga tgaaatcgtt     120

gctgacgtaa gcattcttct ttctgacgta attaacaaaa aagatgatga agataatgaa     180

ataattaaaa actcatggcc taattaggtt gatttaatat cttgatgaga atttctgtat     240

acgcaaattt gtttcctttt tcatagaaga aagtgtggta actgattatt gtgtgtggtt     300

gggtgcagga gaagaaccat ggaacatatg actttatatt cgttgatgct gacaaagaca     360

actacatcaa ctaccacaag cgtttgatcg atcttgtgaa aattggagga gtgattggct     420

acgacaacac tctgtggaat ggttctgtcg tggctcctcc tgatgcacca atgaggaagt     480

acgttcgtta ctacagagac tttgttcttg agcttaacaa ggctcttgct gctgaccctc     540

ggatcgagat ctgtatgctc cctgttggtg atggaatcac tatctgccgt cggatcagtt     600

gatttgactc ctccctactc tgagtttgtc cacagtggat tactttccat cttcttatac     660

ctttcaatcg cattttcacc aaccactaaa atggaccttt ttatgtattt gtgttaagta     720

atatctccat tgtccttgtt ttgctttctt ctgaacaaag aaataatatg taccttactt     780

ttcttcttgg tctcgttctt ttgtttttct ccatgataca acatctaaag aaattatttg     840

tgtcacagca acgtaagtcg ataaaattag ttgaacatat tgagaaaaag ttatcataga     900
```

-continued

```
ccttcaattg ttgaaagtcg atgttggtat ttgtcaattg atattagatt accaaataaa    960
tattagacag taagaaacga acaaagtagg aagatgtagg tcaccggtct ttgaaaattt   1020
atcagataga attcataata cacagttagg tagtttcagt tgagagttaa aagggaaaaa   1080
tatgtaattg tgtgtgataa atacgtcaaa aattagttga tgagcaaaat cgtaaacaaa   1140
aatacttttt tgcattagtt ttgttggatt ccctataaat acgggttccc atatctaact   1200
cgtagttagc ataattataa gcaacaaata aacacaaaat actgaattta gaaattttcc   1260
agaaaattaa ttagagattt tacattattt ttacaaactt tagtgaatta tttcttaaac   1320
gtatgttagt tatttattaa ctgaagtttc acatatttga tagaataaca tttaaataaa   1380
aaaatttgaa gtaaggttag aatgttctta taatacttta taactttttt aaaaggtaca   1440
agccaaaatt atcgcaaatg taaataataa atcattgtaa aaatcttaaa ctaattaaaa   1500
gatctaacgc aatctaaaca aagatttggt atcatcgccc atttatgttt tgatataatc   1560
aaaactggtt aataattaaa ttaaattatc aatttcttaa ttagttagaa ttcttgttaa   1620
tgtaatcaac tcaccattat tttaattatt taaaatatgg gttaatatct cttaatcata   1680
tctaagatga tattttcttc catttatgaa aagaaaaata tgttaattaa gcattaaaaa   1740
gaaggaaaaa ataatttaaa taatattaaa tatatataca tcgtttttag agttcgagtt   1800
cttccgtatt tacagtttct ctttttttcca aagcagggtt tggattggta gtttttctgg   1860
attaattttg tctcaaattc tttcttcttt ttattttttt ttgtgaaatt ctttgtttta   1920
attggtgtga catcgtttcc aaaatatttt caaatttgat tgcttttgaa gttttttttt   1980
tttttctatg ttttggaatt cattatacta gcgttgttgt ttttctttct gcaagagtaa   2040
tggagttttc aatagatcga gacaaaaatc ttctcatggt tgttccagag acacgtatca   2100
aaacaaaaca atttgaaaaa gtttatgtga gaagaaaatc tattaagctt ccacaaaatt   2160
cggtaatttt tccacatgaa atcaaagatc gtggtgaaga agagagtaag gagaaggaat   2220
ttttccatca aggtaaacaa aatctctaat accttaatta cttccgttta gtaattctcc   2280
ttttacttgt ttttttttta atgagagtat gtgacaattt cataaagaaa ttagttgttt   2340
gacatacgag atggtttttt gactaattat attttttgtt ttgaaagatt tccaagctaa   2400
ttttaatgag catatttttg attttattga ttgaggaaat tttcagaatt tcgacattta   2460
agtttttttt ttgttttaaa tatacttttg attcgatgat aagagattgg gaaagcagac   2520
taatgatgtt ttgttgtcac gttcattgat tagagatctc ttatattcat atttgtctac   2580
aatatatcat gcatgtgttg atttgtttcg ttaattcaat tttttttttt tcatgttgac   2640
agatggttca caacacactt atcaaaatgg cgagacaaag aattcaaaag agcatgaaag   2700
aaagtgtgat gaatcagcac atcttcaagg taaataattt taaattcatt cttaaaaaag   2760
ttagcttatt ggtaagttca ttacaattta tatttaacca tcgtcacttt ttatttaacg   2820
agtttgataa gcattttcaa aacctgtcct tcatctgccg atgcagatgt ggttatgttc   2880
atctttgatt ttattgattg aggatttttt cagaatttcg attcatactt gtctgtaata   2940
tatcatccat gttgttttgt aatcagttaa ttcacttatt ttatttttaa cttttattgt   3000
aacagataat tcacaaacca cccataaaaa aaaggagaag aagaattcaa aagaaaagca   3060
tggaataaag cattctgaat cagaacatct tcaaggtaaa tacttttgaa ttcattcatt   3120
aaaaaaacag tttatttgta agttcattac agtttatata tatttaaatt gtttatgata   3180
atgtattttt gcacaatcga ctaatcatta cccactcatt catttatatt ttattttatg   3240
gtgaaagatg atatttcgca acgtgttacc ggaaaaggaa ggagaaggaa ttcaaaaggg   3300
```

-continued

```
acaccaaaaa aactgaggtt taataggcct cggatcttgg aagacggaaa gaaaccaaga   3360
aatcccgcca ccactcgact gagaactata tccaacaaga ggaggaaaaa ggacatagac   3420
agtgaagatg aagttatacc agagcttgca actccaacaa aggaaagctt tccaaagaga   3480
agaaagaacg agaagattaa gagatccgtg gctcggactt taaattttaa gcaagaaatt   3540
gttctgagtt gtcttgagtt cgacaagatt tgtggaccaa tttttccaag agggaaaaag   3600
aggaccacca cacgacgcag atatgatttc ctttgttttt tacttccgat gcctgtttgg   3660
aaaaaacaat caagaaggtc taagcgtagg aaaaatatgg tcagatgggc tagaattgct   3720
tcttcttcaa aactgctaga agaaactttg cctttaatag taagtcatcc gactattaat   3780
ggacaagcag atgcttcttt acacattgat ggtaatcgag ttttttttt gttaatttat    3840
ctgttacatc aaaattgttt atgcttatat ctaaagtatc attgtgtatt attttttgca   3900
gacacactcg tgagacatgt agtctcaaag caaaccaaga aaagtgctaa caatgtcatt   3960
gagcatttaa atcgacaaat aacttatcag aaagatcacg gtctctcatc tctggcagat   4020
gttcctttgc acattgaagg taatctagtc ttatttttgt tctttttaa tatattgatt    4080
aaaaagattg tgatatattt atttaatata tttttgttat attatatcta tattttattg   4140
tttgtacttt tttttgtag atacactaat aaaatcggct agttctgtac tttcagaacg    4200
acccatcaag aaaactaagg atattgctaa gttaatcaaa gatatgggaa gattaaagat   4260
caataaaaag gtaacaacga tgatcaaagc tgacaagaaa ctcgttacgg caaaggttaa   4320
tcttgatcca gagaccatta aagagtggga tgtcttaatg gtgaatgatt caccaagccg   4380
atcatatgac gataaggaga cggaggccaa atggaaaaaa gaaagagaga tttttcaaac   4440
ccggatagat cttttcatta accggatgca tcgcttacaa ggtacattat tgttattatc   4500
attattgtta ttatgatcta tttatacttg tattctaaat tagcttacat atatatataa   4560
ggaatccaag tataagtgag tatgctaagt atatgatcat tttttgaaat tatgtttcct   4620
tccatgatgt ttaaatgatt gtcttgcagg caatagaaag tttaaacagt ggaaaggctc   4680
agttgttgac tcagtggttg gagttttttt gacacaaaat actaccgact atctttcaag   4740
gtaaaatctt tgtttaaatt gttaagaaat ttgaaaaact aattcatata atagatgatc   4800
actttgattg tgagtttcta cagcaacgcg tttatgagcg tggctgcaaa atttcctgtt   4860
gatgcaagag aaggtctatc atactatatt gaggaacctc aagatgctaa aagttctgaa   4920
tgtatcattt tatctgatga gtcaatatca aaggtggaag atcatgagaa tactgcaaaa   4980
aggaaaaacg agaaaaccgg tattatagaa gatgagatag ttgactggaa caatcttaga   5040
aggatgtaca cgaaagaagg atctcgtccc gaaatgcata tggactctgt taattggagt   5100
gacgtgagat tatctggcca aaatgttttg gaaaccacca ttaaaaaacg tggacaattc   5160
aggattcttt cagaaagaat attggtaaga aaaacaaaac ttctaatgaa ctttgtgaat   5220
aatttattca aatgatttaa gactaacact tttttttttt tccttgtttt ctcaagaaat   5280
ttcttaacga tgaagttaac caaaatggaa atattgatct ggaatggctt cgaaatgctc   5340
catcacattt agtgaagtat gtttatgttg gtttttatgt tctcatagat ctcattatta   5400
gtaagcgatc ataaactctt tctattattt tatcaggaga tatctgttgg aaatcgaagg   5460
gatagggctg aaaagtgctg agtgcgtacg actgttagga cttaaacatc atgcgtttcc   5520
ggtatgaaaa tattattatg atttttcatt taacatatat tattaatttt tactgataaa   5580
acccatgtgt taatgtgtag gttgacacaa atgttggtcg tatagcagtt cgactaggtc   5640
```

-continued tggttcctct tgaaccttta ccaaatggag ttcaaatgca tcaactattc gagttatgtt 5700
ttctcattaa tttgattaag aaaatacatt acaagttact aacaactatc tcctatcgat 5760
aaacatgaac tcgtttcagg taccccttcaa tggattcgat tcaaaagtac ctttggccac 5820
gattgtgtaa acttccccaa gaaactttgt aagttcaaat gtttttcctc aatttaagaa 5880
gccaactatt tttacgccat ttgaacacat attacctaat tttatttcta aatattttta 5940
cagatatgaa ctacattatc aaatgataac atttggaaag gtgtgcgtta ctttttttctt 6000 ttttatatta atgaataaaa taatattgtt ggtttaatca aattttgtca actttaggtt 6060
ttctgcacaa aaactattcc taattgtaat gcatgtccaa tgaagtcaga atgcaaatat 6120
tttgcaagtg catatgtcag gtacaatctt ttttctcttt cctactttga tacttagata 6180
taacttaatt tgttaattcc ataaatatta aagaaaaatc ttagaataat cataaaaaat 6240
aattgctaaa cgtctcagct attttatata ataaattttc taaatattga gagtgaattt 6300
gagttttaat aattacatta tatatataaa tatataatgt tagaattgac aaattgtgtt 6360 ttttttttaat agttctaaag ttcttctcga gagtccagaa gaaaagatgc atgagcctaa 6420
tacttttatg aatgcacatt ctcaagacgt tgctgtagat atgacatcaa atataaattt 6480
ggtagaagaa tgtgtttctt ctggatgtag cgatcaagct atatgttata agccactagt 6540
tgagtttcct tcgtccccaa gagcggaaat tcccgagtca acagacattg aagatgttcc 6600
attcatgaat ctttatcagt catatgctag tgttcctaaa attgattttg acttggatgc 6660
attgaagaaa agtgtagaag atgcacttgt aataagtggc aggatgagca gttctgatga 6720
agaaatatca aaagcattag tgattcccac tcctgaaaat gcatgcattc ctatcaaacc 6780
acctcggaaa atgaagtatt ataatcgact aagaactgaa catgtggtgt aagtatcttt 6840
atgtaaatac tgattatacc atataattta tatgcatttt ttgggaatat ataatctaat 6900
acttgttttt tttgcagtta tgtgcttcct gataatcatg agctgctaca cgatgtaagt 6960
atacacatac tttaagctac aaaaaaaatgc aactcttttg tataattaat tagaaaatgc 7020
ttttggtttt ttacatatat tatatagttt gagagaagaa aacttgatga tccaagtcct 7080
taccttcttg cgatttggca accaggtata atacaagcat aatttatcat tgttcacata 7140
actataaact aaatttttca ttcgaataat ttttaggtga aacatcatcc tcgttcgttc 7200
caccaaagaa aaagtgtagt tctgatggat caaagctttg caagataaag aattgttcat 7260
attgttggac tatacgagaa caaaactcca acatttttcg cggaacaatt ttggtaaaca 7320
aaatttacaa tttgatattt taacattggt gacttgaaac tcacataaat tcaattgatc 7380
agattccatg tagaacagca atgcgagggg cctttccact taatggaaca tacttccaaa 7440
ccaatgaggc aagcattttt tcttataatt ttttgtctga gtttttactt aatggtttta 7500
aagagaacac aatggtttat ttttccaggt ttttgctgat catgagacaa gcttaaaccc 7560
cattgtcttt cgtagggagt tgtgtaaggg actagaaaaa cgtgcactat attgtggttc 7620
aacagtgaca tctattttta aacttttaga cacaagacgg attgaacttt gcttttggac 7680
aggtaacaaa cataaatata tattaaattt tttgttgaat tatgaagtta aaataactgt 7740
ggaatgttgt gtggtgctgt gcagggtttt tatgtttgag agcatttgat cgaaagcaac 7800
gagatccaaa agagcttgtc cgacgtctac acactccacc tgatgagaga gggccaaagt 7860
ttatgagtga tgatgatata tagtttcatt ttattctttt tggtctagtt agcaaattat 7920
ttaaacgaac gaatcttttc ttataataac aagcgattca acgattgagt aaatgcacgt 7980
acgtattgtt tcttgattta aatgcatgta cattataatt atttcacaag tggttttcat 8040

-continued

```
atagtagttg tggatgaaaa agaagagagc ccaagagttg gtcttatggt tatgcctggg   8100

ttttggattg gtggcagtgt cattcaaaac cgagtttatg tttctggtgt gaaggtcctt   8160

gagtgaagga tttcaggaac tgtcttaatg cttcttccca ctttgttgtg caacttttat   8220

tttctctttg ttataagcaa gcctatatgt atcaatgata cagtatcatc tattgttcaa   8280

aaaaattgga attaatatct tcttcgtctc aacatctttg ggtcgatcgt tattcgatga   8340

cagtagcaac tagcgagtct cttgtgatat atcctagcca agcgacctca aaactttttt   8400

tacttcgatt gttgtcagta tttctgtttc agacgttttt agcaaaaaag ttctcatggt   8460

gataaaatta ggcttaaaac agtatgactc tgtctttaag actcagtttc agatagtaat   8520

aataaaatta cataaacaaa gagtggtcat agacgtgtat ctgtaagtgt tgtcagagat   8580
```

```
<210> SEQ ID NO 17
<211> LENGTH: 1952
<212> TYPE: PRT
<213> ORGANISM: Oryza sativa
<220> FEATURE:
<223> OTHER INFORMATION: rice DMT1, DMTRICE (1DMTRICE)

<400> SEQUENCE: 17

Met Gln Asp Phe Gly Gln Trp Leu Pro Gln Ser Gln Thr Thr Ala Asp
1               5                   10                  15

Leu Tyr Phe Ser Ser Ile Pro Ile Pro Ser Gln Phe Asp Thr Ser Ile
            20                  25                  30

Glu Thr Gln Thr Arg Thr Ser Ala Val Val Ser Ser Glu Lys Glu Ser
        35                  40                  45

Ala Asn Ser Phe Val Pro His Asn Gly Thr Gly Leu Val Glu Arg Ile
    50                  55                  60

Ser Asn Asp Ala Gly Leu Thr Glu Val Val Gly Ser Ser Ala Gly Pro
65                  70                  75                  80

Thr Glu Cys Ile Asp Leu Asn Lys Thr Pro Ala Arg Lys Pro Lys Lys
                85                  90                  95

Lys Lys His Arg Pro Lys Val Leu Lys Asp Asp Lys Pro Ser Lys Thr
            100                 105                 110

Pro Lys Ser Ala Thr Pro Ile Pro Ser Thr Glu Lys Val Glu Lys Pro
        115                 120                 125

Ser Gly Lys Arg Lys Tyr Val Arg Lys Lys Thr Ser Pro Gly Gln Pro
    130                 135                 140

Pro Ala Glu Gln Ala Ala Ser Ser His Cys Arg Ser Glu Leu Lys Ser
145                 150                 155                 160

Val Lys Arg Ser Leu Asp Phe Gly Gly Glu Val Leu Gln Glu Ser Thr
                165                 170                 175

Gln Ser Gly Ser Gln Val Pro Val Ala Glu Ile Cys Thr Gly Pro Lys
            180                 185                 190

Arg Gln Ser Ile Pro Ser Thr Ile Gln Arg Asp Ser Gln Ser Gln Leu
        195                 200                 205

Ala Cys His Val Val Ser Ser Thr Ser Ser Ile His Thr Ser Ala Ser
    210                 215                 220

Gln Met Val Asn Ala His Leu Phe Pro Pro Asp Asn Met Pro Asn Gly
225                 230                 235                 240

Val Leu Leu Asp Leu Asn Asn Ser Thr Ser Gln Leu Gln Asn Glu His
                245                 250                 255

Ala Lys Phe Val Asp Ser Pro Ala Arg Leu Phe Gly Ser Arg Ile Arg
            260                 265                 270
```

-continued

```
Gln Thr Ser Gly Lys Asn Ser Leu Leu Glu Ile Tyr Ala Gly Met Ser
        275                 280                 285

Asp Arg Asn Val Pro Asp Leu Asn Ser Ser Ile Ser Gln Thr His Ser
    290                 295                 300

Met Ser Thr Asp Phe Ala Gln Tyr Leu Leu Ser Ser Ser Gln Ala Ser
305                 310                 315                 320

Val Arg Glu Thr Gln Met Ala Asn Gln Met Leu Asn Gly His Arg Met
                325                 330                 335

Pro Glu Asn Pro Ile Thr Pro Ser His Cys Ile Glu Arg Ala Ala Leu
            340                 345                 350

Lys Glu His Leu Asn His Val Pro His Ala Lys Ala Ala Val Met Asn
        355                 360                 365

Gly Gln Met Pro His Ser Tyr Arg Leu Ala Gln Asn Pro Ile Leu Pro
    370                 375                 380

Pro Asn His Ile Glu Gly Tyr Gln Val Met Glu Asn Leu Ser Glu Leu
385                 390                 395                 400

Val Thr Thr Asn Asp Tyr Leu Thr Ala Ser Pro Phe Ser Gln Thr Gly
                405                 410                 415

Ala Ala Asn Arg Gln His Asn Ile Gly Asp Ser Met His Ile His Ala
            420                 425                 430

Leu Asp Pro Arg Arg Glu Ser Asn Ala Ser Ser Gly Ser Trp Ile Ser
        435                 440                 445

Leu Gly Val Asn Phe Asn Gln Gln Asn Asn Gly Trp Ala Ser Ala Gly
    450                 455                 460

Ala Ala Asp Ala Ala Ser Ser His Ala Pro Tyr Phe Ser Glu Pro His
465                 470                 475                 480

Lys Arg Met Arg Thr Ala Tyr Leu Asn Asn Tyr Pro Asn Gly Val Val
                485                 490                 495

Gly His Phe Ser Thr Ser Ser Thr Asp Leu Ser Asn Asn Glu Asn Glu
            500                 505                 510

Asn Val Ala Ser Ala Ile Asn Ser Asn Val Phe Thr Leu Ala Asp Ala
        515                 520                 525

Gln Arg Leu Ile Ala Arg Glu Lys Ser Arg Ala Ser Gln Arg Met Ile
    530                 535                 540

Ser Phe Arg Ser Ser Lys Asn Asp Met Val Asn Arg Ser Glu Met Val
545                 550                 555                 560

His Gln His Gly Arg Pro Ala Pro His Gly Ser Ala Cys Arg Glu Ser
                565                 570                 575

Ile Glu Val Pro Asp Lys Gln Phe Gly Leu Met Thr Glu Glu Leu Thr
            580                 585                 590

Gln Leu Pro Ser Met Pro Asn Asn Pro Gln Arg Glu Lys Tyr Ile Pro
        595                 600                 605

Gln Thr Gly Ser Cys Gln Leu Gln Ser Leu Glu His Asp Met Val Lys
    610                 615                 620

Gly His Asn Leu Ala Gly Glu Leu His Lys Gln Val Thr Ser Pro Gln
625                 630                 635                 640

Val Val Ile Gln Ser Asn Phe Cys Val Thr Pro Pro Asp Val Leu Gly
                645                 650                 655

Arg Arg Thr Ser Gly Glu His Leu Arg Thr Leu Ile Ala Pro Thr His
            660                 665                 670

Ala Ser Thr Cys Lys Asp Thr Leu Lys Ala Leu Ser Cys Gln Leu Glu
        675                 680                 685
```

-continued

```
Ser Ser Arg Asp Ile Ile Arg Pro Pro Val Asn Pro Ile Gly Pro Ser
    690                 695                 700

Ser Ala Asp Val Pro Arg Thr Asp Asn His Gln Val Lys Val Ser Glu
705                 710                 715                 720

Glu Thr Val Thr Ala Lys Leu Pro Glu Lys Arg Lys Val Gly Arg Pro
                725                 730                 735

Arg Lys Glu Leu Lys Pro Gly Glu Lys Pro Lys Pro Arg Gly Arg Pro
            740                 745                 750

Arg Lys Gly Lys Val Val Gly Gly Glu Leu Ala Ser Lys Asp Ser His
        755                 760                 765

Thr Asn Pro Leu Gln Asn Glu Ser Thr Ser Cys Ser Tyr Gly Pro Tyr
    770                 775                 780

Ala Gly Glu Ala Ser Val Gly Arg Ala Val Lys Ala Asn Arg Val Gly
785                 790                 795                 800

Glu Asn Ile Ser Gly Ala Met Val Ser Leu Leu Asp Ser Leu Asp Ile
                805                 810                 815

Val Ile Gln Lys Ile Lys Val Leu Asp Ile Asn Lys Ser Glu Asp Pro
            820                 825                 830

Val Thr Ala Glu Pro His Gly Ala Leu Val Pro Tyr Asn Gly Glu Phe
        835                 840                 845

Gly Pro Ile Val Pro Phe Glu Gly Lys Val Lys Arg Lys Arg Ser Arg
    850                 855                 860

Ala Lys Val Asp Leu Asp Pro Val Thr Ala Leu Met Trp Lys Leu Leu
865                 870                 875                 880

Met Gly Pro Asp Met Ser Asp Cys Ala Glu Gly Met Asp Lys Asp Lys
                885                 890                 895

Glu Lys Trp Leu Asn Glu Glu Arg Lys Ile Phe Gln Gly Arg Val Asp
            900                 905                 910

Ser Phe Ile Ala Arg Met His Leu Val Gln Gly Asp Arg Arg Phe Ser
        915                 920                 925

Pro Trp Lys Gly Ser Val Val Asp Ser Val Val Gly Val Phe Leu Thr
    930                 935                 940

Gln Asn Val Ser Asp His Leu Ser Ser Ser Ala Phe Met Ala Leu Ala
945                 950                 955                 960

Ala Lys Phe Pro Val Lys Pro Glu Ala Ser Glu Lys Pro Ala Asn Val
                965                 970                 975

Met Phe His Thr Ile Ser Glu Asn Gly Asp Cys Ser Gly Leu Phe Gly
            980                 985                 990

Asn Ser Val Lys Leu Gln Gly Glu Ile Leu Val Gln Glu Ala Ser Asn
        995                 1000                1005

Thr Ala Ala Ser Phe Ile Thr Thr Glu Asp Lys Glu Gly Ser Asn Ser
   1010                 1015                1020

Val Glu Leu Leu Gly Ser Ser Phe Gly Asp Gly Val Asp Gly Ala Ala
1025                1030                1035                1040

Gly Val Tyr Ser Asn Ile Tyr Glu Asn Leu Pro Ala Arg Leu His Ala
               1045                1050                1055

Thr Arg Arg Pro Val Val Gln Thr Gly Asn Ala Val Glu Ala Glu Asp
           1060                1065                1070

Gly Ser Leu Glu Gly Val Val Ser Ser Glu Asn Ser Thr Ile Ser Ser
       1075                1080                1085

Gln Asn Ser Ser Asp Tyr Leu Phe His Met Ser Asp His Met Phe Ser
   1090                1095                1100

Ser Met Leu Leu Asn Phe Thr Ala Glu Asp Ile Gly Ser Arg Asn Met
```

-continued

```
1105                1110                1115                1120

Pro Lys Ala Thr Arg Thr Thr Tyr Thr Glu Leu Leu Arg Met Gln Glu
                1125                1130                1135

Leu Lys Asn Lys Ser Asn Glu Thr Ile Glu Ser Ser Glu Tyr His Gly
            1140                1145                1150

Val Pro Val Ser Cys Ser Asn Asn Ile Gln Val Leu Asn Gly Ile Gln
        1155                1160                1165

Asn Ile Gly Ser Lys His Gln Pro Leu His Ser Ser Ile Ser Tyr His
    1170                1175                1180

Gln Thr Gly Gln Val His Leu Pro Asp Ile Val His Ala Ser Asp Leu
1185                1190                1195                1200

Glu Gln Ser Val Tyr Thr Gly Leu Asn Arg Val Leu Asp Ser Asn Val
                1205                1210                1215

Thr Gln Thr Ser Tyr Tyr Pro Ser Pro His Pro Gly Ile Ala Cys Asn
            1220                1225                1230

Asn Glu Thr Gln Lys Ala Asp Ser Leu Ser Asn Met Leu Tyr Gly Ile
        1235                1240                1245

Asp Arg Ser Asp Lys Thr Thr Ser Leu Ser Glu Pro Thr Pro Arg Ile
    1250                1255                1260

Asp Asn Cys Phe Gln Pro Leu Ser Ser Glu Lys Met Ser Phe Ala Arg
1265                1270                1275                1280

Glu Gln Ser Ser Ser Glu Asn Tyr Leu Ser Arg Asn Glu Ala Glu Ala
                1285                1290                1295

Ala Phe Val Lys Gln His Gly Thr Ser Asn Val Gln Gly Asp Asn Thr
            1300                1305                1310

Val Arg Thr Glu Gln Asn Gly Gly Glu Asn Ser Gln Ser Gly Tyr Ser
        1315                1320                1325

Gln Gln Asp Asp Asn Val Gly Phe Gln Thr Ala Thr Thr Ser Asn Leu
    1330                1335                1340

Tyr Ser Ser Asn Leu Cys Gln Asn Gln Lys Ala Asn Ser Glu Val Leu
1345                1350                1355                1360

His Gly Val Ser Ser Asn Leu Ile Glu Asn Ser Lys Asp Asp Lys Lys
                1365                1370                1375

Thr Ser Pro Lys Val Pro Val Asp Gly Ser Lys Ala Lys Arg Pro Arg
            1380                1385                1390

Val Gly Ala Gly Lys Lys Lys Thr Tyr Asp Trp Asp Met Leu Arg Lys
        1395                1400                1405

Glu Val Leu Tyr Ser His Gly Asn Lys Glu Arg Ser Gln Asn Ala Lys
    1410                1415                1420

Asp Ser Ile Asp Trp Glu Thr Ile Arg Gln Ala Glu Val Lys Glu Ile
1425                1430                1435                1440

Ser Asp Thr Ile Arg Glu Arg Gly Met Asn Asn Met Leu Ala Glu Arg
                1445                1450                1455

Ile Lys Asp Phe Leu Asn Arg Leu Val Arg Asp His Gly Ser Ile Asp
            1460                1465                1470

Leu Glu Trp Leu Arg Tyr Val Asp Ser Asp Lys Ala Lys Asp Tyr Leu
        1475                1480                1485

Leu Ser Ile Arg Gly Leu Gly Leu Lys Ser Val Glu Cys Val Arg Leu
    1490                1495                1500

Leu Thr Leu His His Met Ala Phe Pro Val Asp Thr Asn Val Gly Arg
1505                1510                1515                1520

Ile Cys Val Arg Leu Gly Trp Val Pro Leu Gln Pro Leu Pro Glu Ser
                1525                1530                1535
```

-continued

```
Leu Gln Leu His Leu Leu Glu Met Tyr Pro Met Leu Glu Asn Ile Gln
            1540                1545                1550

Lys Tyr Leu Trp Pro Arg Leu Cys Lys Leu Asp Gln Arg Thr Leu Tyr
        1555                1560                1565

Glu Leu His Tyr Gln Met Ile Thr Phe Gly Lys Val Phe Cys Thr Lys
    1570                1575                1580

Ser Lys Pro Asn Cys Asn Ala Cys Pro Met Arg Ala Glu Cys Lys His
1585                1590                1595                1600

Phe Ala Ser Ala Phe Ala Ser Ala Arg Leu Ala Leu Pro Gly Pro Glu
                1605                1610                1615

Glu Lys Ser Leu Val Thr Ser Gly Thr Pro Ile Ala Ala Glu Thr Phe
            1620                1625                1630

His Gln Thr Tyr Ile Ser Ser Arg Pro Val Val Ser Gln Leu Glu Trp
        1635                1640                1645

Asn Ser Asn Thr Cys His His Gly Met Asn Asn Arg Gln Pro Ile Ile
    1650                1655                1660

Glu Glu Pro Ala Ser Pro Glu Pro Glu His Glu Thr Glu Glu Met Lys
1665                1670                1675                1680

Glu Cys Ala Ile Glu Asp Ser Phe Val Asp Asp Pro Glu Glu Ile Pro
                1685                1690                1695

Thr Ile Lys Leu Asn Phe Glu Glu Phe Thr Gln Asn Leu Lys Ser Tyr
            1700                1705                1710

Met Gln Ala Asn Asn Ile Glu Ile Glu Asp Ala Asp Met Ser Lys Ala
        1715                1720                1725

Leu Val Ala Ile Thr Pro Glu Val Ala Ser Ile Pro Thr Pro Lys Leu
    1730                1735                1740

Lys Asn Val Ser Arg Leu Arg Thr Glu His Gln Val Tyr Glu Leu Pro
1745                1750                1755                1760

Asp Ser His Pro Leu Leu Glu Gly Phe Asn Gln Arg Glu Pro Asp Asp
                1765                1770                1775

Pro Cys Pro Tyr Leu Leu Ser Ile Trp Thr Pro Gly Glu Thr Ala Gln
            1780                1785                1790

Ser Thr Asp Ala Pro Lys Ser Val Cys Asn Ser Gln Glu Asn Gly Glu
        1795                1800                1805

Leu Cys Ala Ser Asn Thr Cys Phe Ser Cys Asn Ser Ile Arg Glu Ala
    1810                1815                1820

Gln Ala Gln Lys Val Arg Gly Thr Leu Leu Ile Pro Cys Arg Thr Ala
1825                1830                1835                1840

Met Arg Gly Ser Phe Pro Leu Asn Gly Thr Tyr Phe Gln Val Asn Glu
                1845                1850                1855

Val Phe Ala Asp His Asp Ser Ser Arg Asn Pro Ile Asp Val Pro Arg
            1860                1865                1870

Ser Trp Ile Trp Asn Leu Pro Arg Arg Thr Val Tyr Phe Gly Thr Ser
        1875                1880                1885

Ile Pro Thr Ile Phe Lys Gly Leu Thr Thr Glu Glu Ile Gln His Cys
    1890                1895                1900

Phe Trp Arg Gly Phe Val Cys Val Arg Gly Phe Asp Arg Thr Ser Arg
1905                1910                1915                1920

Ala Pro Arg Pro Leu Tyr Ala Arg Leu His Phe Pro Ala Ser Lys Ile
                1925                1930                1935

Thr Arg Asn Lys Lys Ser Ala Gly Ser Ala Pro Gly Arg Asp Asp Glu
            1940                1945                1950
```

-continued

<210> SEQ ID NO 18
<211> LENGTH: 723
<212> TYPE: PRT
<213> ORGANISM: Oryza sativa
<220> FEATURE:
<223> OTHER INFORMATION: DMTRICE novel amino terminus

<400> SEQUENCE: 18

```
Met Gln Asp Phe Gly Gln Trp Leu Pro Gln Ser Gln Thr Thr Ala Asp
1               5                   10                  15

Leu Tyr Phe Ser Ser Ile Pro Ile Pro Ser Gln Phe Asp Thr Ser Ile
            20                  25                  30

Glu Thr Gln Thr Arg Thr Ser Ala Val Val Ser Ser Glu Lys Glu Ser
        35                  40                  45

Ala Asn Ser Phe Val Pro His Asn Gly Thr Gly Leu Val Glu Arg Ile
    50                  55                  60

Ser Asn Asp Ala Gly Leu Thr Glu Val Val Gly Ser Ser Ala Gly Pro
65                  70                  75                  80

Thr Glu Cys Ile Asp Leu Asn Lys Thr Pro Ala Arg Lys Pro Lys Lys
                85                  90                  95

Lys Lys His Arg Pro Lys Val Leu Lys Asp Asp Lys Pro Ser Lys Thr
            100                 105                 110

Pro Lys Ser Ala Thr Pro Ile Pro Ser Thr Glu Lys Val Glu Lys Pro
        115                 120                 125

Ser Gly Lys Arg Lys Tyr Val Arg Lys Lys Thr Ser Pro Gly Gln Pro
    130                 135                 140

Pro Ala Glu Gln Ala Ala Ser Ser His Cys Arg Ser Glu Leu Lys Ser
145                 150                 155                 160

Val Lys Arg Ser Leu Asp Phe Gly Gly Glu Val Leu Gln Glu Ser Thr
                165                 170                 175

Gln Ser Gly Ser Gln Val Pro Val Ala Glu Ile Cys Thr Gly Pro Lys
            180                 185                 190

Arg Gln Ser Ile Pro Ser Thr Ile Gln Arg Asp Ser Gln Ser Gln Leu
        195                 200                 205

Ala Cys His Val Val Ser Ser Thr Ser Ser Ile His Thr Ser Ala Ser
    210                 215                 220

Gln Met Val Asn Ala His Leu Phe Pro Pro Asp Asn Met Pro Asn Gly
225                 230                 235                 240

Val Leu Leu Asp Leu Asn Asn Ser Thr Ser Gln Leu Gln Asn Glu His
                245                 250                 255

Ala Lys Phe Val Asp Ser Pro Ala Arg Leu Phe Gly Ser Arg Ile Arg
            260                 265                 270

Gln Thr Ser Gly Lys Asn Ser Leu Leu Glu Ile Tyr Ala Gly Met Ser
        275                 280                 285

Asp Arg Asn Val Pro Asp Leu Asn Ser Ser Ile Ser Gln Thr His Ser
    290                 295                 300

Met Ser Thr Asp Phe Ala Gln Tyr Leu Leu Ser Ser Ser Gln Ala Ser
305                 310                 315                 320

Val Arg Glu Thr Gln Met Ala Asn Gln Met Leu Asn Gly His Arg Met
                325                 330                 335

Pro Glu Asn Pro Ile Thr Pro Ser His Cys Ile Glu Arg Ala Ala Leu
            340                 345                 350

Lys Glu His Leu Asn His Val Pro His Ala Lys Ala Ala Val Met Asn
        355                 360                 365
```

-continued

```
Gly Gln Met Pro His Ser Tyr Arg Leu Ala Gln Asn Pro Ile Leu Pro
    370                 375                 380

Pro Asn His Ile Glu Gly Tyr Gln Val Met Glu Asn Leu Ser Glu Leu
385                 390                 395                 400

Val Thr Thr Asn Asp Tyr Leu Thr Ala Ser Pro Phe Ser Gln Thr Gly
                405                 410                 415

Ala Ala Asn Arg Gln His Asn Ile Gly Asp Ser Met His Ile His Ala
            420                 425                 430

Leu Asp Pro Arg Arg Glu Ser Asn Ala Ser Ser Gly Ser Trp Ile Ser
        435                 440                 445

Leu Gly Val Asn Phe Asn Gln Gln Asn Asn Gly Trp Ala Ser Ala Gly
    450                 455                 460

Ala Ala Asp Ala Ala Ser Ser His Ala Pro Tyr Phe Ser Glu Pro His
465                 470                 475                 480

Lys Arg Met Arg Thr Ala Tyr Leu Asn Asn Tyr Pro Asn Gly Val Val
                485                 490                 495

Gly His Phe Ser Thr Ser Ser Thr Asp Leu Ser Asn Asn Glu Asn Glu
            500                 505                 510

Asn Val Ala Ser Ala Ile Asn Ser Asn Val Phe Thr Leu Ala Asp Ala
        515                 520                 525

Gln Arg Leu Ile Ala Arg Glu Lys Ser Arg Ala Ser Gln Arg Met Ile
    530                 535                 540

Ser Phe Arg Ser Ser Lys Asn Asp Met Val Asn Arg Ser Glu Met Val
545                 550                 555                 560

His Gln His Gly Arg Pro Ala Pro His Gly Ser Ala Cys Arg Glu Ser
                565                 570                 575

Ile Glu Val Pro Asp Lys Gln Phe Gly Leu Met Thr Glu Glu Leu Thr
            580                 585                 590

Gln Leu Pro Ser Met Pro Asn Asn Pro Gln Arg Glu Lys Tyr Ile Pro
        595                 600                 605

Gln Thr Gly Ser Cys Gln Leu Gln Ser Leu Glu His Asp Met Val Lys
    610                 615                 620

Gly His Asn Leu Ala Gly Glu Leu His Lys Gln Val Thr Ser Pro Gln
625                 630                 635                 640

Val Val Ile Gln Ser Asn Phe Cys Val Thr Pro Pro Asp Val Leu Gly
                645                 650                 655

Arg Arg Thr Ser Gly Glu His Leu Arg Thr Leu Ile Ala Pro Thr His
            660                 665                 670

Ala Ser Thr Cys Lys Asp Thr Leu Lys Ala Leu Ser Cys Gln Leu Glu
        675                 680                 685

Ser Ser Arg Asp Ile Ile Arg Pro Pro Val Asn Pro Ile Gly Pro Ser
    690                 695                 700

Ser Ala Asp Val Pro Arg Thr Asp Asn His Gln Val Lys Val Ser Glu
705                 710                 715                 720

Glu Thr Val


<210> SEQ ID NO 19
<211> LENGTH: 12120
<212> TYPE: DNA
<213> ORGANISM: Oryza sativa
<220> FEATURE:
<223> OTHER INFORMATION: DMTRICE sequence from PAC P0489G09

<400> SEQUENCE: 19

aaatattgct taaatggata taaagttgaa aaatgtactt gagggaagtt gtaggtgcac     60
```

-continued

```
gtggggtccc acaatttttc ttcactagtg cacctttagt tatatatttt ttgcgcaaga    120
ggacaaaggc gctccgtgta attttgagta agggccggcg ggatatttat ttgtgtaaag    180
gacctagcca agaaaagcat gatagtgcat atgtatcctt tctttttctt ttcttttgtt    240
ttcataactg tcttacagaa tttcatgttg gctggtgaca cttgtctcac tcattatttg    300
gtatattttg actaaatgca acgtgttggt gctcggtagt ttatatttgt ttttacgcat    360
tcttcattga ctgtatgtat ttgatgttga taccctgggc tgtcttattt tataggtgga    420
tgctgggagg ccacatagga ggcctgtgtg atccaagtgt gctgctcctg agttgaaatt    480
gcatagccat atagcaacta ctggtgtaaa cttgagagat gaagtagtga aaggaaatat    540
gcaggatttt ggacaatggc tgcctcaatc tcagaccact gccgatctat atttctccag    600
tattccaata ccatcacagt tcgatacttc catagagacg cagactagaa cttctgcagt    660
tgtatcgtca gagaaagaat ctgctaattc gttcgtccct cataatggta ctgggcttgt    720
tgaacgcatt agcaatgatg ctgggctaac tgaagtagtt ggaagtagtg ctggaccaac    780
tgaatgtatt gacttgaaca agacaccagc acggaaaccc aagaagaaaa agcacaggcc    840
aaaggtgcta aaggacgata aaccatcgaa gacacctaaa tctgctactc caataccttc    900
aacagaaaag gtagaaaaac catctggaaa gagaaaatat gtccgcaaga agacatctcc    960
aggccaacct cctgcagaac aggcagctag ctcacactgc agatctgagc tgaagtcagt   1020
taaacgaagt ttggactttg gtggagaagt actgcaagag agtacacaat ctggatctca   1080
agttccggtg gcagaaatat gtactggtcc caagcgtcaa tcaatacctt ctaccatcca   1140
aagagattcg caaagccagt tggcttgcca cgtggtttct agcaccagct caattcacac   1200
ttcagctagt cagatggtta atgcacattt gtttcctcct gataacatgc caaatggagt   1260
attgcttgac ctcaataatt ctactagtca gttacaaaac gaacatgcta aatttgtgga   1320
cagtccggca cgtctttttg gttccagaat aagacagaca tcaggtaaaa attctttgct   1380
agaaatctat gctggcatgt cagatagaaa tgtacctgat ctcaacagtt caatcagtca   1440
gacgcatagc atgtctactg attttgctca atacttgctt tcatcctcac aagcttctgt   1500
aagggaaaca caaatggcca atcagatgct taatggtcat aggatgccag aaaatccaat   1560
tacacctagt cattgtattg aaagggctgc attgaaggaa catttgaatc atgttcctca   1620
cgcaaaagcc gcagtgatga atggccaaat gccccatagt tacaggttgg cgcaaaatcc   1680
catcctacct ccaaatcata ttgaagggta tcaagtgatg gaaaatttga gtgaacttgt   1740
cacgacaaat gactatctaa ctgctagtcc tttcagtcaa actggagctg caaataggca   1800
gcataatatt ggtgactcca tgcatataca tgcattggat cctagaagag agagtaatgc   1860
ttcaagtggt tcttggatat cattaggtgt gaactttaac caacaaaata atggatgggc   1920
atctgcaggt gctgccgatg ctgcgagctc acatgcccca tatttttcag aacctcacaa   1980
aagaatgagg acagcttatc ttaacaatta tccaaatgga gtcgtgggac atttttctac   2040
ctcatctacg gatttgtcaa ataatgagaa tgaaaatgtg gcctcagcaa tcaactcaaa   2100
cgtttttacc cttgctgatg cacaaagatt gatagcccgt gagaaatcac gagcttccca   2160
aagaatgatc agttttagat catctaaaaa tgatatggtt aacagatcag aaatggtcca   2220
tcaacatggc agacctgctc cgcatggctc tgcatgcagg gagtctattg aagtacctga   2280
caaacagttc gggctcatga cagaagaact cacacaatta cctagtatgc caaataaccc   2340
acaaagggaa aaatatattc cgcaaactgg aagttgccaa cttcagtctt tggaacatga   2400
```

-continued

```
catggttaaa gggcataact tggcaggtga attgcataag caagtaactt cacctcaagt   2460
tgttattcag agcaatttct gtgttacccc tcctgatgtg ctcggcagaa gaaccagtgg   2520
ggagcattta agaaccctta tagctccaac acatgcatcg acatgtaagg acactctgaa   2580
agctttaagt tgtcaactgg agagttctag agacattatt aggcctcctg tcaatcctat   2640
agggccatcc tctgccgatg ttccaagaac tgataaccat caagtcaagg tttctgaaga   2700
aaccgttaca gccaaactcc ctgagaagcg aaaagtagga cgtcccagaa aagagttaaa   2760
acctggtgag aaaccaaaac ctagaggccg tccaaggaag ggaaaagttg ttggtggaga   2820
acttgcatca aaggatagtc acactaatcc attgcaaaat gagagtactt catgttctta   2880
tggtccttat gcaggggagg cttctgttgg aagagcagtt aaagcaaata gagttggaga   2940
aaacatttct ggagctatgg tatccctact ggattcttta gatattgtta ttcaaaagat   3000
aaaggtcttg gacataaaca aatcagaaga ccctgtgaca gctgaacctc atggtgctct   3060
tgtcccttac aatggagaat ttggtcctat tgttcctttt gaggggaaag tgaaaagaaa   3120
acgctctcga gccaaagtgg atcttgaccc tgtaactgct ttaatgtgga agttactaat   3180
gggaccagat atgagtgatt gtgctgaagg tatggataag gataaagaga aatggctaaa   3240
tgaagaaaga aaaatattcc aagggcgtgt tgattcattt attgctcgaa tgcatctagt   3300
tcaaggtatt tctatcattt taaaattgtt ttcctaacat gaacatgatg gcttccatct   3360
tgtgattgct gccctcacat tagtgaatgg tctcaaatct tcaatattta ctgtgtaccc   3420
aaatcctatt tcttcatccc aatatattca tgtttgtact cgtactgtcc cattagactt   3480
gcattgtgct gtgaagatca acacctttac ttttaggatt acctctatgt ttgcaggaga   3540
tcggcgtttt tctccttgga aaggatcagt tgtagattct gtagtgggag tatttcttac   3600
acagaatgtt tcggaccatc tttccaggtg aataatgcct agagcctatt tgaaaactgt   3660
gacttgactt gcattgtgag gttatgttgt ttttctgtct gactatttcc tttttttca   3720
gctctgcatt tatggctctt gctgcaaaat ttcctgtaaa gccagaagcc tctgaaaaac   3780
ccgcaaatgt gatgtttcat acaatttcag aaaatggtga ttgttctggg ttgtttggta   3840
attctgtcaa gctacagggt gagatccttg ttcaggaggc cagcaacaca gcagcctctt   3900
ttatcacaac cgaggataag gaaggaagta acagtgtgga attgcttgga agttcttttg   3960
gggatggagt ggatggtgca gcaggagttt attctaatat ttatgagaat ctgccagcta   4020
gactgcatgc tactaggcgt ccagtcgttc aaactggaaa cgctgtcgaa gcggaagatg   4080
ggtcactgga gggtgttgtt tcatcagaaa actccactat ttcatctcaa aattcatcag   4140
attatctatt tcacatgtct gatcatatgt tttcgagcat gttactaaat ttcactgccg   4200
aagacattgg cagcagaaat atgcccaaag caacaagaac cacatataca gaacttctac   4260
gaatgcagga gctgaagaac aagtctaatg aaaccattga atcatcagag tatcatgggg   4320
ttccagtctc atgtagtaac aacattcaag tgctcaatgg aatacaaaat atcggcagta   4380
aacatcagcc tttacattcc tctatttcat atcaccagac tggccaagtt cacctcccag   4440
acatagtaca tgcgagtgat ttggagcaat cagtatacac tggccttaat agagtgcttg   4500
attctaatgt tacacaaacc agttattatc cttcacctca tcctggaatt gcctgtaaca   4560
atgaaacaca aaaggctgac tctttaagca acatgttata tggtatagat agatcagata   4620
agactacttc cctgtctgag cctacaccaa gaatcgataa ctgttttcaa ccattaagtt   4680
cagagaaaat gtcatttgct agggaacagt cctcttctga aaattatctt tcaaggaatg   4740
aagctgaagc tgcatttgtt aaacagcatg gaacatcaaa tgtgcaaggt gataatactg   4800
```

-continued

```
tcaggacaga gcaaaatgga ggtgaaaatt ctcaatcagg atacagccaa caggatgata   4860
atgttggatt tcaaacagcg acaaccagta atctttattc ttcaaactta tgccaaaacc   4920
agaaagcaaa ttctgaagta ctacacggag tttcttccaa cttgatagag aattctaaag   4980
atgacaaaaa gacttccccc aaagttccag tcgatggatc aaaagcaaag aggccaagag   5040
ttggggctgg taaaaagaaa acatatgatt gggatatgtt gagaaaagaa gttctttaca   5100
gtcatggtaa taaagaaaga tcccagaatg ctaaggactc aattgattgg gaaacaataa   5160
gacaagcaga ggtgaaggaa atatctgaca caattagaga gcgaggaatg aataacatgc   5220
tggcagaacg gataaaagta agtatggcat aaaacagttt acattgaaag ttgacataac   5280
tctagtcata tgtgcatgca tgctattcca tatagatttg cttatttgtt ggaattccaa   5340
gttttggatc aaccatactc atctttagca attcatgttg caggacttcc taaaccgatt   5400
ggtgagagac catgggagca tcgatcttga gtggttgcgc tatgtcgatt cagataaagc   5460
gaagtaagct aactaaattt attttgagca aacattcata atgcaattgg cccttgggca   5520
ttctataatt tgtcattttg acctctgcat tgcttagcaa tgacaattgg atgtagtgag   5580
catgggtaat aatgtaagca atgacaattg gatgtagtgg gcatggttaa taattgaaca   5640
tgtctgtgtt tgcgggataa taatgcctat cacctgtgag cctgtgacat gcaaaccttg   5700
aacgttgaac cttgaacccc ctacctcgca ctgtgtgctc tcaaccaact gagcaagtga   5760
gggaccttgt tgtatggaaa aaataatttt aaataaccct tgattcaacc aaagcttcat   5820
aaaagaatat attttctatt attcatttga accagcggtt gaaccagtga accgatggtc   5880
ttgctggtcc ggatttaata ataactatgg ctagaacaga ttagagcacc gaatacttgc   5940
gcgatgctaa atatttcaat ggggacacac ctgctcgtgt gttgcatcaa ctacctaagc   6000
cacacaggca tggcaatcaa atcagcttgc ccatgtaaca tcaactatct gatcgcgaga   6060
aggccggagc tctcacttga tgtttgtcat tcaaaaaata gttattcacc aatgcaatgt   6120
caagctcccg taaagaccat gaatgtagtt tatccttctt tgatcaagtt tttatttata   6180
ttaaagtgtt taccaatgta atcctacatt atttgtacct ggtttttaca tataaataca   6240
ttgtaccttt tgtgtttctt ccagggacta tctcttaagc attagaggac ttggacttaa   6300
aagtgttgag tgtgtgcgtc ttttgacact ccatcacatg gcttttcctg tatgtttcct   6360
ttcacaaata attttcaaga atcttcgttt ctttatttct ggagaagtgg agattttatc   6420
tgtatctgtt gatgatgtag gtggatacaa atgttggtag aatatgtgtg aggcttggat   6480
gggtgccact tcagccccta cccgagtctc ttcagttgca cctgttggag atgtaagtat   6540
cttaaatcca ctggttggct tcactaatgc tggagagtga taggagtttg atcatctgct   6600
attgaaggta tccaatgctg gagaacatac agaaatacct ctggccgagg ttatgcaagc   6660
ttgatcaacg gacattgtga gttttagaaa tgcagttaaa aactatatat ataagagcat   6720
gtcattatct gagagtgtat aacaggttct tgatgatatg taggtatgag cttcactatc   6780
aaatgataac ttttggaaag gtatgagaca acaactttga taaagtgaat tcaacccaat   6840
tactgtgttt tgatggacca tctgtgttac tttccttcta ggtattttgt acaaaaagta   6900
agcccaattg caacgcatgc ccaatgagag ctgagtgcaa gcactttgca agtgcatttg   6960
ccaggtaatt ctcaagatgt acatatttta tatacattct gtgaaatcac ggtgatgatt   7020
gttaggtatg aacaattggc tgagatcccc cccctccccc ctcccatcct tttcctggtc   7080
ctacaagttc tcctaggcta atttaactgg tgcataccac atttatgtta ttttgataca   7140
```

-continued

```
tcaaagatta tgtttgtggt tgtgaggcta tattagtgtg ttgtatgtaa ctcagttttg   7200
caattgtagt tttagttaga acacgttgtt ctctacattt taataaatac tttttgactg   7260
gacatcaatg actggtgtat ttccgatata aaaaggttga ttgttgccga gggatttcaa   7320
ttcggtccga ataggttcga caaatgcagt gggcctatta gtttaagagt gaaagttcta   7380
tcagctgttt gactccactg tgacctttac actttgtact tttgaagaaa cagactaacc   7440
tgctcatatt aaagtcttgg aatgactcca ttgcgacctt tacgctttgt attttagaag   7500
aaacagacta acctgttcat attagagtct tggaactgtg tgtgtgtgtg tttttttttt   7560
ttttgggggg ggggggcat ggagatttaa tccaacattc ctggatgacc ttatattggt   7620
aatgatatgg tttttttatg atatagtgca aggctcgctc ttcctggacc tgaagagaag   7680
agtttagtta catctggaac cccaatagct gcagaaacct tccaccagac atatataagt   7740
tctaggcctg tagtaagtca gcttgagtgg aattcaaaca cctgtcacca tggtatgaac   7800
aatcgccagc caatcattga ggagccagca agcccagaac ctgaacatga gacagaagag   7860
atgaaagagt gtgcaataga ggatagtttt gtcgatgatc cagaagaaat ccctactatc   7920
aagcttaatt ttgaggagtt tacacagaac ctgaagagtt atatgcaagc aaataacatt   7980
gagattgaag atgctgatat gtcaaaggct ttggtcgcta taactcctga agttgcttct   8040
atcccaactc ctaagctcaa gaatgtcagt cgcctaagga cagagcacca agtgtatgat   8100
cttgtccctc ttgcaaaacc aatctcatga atatttacta ttgactatca tgtgttttgc   8160
tgcattgctt acttctctgt tttcaacata tatgtagcta tgaactgcca gattcacatc   8220
cacttcttga aggagtaagt tcataaaaca ttatagaatt ctgtactttc cttatcacca   8280
actgagaata tattgatgct tattttctta caatacacag ttcaaccaaa gagaaccaga   8340
tgatccttgc ccatacctac tctctatatg gaccccaggt aagaagtgca taaacagaac   8400
acaatatcat gggaaccaaa cttttttcaa tggttactta taattgttga aatatgcaac   8460
aggtgaaaca gctcaatcaa ctgatgcacc taagtcggtc tgcaattcac aagagaatgg   8520
tgaactatgt gcaagcaata catgctttag ttgcaacagt ataagagaag cgcaggccca   8580
aaaagttcga gggacactgc tggtaagtag ttgtttctgt aacatatgct cagttgccct   8640
tggttcaaga tgtgctattc aagtttatca tgttcacgaa tagtgataaa gctgctatct   8700
gtcctagcta ttgtccaagc tataacagtt ctgattcact ggttgggcac cagctaggga   8760
ataggatgta aaaaacttat cccgcagttt gttgacaatc tgtttttctt tgttgaaaat   8820
taaaaataga taccatgccg aacagcaatg agaggaagct ttccacttaa tgggacatat   8880
tttcaagtca atgaggtgaa aacagaaagt tcttaaagtt gatcttagtt taattattat   8940
aataccatta aaatatatgc aagtttctac tttctagtat ctcttttatt agtgttcaaa   9000
tgttatgcgg caggtatttg ctgatcatga ctcaagccgg aacccgattg atgttccaag   9060
gagttggata tggaatctcc ctaggagaac tgtttacttt ggaacttcaa ttccgacaat   9120
atttaaaggt atttcactaa taaattttga ccaagaatag gatttttggc agcgccaaat   9180
gtgccactat ctttattgtg tgaagtccat tatgtgattg taataatttg aatcaccaag   9240
aggactaagg cctgctttgg gacatattac gagcagcttt tgcttgcaaa gaaaccagat   9300
tctggtgccg caccttctcc gctcttctgc cacccaagtc cgtccaatac ccctcattga   9360
gcgcttggat cctaacccca tctgccatca tgcatcatcc tgctaacaac tgcttccacc   9420
attgcctgtt tctgttgttg ggaggcactc acgctgcttg ctatagttta ggttttcttt   9480
gtgtcctgat ttagatggaa tttccagctg ctgtctttta cataactagc taaatgtccg   9540
```

-continued

```
cgctttgcta tggataatag aaaatatatt ataatattgt caaataaatt aaatatgttt   9600
tatacgaaat gtgttaacaa tccttttgct atagggaata ttgaccttaa tttgatttta   9660
tatgtggcta tccatttaga tttgtttgtt tttctaataa taataagttc aagggctaat   9720
gtacaaaatt gacaatggga gtaggtgggg tggcagattc actgccacca ccactacctt   9780
cttttaaagg ggtatataga tttgcagcag tggttgcttg atctgtgatt tgaaatgtca   9840
agtacacgct catgcatcag caccatatgt ctacgctcct gacccaacat gcaaccaatg   9900
caattgaggg ttggctctga tacaattact aatgtcctat atccaaaaca actataggcc   9960
tatgaccaaa cataattaat aacctcgctt gcgcttttgt cctcacttgc tccatgtaaa  10020
agggttaacc cgaggttact atgttaggaa tagctgggtt tatgaaacgg ttcaactctc  10080
aactcctcat atagcactaa ttcatgtatt gctgtcagca gtgatttgag ttccagatca  10140
tgctcataag ataggaccaa attgtcctta ctatctactc cctccgtccc aaaatataag  10200
gtatttccgg tcaaaatatc ttatattttg ggatggaggg agtactatac tacggaccca  10260
ccaccaaata gtgccgcaga agagagagag agagagagaa gagggggtgg gggtgggggt  10320
gtatgggtga aataagaata gtgccaagta tttgccaaca aatgaggcgg tcaaatgtgt  10380
cacatcaatt gggaagtatg tcagatcaac tgaaaatttg attgggaaat tattattcat  10440
gcaacaaagc tgtacaactg atcccatgtt tctatcgcag gtttgacaac tgaagaaata  10500
caacattgct tttggagagg taatcatttt tttttgtatg tacgttttgg tttccataac  10560
aaagagagat gaagtgtata ggtactatgt ttactgacaa ggataataat agtagcaagt  10620
atataggcag aggagcatgt ctctattcta ccagtattat tactcataat aactagtata  10680
tcctttttttt tgccatttca gctgatagct actctccagt caaaatattt gccatctcta  10740
ttgaactttt cattgtcttc tgaatgtatc ttactcttgg atcattaata tttcattttg  10800
tcacgatata gtggtatagg acaataaaat catgggaagt atttattttc atcaccaatc  10860
tactcatata attttcaaat gacaattata aatatcttaa aaatatattg ttagttgtcc  10920
tgtataaaat aattgtcaca ccctagtcca cagcgacaag aatttgtgtc tacaggctag  10980
agtgagtact ctagaagtat cttcatagga atcggaataa aatgccaatg tgaatgaaca  11040
aggatatcaa gtataccctc aaaatctcta gagaggattg cgtaaatatg taggtgtaat  11100
taaacaattg tttcatatgg agggttttct taaaggaggt acaagactta tcaatatggg  11160
taaagtagtt tttatccata ggcattgttg gcagaaagct gcttagggta gaatgctact  11220
ccctccgtcc cacaatataa gagattttga gtttttgctt gcaacgtttg accactcggc  11280
ttattcaaaa atttttgaaa ttattattta ttttatttgt gacttacttt attattcaca  11340
gtactttaag tacaactttt cgttttttat atttgcaaaa aaaattgtat aagacgagtg  11400
gtcaaacgtt gtacgcaaaa actcaaaatc ccttatattg tgggacggag ggagtactta  11460
tggatgcctt ttttgtccaa gatgtcagta acattttctt tcagggatgt ggatttttac  11520
ttcttttttc cctaactttt tcaggatttg tgtgcgtgag aggctttgat aggacatcaa  11580
gagcacccag accactgtat gcaagactcc actttccagc aagcaaaatt accaggaata  11640
aaaaatctgc aggttctgct ccaggaagag atgatgaata ggccatctgg aaaaccagaa  11700
aggaaataaa gaggaggtac atatgatctg ccagaagatc actgacctga aatggatcgc  11760
tgaccaataa gttgccgtag gcaattcaat tatttctggc catatacatc tgctgaaagt  11820
tatgaactcc agccactgac gaattcgtgg tgctggtatt cttcggcaac atgatccatc  11880
```

-continued

```
atacagattc tatgcttggt tgttgcaagc aattcttatg cggtgacagt tgctgctgat  11940

agggagaaaa ggcatgtccg gcggctcagc ggctctaact gtactttcat atgagtggaa  12000

ccgattgttg tacatgtgaa aagtttgcca ttcaaaatgg tcattcatgt tgttaggtca  12060

ttcatgtagt cgatgtcaaa ttaatcatca attatttgat ttgattcatt cacaagttta  12120


<210> SEQ ID NO 20
<211> LENGTH: 177
<212> TYPE: PRT
<213> ORGANISM: Zea mays
<220> FEATURE:
<223> OTHER INFORMATION: corn DMT.1 660990 (688512 selclone ID)

<400> SEQUENCE: 20

Glu Pro Asp Asp Pro Cys Pro Tyr Leu Leu Ser Ile Trp Thr Pro Gly
  1               5                  10                  15

Glu Thr Ala Gln Ser Ile Asp Ala Pro Lys Thr Phe Cys Asp Ser Gly
             20                  25                  30

Glu Thr Gly Arg Leu Cys Gly Ser Ser Thr Cys Phe Ser Cys Asn Asn
         35                  40                  45

Ile Arg Glu Met Gln Ala Gln Lys Val Arg Gly Thr Leu Leu Ile Pro
     50                  55                  60

Cys Arg Thr Ala Met Arg Gly Ser Phe Pro Leu Asn Gly Thr Tyr Phe
 65                  70                  75                  80

Gln Val Asn Glu Val Phe Ala Asp His Cys Ser Ser Gln Asn Pro Ile
                 85                  90                  95

Asp Val Pro Arg Ser Trp Ile Trp Asp Leu Pro Arg Arg Thr Val Tyr
            100                 105                 110

Phe Gly Thr Ser Val Pro Thr Ile Phe Arg Gly Leu Thr Thr Glu Glu
        115                 120                 125

Ile Gln Arg Cys Phe Trp Arg Gly Phe Val Cys Val Arg Gly Phe Asp
    130                 135                 140

Arg Thr Val Arg Ala Pro Arg Pro Leu Tyr Ala Arg Leu His Phe Pro
145                 150                 155                 160

Val Ser Lys Val Val Arg Gly Lys Lys Pro Gly Ala Ala Arg Ala Glu
                165                 170                 175

Glu


<210> SEQ ID NO 21
<211> LENGTH: 798
<212> TYPE: DNA
<213> ORGANISM: Zea mays
<220> FEATURE:
<223> OTHER INFORMATION: corn DMT.1 cDNA 660990 (668512 selclone ID)

<400> SEQUENCE: 21

gaaccagatg atccttgtcc atatcttctt tccatatgga ccccaggtga aactgcacaa     60

tcgatcgatg cccccaagac attctgtgat tcaggggaga cgggtagact atgtggaagt    120

tcaacatgct ttagttgcaa caatatacga gaaatgcagg ctcagaaagt cagaggaaca    180

cttttgatac catgccgaac agcaatgaga ggaagcttcc cacttaatgg gacgtatttt    240

caagttaatg aggtatttgc tgaccattgc tcaagtcaaa atccaattga tgtcccacga    300

agttggattt gggacctccc aagacgaact gtttactttg gaacctcagt tcctacaata    360

ttcagaggtt taacgactga agagatacaa cgatgctttt ggagaggatt tgtttgcgtg    420

aggggctttg ataggacagt gcgggcacca aggccccttt atgcaaggtt gcattttcct    480
```

-continued

```
gtcagcaagg ttgttagagg caaaaagcct ggagcagcaa gagcagaaga ataatagaac    540

attgaagaaa tataggggtg ctaaccagat gaggatggat agcccgaaat gagatgctga    600

cccaataggt cgccaaatca cctccaaatt ctaacccaat gacttccatc tgtaatgaat    660

ggcaatacct tgaaaacctg tgatggagat gttttgtggc gacatgatct cttaaattag    720

attccgtctt tggtaacagc ctagctgttc ttgttgagtc gcatattctt tattctgaag    780

atcaatatag caaatggg                                                  798
```

<210> SEQ ID NO 22
<211> LENGTH: 166
<212> TYPE: PRT
<213> ORGANISM: Zea mays
<220> FEATURE:
<221> NAME/KEY: MOD_RES
<222> LOCATION: (1)..(166)
<223> OTHER INFORMATION: corn DMT.2 371537 (441428 selclone ID)
<223> OTHER INFORMATION: Xaa = any amino acid

<400> SEQUENCE: 22

```
Met Ile Thr Phe Gly Lys Val Phe Cys Thr Lys Arg Gln Pro Asn Cys
  1               5                  10                  15

Asn Ala Cys Pro Met Arg Ser Glu Cys Lys His Phe Ala Ser Ala Phe
             20                  25                  30

Ala Ser Ala Arg Leu Ala Leu Pro Ala Pro Gln Glu Glu Ser Leu Val
         35                  40                  45

Lys Leu Ser Asn Pro Phe Ala Phe Gln Asn Ser Ser Met His Ala Met
     50                  55                  60

Asn Ser Thr His Leu Pro Arg Leu Glu Gly Ser Ile His Ser Arg Glu
 65                  70                  75                  80

Phe Leu Pro Lys Asn Ser Glu Pro Ile Ile Glu Glu Pro Ala Ser Pro
                 85                  90                  95

Arg Glu Glu Arg Pro Pro Xaa Thr Met Glu Asn Asp Ile Glu Asp Phe
            100                 105                 110

Tyr Glu Asp Gly Glu Ile Pro Thr Ile Lys Leu Asn Met Glu Ala Phe
        115                 120                 125

Ala Gln Asn Leu Glu Asn Cys Ile Lys Glu Ser Asn Asn Glu Leu Gln
    130                 135                 140

Ser Asp Asp Ile Ala Lys Ala Leu Val Ala Ile Xaa Thr Glu Xaa Ala
145                 150                 155                 160

Ser Ile Pro Xaa Pro Lys
                165
```

<210> SEQ ID NO 23
<211> LENGTH: 506
<212> TYPE: DNA
<213> ORGANISM: Zea mays
<220> FEATURE:
<223> OTHER INFORMATION: corn DMT.2 cDNA 371537 (441428 selclone ID)

<400> SEQUENCE: 23

```
tatcagatga ttacatttgg aaaggtcttt tgtaccaaaa gacagccaaa ttgcaatgca     60

tgcccaatga ggagtgagtg caagcatttt gcaagtgcat ttgcaagtgc aaggcttgca    120

cttcctgctc cccaggagga aagcttagtg aagttgagca atccatttgc tttccagaat    180

agcagcatgc atgctatgaa ttcgactcac ctacctcgcc ttgaggggag tatccattca    240

agggagtttc ttcctaagaa ctcagagcca ataatcgagg agcctgcaag tccaagagag    300

gaaagacctc cakaaaccat ggaaaatgat attgaagatt tttatgaaga tggtgaaatc    360
```

-continued

```
ccaacaataa agcttaacat ggaagctttt gcacaaaact tggagaattg cattaaagaa    420

agcaataacg aactccagtc tgatgatatt gcaaaagcat tggttgctat tarcactgaa    480

rcagcttcsa ttcctgkacc gaaact                                         506


<210> SEQ ID NO 24
<211> LENGTH: 276
<212> TYPE: PRT
<213> ORGANISM: Zea mays
<220> FEATURE:
<223> OTHER INFORMATION: corn DMT.3 218853

<400> SEQUENCE: 24

Met Pro Arg Lys Pro Lys Arg Lys Ala Pro Ala Ser Pro Ala Arg His
1               5                   10                  15

Asp Pro Ser Pro Glu Pro Tyr Pro Ser His Ala Ser Pro Cys Ser Ala
            20                  25                  30

Gln Cys Leu Val Val Arg Asp Ala Leu Leu Ala Phe His Gly Phe Pro
        35                  40                  45

Glu Glu Phe Ala Ala Phe Arg Val Leu Arg Leu Gly Gly Leu Ser Pro
    50                  55                  60

Asn Arg Asp Pro Arg Pro Ser Ser Pro Thr Val Leu Asp Gly Leu Val
65                  70                  75                  80

Thr Thr Leu Leu Ser Gln Asn Thr Thr Asp Ala Ile Ser Arg Arg Ala
                85                  90                  95

Phe Ala Ser Leu Lys Ala Ala Phe Pro Ser Trp Asp Gln Val Val Asp
            100                 105                 110

Glu Glu Gly Lys Arg Leu Glu Asp Ala Ile Arg Cys Gly Gly Leu Ala
        115                 120                 125

Ala Thr Lys Ala Ala Arg Ile Arg Ser Met Leu Arg Asp Val Arg Glu
    130                 135                 140

Arg Arg Gly Lys Ile Cys Leu Glu Tyr Leu Arg Glu Leu Ser Val Asp
145                 150                 155                 160

Glu Val Lys Lys Glu Leu Ser Arg Phe Lys Gly Ile Gly Pro Lys Thr
                165                 170                 175

Val Ala Cys Val Leu Met Phe Tyr Leu Gln Lys Asp Asp Phe Pro Val
            180                 185                 190

Asp Thr His Val Leu Arg Ile Thr Lys Ala Met Gly Trp Val Pro Ala
        195                 200                 205

Thr Ala Ser Arg Glu Lys Ala Tyr Ile His Leu Asn Asn Lys Ile Pro
    210                 215                 220

Asp Asp Leu Lys Phe Asp Leu Asn Cys Leu Phe Val Thr His Gly Lys
225                 230                 235                 240

Leu Cys Gln Ser Cys Thr Lys Lys Val Gly Ser Asp Lys Arg Lys Ser
                245                 250                 255

Ser Asn Ser Ala Cys Pro Leu Ala Gly Tyr Cys Cys Ile Gly Glu Lys
            260                 265                 270

Leu Gln Gln Leu
        275


<210> SEQ ID NO 25
<211> LENGTH: 183
<212> TYPE: PRT
<213> ORGANISM: Triticum sp.
<220> FEATURE:
<223> OTHER INFORMATION: wheat DMT.1 614028 (887053 selclone ID)
```

-continued

<400> SEQUENCE: 25

```
Met Arg Ala Glu Cys Lys His Phe Ala Ser Ala Phe Ala Ser Ala Arg
  1               5                  10                  15

Leu Ala Leu Pro Gly Pro Glu Glu Lys Ser Leu Val Thr Ser Gly Asn
             20                  25                  30

Pro Ile Ala Ser Gly Ser Cys Gln Gln Pro Tyr Ile Ser Ser Met Arg
         35                  40                  45

Leu Asn Gln Leu Asp Trp Asn Ala Asn Ala His Asp His Ile Leu Asp
     50                  55                  60

Asn Arg Gln Pro Ile Ile Glu Glu Pro Ala Ser Pro Glu Pro Glu Pro
 65                  70                  75                  80

Glu Thr Ala Glu Met Arg Glu Ser Ala Ile Glu Asp Ile Phe Leu Asp
                 85                  90                  95

Asp Pro Glu Glu Ile Pro Thr Ile Lys Leu Asn Phe Glu Glu Phe Ala
            100                 105                 110

Gln Asn Leu Lys Asn Tyr Met Gln Val Asn Asn Ile Glu Met Glu Asp
        115                 120                 125

Ala Asp Met Ser Ser Ala Leu Val Ala Ile Thr Pro Glu Ala Ala Ser
    130                 135                 140

Ile Pro Thr Pro Arg Leu Lys Asn Val Ser Arg Leu Arg Thr Glu His
145                 150                 155                 160

Gln Val Tyr Glu Leu Pro Asp Ser His Pro Leu Leu Glu Gly Tyr Asp
                165                 170                 175

Gln Arg Glu Pro Asp Asp Pro
            180
```

<210> SEQ ID NO 26
<211> LENGTH: 557
<212> TYPE: DNA
<213> ORGANISM: Triticum sp.
<220> FEATURE:
<223> OTHER INFORMATION: wheat DMT.1 614028 (887053 selclone ID)

<400> SEQUENCE: 26

```
tgcccaatga gagctgaatg caagcacttt gcaagtgcat ttgcaagtgc tagacttgct      60

cttcctggac ctgaagagaa gagtttggtt acgtcaggaa acccaattgc ttcagggagc     120

tgccagcagc catacataag ttctatgcgt ttaaatcaac ttgactggaa tgcaaatgcc     180

catgaccata ttctggacaa tcgccagcca atcattgagg agccagcaag tccggaacca     240

gaaccagaga ctgcagagat gagagagagt gccatagagg atatttttct tgatgatcct     300

gaagaaattc ctacaatcaa gcttaatttc gaggagtttg cacagaatct caagaattat     360

atgcaagtca ataacattga aatggaagat gctgatatgt caagtgcctt ggttgccata     420

actccggaag ctgcatctat cccgactcct aggctcaaga atgttagtcg cctaagaaca     480

gagcatcaag tctatgaact gccggactca catccacttc tggaaggata cgaccaaaga     540

gagcctgatg atccttg                                                    557
```

<210> SEQ ID NO 27
<211> LENGTH: 145
<212> TYPE: PRT
<213> ORGANISM: Triticum sp.
<220> FEATURE:
<223> OTHER INFORMATION: wheat DMT.2 568842 (908118 selclone ID)

<400> SEQUENCE: 27

```
Asn Arg Val Asp Glu Ser Thr Val Gly Gly Ala Asp Lys Ala Ala Ser
```

-continued

```
  1               5                  10                  15

Pro Lys Lys Thr Arg Thr Thr Arg Lys Lys Asn Thr Glu Asn Phe Asp
            20                  25                  30

Trp Asp Lys Phe Arg Arg Gln Ala Cys Ala Asp Gly His Met Lys Glu
        35                  40                  45

Arg Lys Ser Glu Arg Arg Asp Ser Val Asp Trp Glu Ala Val Arg Cys
    50                  55                  60

Ala Asp Val Gln Arg Ile Ser Gln Ala Ile Arg Glu Arg Gly Met Asn
 65                  70                  75                  80

Asn Val Leu Ser Glu Arg Ile Gln Glu Phe Leu Asn Arg Leu Val Arg
                 85                  90                  95

Asp His Gly Ser Ile Asp Leu Glu Trp Leu Arg Asp Ile Pro Pro Asp
            100                 105                 110

Ser Ala Lys Asp Tyr Leu Leu Ser Ile Arg Gly Leu Gly Leu Lys Ser
        115                 120                 125

Val Glu Cys Val Arg Leu Leu Thr Leu His His Leu Ala Phe Pro Val
    130                 135                 140

Asp
145


<210> SEQ ID NO 28
<211> LENGTH: 439
<212> TYPE: DNA
<213> ORGANISM: Triticum sp.
<220> FEATURE:
<223> OTHER INFORMATION: wheat DMT.2 568842 (908118 selclone ID)

<400> SEQUENCE: 28

caaacagggt ggatgaatct actgtcggag gagcagataa agcagcaagt ccaaagaaaa      60

caagaaccac aagaaaaaaa aatactgaaa acttcgactg ggacaaattt cgaagacagg     120

cctgtgctga tggccacatg aaagaaagga agtctgaaag aagagactct gttgattggg     180

aagcagtacg atgtgcagat gtacaaagaa tttctcaggc catccgggaa cgaggaatga     240

ataatgtttt atcagaacga atccaggaat tcctgaatcg cttggttaga gatcatggaa     300

gcattgatct tgaatggtta agagatatcc cccctgactc agcaaaggac tacttgctta     360

gcatacgtgg actggggctc aaaagtgttg aatgtgttcg tctactgaca ttacatcatc     420

tcgctttccc tgtwgacac                                                  439


<210> SEQ ID NO 29
<211> LENGTH: 108
<212> TYPE: PRT
<213> ORGANISM: Triticum sp.
<220> FEATURE:
<223> OTHER INFORMATION: wheat DMT.3 611792 (838515 selclone ID)

<400> SEQUENCE: 29

Asn Arg Lys Gln Val Asn Glu Val Phe Ala Asp His Lys Ser Ser Tyr
  1               5                  10                  15

Asp Pro Ile Tyr Val Ala Arg Glu Gln Leu Trp Lys Leu Glu Arg Arg
            20                  25                  30

Met Val Tyr Phe Gly Thr Ser Val Pro Ser Ile Phe Lys Gly Leu Thr
        35                  40                  45

Thr Glu Glu Ile Gln Gln Cys Phe Trp Lys Gly Phe Val Cys Val Arg
    50                  55                  60

Gly Phe Glu Arg Glu Thr Gly Ala Pro Arg Pro Leu Cys Gln His Leu
 65                  70                  75                  80
```

-continued

```
His Val Ala Ala Ser Lys Val Pro Arg Ser Arg Asn Ala Ala Ala Ala
                 85                  90                  95

Gly Leu Asn Ser Asp Ser Ala Lys Ala Ser Ala Pro
            100                 105


<210> SEQ ID NO 30
<211> LENGTH: 624
<212> TYPE: DNA
<213> ORGANISM: Triticum sp.
<220> FEATURE:
<223> OTHER INFORMATION: wheat DMT.3 611792 (838515 selclone ID)

<400> SEQUENCE: 30

aatcgaaaac aagttaatga ggtatttgca gaccacaaat ctagctacga tcccatatac      60

gttgcaaggg agcagttatg gaagttggaa agacgaatgg tctactttgg aacttcagtg     120

ccctccatat tcaaaggtct aacaactgaa gaaatacagc agtgcttctg gaaaggattt     180

gtctgtgtgc ggggattcga gagggaaacc ggggcaccaa ggcctctatg ccaacatctg     240

cacgtcgcgg ctagcaaagt gccgagatca cgcaacgcgg cagcagctgg gctgaactcg     300

gattcagcaa aggcatcggc tccatgagta tcatcacacc ggctatcgac ctgtgcatgg     360

gtacgctagt gttggttcct gccgggcwac agccgttytt gtaggaaata aaccsctgcg     420

caaragaatt atcatccagt tggtytgagt gtatacttyt gctgtagkac cttttttttaa    480

aatccctgtg agctytattg taccttgaat ttactttccg accagtttat ccgcttgcaa     540

araggccttt gttatgkacc ggcatcttgt tgtatataca tcatggttcc tctraaaaac     600

ttgtcttgcc akacgacctt acgt                                             624


<210> SEQ ID NO 31
<211> LENGTH: 145
<212> TYPE: PRT
<213> ORGANISM: Triticum sp.
<220> FEATURE:
<223> OTHER INFORMATION: wheat DMT.4 615131 (861906 selclone ID)

<400> SEQUENCE: 31

Met Arg Ser Glu Cys Arg His Phe Ala Ser Ala Phe Ala Ser Ala Arg
  1               5                  10                  15

Leu Ala Leu Pro Ala Pro Gln Glu Lys Ser Leu Val Met Ser Ser Asn
             20                  25                  30

Gln Phe Ser Phe Gln Ser Gly Gly Met Pro Thr Pro Tyr Ser Thr Val
         35                  40                  45

Leu Pro Gln Leu Glu Gly Ser Ala Gln Gly Gln Asp Phe Cys Thr Asn
     50                  55                  60

Asn Ser Glu Pro Ile Ile Glu Glu Pro Ala Ser Pro Ala Arg Glu Glu
 65                  70                  75                  80

Cys Pro Glu Thr Leu Glu Asn Asp Ile Glu Asp Tyr Asp Pro Asp Thr
                 85                  90                  95

Gly Glu Ile Pro Leu Ile Lys Leu Asn Leu Gln Ala Phe Ala Gln Asn
            100                 105                 110

Leu Glu Asn Cys Ile Lys Glu Ser Asn Met Asp Leu Gly Ser Asp Asp
        115                 120                 125

Ile Ala Lys Ala Leu Val Ala Val Ser Thr Gly Ser Ala Ser Ile Pro
    130                 135                 140

Val
145
```

-continued

<210> SEQ ID NO 32
<211> LENGTH: 492
<212> TYPE: DNA
<213> ORGANISM: Triticum sp.
<220> FEATURE:
<223> OTHER INFORMATION: wheat DMT.4 615131 (861906 selclone ID)

<400> SEQUENCE: 32
tacttttgga aaggtgttct gtacaaaaaa caagccaaat tgcaatgctt gtccaatgag 60
aagcgaatgc aggcatttcg caagtgcctt cgcaagtgca cggcttgcac ttcctgcacc 120
tcaggagaaa agtttggtga tgtcgagcaa tcaattcagt ttccagagtg gtggcatgcc 180
aactccatac tcaactgtgc ttcctcagct tgagggaagt gcccagggac aggatttttg 240
cactaacaat tcagagccaa ttattgagga gccagcaagt ccagcacggg aagaatgtcc 300
agaaactctt gaaaatgata ttgaagatta cgatccagat actggtgaaa tcccactaat 360
taagcttaac ttgcaagctt ttgctcagaa cttggaaaac tgcattaaag aaagcaatat 420
ggatcttggg tctgatgata tcgcgaaagc acttgttgct gttagcactg gatcagcttc 480
aattcctgtc cc 492

<210> SEQ ID NO 33
<211> LENGTH: 298
<212> TYPE: PRT
<213> ORGANISM: Glycine max
<220> FEATURE:
<221> NAME/KEY: MOD_RES
<222> LOCATION: (1)..(298)
<223> OTHER INFORMATION: soybean DMT.1 449122 (557119 selclone ID)
<223> OTHER INFORMATION: Xaa = any amino acid

<400> SEQUENCE: 33

Met Asp Ser Leu Asp Trp Asp Ala Val Arg Cys Ala Asp Val Ser Glu
1 5 10 15

Ile Ala Glu Thr Ile Lys Glu Arg Gly Met Asn Asn Arg Leu Ala Asp
20 25 30

Arg Ile Lys Asn Phe Leu Asn Arg Leu Val Glu Glu His Gly Ser Ile
35 40 45

Asp Leu Glu Trp Leu Arg Asp Val Pro Pro Asp Lys Ala Lys Glu Tyr
50 55 60

Leu Leu Ser Ile Arg Gly Leu Gly Leu Lys Ser Val Glu Cys Val Arg
65 70 75 80

Leu Leu Thr Leu His His Leu Ala Phe Pro Val Asp Thr Asn Val Gly
85 90 95

Arg Ile Ala Val Arg Leu Gly Trp Val Pro Leu Gln Pro Leu Pro Glu
100 105 110

Ser Leu Gln Leu His Leu Leu Glu Leu Tyr Pro Val Leu Glu Ser Ile
115 120 125

Gln Lys Tyr Leu Trp Pro Arg Leu Cys Lys Leu Asp Gln Glu Thr Leu
130 135 140

Tyr Glu Leu His Tyr Gln Met Ile Thr Phe Gly Lys Xaa Phe Cys Thr
145 150 155 160

Lys Ser Lys Pro Asn Cys Asn Ala Cys Pro Met Arg Xaa Glu Cys Arg
165 170 175

His Phe Ala Ser Ala Phe Ala Ser Ala Arg Phe Ala Leu Pro Gly Pro
180 185 190

Glu Gln Lys Ser Ile Val Ser Thr Thr Gly Asn Ser Val Ile Asn Gln
195 200 205

-continued

```
Asn Pro Ser Glu Ile Ile Ser Gln Leu His Leu Pro Pro Pro Glu Asn
    210                 215                 220

Thr Ala Gln Glu Asp Glu Ile Gln Leu Thr Glu Val Ser Arg Gln Leu
225                 230                 235                 240

Glu Ser Lys Phe Glu Ile Asn Ile Cys Gln Pro Ile Ile Glu Glu Pro
                245                 250                 255

Arg Thr Pro Glu Pro Glu Cys Leu Gln Glu Ser Gln Thr Asp Ile Glu
            260                 265                 270

Asp Ala Phe Tyr Glu Asp Ser Ser Glu Ile Pro Thr Ile Asn Leu Asn
        275                 280                 285

Ile Glu Glu Phe Thr Leu Asn Leu Gln Asn
    290                 295


<210> SEQ ID NO 34
<211> LENGTH: 638
<212> TYPE: DNA
<213> ORGANISM: Glycine max
<220> FEATURE:
<223> OTHER INFORMATION: soybean DMT.1 449122 (557119 selclone ID)

<400> SEQUENCE: 34

aataaaattt aakagcaagg aacaagaaaa agagaaaaag gatgayttg actgggatag      60

tttaagaatt gaagcacagg ctaaggctgg gaaaagagaa aagacagata acaccatgga    120

ttctttggac tgggatgctg tgagatgtgc agatgtcagt gaaatcgctg agaccatcaa    180

agaaaggggc atgaacaaca ggcttgcaga tcgtattaag aatttcttaa atcgattggt    240

tgaagaacat ggaagcattg accttgaatg gcttagagac gttccacctg acaaagcaaa    300

agaatacttg ctcagcataa gaggattggg actaaaaagt gtggaatgtg tgcggctttt    360

aacactgcac catcttgcct tcccggtaga cacaaatgtc ggacgtatag cagtacgact    420

gggatgggtc cctctacagc cactgcctga gtcactgcag ttgcatctcc tagaattgta    480

cccagtgttg gagtcaatac aaaaatatct ctggcctcga ctatgcaagc tagatcagga    540

aacactatat gagctacatt accagatgat tacatttgga aaggkcttct gtacaaaaag    600

caaaccaaat tgtaatgcat gcccaatgag aggagaat                            638


<210> SEQ ID NO 35
<211> LENGTH: 251
<212> TYPE: PRT
<213> ORGANISM: Glycine max
<220> FEATURE:
<223> OTHER INFORMATION: soybean DMT.2 387990 (473695 selclone ID)

<400> SEQUENCE: 35

Met Arg Met Thr Ile Asp Leu Val Ser Gln Gln Ser Leu Thr Ala Arg
  1               5                  10                  15

Leu Gln Leu Ser Ile Leu Lys Asp Lys Leu Lys Ile Gln Cys Arg Lys
             20                  25                  30

Ala Arg Gly Leu Asp Phe Gly Arg Asn Glu Ser Ser Lys Ile Asp Ser
         35                  40                  45

Ser Pro Val Lys Leu Arg Ser Arg Glu His Gly Lys Glu Lys Lys Asn
     50                  55                  60

Asn Phe Asp Trp Asp Ser Leu Arg Ile Gln Ala Glu Ala Lys Ala Gly
 65                  70                  75                  80

Lys Arg Glu Lys Thr Glu Asn Thr Met Asp Ser Leu Asp Trp Asp Ala
                 85                  90                  95
```

-continued

```
Val Arg Arg Ala Asp Val Ser Glu Ile Ala Asn Ala Ile Lys Glu Arg
            100                 105                 110

Gly Met Asn Asn Met Leu Ala Glu Arg Ile Gln Ser Phe Leu Asn Leu
        115                 120                 125

Leu Val Asp Lys His Gly Gly Ile Asp Leu Glu Trp Leu Arg Asp Val
    130                 135                 140

Pro Pro Asp Gln Ala Lys Glu Phe Leu Leu Ser Ile Arg Gly Leu Gly
145                 150                 155                 160

Leu Lys Ser Val Glu Cys Val Arg Leu Leu Thr Leu His His Leu Ala
                165                 170                 175

Phe Pro Val Asp Thr Asn Val Gly Arg Ile Ala Val Arg Leu Gly Trp
            180                 185                 190

Val Pro Leu Gln Pro Leu Pro Glu Ser Leu Gln Leu His Leu Leu Glu
        195                 200                 205

Leu Tyr Pro Val Leu Glu Ser Ile Gln Lys Tyr Leu Trp Pro Arg Leu
    210                 215                 220

Cys Lys Leu Asp Gln Arg Thr Leu Tyr Glu Leu His Tyr Gln Leu Ile
225                 230                 235                 240

Thr Phe Gly Lys Val Phe Cys Thr Lys Ser Lys
                245                 250


<210> SEQ ID NO 36
<211> LENGTH: 1134
<212> TYPE: DNA
<213> ORGANISM: Glycine max
<220> FEATURE:
<223> OTHER INFORMATION: soybean DMT.2 387990 (473695 selclone ID)

<400> SEQUENCE: 36

gaaaagatag gatcattctc agatagcaac tcagaaatag aagacctgtc tagcgctgcc      60

aagtacaata gttattataa tagaatttct ttcagtgagc ttttagaaat ggcaagttca     120

accatgttgc atgaagttaa cagtcaaaga agcaaatcaa ctgagaactt aggagataca     180

tgtgatcagt ctatagacat gaagcatgac aacctggcag aaaacttgga aaaatcggat     240

gttactcaag gctccgcaga agcacccatc accaatggat atacttttaa aataacccca     300

aactcaggag tacttgaggt taactgttat gatcctctca aaatagaagt cccatcaagt     360

ggctcctcaa agggtaaaga tgagaatgac aatagatcta gtttcccaac agagtctgac     420

tgccaggctg caattgtcca ttctcaagga caaactgaag atccaatgca ggaaagcaag     480

gggactagat tttggtagga atgaaagcag taagatagat tcttcccctg taaaattaag     540

gagcagggag catggaaaag agaaaaagaa taactttgat tgggatagtt taagaataca     600

agcagaagct aaggcaggga aaagagaaaa gacagagaac accatggact ccttggactg     660

ggatgctgtt agacgcgcag atgtcagtga aattgccaat gcaatcaaag aaaggggcat     720

gaacaacatg cttgctgaac gtattcagag tttcctgaat ctattggttg acaagcatgg     780

gggcatcgat cttgagtggc tgagagatgt tccacctgat caagcaaaag aattcttgct     840

cagcataagg ggattgggat tgaaaagtgt ggagtgtgta cgactcttaa cactacacca     900

tcttgccttt ccggtggaca caaatgttgg acgtatagca gtaagattgg gatgggtgcc     960

tctccagcca ctgccagagt cactacagtt gcatcttcta gaattgtacc cagtgttgga    1020

gtccatacaa aaatatctct ggccccggct ctgcaagcta gaccaaagaa cattgtatga    1080

gctgcattac cagctgatta catttggaaa ggtcttctgt actaaaagca agcc          1134
```

-continued

<210> SEQ ID NO 37
<211> LENGTH: 209
<212> TYPE: PRT
<213> ORGANISM: Glycine max
<220> FEATURE:
<221> NAME/KEY: MOD_RES
<222> LOCATION: (1)..(209)
<223> OTHER INFORMATION: soybean DMT.3 657152 (546665 selclone ID)
<223> OTHER INFORMATION: Xaa = any amino acid

<400> SEQUENCE: 37

```
Ile Asn Gln Ala Glu Leu Gln Gln Thr Glu Val Ile Arg Gln Leu Glu
  1               5                  10                  15

Ala Lys Ser Glu Ile Asn Ile Ser Gln Pro Ile Ile Glu Glu Pro Ala
             20                  25                  30

Thr Pro Glu Pro Glu Cys Ser Gln Val Ser Glu Asn Asp Ile Glu Asp
         35                  40                  45

Thr Phe Asn Glu Glu Ser Cys Glu Ile Pro Thr Ile Lys Leu Asp Ile
     50                  55                  60

Glu Glu Phe Thr Leu Asn Leu Gln Asn Tyr Met Gln Glu Asn Met Glu
 65                  70                  75                  80

Leu Gln Glu Gly Glu Met Ser Lys Ala Leu Val Ala Leu His Pro Gly
                 85                  90                  95

Ala Ala Cys Ile Pro Thr Pro Lys Leu Lys Asn Val Ser Arg Leu Arg
            100                 105                 110

Thr Glu His Tyr Val Tyr Glu Leu Pro Asp Ser His Pro Leu Leu Asn
        115                 120                 125

Gly Trp Asn Lys Arg Glu Pro Asp Asp Pro Gly Lys Tyr Leu Leu Ala
    130                 135                 140

Ile Trp Thr Pro Gly Glu Thr Ala Asx Ser Ile Gln Pro Pro Glu Ser
145                 150                 155                 160

Lys Cys Ser Ser Gln Glu Glu Cys Gly Xaa Leu Cys Asn Glu Asn Glu
                165                 170                 175

Cys Phe Ser Cys Asn Ser Phe Arg Glu Ala Xaa Phe Xaa Asp Ser Xaa
            180                 185                 190

Arg Asp Thr Pro Asp Thr Met Ser Asn Ser Xaa Xaa Xaa Gly Ala Phe
        195                 200                 205

His
```

<210> SEQ ID NO 38
<211> LENGTH: 616
<212> TYPE: DNA
<213> ORGANISM: Glycine max
<220> FEATURE:
<223> OTHER INFORMATION: soybean DMT.3 657152 (546665 selclone ID)

<400> SEQUENCE: 38

```
tataaaccaa gcagaacttc aacaaacaga agtgatcagg caactagaag caaaatctga      60

aatcaacatc agccaaccta ttattgaaga gccagcaact ccagagccag aatgctccca     120

agtatccgaa aatgatatag aggatacctt caatgaggaa tcatgtgaaa ttcccaccat     180

caaactagac atagaagagt tcactttgaa cttacaaaac tatatgcaag aaaacatgga     240

acttcaagaa ggtgaaatgt caaaggcctt ggttgctcta catccaggtg ctgcatgcat     300

tcctacaccc aagctgaaga atgtgagccg gttgcgaaca gagcattatg tttatgaact     360

ccctgattca catccccttc tgaatgggtg gaacaagcga gaacctgatg atccaggcaa     420

ataccttcta gctatatgga ctccagggga gacagcagat tctatacagc caccagaaag     480
```

-continued

```
caaatgcagc tctcaggaat gtggccggct ctgtaatgag aatgaatgtt tttcatgcaa    540

cagtttccgt gaagcaaggt tcacagatag ttcgagggac actcctgata ccatgtcgaa    600

cagctwtgar agggag                                                    616


<210> SEQ ID NO 39
<211> LENGTH: 102
<212> TYPE: PRT
<213> ORGANISM: Glycine max
<220> FEATURE:
<223> OTHER INFORMATION: soybean DMT.4 432980 (663678 selclone ID)

<400> SEQUENCE: 39

Glu Ala Ala Ser Ile Pro Met Pro Lys Leu Lys Asn Val Ser Arg Leu
  1               5                  10                  15

Arg Thr Glu His Cys Val Tyr Glu Leu Pro Asp Thr His Pro Leu Leu
             20                  25                  30

Gln Gly Trp Asp Thr Arg Glu Pro Asp Asp Pro Gly Lys Tyr Leu Leu
         35                  40                  45

Ala Ile Trp Thr Pro Gly Glu Thr Ala Asn Ser Ile Gln Pro Pro Glu
     50                  55                  60

Ser Lys Cys Ser Ser Gln Glu Glu Cys Gly Gln Leu Cys Asn Glu Asn
 65                  70                  75                  80

Glu Cys Phe Ser Cys Asn Ser Phe Arg Glu Ala Asn Ser Gln Ile Val
                 85                  90                  95

Arg Gly Thr Leu Leu Val
            100


<210> SEQ ID NO 40
<211> LENGTH: 457
<212> TYPE: DNA
<213> ORGANISM: Glycine max
<220> FEATURE:
<223> OTHER INFORMATION: soybean DMT.4 432980 (663678 selclone ID)

<400> SEQUENCE: 40

agaagctgct tccattccta tgcccaagct aaagaatgtg agccgattac gaacagagca     60

ttgtgtttat gaactcccag atacgcatcc tcttctccaa gggtgggaca cacgagagcc    120

tgatgatcca ggcaaatatc ttcttgctat atggactcca ggtgagacag caaattctat    180

acagccacca gaaagcaaat gcagctctca agaagaatgt ggccaactct gtaatgagaa    240

tgaatgtttc tcgtgcaaca gtttccgtga agcaaattct cagatagtta gagggacact    300

cctggtctga atgcttatca aaatcattgt tttaaccata tgtagcttac taattcttat    360

acattatggg aacaggggag ggaatacatc tccatagaaa ttcaagcatt ataatagact    420

gacttgaatt tatgataaat atgagcagat accatgt                             457


<210> SEQ ID NO 41
<211> LENGTH: 217
<212> TYPE: PRT
<213> ORGANISM: Medicago truncatula
<220> FEATURE:
<223> OTHER INFORMATION: Medicago 6654943

<400> SEQUENCE: 41

Met Glu Leu Gln Glu Gly Glu Met Ser Lys Ala Leu Val Ala Leu Asn
  1               5                  10                  15

Gln Glu Ala Ser Tyr Ile Pro Thr Thr Lys Leu Lys Asn Val Ser Arg
             20                  25                  30
```

-continued

```
Leu Arg Thr Glu His Ser Val Tyr Glu Leu Pro Asp Ser His Pro Leu
        35                  40                  45

Leu Glu Gly Trp Glu Lys Arg Glu Pro Asp Asp Pro Gly Lys Tyr Leu
    50                  55                  60

Leu Ala Ile Trp Thr Pro Gly Glu Thr Ala Asn Ser Ile Gln Pro Pro
65                  70                  75                  80

Asp Arg Arg Cys Ser Ala Gln Asp Cys Gly Gln Leu Cys Asn Glu Glu
                85                  90                  95

Glu Cys Phe Ser Cys Asn Ser Phe Arg Glu Ala Asn Ser Gln Ile Val
            100                 105                 110

Arg Gly Thr Ile Leu Ile Pro Cys Arg Thr Ala Met Arg Gly Ser Phe
        115                 120                 125

Pro Leu Asn Gly Thr Tyr Phe Gln Val Asn Glu Val Phe Ala Asp His
    130                 135                 140

Glu Ser Ser Leu Asn Pro Ile Ser Val Pro Arg Ser Leu Ile Trp Asn
145                 150                 155                 160

Leu Asp Arg Arg Thr Val His Phe Gly Thr Ser Val Thr Ser Ile Phe
                165                 170                 175

Lys Gly Leu Ala Thr Pro Glu Ile Gln Gln Cys Phe Trp Arg Gly Phe
            180                 185                 190

Val Cys Val Arg Ser Phe Glu Arg Ser Thr Arg Ala Pro Arg Pro Leu
        195                 200                 205

Met Ala Arg Leu His Phe Pro Ala Ser
    210                 215
```

<210> SEQ ID NO 42
<211> LENGTH: 657
<212> TYPE: DNA
<213> ORGANISM: Medicago truncatula
<220> FEATURE:
<223> OTHER INFORMATION: Medicago 6654943 EST306265

<400> SEQUENCE: 42

```
gagaacatgg aacttcaaga aggtgaaatg tcaaaggcct tggttgctct aaatcaagaa      60

gcttcttaca ttcctacaac gaagctgaag aacgtgagtc ggttgcgcac agagcattct     120

gtttatgaac tcccagattc tcatcctctt ctggaagggt gggaaaagcg agaacctgat     180

gatccaggaa aataccttct agctatatgg acgccaggtg agactgcaaa ttctatacag     240

ccaccagaca gaagatgcag cgctcaagat tgtggccaac tctgtaatga ggaggaatgt     300

ttttcgtgca acagcttccg tgaagcaaat tcacagatag ttcgagggac aatcctgata     360

ccatgtcgaa cagctatgag agggagcttt ccgctaaacg gaacctattt tcaagtcaat     420

gaggtttttg cagaccatga atcaagtctt aatccgatta gcgttcccag aagtttgata     480

tggaaccttg ataggaggac agtgcatttt ggaacctccg taacaagcat attcaaaggt     540

ttagcaacac cagaaattca acagtgcttc tggagagggt ttgtctgtgt gcggagcttt     600

gaaaggtcaa cgagagcacc ccgtccttta atggccagac tgcatttccc agcaagc        657
```

<210> SEQ ID NO 43
<211> LENGTH: 210
<212> TYPE: PRT
<213> ORGANISM: Lycopersicon esculentum
<220> FEATURE:
<223> OTHER INFORMATION: tomato 12624037

<400> SEQUENCE: 43

```
Met Glu Leu Gln Glu Gly Glu Met Ser Lys Ala Leu Val Ala Leu Asn
```

-continued

```
 1               5                   10                  15

Gln Glu Ala Ser Tyr Ile Pro Thr Thr Lys Leu Lys Asn Val Ser Arg
            20                  25                  30

Leu Arg Thr Glu His Ser Val Tyr Glu Leu Pro Asp Ser His Pro Leu
        35                  40                  45

Leu Glu Gly Trp Glu Lys Arg Glu Pro Asp Asp Pro Gly Lys Tyr Leu
     50                  55                  60

Leu Ala Ile Trp Thr Pro Gly Glu Thr Ala Asn Ser Ile Gln Pro Pro
 65                  70                  75                  80

Asp Arg Arg Cys Ser Ala Gln Asp Cys Gly Gln Leu Cys Asn Glu Glu
                85                  90                  95

Glu Cys Phe Ser Cys Asn Ser Phe Arg Glu Ala Asn Ser Gln Ile Val
            100                 105                 110

Arg Gly Thr Ile Leu Ile Pro Cys Arg Thr Ala Met Arg Gly Ser Phe
        115                 120                 125

Pro Leu Asn Gly Thr Tyr Phe Gln Val Asn Glu Val Phe Ala Asp His
    130                 135                 140

Glu Ser Ser Leu Asn Pro Ile Ser Val Pro Arg Ser Leu Ile Trp Asn
145                 150                 155                 160

Leu Asp Arg Arg Thr Val His Phe Gly Thr Ser Val Thr Ser Ile Phe
                165                 170                 175

Lys Gly Leu Ala Thr Pro Glu Ile Gln Gln Cys Phe Trp Arg Gly Phe
            180                 185                 190

Val Cys Val Arg Ser Phe Glu Arg Ser Thr Arg Ala Pro Arg Pro Leu
        195                 200                 205

Met Ala
    210
```

<210> SEQ ID NO 44
<211> LENGTH: 758
<212> TYPE: DNA
<213> ORGANISM: Lycopersicon esculentum
<220> FEATURE:
<223> OTHER INFORMATION: tomato 12624037 EST469495

<400> SEQUENCE: 44

```
gcttgagaaa ggaagtccaa tcaaagagtg ggaaaaaaga aagaagcaag gatgcaatgg     60

actcattgaa ctacgaagca gtcagaagtg cagcagttaa agaaatttct gatgctatta    120

aggaacgagg gatgaacaac atgctggcag agcgaattaa ggacttcctc gatagactgg    180

tgagggatca tggaagtatt gacctagaat ggttgagaga tgtggcccca gacaaagcga    240

aagagtatct tttgagtatt cgtggactgg gtctgaaaag tgtagaatgt gtgcggctat    300

taacacttca taaccttgct tttccagttg acacaaatgt tggacgaata gctgtgagat    360

taggatgggt tcctctccaa ccacttcctg agtccctgca gttgcatctt cttgaactgt    420

atccaattct ggagtcaatt cagaagtatc tctggccacg actctgcaag ctcgatcaga    480

gaacactgta tgagttgcac taccacatga ttacctttgg aaaggttttc tgcaccaaaa    540

gtaagcctaa ctgtaatgca tgcccactga gagctgaatg cagacacttt gctagtgctt    600

acgcaagtgc aagacttgcc cttcctggcc cagaggagaa gagtatagtg agttcagcag    660

ttccgatccc tagtgaggga aatgcagctg ccgcattcaa gcccatgcta ttacccccag    720

agctgaagta gggatggcgt acccatatgc tccaattg                            758
```

<210> SEQ ID NO 45

-continued

<211> LENGTH: 203
<212> TYPE: PRT
<213> ORGANISM: Hordeum vulgare
<220> FEATURE:
<221> NAME/KEY: MOD_RES
<222> LOCATION: (1)..(203)
<223> OTHER INFORMATION: barley 13256964
<223> OTHER INFORMATION: Xaa = any amino acid

<400> SEQUENCE: 45

```
Met Ala Ser Glu Thr Glu Thr Phe Ala Phe Gln Ala Glu Ile Asn Gln
  1               5                  10                  15

Leu Leu Ser Leu Ile Ile Asn Thr Phe Tyr Ser Asn Lys Glu Ile Phe
             20                  25                  30

Leu Arg Glu Leu Ile Ser Asn Ala Ser Asp Ala Leu Asp Lys Ile Arg
         35                  40                  45

Phe Glu Ser Leu Thr Asp Lys Ser Lys Leu Asp Ala Gln Pro Glu Leu
     50                  55                  60

Phe Ile His Ile Ile Pro Asp Lys Ala Thr Asn Thr Leu Thr Leu Ile
 65                  70                  75                  80

Asp Ser Gly Ile Gly Met Thr Lys Ser Asp Leu Val Asn Asn Leu Gly
                 85                  90                  95

Thr Ile Ala Arg Ser Gly Thr Lys Asp Phe Met Glu Ala Leu Ala Ala
            100                 105                 110

Gly Ala Asp Val Ser Met Ile Gly Gln Phe Gly Val Gly Phe Tyr Ser
        115                 120                 125

Ala Tyr Pro Cys Ala Glu Arg Val Xaa Val Thr Ser Lys His Asn Asp
    130                 135                 140

Asp Glu Gln Tyr Gly Gly Glu Xaa Gln Ala Gly Trp Leu Leu Tyr Cys
145                 150                 155                 160

Gly His Val Ile Leu Leu Glu Ser Pro Phe Gly Gly Val Leu Arg Ser
                165                 170                 175

Pro Ser Thr Ser Arg Thr Asn Ser Trp Ser Thr Leu Glu Arg Arg Ala
            180                 185                 190

Phe Lys Asp Leu Gly Lys Asn Thr Pro Ser Ser
        195                 200
```

<210> SEQ ID NO 46
<211> LENGTH: 883
<212> TYPE: DNA
<213> ORGANISM: Hordeum vulgare
<220> FEATURE:
<221> NAME/KEY: modified_base
<222> LOCATION: (1)..(883)
<223> OTHER INFORMATION: barley 13256964 HVSMEi0014B12f
<223> OTHER INFORMATION: n = g, a, c or t

<400> SEQUENCE: 46

```
cgagaacccc gctccaaagc cctaacccta ggccatcccc tctccctccc ctcaaccctc      60

gtcgactccg cgcgcgcctg cgttccagga gcttccgctg ccggcggcgc catggcctca     120

gagaccgaga ccttcgcctt ccaggcggag atcaaccagc tgctctcgct catcatcaac     180

accttctact ccaacaagga gatcttcctc cgcgagctca tctccaacgc ctccgatgcg     240

ttggataaga tcaggtttga gagcctcact gacaagagca agctggatgc tcagccagag     300

ctgttcatcc acattatccc tgacaaggcc accaacacac tcacccttat cgacagtggc     360

attggtatga ccaagtcaga cctcgtgaac aaccttggta ccattgcaag gtctggcacc     420

aaggatttca tggaggcatt ggctgctggt gccgatgtgt ccatgattgg tcagtttggt     480
```

-continued

```
gttggtttct actctgctta cccttgtgct gagagagtcg ntgtgaccag caagcacaac    540

gatgacgagc agtatggggg ggagtnccag gctgggtggc ttctttactg tggacacgtg    600

atactcttgg agagcccctt tggaggggta ctaagatccc cctctacctc aaggacgaac    660

agttggagta ccttggagag gcgcgccttt aaggatttgg ggaaaaacac tccgagttca    720

taactttttc atctcctctg gacggggaaa acccctgaaa aggaattttt gcgctggaaa    780

gtgggtggaa aaatgggttc ctgggggggc ccggttgagg gattgttggt cacataaaca    840

actatcgtct tctatcttag cacctaatag tccttcacat gag                      883
```

<210> SEQ ID NO 47
<211> LENGTH: 164
<212> TYPE: PRT
<213> ORGANISM: Zea mays
<220> FEATURE:
<223> OTHER INFORMATION: corn BE511860

<400> SEQUENCE: 47

```
Leu Leu Glu Gly Phe Glu Gln Arg Glu Pro Asp Asp Pro Cys Pro Tyr
  1               5                  10                  15

Leu Leu Ser Ile Trp Thr Pro Gly Glu Thr Ala Gln Ser Ile Asp Ala
             20                  25                  30

Pro Lys Thr Phe Cys Asp Ser Gly Glu Thr Gly Arg Leu Cys Gly Ser
         35                  40                  45

Ser Thr Cys Phe Ser Cys Asn Asn Ile Arg Glu Met Gln Ala Gln Lys
     50                  55                  60

Val Arg Gly Thr Leu Leu Ile Pro Cys Arg Thr Ala Met Arg Gly Ser
 65                  70                  75                  80

Phe Pro Leu Asn Gly Thr Tyr Phe Gln Val Asn Glu Val Phe Ala Asp
                 85                  90                  95

His Cys Ser Ser Gln Asn Pro Ile Asp Val Pro Arg Ser Trp Ile Trp
            100                 105                 110

Asp Leu Pro Arg Arg Thr Val Tyr Phe Gly Thr Ser Val Pro Thr Ile
        115                 120                 125

Phe Arg Gly Leu Thr Thr Glu Glu Ile Gln Arg Cys Phe Trp Arg Gly
    130                 135                 140

Phe Val Cys Val Arg Gly Phe Asp Arg Thr Val Arg Ala Pro Arg Ala
145                 150                 155                 160

Leu Tyr Ala Arg
```

<210> SEQ ID NO 48
<211> LENGTH: 517
<212> TYPE: DNA
<213> ORGANISM: Zea mays
<220> FEATURE:
<223> OTHER INFORMATION: corn BE511860 EST946063H01.Y1 946

<400> SEQUENCE: 48

```
tatgaactgc cagattcaca cgcctcttct ggaaggattc gaacagagag aaccagatga     60

tccctgtcca tatcttcttt ccatatggac cccaggtgaa actgcacaat cgatcgatgc    120

ccccaagaca ttctgtgatt caggggagac gggtagacta tgtggaagtt caacatgctt    180

tagttgcaac aatatacgag aaatgcaggc tcagaaagtc agaggaacac ttttgatacc    240

atgccgaaca gcaatgagag gaagcttccc acttaatggg acgtattttc aagttaatga    300

ggtatttgct gaccattgct caagtcaaaa tccaattgat gtcccacgaa gttggatttg    360

ggacctccca agacgaactg tttactttgg aacctcagtt cctacaatat tcagaggttt    420
```

-continued

```
aacgactgaa gagatacaac gatgcttttg gagaggattt gtttgcgtga ggggctttga    480

taggacagtg cgggcaccaa gggcccttta tgcaagg                             517
```

<210> SEQ ID NO 49
<211> LENGTH: 137
<212> TYPE: PRT
<213> ORGANISM: Gossypium arboreum
<220> FEATURE:
<223> OTHER INFORMATION: cotton 11206330

<400> SEQUENCE: 49

```
Met Gln Gly Asn Met Glu Leu Gln Glu Gly Asp Leu Ser Lys Ala Leu
  1               5                  10                  15

Val Ala Leu Asn Pro Asp Ala Ala Ser Ile Pro Thr Pro Lys Leu Lys
             20                  25                  30

Asn Val Ser Arg Leu Arg Thr Glu His Tyr Val Tyr Glu Leu Pro Asp
         35                  40                  45

Lys His Pro Leu Leu Lys Gln Met Glu Lys Arg Glu Pro Asp Asp Pro
     50                  55                  60

Ser Pro Tyr Leu Leu Ala Ile Trp Thr Pro Gly Glu Thr Ala Asn Ser
 65                  70                  75                  80

Ile Gln Pro Pro Glu Gln Ser Cys Gly Ser Gln Glu Pro Gly Arg Leu
                 85                  90                  95

Cys Asn Glu Lys Thr Cys Phe Ala Cys Asn Ser Val Arg Glu Ala Asn
            100                 105                 110

Thr Glu Thr Val Arg Gly Thr Ile Leu Ile Pro Cys Arg Asn Ala Met
        115                 120                 125

Arg Gly Ser Phe Ser Leu Asn Gly Thr
    130                 135
```

<210> SEQ ID NO 50
<211> LENGTH: 766
<212> TYPE: DNA
<213> ORGANISM: Gossypium arboreum
<220> FEATURE:
<223> OTHER INFORMATION: cotton 11206330 GA_Eb0023J04f

<400> SEQUENCE: 50

```
ctccgccagt gcataacttg cttaaagtag ggcctaatgt tggcaacaat gaacctatca     60

ttgaggagcc tgcaacacct gaaccagagc atgcagaagg atcagagagt gatattgaag    120

atgcaagcta tgatgatcca gatgaaattc ccacaataaa actcaacatt gaagagttca    180

cagcaaacct acagcattac atgcagggca atatggaact ccaagaaggg gacttgtcaa    240

aggctttagt agctttgaat cctgatgctg cttctatccc tactccaaaa ttgaagaatg    300

taagcaggct acgaacagag cactatgtat atgagcttcc agataaacat cctctcttga    360

aacagatgga aaagcgggaa cctgatgatc ctagccccta tcttcttgca atatggacac    420

caggtgaaac tgcaaactca attcaaccac cagaacaaag ttgtgggtcc caagaaccag    480

gaagactgtg caatgagaag acctgctttg cttgcaacag tgtaagagaa gctaacactg    540

agacagtccg aggaaccatc ttgatacctt gtagaaatgc aatgagagga agcttttccc    600

ttaatgggac ttaattttca agttaatgag gtcttttgca gatcatgaat caagcctcaa    660

cccaatcgac gttccaaggg gaatggattg ggaatttaac aagaacgaac tgtatacttg    720

gaacatcctg gttcatcaat atttaaagga cttttcgacg agggaa                   766
```

-continued

<210> SEQ ID NO 51
<211> LENGTH: 179
<212> TYPE: PRT
<213> ORGANISM: Glycine max
<220> FEATURE:
<221> NAME/KEY: MOD_RES
<222> LOCATION: (167)
<223> OTHER INFORMATION: soybean 5606759
<223> OTHER INFORMATION: Xaa = His or Gln

<400> SEQUENCE: 51

```
Met Gly Trp Val Pro Leu Gln Pro Leu Pro Glu Ser Leu Gln Leu His
  1               5                  10                  15

Leu Leu Glu Leu Tyr Pro Val Leu Glu Ser Ile Gln Lys Tyr Leu Trp
             20                  25                  30

Pro Arg Leu Cys Lys Leu Asp Gln Glu Thr Leu Tyr Glu Leu His Tyr
         35                  40                  45

Gln Met Ile Thr Phe Gly Lys Val Phe Cys Thr Lys Ser Lys Pro Asn
     50                  55                  60

Cys Asn Ala Cys Pro Met Arg Ala Glu Cys Arg His Phe Ala Ser Ala
 65                  70                  75                  80

Phe Ala Ser Ala Arg Phe Ala Leu Pro Gly Pro Glu Gln Lys Ser Ile
                 85                  90                  95

Val Ser Thr Thr Gly Asn Ser Val Ile Asn Gln Asn Pro Ser Glu Ile
            100                 105                 110

Ile Ser Gln Leu His Leu Pro Pro Pro Glu Asn Thr Ala Gln Glu Asp
        115                 120                 125

Glu Ile Gln Leu Thr Glu Val Ser Arg Gln Leu Glu Ser Lys Phe Glu
    130                 135                 140

Ile Tyr Ile Cys Gln Pro Ile Ile Glu Glu Pro Arg Thr Pro Glu Pro
145                 150                 155                 160

Glu Cys Leu Gln Glu Ser Xaa Thr Asp Ile Glu Asp Ala Val Tyr Glu
                165                 170                 175

Asp Ser Ser
```

<210> SEQ ID NO 52
<211> LENGTH: 583
<212> TYPE: DNA
<213> ORGANISM: Glycine max
<220> FEATURE:
<221> NAME/KEY: modified_base
<222> LOCATION: (546)
<223> OTHER INFORMATION: soybean 5606759 sb95c12.y1
<223> OTHER INFORMATION: n = g, a, c or t

<400> SEQUENCE: 52

```
acgagcttcc cggtagacac aaatgtcgga cgtattgccg tacgactggg atgggtgcct      60

ctgcagccac tgcctgagtc actgcagttg catctcctag aattgtaccc ggtgttggag     120

tcaatacaaa aatatctctg gcctcgactg tgcaagctag atcaggaaac actatatgag     180

ctacattacc agatgattac atttggaaag gtcttctgta caaaaagcaa accaaattgt     240

aatgcatgcc caatgagagc agaatgtaga cactttgcta gtgcatttgc aagtgcaagg     300

tttgcactgc ctggaccaga gcagaagagt atagttagca caactggaaa tagtgtgatt     360

aaccagaacc catctgaaat catcagtcag ttgcacttgc ctccacctga gaacacagcc     420

caagaagatg aaattcaact aacagaagtg agcagacaat tggaatcaaa atttgaaata     480

tatatttgcc aacctatcat tgaagagccc agaactccag agccagaatg cttgcaagaa     540

tcacanactg atatagagga tgctgtctat gaggattcaa gtg                      583
```

-continued

<210> SEQ ID NO 53
<211> LENGTH: 155
<212> TYPE: PRT
<213> ORGANISM: Triticum aestivum
<220> FEATURE:
<223> OTHER INFORMATION: wheat 12019155

<400> SEQUENCE: 53

```
Met Phe His Cys His Gly Thr Arg Gly Ser Asp Leu Gly Phe Asp Leu
  1               5                  10                  15

Asn Lys Thr Pro Glu Gln Lys Ala Pro Gln Arg Arg Lys His Arg Pro
             20                  25                  30

Lys Val Ile Lys Glu Ala Lys Pro Lys Ser Thr Arg Lys Pro Ala Thr
         35                  40                  45

Gln Lys Thr Gln Met Lys Glu Asn Pro His Lys Lys Arg Lys Tyr Val
     50                  55                  60

Arg Lys Thr Ala Ala Thr Pro Gln Thr Asn Val Thr Glu Glu Ser Val
 65                  70                  75                  80

Asp Ser Ile Val Ala Thr Lys Lys Ser Cys Arg Arg Ala Leu Asn Phe
                 85                  90                  95

Asp Leu Glu His Asn Lys Tyr Ala Ser Gln Ser Thr Ile Ser Cys Gln
            100                 105                 110

Gln Glu Ile Asp His Arg Asn Glu Lys Ala Phe Asn Thr Thr Ser Asp
        115                 120                 125

His Lys Ala Lys Glu Pro Lys Asn Thr Asp Asp Asn Thr Leu Leu Leu
    130                 135                 140

His Glu Lys Gln Ala Asn Asn Phe Gln Ser Glu
145                 150                 155
```

<210> SEQ ID NO 54
<211> LENGTH: 902
<212> TYPE: DNA
<213> ORGANISM: Triticum aestivum
<220> FEATURE:
<221> NAME/KEY: modified_base
<222> LOCATION: (1)..(902)
<223> OTHER INFORMATION: wheat 12019155 ESTBRY_901
<223> OTHER INFORMATION: n = g, a, c or t

<400> SEQUENCE: 54

```
aacagtcagg acaaaggcaa caagatcagc agtcaggaca agggcagcaa ccgggacaaa     60

ggcagccagg gtactactca acttctccgc aacaattagg acaaggccaa ccaaggtact    120

acccaacttc tccgcagcag ccaggacaag agcagcagcc aagacaattg caacaaccag    180

aacaagggca acaaggtcag cagccagaac aagggcagca aggtcagcag caaagacaag    240

gggagcaagg tcagcagcca ggacaagggc aacaagggca gcaaccggga caagggcagc    300

cagggtacta cccaacttct ccgcagcagt caggacaagg gcaaccaggg tactacccaa    360

cttctccaca gcagtcagga caattgcaac aaccagcaca agggcagcaa ccaggacaag    420

agcaacaagg tcaacagcca ggacaagggc agcaaccggg acaagggcaa gccagggtac    480

tacccaactt ctccgcagca gtcaggacaa gagcaacagc tagaacaatg gcaacagtca    540

ggacaggggc aaccagggca ctacccaact tctccgttgc aagccaggac aagggcaacc    600

agggtactac ccaacttctc acaacagata ggacaagggc agcagccaag aacaatttgc    660

acaaccaaca caagggcaac aangggcagc aaccaaggac aangggcaac aaggtcaaca    720

gcccangaaa aaaggcaaca aaggtcaagc aaccaagnac aaggggcagc aanccaggac    780
```

-continued

```
aagggcagcc anggtcctac ccaacttntt ttgagcaagt canggaaaag gggcaccanc    840

cnagganaaa tgggnaccac ccagnacaag gacaaccccg ggtcttcccc aaantttttn    900

cn                                                                   902
```

<210> SEQ ID NO 55
<211> LENGTH: 255
<212> TYPE: PRT
<213> ORGANISM: Lycopersicon esculentum
<220> FEATURE:
<221> NAME/KEY: MOD_RES
<222> LOCATION: (1)..(255)
<223> OTHER INFORMATION: tomato 8106032
<223> OTHER INFORMATION: Xaa = any amino acid

<400> SEQUENCE: 55

```
Met Ser Leu Ala Ala His Phe Pro Leu Lys Thr Asp Ser Thr Gln Lys
  1               5                  10                  15

His Glu Gly Asn Thr Gly Ile Ile Ile Glu Glu Pro Glu Glu Cys Ala
             20                  25                  30

Thr Asp Pro Asn Val Ser Ile Arg Trp Tyr Glu Asp Gln Pro Asn Gln
         35                  40                  45

Ser Thr His Cys Gln Asp Ser Ser Gly Val Tyr Asn Thr Asp Ser Asn
     50                  55                  60

Glu Glu Lys Pro Ala Val Asn Asp Ser Glu Ser Ser Glu Asn Ser Thr
 65                  70                  75                  80

Glu Cys Ile Lys Ser Ala Glu Cys Ser Val Ile Leu Gln Ser Asp Ser
                 85                  90                  95

Ser Arg Glu Gly Ser Asp Leu Tyr His Gly Ser Thr Val Thr Ser Ser
            100                 105                 110

Gln Asp Arg Lys Glu Leu Asn Asp Leu Pro Ser Ser Pro Ser Ser Val
        115                 120                 125

Val Ser Ser Glu Ile Ser Ala Val Ile Gln Ala Ser Glu Gly Thr Asp
    130                 135                 140

Ser Ser Asn Phe Cys Ser Ser Thr Ser Phe Leu Lys Leu Leu Gln Met
145                 150                 155                 160

Ala Gly Thr Ser Gly Ala Gln Gly Thr Arg Cys Thr Glu His Leu His
                165                 170                 175

Asn Gln His Lys Gly Asn Xaa Gly Gln Gln Pro Arg Thr Xaa Gly Asn
            180                 185                 190

Lys Val Asn Ser Pro Xaa Lys Lys Ala Thr Lys Val Lys Gln Pro Xaa
        195                 200                 205

Thr Arg Gly Ser Xaa Pro Gly Gln Gly Gln Pro Xaa Ser Tyr Pro Thr
    210                 215                 220

Xaa Phe Glu Gln Val Xaa Glu Lys Gly His Xaa Pro Arg Xaa Asn Gly
225                 230                 235                 240

Xaa His Pro Xaa Gln Gly Gln Pro Arg Val Phe Pro Lys Xaa Phe
                245                 250                 255
```

<210> SEQ ID NO 56
<211> LENGTH: 589
<212> TYPE: DNA
<213> ORGANISM: Lycopersicon esculentum
<220> FEATURE:
<223> OTHER INFORMATION: tomato 8106032 EST356474

<400> SEQUENCE: 56

```
ctcgtgccgg ttggggtata tcttacacag aatgtttcag atcacctttc tagttctgca     60
```

-continued

```
ttcatgtcac tcgctgccca ctttcctctg aaaacagaca gtactcagaa gcatgaagga    120

aatacaggta ttataattga agaacctgaa gagtgtgcaa cagaccccaa tgtttccatc    180

agatggtatg aagatcaacc aaatcagtca acccattgtc aggattcttc aggagtctat    240

aatacagatt caaatgaaga aaaaccagct gtcaatgact ctgaatcaag tgaaaatagc    300

acagaatgca taaaatcagc agaatgttct gtaattctgc aatcagattc ttctagagaa    360

ggctcagatc tgtatcatgg atcaacagtt acaagttccc aagatcgaaa agagttgaat    420

gatttgcctt cttctccgag ttctgttgtt tcttctgaga tctctgctgt tattcaagct    480

tcagaaggaa ctgactcaag caacttttgc agctccactt ctttttgaa gctattacag    540

atggcaggaa cttcaggagc acaaggaacc aggtgcactg aacatctac               589
```

<210> SEQ ID NO 57
<211> LENGTH: 179
<212> TYPE: PRT
<213> ORGANISM: Zea mays
<220> FEATURE:
<223> OTHER INFORMATION: corn AW042334

<400> SEQUENCE: 57

```
Asp Ala His Pro Leu Leu Gln Gln Leu Gly Leu Asp Gln Arg Glu His
  1               5                  10                  15

Asp Asp Pro Thr Pro Tyr Leu Leu Ala Ile Trp Thr Pro Asp Gly Ile
             20                  25                  30

Lys Glu Ile Thr Lys Thr Pro Lys Pro Cys Cys Asp Pro Gln Met Gly
         35                  40                  45

Gly Asp Leu Cys Asn Asn Glu Met Cys His Asn Cys Thr Ala Glu Lys
     50                  55                  60

Glu Asn Gln Ser Arg Tyr Val Arg Gly Thr Ile Leu Val Pro Cys Arg
 65                  70                  75                  80

Thr Ala Met Arg Gly Ser Phe Pro Leu Asn Gly Thr Tyr Phe Gln Val
                 85                  90                  95

Asn Glu Val Phe Ala Asp His Arg Ser Ser His Asn Pro Ile His Val
            100                 105                 110

Glu Arg Glu Met Leu Trp Asn Leu Gln Arg Arg Met Val Phe Phe Gly
        115                 120                 125

Thr Ser Val Pro Thr Ile Phe Lys Gly Leu Arg Thr Glu Glu Ile Gln
    130                 135                 140

Gln Cys Phe Trp Arg Gly Phe Val Cys Val Arg Gly Phe Asp Met Glu
145                 150                 155                 160

Thr Arg Ala Pro Arg Pro Leu Cys Pro His Leu His Val Ile Ala Arg
                165                 170                 175

Pro Lys Ala
```

<210> SEQ ID NO 58
<211> LENGTH: 595
<212> TYPE: DNA
<213> ORGANISM: Zea mays
<220> FEATURE:
<223> OTHER INFORMATION: corn AW042334 EST614027C01.y1 614

<400> SEQUENCE: 58

```
gaattcggca ccagcagatg cacatccact tttacaacag ctaggacttg accaacggga     60

acatgatgat cctaccccat acttattggc catatggaca ccagatggaa taaaggaaat    120

aactaagaca ccaaaaccat gctgtgaccc tcaaatggga ggcgatttat gcaataatga    180
```

-continued

```
aatgtgccac aattgtactg cagagaaaga aaaccaatct agatatgtca gaggcacaat    240

tctggttcct tgtcgaacag ctatgagggg tagtttccca cttaatggca cttactttca    300

agtcaatgag gtatttgctg accacagatc tagccacaac ccaatccatg tggaaaggga    360

gatgctatgg aacttgcaaa ggcgcatggt ctttttcggg acttcagtac ccaccatatt    420

caaaggtcta agaacagaag aaatacaaca atgcttctgg aggggatttg tctgtgtgcg    480

aggattcgac atggagacta gagcaccaag gcctctgtgc ccccatttgc acgttatagc    540

aaggccgaaa gcccgcaaga cagcagcaac tgagcaagta ctctaatcag caaag         595
```

```
<210> SEQ ID NO 59
<211> LENGTH: 150
<212> TYPE: PRT
<213> ORGANISM: Zea mays
<220> FEATURE:
<223> OTHER INFORMATION: corn AW076298

<400> SEQUENCE: 59

Pro Cys Arg Thr Ala Met Arg Gly Ser Phe Pro Leu Asn Gly Thr Tyr
  1               5                  10                  15

Phe Gln Val Asn Glu Val Phe Ala Asp His Cys Ser Ser Gln Asn Pro
             20                  25                  30

Ile Asp Val Pro Arg Ser Trp Ile Trp Asp Leu Pro Arg Arg Thr Val
         35                  40                  45

Tyr Phe Gly Thr Ser Val Pro Thr Ile Phe Arg Gly Leu Ser Thr Glu
     50                  55                  60

Gln Ile Gln Phe Cys Phe Trp Lys Gly Phe Val Cys Val Arg Gly Phe
 65                  70                  75                  80

Glu Gln Lys Thr Arg Ala Pro Arg Pro Leu Met Ala Arg Leu His Phe
                 85                  90                  95

Pro Ala Ser Lys Leu Lys Asn Asn Lys Leu Thr Thr Glu Glu Ile Gln
            100                 105                 110

Gln Cys Phe Trp Arg Gly Phe Val Cys Val Arg Gly Phe Asp Arg Thr
        115                 120                 125

Val Arg Ala Pro Arg Pro Leu Tyr Ala Arg Leu His Phe Pro Ala Ser
    130                 135                 140

Lys Val Val Arg Gly Lys
145                 150
```

```
<210> SEQ ID NO 60
<211> LENGTH: 640
<212> TYPE: DNA
<213> ORGANISM: Zea mays
<220> FEATURE:
<223> OTHER INFORMATION: corn AW076298 EST614065C03.y1 614

<400> SEQUENCE: 60

cggccccaga ccatgccgga cagcaatgag aggaagcttc ccacttaatg ggacatattt     60

tcaagttaat gaggtatttg ctgaccattg ttcaagccaa aatccaattg atgtcccacg    120

aagttggata tgggacctcc caagacgaac tgtttacttt ggaacctcag ttcctacaat    180

atttagaggt ttaacgactg aagagataca acaatgcttt tggagaggat tcgtttgtgt    240

gaggggcttt gataggacag taagggcacc aaggcccctt tatgcaaggt tgcattttcc    300

tgccagcaag gttgttagag gcaaaaagcc tggagcggca agcgtcgaag aataataggt    360

acatcgaaga aatatagagg agctaacaaa acggatggat agccctaaat gagatgctga    420
```

-continued

```
cccaataagt cgccgaatca cctccaagtt ctaacccaat ttttgaggcg acatgacctg    480

ttaaattatg ttccatctat ggtaacagct tagatgttct tgtgagtcgc atattcttta    540

ctctgaaatt caatatagca aatgaaaaaa aacacagtgc atagtctagt tctaattgta    600

cctgtgagtg gaatcagttg ttgtacaaca tgaagatggg                          640
```

<210> SEQ ID NO 61
<211> LENGTH: 140
<212> TYPE: PRT
<213> ORGANISM: Zea mays
<220> FEATURE:
<223> OTHER INFORMATION: corn BE639158

<400> SEQUENCE: 61

```
Lys Asn Ser Glu Pro Ile Ile Glu Glu Pro Ala Ser Pro Arg Glu Glu
  1               5                  10                  15

Arg Pro Pro Glu Thr Met Glu Asn Asp Ile Glu Asp Phe Tyr Glu Asp
             20                  25                  30

Gly Glu Ile Pro Thr Ile Lys Leu Asn Met Glu Ala Phe Ala Gln Asn
         35                  40                  45

Leu Glu Asn Cys Ile Lys Glu Ser Asn Asn Glu Leu Gln Ser Asp Asp
     50                  55                  60

Ile Ala Lys Ala Leu Val Ala Ile Ser Thr Glu Ala Ala Ser Ile Pro
 65                  70                  75                  80

Val Pro Lys Leu Lys Asn Val Leu Arg Leu Arg Thr Glu His Tyr Val
                 85                  90                  95

Tyr Glu Leu Pro Asp Ala His Pro Leu Leu Gln Gln Leu Gly Leu Asp
            100                 105                 110

Gln Arg Glu His Asp Asp Pro Thr Pro Tyr Leu Leu Ala Ile Trp Thr
        115                 120                 125

Pro Asp Gly Ile Lys Glu Ile Thr Lys Thr Pro Lys
    130                 135                 140
```

<210> SEQ ID NO 62
<211> LENGTH: 561
<212> TYPE: DNA
<213> ORGANISM: Zea mays
<220> FEATURE:
<223> OTHER INFORMATION: corn BE639158 EST946021E09.y1 946

<400> SEQUENCE: 62

```
tgagctgcat tatcagatga ttacatttgg aaaggtcttt tgtaccaaaa gacagccaaa     60

ttgcaatgca tgctatgaat tcgactcacc tacctcgcct tgaggggagt atccattcaa    120

gggagtttct tcctaagaat tcagagccaa taatcgagga gcctgcaagt ccaagagagg    180

aaagacctcc agaaaccatg gaaaatgata ttgaagattt ttatgaagat ggtgaaatcc    240

caacaataaa gcttaacatg gaagcttttg cacaaaactt ggagaattgc attaaagaaa    300

gcaataacga actccagtct gatgatattg caaaagcatt ggttgctatt agcactgaag    360

cagcttcgat tcctgtaccg aaactaaaga atgtgcttag gcttcgaaca gaacactatg    420

tgtatgagct tccagatgca catccacttt tacaacagct aggacttgac caacgggaac    480

atgatgatcc taccccatac ttattggcca tatggacacc agatggaata aaggaaataa    540

ctaagacacc aaaaccatgc t                                              561
```

<210> SEQ ID NO 63
<211> LENGTH: 138
<212> TYPE: PRT

-continued

```
<213> ORGANISM: Zea mays
<220> FEATURE:
<221> NAME/KEY: MOD_RES
<222> LOCATION: (63)
<223> OTHER INFORMATION: corn T25243
<220> FEATURE:
<221> NAME/KEY: MOD_RES
<222> LOCATION: (114)
<223> OTHER INFORMATION: Xaa = Asp or Glu
<223> OTHER INFORMATION: Xaa = Cys, Trp, Arg, Ser or Gly

<400> SEQUENCE: 63

Asn His Gln Pro Ile Ile Glu Glu Pro Leu Ser Pro Glu Cys Glu Thr
  1               5                  10                  15

Glu Asn Ile Glu Ala His Glu Gly Ala Ile Glu Asp Phe Phe Cys Glu
             20                  25                  30

Glu Ser Asp Glu Ile Pro Thr Ile Asn Leu Asn Ile Glu Glu Phe Thr
         35                  40                  45

Gln Asn Leu Lys Asp Tyr Met Gln Ala Asn Asn Val Glu Ile Xaa Tyr
     50                  55                  60

Ala Asp Met Ser Lys Ala Leu Val Ala Ile Thr Pro Asp Ala Ala Ser
 65                  70                  75                  80

Ile Pro Thr Pro Lys Leu Lys Asn Val Asn Arg Leu Arg Thr Glu His
                 85                  90                  95

Gln Val Tyr Glu Leu Pro Asp Ser His Pro Leu Leu Glu Gly Phe Glu
            100                 105                 110

Gln Xaa Glu Pro Asp Asp Pro Cys Pro Tyr Leu Leu Ser Ile Trp Thr
        115                 120                 125

Pro Gly Glu Leu His Asn Arg Ser Met Pro
    130                 135


<210> SEQ ID NO 64
<211> LENGTH: 422
<212> TYPE: DNA
<213> ORGANISM: Zea mays
<220> FEATURE:
<221> NAME/KEY: modified_base
<222> LOCATION: (1)..(422)
<223> OTHER INFORMATION: corn T25243 EST5c10h02
<223> OTHER INFORMATION: n = g, a, c or t

<400> SEQUENCE: 64

ctggtaatca tcagccaatc atcgaggaac cactgagccc agaatgtgaa actgaaaata      60

tagaggcaca tgagggtgca attgaggatt tcttttgtga agaatctgat gaaattccta     120

ccattaatct taatatcgag gagttcacac aaaacttgaa ggactatatg caagcaaaca     180

atgttgagat tgantatgct gacatgtcaa aggcattggt tgccatcacg cctgatgctg     240

cttccattcc aactccaaag ctcaagaatg tcaatcgtct gaggacagaa caccaagttt     300

atgaactgcc agattcacac cctcttctgg aaggattcga acagngngaa ccagatgatc     360

cctgtccata tcttctttcc atatggaccc caggtgaact gcacaatcga tcgatgcccc     420

aa                                                                    422


<210> SEQ ID NO 65
<211> LENGTH: 89
<212> TYPE: PRT
<213> ORGANISM: Zea mays
<220> FEATURE:
<223> OTHER INFORMATION: corn AW453174

<400> SEQUENCE: 65
```

-continued

```
Phe Gln Gly Asn Glu Val Phe Ala Asp His Cys Ser Arg Gln Asn Pro
  1               5                  10                  15

Ile Asp Gly Pro Arg Ser Trp Ile Trp Asp Leu Pro Arg Arg Thr Gly
             20                  25                  30

Tyr Phe Gly Thr Ser Gly Pro Thr Ile Phe Arg Gly Leu Thr Thr Glu
         35                  40                  45

Glu Ile Gln Arg Cys Phe Trp Arg Gly Phe Val Cys Val Arg Gly Phe
     50                  55                  60

Asp Arg Thr Val Arg Ala Pro Arg Pro Leu Tyr Ala Arg Leu His Phe
 65                  70                  75                  80

Pro Val Ser Lys Val Val Arg Gly Lys
                 85
```

<210> SEQ ID NO 66
<211> LENGTH: 488
<212> TYPE: DNA
<213> ORGANISM: Zea mays
<220> FEATURE:
<223> OTHER INFORMATION: corn AW453174 EST 660032D01.y1 660

<400> SEQUENCE: 66

```
catgccgaac agcaatgaga ggaagcttcc cacttaatgg gacgattttc aaggtaatga      60

ggtatttgct gaccattgct caaggcaaaa tccaattgat ggcccacgaa gttggatttg     120

ggaccttcca agacgaactg gttactttgg aacctcaggt cctacaatat tcagagggtt     180

aacgactgaa gagatacaac gatgcttttg gagaggattt gtttgcgtga ggggctttga     240

taggacagtg cgggcaccaa ggcccccttta tgcaaggttg cattttcctg tcagcaaggt     300

tgttagaggc aaaaagcctg gagcagcaag agcagaagaa taatagaaca ttgaagaaat     360

ataggggtgc taaccagatg aggatggata gcccgaaatg agatgctgac ccaataggtc     420

gccaaatcac ctccaaattc taacccaatg acttccatct gtaatgaatg gcaatacctt     480

gaaaacct                                                              488
```

<210> SEQ ID NO 67
<211> LENGTH: 93
<212> TYPE: PRT
<213> ORGANISM: Zea mays
<220> FEATURE:
<223> OTHER INFORMATION: corn BE509759

<400> SEQUENCE: 67

```
Asn Gly Thr Tyr Phe Gln Val Asn Glu Val Phe Ala Asp His Arg Ser
  1               5                  10                  15

Ser His Asn Pro Ile His Val Glu Arg Glu Met Leu Trp Asn Leu Gln
             20                  25                  30

Arg Arg Met Val Phe Phe Gly Thr Ser Val Pro Thr Ile Phe Lys Gly
         35                  40                  45

Leu Arg Thr Glu Glu Ile Gln Gln Cys Phe Trp Arg Gly Phe Val Cys
     50                  55                  60

Val Arg Gly Phe Asp Met Glu Thr Arg Ala Pro Arg Pro Leu Cys Pro
 65                  70                  75                  80

His Leu His Ile Ile Ala Arg Pro Lys Ala Arg Lys Thr
                 85                  90
```

<210> SEQ ID NO 68
<211> LENGTH: 570
<212> TYPE: DNA
<213> ORGANISM: Zea mays

-continued

<220> FEATURE:
<223> OTHER INFORMATION: corn BE509759 EST946021E09.x1 946

<400> SEQUENCE: 68
tggcatctta catggactaa cagctagatg ctaatttaca tacagtagat ctgaaacaaa 60
aaagtgaaaa ttattggtgc ttcctgatgc ttcattagtc ctctcgtctc agaaactaac 120
agtctcggac cccatccatg gcttaaattt cctaaacaat ggctcttttt taggcaggaa 180
gtaatatgat tccatgcata ggtcgagagc tattgatgtc atatcacaat aaacatgatg 240
ttcataaaac tgatatcttt gctgattaga gtacttgctc agttgctgct gtcttgcggg 300
ccttcggcct tgctataatg tgcaaatggg ggcacagagg ccttggtgct ctagtctcca 360
tgtcgaatcc tcgcacacag acaaatcccc tccagaagca ttgttgtatt tcttctgttc 420
ttagaccttt gaatatggtg ggtactgaag tcccgaaaaa gaccatgcgc ctttgcaagt 480
tccatagcat ctccctttcc acatggattg ggttgtggct agatctgtgg tcagcaaata 540
cctcattgac ttgaaagtaa gtgccattaa 570

<210> SEQ ID NO 69
<211> LENGTH: 71
<212> TYPE: PRT
<213> ORGANISM: Zea mays
<220> FEATURE:
<223> OTHER INFORMATION: corn AW017984

<400> SEQUENCE: 69

Val Pro Arg Ser Trp Ile Trp Asp Leu Pro Arg Arg Thr Val Tyr Phe
1 5 10 15

Gly Thr Ser Val Pro Thr Ile Phe Arg Gly Leu Thr Thr Glu Glu Ile
20 25 30

Gln Gln Cys Phe Trp Arg Gly Phe Val Cys Val Arg Gly Phe Asp Arg
35 40 45

Thr Val Arg Ala Pro Arg Pro Leu Tyr Ala Arg Leu His Phe Pro Ala
50 55 60

Ser Lys Val Val Arg Gly Lys
65 70

<210> SEQ ID NO 70
<211> LENGTH: 613
<212> TYPE: DNA
<213> ORGANISM: Zea mays
<220> FEATURE:
<223> OTHER INFORMATION: corn AW017984 EST614065C03.x1 614

<400> SEQUENCE: 70
cctgaaacaa tcaaataacg gccgatgagg ttacattgtt tatagtatat gatcaaagaa 60
catgtatgac cattgtacaa ataggcccat cttcatgttg tacaacaact gattccactc 120
acaggtacaa ttagaactag actatgcact gtgttttttt tcatttgcta tattgaattt 180
cagagtaaag aatatgcgac tcacaagaac atctaagctg ttaccataga tggaacataa 240
tttaacaggt catgtcgcct caaaaattgg gttagaactt ggaggtgatt cggcgactta 300
ttgggtcagc atctcattta gggctatcca tccgttttgt tagctcctct atatttcttc 360
gatgtaccta ttattcttcg acgcttgccg ctccaggctt tttgcctcta acaaccttgc 420
tggcaggaaa atgcaacctt gcataaaggg gccttggtgc ccttactgtc ctatcaaagc 480
ccctcacaca aacgaatcct ctccaaaagc attgttgtat ctcttcagtc gttaaacctc 540
taaatattgt aggaactgag gttccaaagt aaacagttcg tcttgggagg tcccatatcc 600

-continued

```
aacttcgtgg gac                                                        613


<210> SEQ ID NO 71
<211> LENGTH: 90
<212> TYPE: PRT
<213> ORGANISM: Artificial Sequence
<220> FEATURE:
<223> OTHER INFORMATION: Description of Artificial Sequence:DMT Domain A
      consensus sequence
<220> FEATURE:
<221> NAME/KEY: MOD_RES
<222> LOCATION: (3)
<223> OTHER INFORMATION: Xaa = any amino acid
<220> FEATURE:
<221> NAME/KEY: MOD_RES
<222> LOCATION: (4)
<223> OTHER INFORMATION: Xaa = Ile or Leu
<220> FEATURE:
<221> NAME/KEY: MOD_RES
<222> LOCATION: (6)
<223> OTHER INFORMATION: Xaa = Asp or Pro
<220> FEATURE:
<221> NAME/KEY: MOD_RES
<222> LOCATION: (7)
<223> OTHER INFORMATION: Xaa = Glu or Val
<220> FEATURE:
<221> NAME/KEY: MOD_RES
<222> LOCATION: (9)..(11)
<223> OTHER INFORMATION: Xaa = any amino acid
<220> FEATURE:
<221> NAME/KEY: MOD_RES
<222> LOCATION: (13)
<223> OTHER INFORMATION: Xaa = any amino acid
<220> FEATURE:
<221> NAME/KEY: MOD_RES
<222> LOCATION: (14)
<223> OTHER INFORMATION: Xaa = Leu or Val
<220> FEATURE:
<221> NAME/KEY: MOD_RES
<222> LOCATION: (16)
<223> OTHER INFORMATION: Xaa = Met or Leu
<220> FEATURE:
<221> NAME/KEY: MOD_RES
<222> LOCATION: (17)
<223> OTHER INFORMATION: Xaa = Glu or Asp
<220> FEATURE:
<221> NAME/KEY: MOD_RES
<222> LOCATION: (18)..(19)
<223> OTHER INFORMATION: Xaa = any amino acid, Xaa at positions 18 and
      19 may be present or absent
<220> FEATURE:
<221> NAME/KEY: MOD_RES
<222> LOCATION: (21)
<223> OTHER INFORMATION: Xaa = Lys or Glu
<220> FEATURE:
<221> NAME/KEY: MOD_RES
<222> LOCATION: (22)
<223> OTHER INFORMATION: Xaa = any amino acid
<220> FEATURE:
<221> NAME/KEY: MOD_RES
<222> LOCATION: (23)
<223> OTHER INFORMATION: Xaa = Lys or Thr
<220> FEATURE:
<221> NAME/KEY: MOD_RES
<222> LOCATION: (24)
<223> OTHER INFORMATION: Xaa = any amino acid
<220> FEATURE:
<221> NAME/KEY: MOD_RES
<222> LOCATION: (25)
<223> OTHER INFORMATION: Xaa = Lys or Ala
<220> FEATURE:
<221> NAME/KEY: MOD_RES
<222> LOCATION: (26)
<223> OTHER INFORMATION: Xaa = Trp or Lys
<220> FEATURE:
<221> NAME/KEY: MOD_RES
<222> LOCATION: (27)
```

-continued

<223> OTHER INFORMATION: Xaa = Trp or Leu
<220> FEATURE:
<221> NAME/KEY: MOD_RES
<222> LOCATION: (28)
<223> OTHER INFORMATION: Xaa = any amino acid
<220> FEATURE:
<221> NAME/KEY: MOD_RES
<222> LOCATION: (32)..(33)
<223> OTHER INFORMATION: Xaa = any amino acid
<220> FEATURE:
<221> NAME/KEY: MOD_RES
<222> LOCATION: (35)
<223> OTHER INFORMATION: Xaa = any amino acid
<220> FEATURE:
<221> NAME/KEY: MOD_RES
<222> LOCATION: (36)
<223> OTHER INFORMATION: Xaa = Gly or Thr
<220> FEATURE:
<221> NAME/KEY: MOD_RES
<222> LOCATION: (38)
<223> OTHER INFORMATION: Xaa = any amino acid
<220> FEATURE:
<221> NAME/KEY: MOD_RES
<222> LOCATION: (39)
<223> OTHER INFORMATION: Xaa = Asp or Asn
<220> FEATURE:
<221> NAME/KEY: MOD_RES
<222> LOCATION: (40)
<223> OTHER INFORMATION: Xaa = Ser or Leu
<220> FEATURE:
<221> NAME/KEY: MOD_RES
<222> LOCATION: (43)
<223> OTHER INFORMATION: Xaa = Ala or Asn
<220> FEATURE:
<221> NAME/KEY: MOD_RES
<222> LOCATION: (46)
<223> OTHER INFORMATION: Xaa = His or Arg
<220> FEATURE:
<221> NAME/KEY: MOD_RES
<222> LOCATION: (47)
<223> OTHER INFORMATION: Xaa = any amino acid
<220> FEATURE:
<221> NAME/KEY: MOD_RES
<222> LOCATION: (48)
<223> OTHER INFORMATION: Xaa = Val or Leu
<220> FEATURE:
<221> NAME/KEY: MOD_RES
<222> LOCATION: (51)
<223> OTHER INFORMATION: Xaa = Asp or Asn
<220> FEATURE:
<221> NAME/KEY: MOD_RES
<222> LOCATION: (53)
<223> OTHER INFORMATION: Xaa = any amino acid
<220> FEATURE:
<221> NAME/KEY: MOD_RES
<222> LOCATION: (55)
<223> OTHER INFORMATION: Xaa = any amino acid
<220> FEATURE:
<221> NAME/KEY: MOD_RES
<222> LOCATION: (56)
<223> OTHER INFORMATION: Xaa = Pro or Gln
<220> FEATURE:
<221> NAME/KEY: MOD_RES
<222> LOCATION: (66)
<223> OTHER INFORMATION: Xaa = Ile or Val
<220> FEATURE:
<221> NAME/KEY: MOD_RES
<222> LOCATION: (74)
<223> OTHER INFORMATION: Xaa = Val or Thr
<220> FEATURE:
<221> NAME/KEY: MOD_RES
<222> LOCATION: (76)
<223> OTHER INFORMATION: Xaa = Val or Thr
<220> FEATURE:
<221> NAME/KEY: MOD_RES
<222> LOCATION: (77)
<223> OTHER INFORMATION: Xaa = Leu or Ser
<220> FEATURE:
<221> NAME/KEY: MOD_RES -continued

```
<222> LOCATION: (80)
<223> OTHER INFORMATION: Xaa = Ser or Asn
<220> FEATURE:
<221> NAME/KEY: MOD_RES
<222> LOCATION: (82)
<223> OTHER INFORMATION: Xaa = Phe or Tyr
<220> FEATURE:
<221> NAME/KEY: MOD_RES
<222> LOCATION: (84)
<223> OTHER INFORMATION: Xaa = any amino acid
<220> FEATURE:
<221> NAME/KEY: MOD_RES
<222> LOCATION: (85)
<223> OTHER INFORMATION: Xaa = Leu or Val
<220> FEATURE:
<221> NAME/KEY: MOD_RES
<222> LOCATION: (87)
<223> OTHER INFORMATION: Xaa = Ala or Ser
<220> FEATURE:
<221> NAME/KEY: MOD_RES
<222> LOCATION: (88)
<223> OTHER INFORMATION: Xaa = any amino acid

<400> SEQUENCE: 71

Lys Val Xaa Xaa Asp Xaa Xaa Thr Xaa Xaa Xaa Trp Xaa Xaa Leu Xaa
  1               5                  10                  15

Xaa Xaa Xaa Asp Xaa Xaa Xaa Xaa Xaa Xaa Xaa Xaa Xaa Glu Arg Xaa
             20                  25                  30

Xaa Phe Xaa Xaa Arg Xaa Xaa Xaa Phe Ile Xaa Arg Met Xaa Xaa Xaa
         35                  40                  45

Gln Gly Xaa Arg Xaa Phe Xaa Xaa Trp Lys Gly Ser Val Val Asp Ser
     50                  55                  60

Val Xaa Gly Val Phe Leu Thr Gln Asn Xaa Asp Xaa Xaa Ser Ser Xaa
 65                  70                  75                  80

Ala Xaa Met Xaa Xaa Ala Xaa Xaa Phe Pro
                 85                  90


<210> SEQ ID NO 72
<211> LENGTH: 230
<212> TYPE: PRT
<213> ORGANISM: Artificial Sequence
<220> FEATURE:
<223> OTHER INFORMATION: Description of Artificial Sequence:DMT Domain B
      consensus sequence
<220> FEATURE:
<221> NAME/KEY: MOD_RES
<222> LOCATION: (2)
<223> OTHER INFORMATION: Xaa = Asp or Asn
<220> FEATURE:
<221> NAME/KEY: MOD_RES
<222> LOCATION: (3)
<223> OTHER INFORMATION: Xaa = any amino acid
<220> FEATURE:
<221> NAME/KEY: MOD_RES
<222> LOCATION: (4)
<223> OTHER INFORMATION: Xaa = Leu or Phe
<220> FEATURE:
<221> NAME/KEY: MOD_RES
<222> LOCATION: (6)..(10)
<223> OTHER INFORMATION: Xaa = any amino acid
<220> FEATURE:
<221> NAME/KEY: MOD_RES
<222> LOCATION: (12)..(17)
<223> OTHER INFORMATION: Xaa = any amino acid, Xaa at positions 15-17
      may be present or absent
<220> FEATURE:
<221> NAME/KEY: MOD_RES
<222> LOCATION: (19)
<223> OTHER INFORMATION: Xaa = Ser or Thr
<220> FEATURE:
<221> NAME/KEY: MOD_RES
<222> LOCATION: (20)
```

-continued

<223> OTHER INFORMATION: Xaa = any amino acid
<220> FEATURE:
<221> NAME/KEY: MOD_RES
<222> LOCATION: (21)
<223> OTHER INFORMATION: Xaa = Asp or Asn
<220> FEATURE:
<221> NAME/KEY: MOD_RES
<222> LOCATION: (22)
<223> OTHER INFORMATION: Xaa = Tyr or Trp
<220> FEATURE:
<221> NAME/KEY: MOD_RES
<222> LOCATION: (23)..(25)
<223> OTHER INFORMATION: Xaa = any amino acid
<220> FEATURE:
<221> NAME/KEY: MOD_RES
<222> LOCATION: (27)..(36)
<223> OTHER INFORMATION: Xaa = any amino acid
<220> FEATURE:
<221> NAME/KEY: MOD_RES
<222> LOCATION: (38)..(39)
<223> OTHER INFORMATION: Xaa = any amino acid
<220> FEATURE:
<221> NAME/KEY: MOD_RES
<222> LOCATION: (42)
<223> OTHER INFORMATION: Xaa = Met or Gln
<220> FEATURE:
<221> NAME/KEY: MOD_RES
<222> LOCATION: (43)
<223> OTHER INFORMATION: Xaa = Asn or Phe
<220> FEATURE:
<221> NAME/KEY: MOD_RES
<222> LOCATION: (44)..(45)
<223> OTHER INFORMATION: Xaa = any amino acid
<220> FEATURE:
<221> NAME/KEY: MOD_RES
<222> LOCATION: (47)
<223> OTHER INFORMATION: Xaa = Ala or Ser
<220> FEATURE:
<221> NAME/KEY: MOD_RES
<222> LOCATION: (48)
<223> OTHER INFORMATION: Xaa = any amino acid
<220> FEATURE:
<221> NAME/KEY: MOD_RES
<222> LOCATION: (51)..(62)
<223> OTHER INFORMATION: Xaa = any amino acid, Xaa at positions 53-62
      may be present or absent
<220> FEATURE:
<221> NAME/KEY: MOD_RES
<222> LOCATION: (65)..(67)
<223> OTHER INFORMATION: Xaa = any amino acid
<220> FEATURE:
<221> NAME/KEY: MOD_RES
<222> LOCATION: (69)..(70)
<223> OTHER INFORMATION: Xaa = any amino acid
<220> FEATURE:
<221> NAME/KEY: MOD_RES
<222> LOCATION: (71)
<223> OTHER INFORMATION: Xaa = His or Asn
<220> FEATURE:
<221> NAME/KEY: MOD_RES
<222> LOCATION: (73)
<223> OTHER INFORMATION: Xaa = any amino acid
<220> FEATURE:
<221> NAME/KEY: MOD_RES
<222> LOCATION: (81)..(82)
<223> OTHER INFORMATION: Xaa = any amino acid
<220> FEATURE:
<221> NAME/KEY: MOD_RES
<222> LOCATION: (83)
<223> OTHER INFORMATION: Xaa = Pro or Asp
<220> FEATURE:
<221> NAME/KEY: MOD_RES
<222> LOCATION: (84)
<223> OTHER INFORMATION: Xaa = Pro or Ser
<220> FEATURE:
<221> NAME/KEY: MOD_RES
<222> LOCATION: (85)
<223> OTHER INFORMATION: Xaa = Asp or His
<220> FEATURE:

-continued

<221> NAME/KEY: MOD_RES
<222> LOCATION: (86)
<223> OTHER INFORMATION: Xaa = any amino acid
<220> FEATURE:
<221> NAME/KEY: MOD_RES
<222> LOCATION: (87)
<223> OTHER INFORMATION: Xaa = Ala or Val
<220> FEATURE:
<221> NAME/KEY: MOD_RES
<222> LOCATION: (89)
<223> OTHER INFORMATION: Xaa = any amino acid
<220> FEATURE:
<221> NAME/KEY: MOD_RES
<222> LOCATION: (90)
<223> OTHER INFORMATION: Xaa = Tyr or Phe
<220> FEATURE:
<221> NAME/KEY: MOD_RES
<222> LOCATION: (93)
<223> OTHER INFORMATION: Xaa = Ser or Glu
<220> FEATURE:
<221> NAME/KEY: MOD_RES
<222> LOCATION: (94)
<223> OTHER INFORMATION: Xaa = Ile or Phe
<220> FEATURE:
<221> NAME/KEY: MOD_RES
<222> LOCATION: (95)
<223> OTHER INFORMATION: Xaa = any amino acid
<220> FEATURE:
<221> NAME/KEY: MOD_RES
<222> LOCATION: (97)
<223> OTHER INFORMATION: Xaa = Leu or Ile
<220> FEATURE:
<221> NAME/KEY: MOD_RES
<222> LOCATION: (102)
<223> OTHER INFORMATION: Xaa = Val or Ala
<220> FEATURE:
<221> NAME/KEY: MOD_RES
<222> LOCATION: (109)
<223> OTHER INFORMATION: Xaa = any amino acid
<220> FEATURE:
<221> NAME/KEY: MOD_RES
<222> LOCATION: (111)
<223> OTHER INFORMATION: Xaa = His or Lys
<220> FEATURE:
<221> NAME/KEY: MOD_RES
<222> LOCATION: (112)..(113)
<223> OTHER INFORMATION: Xaa = any amino acid
<220> FEATURE:
<221> NAME/KEY: MOD_RES
<222> LOCATION: (125)
<223> OTHER INFORMATION: Xaa = Ala or Cys
<220> FEATURE:
<221> NAME/KEY: MOD_RES
<222> LOCATION: (128)
<223> OTHER INFORMATION: Xaa = Met or Leu
<220> FEATURE:
<221> NAME/KEY: MOD_RES
<222> LOCATION: (130)
<223> OTHER INFORMATION: Xaa = Trp or Leu
<220> FEATURE:
<221> NAME/KEY: MOD_RES
<222> LOCATION: (134)
<223> OTHER INFORMATION: Xaa = Gln or Glu
<220> FEATURE:
<221> NAME/KEY: MOD_RES
<222> LOCATION: (138)..(139)
<223> OTHER INFORMATION: Xaa = any amino acid
<220> FEATURE:
<221> NAME/KEY: MOD_RES
<222> LOCATION: (140)
<223> OTHER INFORMATION: Xaa = Leu or Val
<220> FEATURE:
<221> NAME/KEY: MOD_RES
<222> LOCATION: (142)
<223> OTHER INFORMATION: Xaa = Leu or Met
<220> FEATURE:
<221> NAME/KEY: MOD_RES
<222> LOCATION: (144)
<223> OTHER INFORMATION: Xaa = Leu or Gln -continued

```
<220> FEATURE:
<221> NAME/KEY: MOD_RES
<222> LOCATION: (146)
<223> OTHER INFORMATION: Xaa = Glu or Phe
<220> FEATURE:
<221> NAME/KEY: MOD_RES
<222> LOCATION: (147)
<223> OTHER INFORMATION: Xaa = any amino acid
<220> FEATURE:
<221> NAME/KEY: MOD_RES
<222> LOCATION: (150)
<223> OTHER INFORMATION: Xaa = any amino acid
<220> FEATURE:
<221> NAME/KEY: MOD_RES
<222> LOCATION: (151)
<223> OTHER INFORMATION: Xaa = Leu or Met
<220> FEATURE:
<221> NAME/KEY: MOD_RES
<222> LOCATION: (152)
<223> OTHER INFORMATION: Xaa = Glu or Asp
<220> FEATURE:
<221> NAME/KEY: MOD_RES
<222> LOCATION: (153)
<223> OTHER INFORMATION: Xaa = Ser or Asn
<220> FEATURE:
<221> NAME/KEY: MOD_RES
<222> LOCATION: (154)
<223> OTHER INFORMATION: Xaa = Ile or Val
<220> FEATURE:
<221> NAME/KEY: MOD_RES
<222> LOCATION: (166)
<223> OTHER INFORMATION: Xaa = Asp or Pro
<220> FEATURE:
<221> NAME/KEY: MOD_RES
<222> LOCATION: (168)
<223> OTHER INFORMATION: Xaa = any amino acid
<220> FEATURE:
<221> NAME/KEY: MOD_RES
<222> LOCATION: (176)
<223> OTHER INFORMATION: Xaa = Gln or His
<220> FEATURE:
<221> NAME/KEY: MOD_RES
<222> LOCATION: (177)
<223> OTHER INFORMATION: Xaa = Leu or Met
<220> FEATURE:
<221> NAME/KEY: MOD_RES
<222> LOCATION: (183)..(184)
<223> OTHER INFORMATION: Xaa = any amino acid, Xaa at positions 183 and
      184 may be present of absent
<220> FEATURE:
<221> NAME/KEY: MOD_RES
<222> LOCATION: (189)..(190)
<223> OTHER INFORMATION: Xaa = any amino acid
<220> FEATURE:
<221> NAME/KEY: MOD_RES
<222> LOCATION: (199)
<223> OTHER INFORMATION: Xaa = Arg or Lys
<220> FEATURE:
<221> NAME/KEY: MOD_RES
<222> LOCATION: (200)..(201)
<223> OTHER INFORMATION: Xaa = any amino acid, Xaa at positions 200 and
      201 may be present or absent
<220> FEATURE:
<221> NAME/KEY: MOD_RES
<222> LOCATION: (204)
<223> OTHER INFORMATION: Xaa = Arg or Lys
<220> FEATURE:
<221> NAME/KEY: MOD_RES
<222> LOCATION: (205)
<223> OTHER INFORMATION: Xaa = His or Tyr
<220> FEATURE:
<221> NAME/KEY: MOD_RES
<222> LOCATION: (206)
<223> OTHER INFORMATION: Xaa = Phe or Tyr
<220> FEATURE:
<221> NAME/KEY: MOD_RES
<222> LOCATION: (207)
<223> OTHER INFORMATION: Xaa = Ala or Ser
<220> FEATURE:
```

-continued

```
<221> NAME/KEY: MOD_RES
<222> LOCATION: (210)
<223> OTHER INFORMATION: Xaa = any amino acid
<220> FEATURE:
<221> NAME/KEY: MOD_RES
<222> LOCATION: (211)
<223> OTHER INFORMATION: Xaa = Ala or Val
<220> FEATURE:
<221> NAME/KEY: MOD_RES
<222> LOCATION: (212)..(221)
<223> OTHER INFORMATION: Xaa = any amino acid, Xaa at positions 212-221
      may be present or absent
<220> FEATURE:
<221> NAME/KEY: MOD_RES
<222> LOCATION: (223)
<223> OTHER INFORMATION: Xaa = Ala or Ser
<220> FEATURE:
<221> NAME/KEY: MOD_RES
<222> LOCATION: (224)
<223> OTHER INFORMATION: Xaa = Arg or Lys
<220> FEATURE:
<221> NAME/KEY: MOD_RES
<222> LOCATION: (225)
<223> OTHER INFORMATION: Xaa = any amino acid
<220> FEATURE:
<221> NAME/KEY: MOD_RES
<222> LOCATION: (226)
<223> OTHER INFORMATION: Xaa = Ala or Leu
<220> FEATURE:
<221> NAME/KEY: MOD_RES
<222> LOCATION: (228)
<223> OTHER INFORMATION: Xaa = Pro or Glu
<220> FEATURE:
<221> NAME/KEY: MOD_RES
<222> LOCATION: (229)
<223> OTHER INFORMATION: Xaa = any amino acid
<220> FEATURE:
<221> NAME/KEY: MOD_RES
<222> LOCATION: (230)
<223> OTHER INFORMATION: Xaa = Pro or Thr

<400> SEQUENCE: 72

Trp Xaa Xaa Xaa Arg Xaa Xaa Xaa Xaa Xaa Glu Xaa Xaa Xaa Xaa Xaa
  1               5                  10                  15

Xaa Asp Xaa Xaa Xaa Xaa Xaa Xaa Xaa Arg Xaa Xaa Xaa Xaa Xaa Xaa
             20                  25                  30

Xaa Xaa Xaa Xaa Ile Xaa Xaa Arg Gly Xaa Xaa Xaa Xaa Leu Xaa Xaa
         35                  40                  45

Arg Ile Xaa Xaa Xaa Xaa Xaa Xaa Xaa Xaa Xaa Xaa Xaa Xaa Phe Leu
     50                  55                  60

Xaa Xaa Xaa Val Xaa Xaa Xaa Gly Xaa Ile Asp Leu Glu Trp Leu Arg
 65                  70                  75                  80

Xaa Xaa Xaa Xaa Xaa Xaa Xaa Lys Xaa Xaa Leu Leu Xaa Xaa Xaa Gly
                 85                  90                  95

Xaa Gly Leu Lys Ser Xaa Glu Cys Val Arg Leu Leu Xaa Leu Xaa Xaa
            100                 105                 110

Xaa Ala Phe Pro Val Asp Thr Asn Val Gly Arg Ile Xaa Val Arg Xaa
        115                 120                 125

Gly Xaa Val Pro Leu Xaa Pro Leu Pro Xaa Xaa Xaa Gln Xaa His Xaa
    130                 135                 140

Leu Xaa Xaa Tyr Pro Xaa Xaa Xaa Xaa Xaa Gln Lys Xaa Leu Trp Pro
145                 150                 155                 160

Arg Leu Cys Lys Leu Xaa Gln Xaa Thr Leu Tyr Glu Leu His Tyr Xaa
                165                 170                 175

Xaa Ile Thr Phe Gly Lys Xaa Xaa Phe Cys Thr Lys Xaa Xaa Pro Asn
            180                 185                 190
```

-continued

```
Cys Asn Ala Cys Pro Met Xaa Xaa Xaa Glu Cys Xaa Xaa Xaa Xaa Ser
        195                 200                 205

Ala Xaa Xaa Xaa Xaa Xaa Xaa Xaa Xaa Xaa Xaa Xaa Xaa Ser Xaa Xaa
    210                 215                 220

Xaa Xaa Leu Xaa Xaa Xaa
225                 230
```

```
<210> SEQ ID NO 73
<211> LENGTH: 292
<212> TYPE: PRT
<213> ORGANISM: Artificial Sequence
<220> FEATURE:
<223> OTHER INFORMATION: Description of Artificial Sequence:DMT Domain C
      consensus sequence
<220> FEATURE:
<221> NAME/KEY: MOD_RES
<222> LOCATION: (2)
<223> OTHER INFORMATION: Xaa = Ile or Leu
<220> FEATURE:
<221> NAME/KEY: MOD_RES
<222> LOCATION: (3)
<223> OTHER INFORMATION: Xaa = Ile or Val
<220> FEATURE:
<221> NAME/KEY: MOD_RES
<222> LOCATION: (5)
<223> OTHER INFORMATION: Xaa = Glu or Phe
<220> FEATURE:
<221> NAME/KEY: MOD_RES
<222> LOCATION: (7)
<223> OTHER INFORMATION: Xaa = any amino acid
<220> FEATURE:
<221> NAME/KEY: MOD_RES
<222> LOCATION: (8)
<223> OTHER INFORMATION: Xaa = Ser or Thr
<220> FEATURE:
<221> NAME/KEY: MOD_RES
<222> LOCATION: (10)..(14)
<223> OTHER INFORMATION: Xaa = any amino acid, Xaa at positions 12-14
      may be present or absent
<220> FEATURE:
<221> NAME/KEY: MOD_RES
<222> LOCATION: (16)..(30)
<223> OTHER INFORMATION: Xaa = any amino acid, Xaa at positions 16-30
      may be present or absent
<220> FEATURE:
<221> NAME/KEY: MOD_RES
<222> LOCATION: (31)
<223> OTHER INFORMATION: Xaa = Asp or Ala
<220> FEATURE:
<221> NAME/KEY: MOD_RES
<222> LOCATION: (34)
<223> OTHER INFORMATION: Xaa = Asp or Glu
<220> FEATURE:
<221> NAME/KEY: MOD_RES
<222> LOCATION: (35)..(57)
<223> OTHER INFORMATION: Xaa = any amino acid, Xaa at positions 39-57
      may be present or absent
<220> FEATURE:
<221> NAME/KEY: MOD_RES
<222> LOCATION: (58)
<223> OTHER INFORMATION: Xaa = Ile or Val
<220> FEATURE:
<221> NAME/KEY: MOD_RES
<222> LOCATION: (60)
<223> OTHER INFORMATION: Xaa = any amino acid
<220> FEATURE:
<221> NAME/KEY: MOD_RES
<222> LOCATION: (62)
<223> OTHER INFORMATION: Xaa = any amino acid
<220> FEATURE:
<221> NAME/KEY: MOD_RES
<222> LOCATION: (63)
<223> OTHER INFORMATION: Xaa = Leu or Phe
<220> FEATURE:
<221> NAME/KEY: MOD_RES
<222> LOCATION: (64)
```

-continued

<223> OTHER INFORMATION: Xaa = Asn or Asp
<220> FEATURE:
<221> NAME/KEY: MOD_RES
<222> LOCATION: (65)..(81)
<223> OTHER INFORMATION: Xaa = any amino acid, Xaa at positions 73-81
may be present or absent
<220> FEATURE:
<221> NAME/KEY: MOD_RES
<222> LOCATION: (82)
<223> OTHER INFORMATION: Xaa = Ser or Ala
<220> FEATURE:
<221> NAME/KEY: MOD_RES
<222> LOCATION: (83)
<223> OTHER INFORMATION: Xaa = any amino acid
<220> FEATURE:
<221> NAME/KEY: MOD_RES
<222> LOCATION: (84)
<223> OTHER INFORMATION: Xaa = Ala or Asp
<220> FEATURE:
<221> NAME/KEY: MOD_RES
<222> LOCATION: (87)..(94)
<223> OTHER INFORMATION: Xaa = any amino acid
<220> FEATURE:
<221> NAME/KEY: MOD_RES
<222> LOCATION: (95)
<223> OTHER INFORMATION: Xaa = Ile or Leu
<220> FEATURE:
<221> NAME/KEY: MOD_RES
<222> LOCATION: (97)..(101)
<223> OTHER INFORMATION: Xaa = any amino acid, Xaa at positions 99-101
may be present or absent
<220> FEATURE:
<221> NAME/KEY: MOD_RES
<222> LOCATION: (102)
<223> OTHER INFORMATION: Xaa = Lys or Arg
<220> FEATURE:
<221> NAME/KEY: MOD_RES
<222> LOCATION: (103)
<223> OTHER INFORMATION: Xaa = Leu or Met
<220> FEATURE:
<221> NAME/KEY: MOD_RES
<222> LOCATION: (105)..(108)
<223> OTHER INFORMATION: Xaa = any amino acid
<220> FEATURE:
<221> NAME/KEY: MOD_RES
<222> LOCATION: (114)
<223> OTHER INFORMATION: Xaa = any amino acid
<220> FEATURE:
<221> NAME/KEY: MOD_RES
<222> LOCATION: (116)
<223> OTHER INFORMATION: Xaa = Tyr or Phe
<220> FEATURE:
<221> NAME/KEY: MOD_RES
<222> LOCATION: (117)
<223> OTHER INFORMATION: Xaa = Glu or Val
<220> FEATURE:
<221> NAME/KEY: MOD_RES
<222> LOCATION: (121)
<223> OTHER INFORMATION: Xaa = any amino acid
<220> FEATURE:
<221> NAME/KEY: MOD_RES
<222> LOCATION: (123)
<223> OTHER INFORMATION: Xaa = any amino acid
<220> FEATURE:
<221> NAME/KEY: MOD_RES
<222> LOCATION: (124)
<223> OTHER INFORMATION: Xaa = Leu or Ile
<220> FEATURE:
<221> NAME/KEY: MOD_RES
<222> LOCATION: (126)
<223> OTHER INFORMATION: Xaa = Glu or Lys
<220> FEATURE:
<221> NAME/KEY: MOD_RES
<222> LOCATION: (127)
<223> OTHER INFORMATION: Xaa = any amino acid
<220> FEATURE:
<221> NAME/KEY: MOD_RES
<222> LOCATION: (128)
<223> OTHER INFORMATION: Xaa = Asp or Glu -continued
<220> FEATURE:
<221> NAME/KEY: MOD_RES
<222> LOCATION: (130)
<223> OTHER INFORMATION: Xaa = Pro or Ile
<220> FEATURE:
<221> NAME/KEY: MOD_RES
<222> LOCATION: (131)..(132)
<223> OTHER INFORMATION: Xaa = any amino acid
<220> FEATURE:
<221> NAME/KEY: MOD_RES
<222> LOCATION: (136)
<223> OTHER INFORMATION: Xaa = Ala or Ser
<220> FEATURE:
<221> NAME/KEY: MOD_RES
<222> LOCATION: (139)
<223> OTHER INFORMATION: Xaa = Thr or Gln
<220> FEATURE:
<221> NAME/KEY: MOD_RES
<222> LOCATION: (141)
<223> OTHER INFORMATION: Xaa = Gly or Asp
<220> FEATURE:
<221> NAME/KEY: MOD_RES
<222> LOCATION: (142)
<223> OTHER INFORMATION: Xaa = Glu or Gly
<220> FEATURE:
<221> NAME/KEY: MOD_RES
<222> LOCATION: (143)..(150)
<223> OTHER INFORMATION: Xaa = any amino acid, Xaa at positions 149 and
      150 May be present or absent
<220> FEATURE:
<221> NAME/KEY: MOD_RES
<222> LOCATION: (151)
<223> OTHER INFORMATION: Xaa = Pro or Ser
<220> FEATURE:
<221> NAME/KEY: MOD_RES
<222> LOCATION: (152)..(154)
<223> OTHER INFORMATION: Xaa = any amino acid
<220> FEATURE:
<221> NAME/KEY: MOD_RES
<222> LOCATION: (156)..(165)
<223> OTHER INFORMATION: Xaa = any amino acid, Xaa at positions 162-165
      may be present or absent
<220> FEATURE:
<221> NAME/KEY: MOD_RES
<222> LOCATION: (166)
<223> OTHER INFORMATION: Xaa = Met or Leu
<220> FEATURE:
<221> NAME/KEY: MOD_RES
<222> LOCATION: (168)..(171)
<223> OTHER INFORMATION: Xaa = any amino acid
<220> FEATURE:
<221> NAME/KEY: MOD_RES
<222> LOCATION: (173)..(174)
<223> OTHER INFORMATION: Xaa = any amino acid
<220> FEATURE:
<221> NAME/KEY: MOD_RES
<222> LOCATION: (176)..(178)
<223> OTHER INFORMATION: Xaa = any amino acid
<220> FEATURE:
<221> NAME/KEY: MOD_RES
<222> LOCATION: (179)
<223> OTHER INFORMATION: Xaa = Arg or Lys
<220> FEATURE:
<221> NAME/KEY: MOD_RES
<222> LOCATION: (181)..(185)
<223> OTHER INFORMATION: Xaa = any amino acid
<220> FEATURE:
<221> NAME/KEY: MOD_RES
<222> LOCATION: (186)
<223> OTHER INFORMATION: Xaa = Val or Phe
<220> FEATURE:
<221> NAME/KEY: MOD_RES
<222> LOCATION: (190)
<223> OTHER INFORMATION: Xaa = Leu or Ile
<220> FEATURE:
<221> NAME/KEY: MOD_RES
<222> LOCATION: (192)..(213)
<223> OTHER INFORMATION: Xaa = any amino acid, Xaa at positions 192-213
      may be present or absent -continued <220> FEATURE:
<221> NAME/KEY: MOD_RES
<222> LOCATION: (214)
<223> OTHER INFORMATION: Xaa = Leu or Val
<220> FEATURE:
<221> NAME/KEY: MOD_RES
<222> LOCATION: (219)
<223> OTHER INFORMATION: Xaa = any amino acid
<220> FEATURE:
<221> NAME/KEY: MOD_RES
<222> LOCATION: (220)
<223> OTHER INFORMATION: Xaa = Ser or Thr
<220> FEATURE:
<221> NAME/KEY: MOD_RES
<222> LOCATION: (221)
<223> OTHER INFORMATION: Xaa = Ser or Arg
<220> FEATURE:
<221> NAME/KEY: MOD_RES
<222> LOCATION: (222)..(223)
<223> OTHER INFORMATION: Xaa = any amino acid
<220> FEATURE:
<221> NAME/KEY: MOD_RES
<222> LOCATION: (226)..(228)
<223> OTHER INFORMATION: Xaa = any amino acid
<220> FEATURE:
<221> NAME/KEY: MOD_RES
<222> LOCATION: (229)
<223> OTHER INFORMATION: Xaa = Arg or Thr
<220> FEATURE:
<221> NAME/KEY: MOD_RES
<222> LOCATION: (230)..(232)
<223> OTHER INFORMATION: Xaa = any amino acid
<220> FEATURE:
<221> NAME/KEY: MOD_RES
<222> LOCATION: (233)
<223> OTHER INFORMATION: Xaa = Trp or Lys
<220> FEATURE:
<221> NAME/KEY: MOD_RES
<222> LOCATION: (234)
<223> OTHER INFORMATION: Xaa = any amino acid
<220> FEATURE:
<221> NAME/KEY: MOD_RES
<222> LOCATION: (236)
<223> OTHER INFORMATION: Xaa = any amino acid
<220> FEATURE:
<221> NAME/KEY: MOD_RES
<222> LOCATION: (237)
<223> OTHER INFORMATION: Xaa = Arg or Lys
<220> FEATURE:
<221> NAME/KEY: MOD_RES
<222> LOCATION: (239)..(242)
<223> OTHER INFORMATION: Xaa = any amino acid
<220> FEATURE:
<221> NAME/KEY: MOD_RES
<222> LOCATION: (244)
<223> OTHER INFORMATION: Xaa = Thr or Ser
<220> FEATURE:
<221> NAME/KEY: MOD_RES
<222> LOCATION: (245)
<223> OTHER INFORMATION: Xaa = Ser or Thr
<220> FEATURE:
<221> NAME/KEY: MOD_RES
<222> LOCATION: (246)..(247)
<223> OTHER INFORMATION: Xaa = any amino acid
<220> FEATURE:
<221> NAME/KEY: MOD_RES
<222> LOCATION: (248)
<223> OTHER INFORMATION: Xaa = Ser or Thr
<220> FEATURE:
<221> NAME/KEY: MOD_RES
<222> LOCATION: (250)
<223> OTHER INFORMATION: Xaa = Phe or Cys
<220> FEATURE:
<221> NAME/KEY: MOD_RES
<222> LOCATION: (251)
<223> OTHER INFORMATION: Xaa = Arg or Lys
<220> FEATURE:
<221> NAME/KEY: MOD_RES
<222> LOCATION: (252)

-continued

<223> OTHER INFORMATION: Xaa = Gly or Leu
<220> FEATURE:
<221> NAME/KEY: MOD_RES
<222> LOCATION: (254)
<223> OTHER INFORMATION: Xaa = any amino acid
<220> FEATURE:
<221> NAME/KEY: MOD_RES
<222> LOCATION: (255)
<223> OTHER INFORMATION: Xaa = Thr or Val
<220> FEATURE:
<221> NAME/KEY: MOD_RES
<222> LOCATION: (256)..(257)
<223> OTHER INFORMATION: Xaa = any amino acid
<220> FEATURE:
<221> NAME/KEY: MOD_RES
<222> LOCATION: (259)..(260)
<223> OTHER INFORMATION: Xaa = any amino acid
<220> FEATURE:
<221> NAME/KEY: MOD_RES
<222> LOCATION: (261)
<223> OTHER INFORMATION: Xaa = Cys or Asn
<220> FEATURE:
<221> NAME/KEY: MOD_RES
<222> LOCATION: (263)
<223> OTHER INFORMATION: Xaa = Trp or Gln
<220> FEATURE:
<221> NAME/KEY: MOD_RES
<222> LOCATION: (264)
<223> OTHER INFORMATION: Xaa = any amino acid
<220> FEATURE:
<221> NAME/KEY: MOD_RES
<222> LOCATION: (266)
<223> OTHER INFORMATION: Xaa = Phe or Tyr
<220> FEATURE:
<221> NAME/KEY: MOD_RES
<222> LOCATION: (267)
<223> OTHER INFORMATION: Xaa = Val or Leu
<220> FEATURE:
<221> NAME/KEY: MOD_RES
<222> LOCATION: (269)
<223> OTHER INFORMATION: Xaa = Val or Leu
<220> FEATURE:
<221> NAME/KEY: MOD_RES
<222> LOCATION: (271)
<223> OTHER INFORMATION: Xaa = any amino acid
<220> FEATURE:
<221> NAME/KEY: MOD_RES
<222> LOCATION: (273)
<223> OTHER INFORMATION: Xaa = Glu or Asp
<220> FEATURE:
<221> NAME/KEY: MOD_RES
<222> LOCATION: (274)..(276)
<223> OTHER INFORMATION: Xaa = any amino acid
<220> FEATURE:
<221> NAME/KEY: MOD_RES
<222> LOCATION: (277)
<223> OTHER INFORMATION: Xaa = Arg or Gly
<220> FEATURE:
<221> NAME/KEY: MOD_RES
<222> LOCATION: (278)
<223> OTHER INFORMATION: Xaa = any amino acid
<220> FEATURE:
<221> NAME/KEY: MOD_RES
<222> LOCATION: (280)
<223> OTHER INFORMATION: Xaa = Arg or Lys
<220> FEATURE:
<221> NAME/KEY: MOD_RES
<222> LOCATION: (281)
<223> OTHER INFORMATION: Xaa = any amino acid
<220> FEATURE:
<221> NAME/KEY: MOD_RES
<222> LOCATION: (283)..(284)
<223> OTHER INFORMATION: Xaa = any amino acid
<220> FEATURE:
<221> NAME/KEY: MOD_RES
<222> LOCATION: (285)
<223> OTHER INFORMATION: Xaa = Arg or His
<220> FEATURE:
<221> NAME/KEY: MOD_RES -continued
<222> LOCATION: (288)..(289)
<223> OTHER INFORMATION: Xaa = any amino acid
<220> FEATURE:
<221> NAME/KEY: MOD_RES
<222> LOCATION: (290)
<223> OTHER INFORMATION: Xaa = Ala or Val

<400> SEQUENCE: 73

```
Pro Xaa Xaa Glu Xaa Pro Xaa Xaa Pro Xaa Xaa Xaa Xaa Xaa Glu Xaa
  1               5                  10                  15

Xaa Xaa Xaa Xaa Xaa Xaa Xaa Xaa Xaa Xaa Xaa Xaa Xaa Xaa Xaa Ile
             20                  25                  30

Glu Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Pro Xaa Ile Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Leu Val Xaa Xaa Xaa Xaa Xaa Xaa Xaa Xaa Xaa Pro
                 85                  90                  95

Xaa Xaa Xaa Xaa Xaa Xaa Xaa Lys Xaa Xaa Xaa Xaa Leu Arg Thr Glu
            100                 105                 110

His Xaa Val Xaa Xaa Leu Pro Asp Xaa His Xaa Xaa Leu Xaa Xaa Xaa
        115                 120                 125

Asp Xaa Xaa Xaa Tyr Leu Leu Xaa Ile Trp Xaa Pro Xaa Xaa Xaa Xaa
    130                 135                 140

Xaa Xaa Xaa Xaa Xaa Xaa Xaa Xaa Xaa Xaa Cys Xaa Xaa Xaa Xaa Xaa
145                 150                 155                 160

Xaa Xaa Xaa Xaa Xaa Xaa Cys Xaa Xaa Xaa Xaa Cys Xaa Xaa Cys Xaa
                165                 170                 175

Xaa Xaa Xaa Glu Xaa Xaa Xaa Xaa Xaa Xaa Arg Gly Thr Xaa Leu Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Phe Ala Asp His Xaa Xaa Xaa Xaa Xaa Pro
    210                 215                 220

Ile Xaa Xaa Xaa Xaa Xaa Xaa Xaa Xaa Xaa Leu Xaa Xaa Arg Xaa Xaa
225                 230                 235                 240

Xaa Xaa Gly Xaa Xaa Xaa Xaa Xaa Ile Xaa Xaa Xaa Leu Xaa Xaa Xaa
                245                 250                 255

Xaa Ile Xaa Xaa Xaa Phe Xaa Xaa Gly Xaa Xaa Cys Xaa Arg Xaa Phe
            260                 265                 270

Xaa Xaa Xaa Xaa Xaa Xaa Pro Xaa Xaa Leu Xaa Xaa Xaa Leu His Xaa
        275                 280                 285

Xaa Xaa Ser Lys
    290
```

<210> SEQ ID NO 74
<211> LENGTH: 1269
<212> TYPE: PRT
<213> ORGANISM: Artificial Sequence
<220> FEATURE:
<223> OTHER INFORMATION: Description of Artificial Sequence:DMT
consensus sequence spanning Domains A, B and C
<220> FEATURE:
<221> NAME/KEY: MOD_RES
<222> LOCATION: (1)..(14)
<223> OTHER INFORMATION: Xaa = any amino acid, Xaa at positions 10-14
may be present or absent -continued <220> FEATURE:
<221> NAME/KEY: MOD_RES
<222> LOCATION: (15)
<223> OTHER INFORMATION: Xaa = Thr or Gln
<220> FEATURE:
<221> NAME/KEY: MOD_RES
<222> LOCATION: (16)
<223> OTHER INFORMATION: Xaa = Ala or Ile
<220> FEATURE:
<221> NAME/KEY: MOD_RES
<222> LOCATION: (17)
<223> OTHER INFORMATION: Xaa = Ser or Lys
<220> FEATURE:
<221> NAME/KEY: MOD_RES
<222> LOCATION: (18)
<223> OTHER INFORMATION: Xaa = Ile or Leu
<220> FEATURE:
<221> NAME/KEY: MOD_RES
<222> LOCATION: (19)..(21)
<223> OTHER INFORMATION: Xaa = any amino acid
<220> FEATURE:
<221> NAME/KEY: MOD_RES
<222> LOCATION: (22)
<223> OTHER INFORMATION: Xaa = Ala or Arg
<220> FEATURE:
<221> NAME/KEY: MOD_RES
<222> LOCATION: (23)
<223> OTHER INFORMATION: Xaa = Ser or Lys
<220> FEATURE:
<221> NAME/KEY: MOD_RES
<222> LOCATION: (24)
<223> OTHER INFORMATION: Xaa = any amino acid
<220> FEATURE:
<221> NAME/KEY: MOD_RES
<222> LOCATION: (25)
<223> OTHER INFORMATION: Xaa = Gly or Met
<220> FEATURE:
<221> NAME/KEY: MOD_RES
<222> LOCATION: (26)..(27)
<223> OTHER INFORMATION: Xaa = any amino acid
<220> FEATURE:
<221> NAME/KEY: MOD_RES
<222> LOCATION: (28)
<223> OTHER INFORMATION: Xaa = Ser or Arg
<220> FEATURE:
<221> NAME/KEY: MOD_RES
<222> LOCATION: (29)
<223> OTHER INFORMATION: Xaa = Pro or Lys
<220> FEATURE:
<221> NAME/KEY: MOD_RES
<222> LOCATION: (30)..(31)
<223> OTHER INFORMATION: Xaa = any amino acid
<220> FEATURE:
<221> NAME/KEY: MOD_RES
<222> LOCATION: (32)
<223> OTHER INFORMATION: Xaa = Lys or Phe
<220> FEATURE:
<221> NAME/KEY: MOD_RES
<222> LOCATION: (33)..(34)
<223> OTHER INFORMATION: Xaa = any amino acid
<220> FEATURE:
<221> NAME/KEY: MOD_RES
<222> LOCATION: (35)
<223> OTHER INFORMATION: Xaa = Glu or Leu
<220> FEATURE:
<221> NAME/KEY: MOD_RES
<222> LOCATION: (37)
<223> OTHER INFORMATION: Xaa = any amino acid, Xaa at position 37 may be
present or absent
<220> FEATURE:
<221> NAME/KEY: MOD_RES
<222> LOCATION: (39)..(41)
<223> OTHER INFORMATION: Xaa = any amino acid, Xaa at positions 39-41
may be present or absent
<220> FEATURE:
<221> NAME/KEY: MOD_RES
<222> LOCATION: (42)
<223> OTHER INFORMATION: Xaa = Pro or Arg
<220> FEATURE:

-continued

<221> NAME/KEY: MOD_RES
<222> LOCATION: (43)..(44)
<223> OTHER INFORMATION: Xaa = any amino acid
<220> FEATURE:
<221> NAME/KEY: MOD_RES
<222> LOCATION: (45)
<223> OTHER INFORMATION: Xaa = Pro or Arg
<220> FEATURE:
<221> NAME/KEY: MOD_RES
<222> LOCATION: (46)
<223> OTHER INFORMATION: Xaa = any amino acid
<220> FEATURE:
<221> NAME/KEY: MOD_RES
<222> LOCATION: (47)
<223> OTHER INFORMATION: Xaa = Lys or Arg
<220> FEATURE:
<221> NAME/KEY: MOD_RES
<222> LOCATION: (48)
<223> OTHER INFORMATION: Xaa = Lys or Arg
<220> FEATURE:
<221> NAME/KEY: MOD_RES
<222> LOCATION: (49)
<223> OTHER INFORMATION: Xaa = Gly or Asp
<220> FEATURE:
<221> NAME/KEY: MOD_RES
<222> LOCATION: (50)
<223> OTHER INFORMATION: Xaa = Arg or Lys
<220> FEATURE:
<221> NAME/KEY: MOD_RES
<222> LOCATION: (51)
<223> OTHER INFORMATION: Xaa = any amino acid
<220> FEATURE:
<221> NAME/KEY: MOD_RES
<222> LOCATION: (52)
<223> OTHER INFORMATION: Xaa = Gly or Val
<220> FEATURE:
<221> NAME/KEY: MOD_RES
<222> LOCATION: (53)
<223> OTHER INFORMATION: Xaa = any amino acid
<220> FEATURE:
<221> NAME/KEY: MOD_RES
<222> LOCATION: (54)
<223> OTHER INFORMATION: Xaa = Lys or Gly
<220> FEATURE:
<221> NAME/KEY: MOD_RES
<222> LOCATION: (55)..(59)
<223> OTHER INFORMATION: Xaa = any amino acid, Xaa at positions 58 and
59 may be present or absent
<220> FEATURE:
<221> NAME/KEY: MOD_RES
<222> LOCATION: (60)
<223> OTHER INFORMATION: Xaa = Pro or Ser
<220> FEATURE:
<221> NAME/KEY: MOD_RES
<222> LOCATION: (61)
<223> OTHER INFORMATION: Xaa = Pro or Lys
<220> FEATURE:
<221> NAME/KEY: MOD_RES
<222> LOCATION: (62)..(64)
<223> OTHER INFORMATION: Xaa = any amino acid
<220> FEATURE:
<221> NAME/KEY: MOD_RES
<222> LOCATION: (65)
<223> OTHER INFORMATION: Xaa = Ser or Asn
<220> FEATURE:
<221> NAME/KEY: MOD_RES
<222> LOCATION: (66)
<223> OTHER INFORMATION: Xaa = any amino acid
<220> FEATURE:
<221> NAME/KEY: MOD_RES
<222> LOCATION: (67)
<223> OTHER INFORMATION: Xaa = Ile or Leu
<220> FEATURE:
<221> NAME/KEY: MOD_RES
<222> LOCATION: (68)..(69)
<223> OTHER INFORMATION: Xaa = any amino acid, Xaa at positions 68 and
69 may be present or absent
<220> FEATURE:
<221> NAME/KEY: MOD_RES -continued
<222> LOCATION: (70)
<223> OTHER INFORMATION: Xaa = Gln or Asp
<220> FEATURE:
<221> NAME/KEY: MOD_RES
<222> LOCATION: (71)..(79)
<223> OTHER INFORMATION: Xaa = any amino acid
<220> FEATURE:
<221> NAME/KEY: MOD_RES
<222> LOCATION: (80)
<223> OTHER INFORMATION: Xaa = Pro or Gln
<220> FEATURE:
<221> NAME/KEY: MOD_RES
<222> LOCATION: (81)..(84)
<223> OTHER INFORMATION: Xaa = any amino acid
<220> FEATURE:
<221> NAME/KEY: MOD_RES
<222> LOCATION: (85)
<223> OTHER INFORMATION: Xaa = Lys or Ala
<220> FEATURE:
<221> NAME/KEY: MOD_RES
<222> LOCATION: (86)
<223> OTHER INFORMATION: Xaa = Pro or Ser
<220> FEATURE:
<221> NAME/KEY: MOD_RES
<222> LOCATION: (87)..(102)
<223> OTHER INFORMATION: Xaa = any amino acid, Xaa at positions 100-102
may be present or absent
<220> FEATURE:
<221> NAME/KEY: MOD_RES
<222> LOCATION: (103)
<223> OTHER INFORMATION: Xaa = Pro or Ala
<220> FEATURE:
<221> NAME/KEY: MOD_RES
<222> LOCATION: (104)..(107)
<223> OTHER INFORMATION: Xaa = any amino acid
<220> FEATURE:
<221> NAME/KEY: MOD_RES
<222> LOCATION: (109)..(118)
<223> OTHER INFORMATION: Xaa = any amino acid, Xaa at positions 109-118
may be present or absent
<220> FEATURE:
<221> NAME/KEY: MOD_RES
<222> LOCATION: (120)
<223> OTHER INFORMATION: Xaa = any amino acid
<220> FEATURE:
<221> NAME/KEY: MOD_RES
<222> LOCATION: (121)
<223> OTHER INFORMATION: Xaa = Ile or Leu
<220> FEATURE:
<221> NAME/KEY: MOD_RES
<222> LOCATION: (122)..(125)
<223> OTHER INFORMATION: Xaa = any amino acid, Xaa at positions 122-125
may be present or absent
<220> FEATURE:
<221> NAME/KEY: MOD_RES
<222> LOCATION: (126)
<223> OTHER INFORMATION: Xaa = Leu or Asn
<220> FEATURE:
<221> NAME/KEY: MOD_RES
<222> LOCATION: (127)..(172)
<223> OTHER INFORMATION: Xaa = any amino acid, Xaa at positions 138-172
may be present or absent
<220> FEATURE:
<221> NAME/KEY: MOD_RES
<222> LOCATION: (173)
<223> OTHER INFORMATION: Xaa = Lys or Asp
<220> FEATURE:
<221> NAME/KEY: MOD_RES
<222> LOCATION: (174)..(180)
<223> OTHER INFORMATION: Xaa = any amino acid, Xaa at positions 176-180
may be present or absent
<220> FEATURE:
<221> NAME/KEY: MOD_RES
<222> LOCATION: (181)
<223> OTHER INFORMATION: Xaa = Pro or Ala
<220> FEATURE:
<221> NAME/KEY: MOD_RES
<222> LOCATION: (184)
<223> OTHER INFORMATION: Xaa = any amino acid -continued
<220> FEATURE:
<221> NAME/KEY: MOD_RES
<222> LOCATION: (185)
<223> OTHER INFORMATION: Xaa = Ile or Leu
<220> FEATURE:
<221> NAME/KEY: MOD_RES
<222> LOCATION: (187)
<223> OTHER INFORMATION: Xaa = Asp or Pro
<220> FEATURE:
<221> NAME/KEY: MOD_RES
<222> LOCATION: (188)
<223> OTHER INFORMATION: Xaa = Glu or Val
<220> FEATURE:
<221> NAME/KEY: MOD_RES
<222> LOCATION: (190)..(192)
<223> OTHER INFORMATION: Xaa = any amino acid
<220> FEATURE:
<221> NAME/KEY: MOD_RES
<222> LOCATION: (194)
<223> OTHER INFORMATION: Xaa = any amino acid
<220> FEATURE:
<221> NAME/KEY: MOD_RES
<222> LOCATION: (195)
<223> OTHER INFORMATION: Xaa = Leu or Val
<220> FEATURE:
<221> NAME/KEY: MOD_RES
<222> LOCATION: (197)
<223> OTHER INFORMATION: Xaa = Met or Leu
<220> FEATURE:
<221> NAME/KEY: MOD_RES
<222> LOCATION: (198)
<223> OTHER INFORMATION: Xaa = Glu or Asp
<220> FEATURE:
<221> NAME/KEY: MOD_RES
<222> LOCATION: (199)..(200)
<223> OTHER INFORMATION: Xaa = any amino acid, Xaa at positions 199 and
200 may be present or absent
<220> FEATURE:
<221> NAME/KEY: MOD_RES
<222> LOCATION: (202)
<223> OTHER INFORMATION: Xaa = Lys or Glu
<220> FEATURE:
<221> NAME/KEY: MOD_RES
<222> LOCATION: (203)
<223> OTHER INFORMATION: Xaa = any amino acid
<220> FEATURE:
<221> NAME/KEY: MOD_RES
<222> LOCATION: (204)
<223> OTHER INFORMATION: Xaa = Lys or Thr
<220> FEATURE:
<221> NAME/KEY: MOD_RES
<222> LOCATION: (205)
<223> OTHER INFORMATION: Xaa = any amino acid
<220> FEATURE:
<221> NAME/KEY: MOD_RES
<222> LOCATION: (206)
<223> OTHER INFORMATION: Xaa = Lys or Ala
<220> FEATURE:
<221> NAME/KEY: MOD_RES
<222> LOCATION: (207)
<223> OTHER INFORMATION: Xaa = Trp or Lys
<220> FEATURE:
<221> NAME/KEY: MOD_RES
<222> LOCATION: (208)
<223> OTHER INFORMATION: Xaa = Trp or Leu
<220> FEATURE:
<221> NAME/KEY: MOD_RES
<222> LOCATION: (209)
<223> OTHER INFORMATION: Xaa = any amino acid
<220> FEATURE:
<221> NAME/KEY: MOD_RES
<222> LOCATION: (210)
<223> OTHER INFORMATION: Xaa = Glu or Lys
<220> FEATURE:
<221> NAME/KEY: MOD_RES
<222> LOCATION: (213)..(214)
<223> OTHER INFORMATION: Xaa = any amino acid
<220> FEATURE:
<221> NAME/KEY: MOD_RES -continued
<222> LOCATION: (216)
<223> OTHER INFORMATION: Xaa = any amino acid
<220> FEATURE:
<221> NAME/KEY: MOD_RES
<222> LOCATION: (217)
<223> OTHER INFORMATION: Xaa = Gly or Thr
<220> FEATURE:
<221> NAME/KEY: MOD_RES
<222> LOCATION: (219)
<223> OTHER INFORMATION: Xaa = any amino acid
<220> FEATURE:
<221> NAME/KEY: MOD_RES
<222> LOCATION: (220)
<223> OTHER INFORMATION: Xaa = Asp or Asn
<220> FEATURE:
<221> NAME/KEY: MOD_RES
<222> LOCATION: (221)
<223> OTHER INFORMATION: Xaa = Ser or Leu
<220> FEATURE:
<221> NAME/KEY: MOD_RES
<222> LOCATION: (224)
<223> OTHER INFORMATION: Xaa = Ala or Asn
<220> FEATURE:
<221> NAME/KEY: MOD_RES
<222> LOCATION: (227)
<223> OTHER INFORMATION: Xaa = His or Arg
<220> FEATURE:
<221> NAME/KEY: MOD_RES
<222> LOCATION: (228)
<223> OTHER INFORMATION: Xaa = any amino acid
<220> FEATURE:
<221> NAME/KEY: MOD_RES
<222> LOCATION: (229)
<223> OTHER INFORMATION: Xaa = Val or Leu
<220> FEATURE:
<221> NAME/KEY: MOD_RES
<222> LOCATION: (232)
<223> OTHER INFORMATION: Xaa = Asp or Asn
<220> FEATURE:
<221> NAME/KEY: MOD_RES
<222> LOCATION: (234)
<223> OTHER INFORMATION: Xaa = any amino acid
<220> FEATURE:
<221> NAME/KEY: MOD_RES
<222> LOCATION: (236)
<223> OTHER INFORMATION: Xaa = any amino acid
<220> FEATURE:
<221> NAME/KEY: MOD_RES
<222> LOCATION: (237)
<223> OTHER INFORMATION: Xaa = Pro or Gln
<220> FEATURE:
<221> NAME/KEY: MOD_RES
<222> LOCATION: (247)
<223> OTHER INFORMATION: Xaa = Ile or Val
<220> FEATURE:
<221> NAME/KEY: MOD_RES
<222> LOCATION: (255)
<223> OTHER INFORMATION: Xaa = Val or Thr
<220> FEATURE:
<221> NAME/KEY: MOD_RES
<222> LOCATION: (257)
<223> OTHER INFORMATION: Xaa = His or Tyr
<220> FEATURE:
<221> NAME/KEY: MOD_RES
<222> LOCATION: (258)
<223> OTHER INFORMATION: Xaa = Leu or Ser
<220> FEATURE:
<221> NAME/KEY: MOD_RES
<222> LOCATION: (261)
<223> OTHER INFORMATION: Xaa = Ser or Asn
<220> FEATURE:
<221> NAME/KEY: MOD_RES
<222> LOCATION: (263)
<223> OTHER INFORMATION: Xaa = Phe or Tyr
<220> FEATURE:
<221> NAME/KEY: MOD_RES
<222> LOCATION: (265)
<223> OTHER INFORMATION: Xaa = any amino acid
<220> FEATURE:

-continued

<221> NAME/KEY: MOD_RES
<222> LOCATION: (266)
<223> OTHER INFORMATION: Xaa = Leu or Val
<220> FEATURE:
<221> NAME/KEY: MOD_RES
<222> LOCATION: (268)
<223> OTHER INFORMATION: Xaa = Ala or Ser
<220> FEATURE:
<221> NAME/KEY: MOD_RES
<222> LOCATION: (269)
<223> OTHER INFORMATION: Xaa = any amino acid
<220> FEATURE:
<221> NAME/KEY: MOD_RES
<222> LOCATION: (272)..(287)
<223> OTHER INFORMATION: Xaa = any amino acid, Xaa from positions
272-287 may be present or absent
<220> FEATURE:
<221> NAME/KEY: MOD_RES
<222> LOCATION: (288)
<223> OTHER INFORMATION: Xaa = Pro or Val
<220> FEATURE:
<221> NAME/KEY: MOD_RES
<222> LOCATION: (289)..(303)
<223> OTHER INFORMATION: Xaa = any amino acid, Xaa at positions 295-303
may be present or absent
<220> FEATURE:
<221> NAME/KEY: MOD_RES
<222> LOCATION: (304)
<223> OTHER INFORMATION: Xaa = Ser or His
<220> FEATURE:
<221> NAME/KEY: MOD_RES
<222> LOCATION: (305)..(307)
<223> OTHER INFORMATION: Xaa = any amino acid
<220> FEATURE:
<221> NAME/KEY: MOD_RES
<222> LOCATION: (308)
<223> OTHER INFORMATION: Xaa = Glu or Asp
<220> FEATURE:
<221> NAME/KEY: MOD_RES
<222> LOCATION: (309)..(332)
<223> OTHER INFORMATION: Xaa = any amino acid, Xaa at positions 319-332
may be present or absent
<220> FEATURE:
<221> NAME/KEY: MOD_RES
<222> LOCATION: (333)
<223> OTHER INFORMATION: Xaa = Ser or Thr
<220> FEATURE:
<221> NAME/KEY: MOD_RES
<222> LOCATION: (334)
<223> OTHER INFORMATION: Xaa = any amino acid
<220> FEATURE:
<221> NAME/KEY: MOD_RES
<222> LOCATION: (335)
<223> OTHER INFORMATION: Xaa = Ser or Glu
<220> FEATURE:
<221> NAME/KEY: MOD_RES
<222> LOCATION: (336)..(341)
<223> OTHER INFORMATION: Xaa = any amino acid
<220> FEATURE:
<221> NAME/KEY: MOD_RES
<222> LOCATION: (342)
<223> OTHER INFORMATION: Xaa = Lys or Asn
<220> FEATURE:
<221> NAME/KEY: MOD_RES
<222> LOCATION: (343)..(397)
<223> OTHER INFORMATION: Xaa = any amino acid, Xaa at positions 351-397
may be present or absent
<220> FEATURE:
<221> NAME/KEY: MOD_RES
<222> LOCATION: (398)
<223> OTHER INFORMATION: Xaa = Glu or Ile
<220> FEATURE:
<221> NAME/KEY: MOD_RES
<222> LOCATION: (399)..(407)
<223> OTHER INFORMATION: Xaa = any amino acid, Xaa at position 407 may
be present or absent
<220> FEATURE:
<221> NAME/KEY: MOD_RES
<222> LOCATION: (408)

-continued

<223> OTHER INFORMATION: Xaa = Ile or Val
<220> FEATURE:
<221> NAME/KEY: MOD_RES
<222> LOCATION: (409)
<223> OTHER INFORMATION: Xaa = any amino acid
<220> FEATURE:
<221> NAME/KEY: MOD_RES
<222> LOCATION: (410)
<223> OTHER INFORMATION: Xaa = Asn or Ser
<220> FEATURE:
<221> NAME/KEY: MOD_RES
<222> LOCATION: (411)..(414)
<223> OTHER INFORMATION: Xaa = any amino acid, Xaa at positions 412-414
may be present or absent
<220> FEATURE:
<221> NAME/KEY: MOD_RES
<222> LOCATION: (415)
<223> OTHER INFORMATION: Xaa = Glu or Asp
<220> FEATURE:
<221> NAME/KEY: MOD_RES
<222> LOCATION: (416)
<223> OTHER INFORMATION: Xaa = any amino acid
<220> FEATURE:
<221> NAME/KEY: MOD_RES
<222> LOCATION: (417)
<223> OTHER INFORMATION: Xaa = Glu or Ser
<220> FEATURE:
<221> NAME/KEY: MOD_RES
<222> LOCATION: (418)..(421)
<223> OTHER INFORMATION: Xaa = any amino acid
<220> FEATURE:
<221> NAME/KEY: MOD_RES
<222> LOCATION: (422)
<223> OTHER INFORMATION: Xaa = Gln or Leu
<220> FEATURE:
<221> NAME/KEY: MOD_RES
<222> LOCATION: (423)..(433)
<223> OTHER INFORMATION: Xaa = any amino acid, Xaa at positions 423-433
may be present or absent
<220> FEATURE:
<221> NAME/KEY: MOD_RES
<222> LOCATION: (434)
<223> OTHER INFORMATION: Xaa = Asp or His
<220> FEATURE:
<221> NAME/KEY: MOD_RES
<222> LOCATION: (435)
<223> OTHER INFORMATION: Xaa = any amino acid
<220> FEATURE:
<221> NAME/KEY: MOD_RES
<222> LOCATION: (436)
<223> OTHER INFORMATION: Xaa = Phe or Met
<220> FEATURE:
<221> NAME/KEY: MOD_RES
<222> LOCATION: (437)..(441)
<223> OTHER INFORMATION: Xaa = any amino acid
<220> FEATURE:
<221> NAME/KEY: MOD_RES
<222> LOCATION: (442)
<223> OTHER INFORMATION: Xaa = Gln or Asn
<220> FEATURE:
<221> NAME/KEY: MOD_RES
<222> LOCATION: (443)..(445)
<223> OTHER INFORMATION: Xaa = any amino acid, Xaa at positions 443-445
may be present or absent
<220> FEATURE:
<221> NAME/KEY: MOD_RES
<222> LOCATION: (446)
<223> OTHER INFORMATION: Xaa = Gly or Glu
<220> FEATURE:
<221> NAME/KEY: MOD_RES
<222> LOCATION: (447)..(448)
<223> OTHER INFORMATION: Xaa = any amino acid
<220> FEATURE:
<221> NAME/KEY: MOD_RES
<222> LOCATION: (449)
<223> OTHER INFORMATION: Xaa = Gly or Asp
<220> FEATURE:
<221> NAME/KEY: MOD_RES
<222> LOCATION: (451)

```
<223> OTHER INFORMATION: Xaa = any amino acid
<220> FEATURE:
<221> NAME/KEY: MOD_RES
<222> LOCATION: (452)
<223> OTHER INFORMATION: Xaa = Lys or Asp
<220> FEATURE:
<221> NAME/KEY: MOD_RES
<222> LOCATION: (453)..(463)
<223> OTHER INFORMATION: Xaa = any amino acid, Xaa at positions 460-463
      may be present or absent
<220> FEATURE:
<221> NAME/KEY: MOD_RES
<222> LOCATION: (464)
<223> OTHER INFORMATION: Xaa = Thr or Met
<220> FEATURE:
<221> NAME/KEY: MOD_RES
<222> LOCATION: (465)..(466)
<223> OTHER INFORMATION: Xaa = any amino acid
<220> FEATURE:
<221> NAME/KEY: MOD_RES
<222> LOCATION: (467)
<223> OTHER INFORMATION: Xaa = Val or Leu
<220> FEATURE:
<221> NAME/KEY: MOD_RES
<222> LOCATION: (468)..(470)
<223> OTHER INFORMATION: Xaa = any amino acid
<220> FEATURE:
<221> NAME/KEY: MOD_RES
<222> LOCATION: (471)
<223> OTHER INFORMATION: Xaa = Ser or Gln
<220> FEATURE:
<221> NAME/KEY: MOD_RES
<222> LOCATION: (472)..(481)
<223> OTHER INFORMATION: Xaa = any amino acid, Xaa at positions 478-481
      may be present or absent
<220> FEATURE:
<221> NAME/KEY: MOD_RES
<222> LOCATION: (482)
<223> OTHER INFORMATION: Xaa = Ser or Glu
<220> FEATURE:
<221> NAME/KEY: MOD_RES
<222> LOCATION: (483)..(485)
<223> OTHER INFORMATION: Xaa = any amino acid, Xaa at position 485 may
      be present or absent
<220> FEATURE:
<221> NAME/KEY: MOD_RES
<222> LOCATION: (486)
<223> OTHER INFORMATION: Xaa = Ser or Val
<220> FEATURE:
<221> NAME/KEY: MOD_RES
<222> LOCATION: (487)..(511)
<223> OTHER INFORMATION: Xaa = any amino acid, Xaa at positions 506-511
      may be present or absent
<220> FEATURE:
<221> NAME/KEY: MOD_RES
<222> LOCATION: (512)
<223> OTHER INFORMATION: Xaa = Thr or Ser
<220> FEATURE:
<221> NAME/KEY: MOD_RES
<222> LOCATION: (513)..(540)
<223> OTHER INFORMATION: Xaa = any amino acid, Xaa at positions 529-540
      may be present or absent
<220> FEATURE:
<221> NAME/KEY: MOD_RES
<222> LOCATION: (541)
<223> OTHER INFORMATION: Xaa = Arg or Ser
<220> FEATURE:
<221> NAME/KEY: MOD_RES
<222> LOCATION: (542)..(547)
<223> OTHER INFORMATION: Xaa = any amino acid, Xaa at positions 544-547
      may be present or absent
<220> FEATURE:
<221> NAME/KEY: MOD_RES
<222> LOCATION: (548)
<223> OTHER INFORMATION: Xaa = Thr or Pro
<220> FEATURE:
<221> NAME/KEY: MOD_RES
<222> LOCATION: (549)..(553)
<223> OTHER INFORMATION: Xaa = any amino acid
```

-continued

```
<220> FEATURE:
<221> NAME/KEY: MOD_RES
<222> LOCATION: (554)
<223> OTHER INFORMATION: Xaa = Pro or Lys
<220> FEATURE:
<221> NAME/KEY: MOD_RES
<222> LOCATION: (555)..(564)
<223> OTHER INFORMATION: Xaa = any amino acid
<220> FEATURE:
<221> NAME/KEY: MOD_RES
<222> LOCATION: (565)
<223> OTHER INFORMATION: Xaa = Gln or Glu
<220> FEATURE:
<221> NAME/KEY: MOD_RES
<222> LOCATION: (566)..(569)
<223> OTHER INFORMATION: Xaa = any amino acid
<220> FEATURE:
<221> NAME/KEY: MOD_RES
<222> LOCATION: (570)
<223> OTHER INFORMATION: Xaa = Asp or Ser
<220> FEATURE:
<221> NAME/KEY: MOD_RES
<222> LOCATION: (571)..(574)
<223> OTHER INFORMATION: Xaa = any amino acid, Xaa at positions 572-574
      may be present or absent
<220> FEATURE:
<221> NAME/KEY: MOD_RES
<222> LOCATION: (575)
<223> OTHER INFORMATION: Xaa = Ser or Arg
<220> FEATURE:
<221> NAME/KEY: MOD_RES
<222> LOCATION: (576)..(580)
<223> OTHER INFORMATION: Xaa = any amino acid
<220> FEATURE:
<221> NAME/KEY: MOD_RES
<222> LOCATION: (581)
<223> OTHER INFORMATION: Xaa = Asp or Pro
<220> FEATURE:
<221> NAME/KEY: MOD_RES
<222> LOCATION: (582)..(584)
<223> OTHER INFORMATION: Xaa = any amino acid
<220> FEATURE:
<221> NAME/KEY: MOD_RES
<222> LOCATION: (585)
<223> OTHER INFORMATION: Xaa = Asn or Asp
<220> FEATURE:
<221> NAME/KEY: MOD_RES
<222> LOCATION: (586)..(588)
<223> OTHER INFORMATION: Xaa = any amino acid
<220> FEATURE:
<221> NAME/KEY: MOD_RES
<222> LOCATION: (589)
<223> OTHER INFORMATION: Xaa = Pro or Tyr
<220> FEATURE:
<221> NAME/KEY: MOD_RES
<222> LOCATION: (590)..(591)
<223> OTHER INFORMATION: Xaa = any amino acid
<220> FEATURE:
<221> NAME/KEY: MOD_RES
<222> LOCATION: (592)
<223> OTHER INFORMATION: Xaa = Phe or Ser
<220> FEATURE:
<221> NAME/KEY: MOD_RES
<222> LOCATION: (593)
<223> OTHER INFORMATION: Xaa = any amino acid
<220> FEATURE:
<221> NAME/KEY: MOD_RES
<222> LOCATION: (594)
<223> OTHER INFORMATION: Xaa = Arg or Lys
<220> FEATURE:
<221> NAME/KEY: MOD_RES
<222> LOCATION: (595)
<223> OTHER INFORMATION: Xaa = any amino acid
<220> FEATURE:
<221> NAME/KEY: MOD_RES
<222> LOCATION: (596)
<223> OTHER INFORMATION: Xaa = Gly or Ser
<220> FEATURE:
<221> NAME/KEY: MOD_RES
```

-continued

<222> LOCATION: (597)
<223> OTHER INFORMATION: Xaa = any amino acid
<220> FEATURE:
<221> NAME/KEY: MOD_RES
<222> LOCATION: (598)
<223> OTHER INFORMATION: Xaa = Ser or Ala
<220> FEATURE:
<221> NAME/KEY: MOD_RES
<222> LOCATION: (599)
<223> OTHER INFORMATION: Xaa = Val or Arg
<220> FEATURE:
<221> NAME/KEY: MOD_RES
<222> LOCATION: (600)
<223> OTHER INFORMATION: Xaa = Pro or Glu
<220> FEATURE:
<221> NAME/KEY: MOD_RES
<222> LOCATION: (601)..(603)
<223> OTHER INFORMATION: Xaa = any amino acid
<220> FEATURE:
<221> NAME/KEY: MOD_RES
<222> LOCATION: (604)
<223> OTHER INFORMATION: Xaa = Thr or Ser
<220> FEATURE:
<221> NAME/KEY: MOD_RES
<222> LOCATION: (605)..(610)
<223> OTHER INFORMATION: Xaa = any amino acid, Xaa at positions 608-610
may be present or absent
<220> FEATURE:
<221> NAME/KEY: MOD_RES
<222> LOCATION: (611)
<223> OTHER INFORMATION: Xaa = Ile or Leu
<220> FEATURE:
<221> NAME/KEY: MOD_RES
<222> LOCATION: (612)..(614)
<223> OTHER INFORMATION: Xaa = any amino acid
<220> FEATURE:
<221> NAME/KEY: MOD_RES
<222> LOCATION: (615)
<223> OTHER INFORMATION: Xaa = Pro or Glu
<220> FEATURE:
<221> NAME/KEY: MOD_RES
<222> LOCATION: (616)
<223> OTHER INFORMATION: Xaa = any amino acid
<220> FEATURE:
<221> NAME/KEY: MOD_RES
<222> LOCATION: (618)..(622)
<223> OTHER INFORMATION: Xaa = any amino acid,Xaa at positions 621 and
622 may be present or absent
<220> FEATURE:
<221> NAME/KEY: MOD_RES
<222> LOCATION: (623)
<223> OTHER INFORMATION: Xaa = Leu or Gln
<220> FEATURE:
<221> NAME/KEY: MOD_RES
<222> LOCATION: (624)
<223> OTHER INFORMATION: Xaa = any amino acid
<220> FEATURE:
<221> NAME/KEY: MOD_RES
<222> LOCATION: (625)
<223> OTHER INFORMATION: Xaa = Gly or Cys
<220> FEATURE:
<221> NAME/KEY: MOD_RES
<222> LOCATION: (626)
<223> OTHER INFORMATION: Xaa = any amino acid
<220> FEATURE:
<221> NAME/KEY: MOD_RES
<222> LOCATION: (627)
<223> OTHER INFORMATION: Xaa = Ser or His
<220> FEATURE:
<221> NAME/KEY: MOD_RES
<222> LOCATION: (628)
<223> OTHER INFORMATION: Xaa = Ser or Asn
<220> FEATURE:
<221> NAME/KEY: MOD_RES
<222> LOCATION: (629)
<223> OTHER INFORMATION: Xaa = any amino acid
<220> FEATURE:
<221> NAME/KEY: MOD_RES
<222> LOCATION: (630)

-continued

<223> OTHER INFORMATION: Xaa = Val or Gln
<220> FEATURE:
<221> NAME/KEY: MOD_RES
<222> LOCATION: (631)
<223> OTHER INFORMATION: Xaa = any amino acid
<220> FEATURE:
<221> NAME/KEY: MOD_RES
<222> LOCATION: (632)
<223> OTHER INFORMATION: Xaa = Glu or Asp
<220> FEATURE:
<221> NAME/KEY: MOD_RES
<222> LOCATION: (633)..(635)
<223> OTHER INFORMATION: Xaa = any amino acid
<220> FEATURE:
<221> NAME/KEY: MOD_RES
<222> LOCATION: (637)
<223> OTHER INFORMATION: Xaa = Gln or Glu
<220> FEATURE:
<221> NAME/KEY: MOD_RES
<222> LOCATION: (638)..(639)
<223> OTHER INFORMATION: Xaa = any amino acid, Xaa at position 639 may
be present or absent
<220> FEATURE:
<221> NAME/KEY: MOD_RES
<222> LOCATION: (640)
<223> OTHER INFORMATION: Xaa = Asn or Gly
<220> FEATURE:
<221> NAME/KEY: MOD_RES
<222> LOCATION: (641)..(643)
<223> OTHER INFORMATION: Xaa = any amino acid
<220> FEATURE:
<221> NAME/KEY: MOD_RES
<222> LOCATION: (644)
<223> OTHER INFORMATION: Xaa = Glu or Asn
<220> FEATURE:
<221> NAME/KEY: MOD_RES
<222> LOCATION: (645)..(674)
<223> OTHER INFORMATION: Xaa = any amino acid, Xaa at positions 665-674
may be present or absent
<220> FEATURE:
<221> NAME/KEY: MOD_RES
<222> LOCATION: (675)
<223> OTHER INFORMATION: Xaa = Asn or Ala
<220> FEATURE:
<221> NAME/KEY: MOD_RES
<222> LOCATION: (676)
<223> OTHER INFORMATION: Xaa = Pro or Gly
<220> FEATURE:
<221> NAME/KEY: MOD_RES
<222> LOCATION: (677)..(682)
<223> OTHER INFORMATION: Xaa = any amino acid, Xaa at positions 678-682
may be present or absent
<220> FEATURE:
<221> NAME/KEY: MOD_RES
<222> LOCATION: (683)
<223> OTHER INFORMATION: Xaa = Ser or Leu
<220> FEATURE:
<221> NAME/KEY: MOD_RES
<222> LOCATION: (684)..(729)
<223> OTHER INFORMATION: Xaa = any amino acid, Xaa at positions 709-729
may be present or absent
<220> FEATURE:
<221> NAME/KEY: MOD_RES
<222> LOCATION: (730)
<223> OTHER INFORMATION: Xaa = Gln or Asp
<220> FEATURE:
<221> NAME/KEY: MOD_RES
<222> LOCATION: (732)
<223> OTHER INFORMATION: Xaa = Asp or Asn
<220> FEATURE:
<221> NAME/KEY: MOD_RES
<222> LOCATION: (733)
<223> OTHER INFORMATION: Xaa = any amino acid
<220> FEATURE:
<221> NAME/KEY: MOD_RES
<222> LOCATION: (734)
<223> OTHER INFORMATION: Xaa = Leu or Phe
<220> FEATURE:
<221> NAME/KEY: MOD_RES -continued
<222> LOCATION: (736)..(740)
<223> OTHER INFORMATION: Xaa = any amino acid
<220> FEATURE:
<221> NAME/KEY: MOD_RES
<222> LOCATION: (742)..(747)
<223> OTHER INFORMATION: Xaa = any amino acid, Xaa at positions 745-747
may be present or absent
<220> FEATURE:
<221> NAME/KEY: MOD_RES
<222> LOCATION: (749)
<223> OTHER INFORMATION: Xaa = Ser or Thr
<220> FEATURE:
<221> NAME/KEY: MOD_RES
<222> LOCATION: (750)
<223> OTHER INFORMATION: Xaa = any amino acid
<220> FEATURE:
<221> NAME/KEY: MOD_RES
<222> LOCATION: (751)
<223> OTHER INFORMATION: Xaa = Asp or Asn
<220> FEATURE:
<221> NAME/KEY: MOD_RES
<222> LOCATION: (752)
<223> OTHER INFORMATION: Xaa = Tyr or Trp
<220> FEATURE:
<221> NAME/KEY: MOD_RES
<222> LOCATION: (753)..(755)
<223> OTHER INFORMATION: Xaa = any amino acid
<220> FEATURE:
<221> NAME/KEY: MOD_RES
<222> LOCATION: (757)..(766)
<223> OTHER INFORMATION: Xaa = any amino acid
<220> FEATURE:
<221> NAME/KEY: MOD_RES
<222> LOCATION: (768)..(769)
<223> OTHER INFORMATION: Xaa = any amino acid
<220> FEATURE:
<221> NAME/KEY: MOD_RES
<222> LOCATION: (772)
<223> OTHER INFORMATION: Xaa = Met or Gln
<220> FEATURE:
<221> NAME/KEY: MOD_RES
<222> LOCATION: (773)
<223> OTHER INFORMATION: Xaa = Asn or Phe
<220> FEATURE:
<221> NAME/KEY: MOD_RES
<222> LOCATION: (774)..(775)
<223> OTHER INFORMATION: Xaa = any amino acid
<220> FEATURE:
<221> NAME/KEY: MOD_RES
<222> LOCATION: (777)
<223> OTHER INFORMATION: Xaa = Ala or Ser
<220> FEATURE:
<221> NAME/KEY: MOD_RES
<222> LOCATION: (778)
<223> OTHER INFORMATION: Xaa = any amino acid
<220> FEATURE:
<221> NAME/KEY: MOD_RES
<222> LOCATION: (781)..(792)
<223> OTHER INFORMATION: Xaa = any amino acid, Xaa at positions 783-792
may be present or absent
<220> FEATURE:
<221> NAME/KEY: MOD_RES
<222> LOCATION: (795)..(797)
<223> OTHER INFORMATION: Xaa = any amino acid
<220> FEATURE:
<221> NAME/KEY: MOD_RES
<222> LOCATION: (799)..(800)
<223> OTHER INFORMATION: Xaa = any amino acid
<220> FEATURE:
<221> NAME/KEY: MOD_RES
<222> LOCATION: (801)
<223> OTHER INFORMATION: Xaa = His or Asn
<220> FEATURE:
<221> NAME/KEY: MOD_RES
<222> LOCATION: (803)
<223> OTHER INFORMATION: Xaa = any amino acid
<220> FEATURE:
<221> NAME/KEY: MOD_RES
<222> LOCATION: (811)..(812)

-continued

<223> OTHER INFORMATION: Xaa = any amino acid
<220> FEATURE:
<221> NAME/KEY: MOD_RES
<222> LOCATION: (813)
<223> OTHER INFORMATION: Xaa = Pro or Asp
<220> FEATURE:
<221> NAME/KEY: MOD_RES
<222> LOCATION: (814)
<223> OTHER INFORMATION: Xaa = Pro or Ser
<220> FEATURE:
<221> NAME/KEY: MOD_RES
<222> LOCATION: (815)
<223> OTHER INFORMATION: Xaa = Asp or His
<220> FEATURE:
<221> NAME/KEY: MOD_RES
<222> LOCATION: (816)
<223> OTHER INFORMATION: Xaa = any amino acid
<220> FEATURE:
<221> NAME/KEY: MOD_RES
<222> LOCATION: (817)
<223> OTHER INFORMATION: Xaa = Ala or Val
<220> FEATURE:
<221> NAME/KEY: MOD_RES
<222> LOCATION: (819)
<223> OTHER INFORMATION: Xaa = any amino acid
<220> FEATURE:
<221> NAME/KEY: MOD_RES
<222> LOCATION: (820)
<223> OTHER INFORMATION: Xaa = Tyr or Phe
<220> FEATURE:
<221> NAME/KEY: MOD_RES
<222> LOCATION: (823)
<223> OTHER INFORMATION: Xaa = Ser or Glu
<220> FEATURE:
<221> NAME/KEY: MOD_RES
<222> LOCATION: (824)
<223> OTHER INFORMATION: Xaa = Ile or Phe
<220> FEATURE:
<221> NAME/KEY: MOD_RES
<222> LOCATION: (825)
<223> OTHER INFORMATION: Xaa = any amino acid
<220> FEATURE:
<221> NAME/KEY: MOD_RES
<222> LOCATION: (827)
<223> OTHER INFORMATION: Xaa = Leu or Ile
<220> FEATURE:
<221> NAME/KEY: MOD_RES
<222> LOCATION: (832)
<223> OTHER INFORMATION: Xaa = Val or Ala
<220> FEATURE:
<221> NAME/KEY: MOD_RES
<222> LOCATION: (839)
<223> OTHER INFORMATION: Xaa = any amino acid
<220> FEATURE:
<221> NAME/KEY: MOD_RES
<222> LOCATION: (841)
<223> OTHER INFORMATION: Xaa = His or Lys
<220> FEATURE:
<221> NAME/KEY: MOD_RES
<222> LOCATION: (842)..(843)
<223> OTHER INFORMATION: Xaa = any amino acid
<220> FEATURE:
<221> NAME/KEY: MOD_RES
<222> LOCATION: (855)
<223> OTHER INFORMATION: Xaa = Ala or Cys
<220> FEATURE:
<221> NAME/KEY: MOD_RES
<222> LOCATION: (858)
<223> OTHER INFORMATION: Xaa = Met or Leu
<220> FEATURE:
<221> NAME/KEY: MOD_RES
<222> LOCATION: (860)
<223> OTHER INFORMATION: Xaa = Trp or Leu
<220> FEATURE:
<221> NAME/KEY: MOD_RES
<222> LOCATION: (864)
<223> OTHER INFORMATION: Xaa = Gln or Glu
<220> FEATURE:
<221> NAME/KEY: MOD_RES -continued
<222> LOCATION: (868)..(869)
<223> OTHER INFORMATION: Xaa = any amino acid
<220> FEATURE:
<221> NAME/KEY: MOD_RES
<222> LOCATION: (870)
<223> OTHER INFORMATION: Xaa = Leu or Val
<220> FEATURE:
<221> NAME/KEY: MOD_RES
<222> LOCATION: (872)
<223> OTHER INFORMATION: Xaa = Leu or Met
<220> FEATURE:
<221> NAME/KEY: MOD_RES
<222> LOCATION: (874)
<223> OTHER INFORMATION: Xaa = Leu or Gln
<220> FEATURE:
<221> NAME/KEY: MOD_RES
<222> LOCATION: (876)
<223> OTHER INFORMATION: Xaa = Glu or Phe
<220> FEATURE:
<221> NAME/KEY: MOD_RES
<222> LOCATION: (877)
<223> OTHER INFORMATION: Xaa = any amino acid
<220> FEATURE:
<221> NAME/KEY: MOD_RES
<222> LOCATION: (880)
<223> OTHER INFORMATION: Xaa = any amino acid
<220> FEATURE:
<221> NAME/KEY: MOD_RES
<222> LOCATION: (881)
<223> OTHER INFORMATION: Xaa = Leu or Met
<220> FEATURE:
<221> NAME/KEY: MOD_RES
<222> LOCATION: (882)
<223> OTHER INFORMATION: Xaa = Glu or Asp
<220> FEATURE:
<221> NAME/KEY: MOD_RES
<222> LOCATION: (883)
<223> OTHER INFORMATION: Xaa = Ser or Asn
<220> FEATURE:
<221> NAME/KEY: MOD_RES
<222> LOCATION: (884)
<223> OTHER INFORMATION: Xaa = Ile or Val
<220> FEATURE:
<221> NAME/KEY: MOD_RES
<222> LOCATION: (887)
<223> OTHER INFORMATION: Xaa = Phe or Tyr
<220> FEATURE:
<221> NAME/KEY: MOD_RES
<222> LOCATION: (896)
<223> OTHER INFORMATION: Xaa = Asp or Pro
<220> FEATURE:
<221> NAME/KEY: MOD_RES
<222> LOCATION: (898)
<223> OTHER INFORMATION: Xaa = any amino acid
<220> FEATURE:
<221> NAME/KEY: MOD_RES
<222> LOCATION: (906)
<223> OTHER INFORMATION: Xaa = Gln or His
<220> FEATURE:
<221> NAME/KEY: MOD_RES
<222> LOCATION: (907)
<223> OTHER INFORMATION: Xaa = Leu or Met
<220> FEATURE:
<221> NAME/KEY: MOD_RES
<222> LOCATION: (913)..(914)
<223> OTHER INFORMATION: Xaa = any amino acid, Xaa at positions 913 and
914 may be present or absent
<220> FEATURE:
<221> NAME/KEY: MOD_RES
<222> LOCATION: (919)..(920)
<223> OTHER INFORMATION: Xaa = any amino acid
<220> FEATURE:
<221> NAME/KEY: MOD_RES
<222> LOCATION: (929)
<223> OTHER INFORMATION: Xaa = Arg or Lys
<220> FEATURE:
<221> NAME/KEY: MOD_RES
<222> LOCATION: (930)..(931)
<223> OTHER INFORMATION: Xaa = any amino acid, Xaa at positions 930 and

```
     931 may be present or absent
<220> FEATURE:
<221> NAME/KEY: MOD_RES
<222> LOCATION: (934)
<223> OTHER INFORMATION: Xaa = Arg or Lys
<220> FEATURE:
<221> NAME/KEY: MOD_RES
<222> LOCATION: (935)
<223> OTHER INFORMATION: Xaa = His or Tyr
<220> FEATURE:
<221> NAME/KEY: MOD_RES
<222> LOCATION: (936)
<223> OTHER INFORMATION: Xaa = Phe or Tyr
<220> FEATURE:
<221> NAME/KEY: MOD_RES
<222> LOCATION: (937)
<223> OTHER INFORMATION: Xaa = Ala or Ser
<220> FEATURE:
<221> NAME/KEY: MOD_RES
<222> LOCATION: (940)
<223> OTHER INFORMATION: Xaa = any amino acid
<220> FEATURE:
<221> NAME/KEY: MOD_RES
<222> LOCATION: (941)
<223> OTHER INFORMATION: Xaa = Ala or Val
<220> FEATURE:
<221> NAME/KEY: MOD_RES
<222> LOCATION: (942)..(951)
<223> OTHER INFORMATION: Xaa = any amino acid, Xaa at positions 942-951
      may be present or absent
<220> FEATURE:
<221> NAME/KEY: MOD_RES
<222> LOCATION: (953)
<223> OTHER INFORMATION: Xaa = Ala or Ser
<220> FEATURE:
<221> NAME/KEY: MOD_RES
<222> LOCATION: (954)
<223> OTHER INFORMATION: Xaa = Arg or Lys
<220> FEATURE:
<221> NAME/KEY: MOD_RES
<222> LOCATION: (955)
<223> OTHER INFORMATION: Xaa = any amino acid
<220> FEATURE:
<221> NAME/KEY: MOD_RES
<222> LOCATION: (956)
<223> OTHER INFORMATION: Xaa = Ala or Leu
<220> FEATURE:
<221> NAME/KEY: MOD_RES
<222> LOCATION: (958)
<223> OTHER INFORMATION: Xaa = Pro or Glu
<220> FEATURE:
<221> NAME/KEY: MOD_RES
<222> LOCATION: (959)
<223> OTHER INFORMATION: Xaa = any amino acid
<220> FEATURE:
<221> NAME/KEY: MOD_RES
<222> LOCATION: (960)
<223> OTHER INFORMATION: Xaa = Pro or Thr
<220> FEATURE:
<221> NAME/KEY: MOD_RES
<222> LOCATION: (961)
<223> OTHER INFORMATION: Xaa = Glu or Gln
<220> FEATURE:
<221> NAME/KEY: MOD_RES
<222> LOCATION: (962)..(977)
<223> OTHER INFORMATION: Xaa = any amino acid, Xaa at positions 969-977
      may be present or absent
<220> FEATURE:
<221> NAME/KEY: MOD_RES
<222> LOCATION: (979)
<223> OTHER INFORMATION: Xaa = Ile or Leu
<220> FEATURE:
<221> NAME/KEY: MOD_RES
<222> LOCATION: (980)
<223> OTHER INFORMATION: Xaa = Ile or Val
<220> FEATURE:
<221> NAME/KEY: MOD_RES
<222> LOCATION: (982)
<223> OTHER INFORMATION: Xaa = Glu or Phe
```

-continued

```
<220> FEATURE:
<221> NAME/KEY: MOD_RES
<222> LOCATION: (984)
<223> OTHER INFORMATION: Xaa = any amino acid
<220> FEATURE:
<221> NAME/KEY: MOD_RES
<222> LOCATION: (985)
<223> OTHER INFORMATION: Xaa = Ser or Thr
<220> FEATURE:
<221> NAME/KEY: MOD_RES
<222> LOCATION: (987)..(991)
<223> OTHER INFORMATION: Xaa = any amino acid, Xaa at positions 989-991
      may be present or absent
<220> FEATURE:
<221> NAME/KEY: MOD_RES
<222> LOCATION: (993)..(1007)
<223> OTHER INFORMATION: Xaa = any amino acid, Xaa at positions 993-1007
      may be present or absent
<220> FEATURE:
<221> NAME/KEY: MOD_RES
<222> LOCATION: (1008)
<223> OTHER INFORMATION: Xaa = Asp or Ala
<220> FEATURE:
<221> NAME/KEY: MOD_RES
<222> LOCATION: (1011)
<223> OTHER INFORMATION: Xaa = Asp or Glu
<220> FEATURE:
<221> NAME/KEY: MOD_RES
<222> LOCATION: (1012)..(1034)
<223> OTHER INFORMATION: Xaa = any amino acid, Xaa at positions
      1016-1034 may be present or absent
<220> FEATURE:
<221> NAME/KEY: MOD_RES
<222> LOCATION: (1035)
<223> OTHER INFORMATION: Xaa = Ile or Val
<220> FEATURE:
<221> NAME/KEY: MOD_RES
<222> LOCATION: (1037)
<223> OTHER INFORMATION: Xaa = any amino acid
<220> FEATURE:
<221> NAME/KEY: MOD_RES
<222> LOCATION: (1039)
<223> OTHER INFORMATION: Xaa = any amino acid
<220> FEATURE:
<221> NAME/KEY: MOD_RES
<222> LOCATION: (1040)
<223> OTHER INFORMATION: Xaa = Leu or Phe
<220> FEATURE:
<221> NAME/KEY: MOD_RES
<222> LOCATION: (1041)
<223> OTHER INFORMATION: Xaa = Asn or Asp
<220> FEATURE:
<221> NAME/KEY: MOD_RES
<222> LOCATION: (1042)..(1058)
<223> OTHER INFORMATION: Xaa = any amino acid, Xaa at positions
      1050-1058 may be present or absent
<220> FEATURE:
<221> NAME/KEY: MOD_RES
<222> LOCATION: (1059)
<223> OTHER INFORMATION: Xaa = Ser or Ala
<220> FEATURE:
<221> NAME/KEY: MOD_RES
<222> LOCATION: (1060)
<223> OTHER INFORMATION: Xaa = any amino acid
<220> FEATURE:
<221> NAME/KEY: MOD_RES
<222> LOCATION: (1061)
<223> OTHER INFORMATION: Xaa = Ala or Asp
<220> FEATURE:
<221> NAME/KEY: MOD_RES
<222> LOCATION: (1064)..(1071)
<223> OTHER INFORMATION: Xaa = any amino acid
<220> FEATURE:
<221> NAME/KEY: MOD_RES
<222> LOCATION: (1072)
<223> OTHER INFORMATION: Xaa = Ile or Leu
<220> FEATURE:
<221> NAME/KEY: MOD_RES
<222> LOCATION: (1074)..(1078)
```

-continued

<223> OTHER INFORMATION: Xaa = any amino acid, Xaa at positions
      1076-1078 may be present or absent
<220> FEATURE:
<221> NAME/KEY: MOD_RES
<222> LOCATION: (1079)
<223> OTHER INFORMATION: Xaa = Lys or Arg
<220> FEATURE:
<221> NAME/KEY: MOD_RES
<222> LOCATION: (1080)
<223> OTHER INFORMATION: Xaa = Leu or Met
<220> FEATURE:
<221> NAME/KEY: MOD_RES
<222> LOCATION: (1082)..(1085)
<223> OTHER INFORMATION: Xaa = any amino acid
<220> FEATURE:
<221> NAME/KEY: MOD_RES
<222> LOCATION: (1091)
<223> OTHER INFORMATION: Xaa = any amino acid
<220> FEATURE:
<221> NAME/KEY: MOD_RES
<222> LOCATION: (1093)
<223> OTHER INFORMATION: Xaa = Tyr or Phe
<220> FEATURE:
<221> NAME/KEY: MOD_RES
<222> LOCATION: (1094)
<223> OTHER INFORMATION: Xaa = Glu or Val
<220> FEATURE:
<221> NAME/KEY: MOD_RES
<222> LOCATION: (1098)
<223> OTHER INFORMATION: Xaa = any amino acid
<220> FEATURE:
<221> NAME/KEY: MOD_RES
<222> LOCATION: (1100)
<223> OTHER INFORMATION: Xaa = any amino acid
<220> FEATURE:
<221> NAME/KEY: MOD_RES
<222> LOCATION: (1101)
<223> OTHER INFORMATION: Xaa = Leu or Ile
<220> FEATURE:
<221> NAME/KEY: MOD_RES
<222> LOCATION: (1103)
<223> OTHER INFORMATION: Xaa = Glu or Lys
<220> FEATURE:
<221> NAME/KEY: MOD_RES
<222> LOCATION: (1104)
<223> OTHER INFORMATION: Xaa = any amino acid
<220> FEATURE:
<221> NAME/KEY: MOD_RES
<222> LOCATION: (1105)
<223> OTHER INFORMATION: Xaa = Asp or Glu
<220> FEATURE:
<221> NAME/KEY: MOD_RES
<222> LOCATION: (1107)
<223> OTHER INFORMATION: Xaa = Pro or Ile
<220> FEATURE:
<221> NAME/KEY: MOD_RES
<222> LOCATION: (1108)..(1109)
<223> OTHER INFORMATION: Xaa = any amino acid
<220> FEATURE:
<221> NAME/KEY: MOD_RES
<222> LOCATION: (1113)
<223> OTHER INFORMATION: Xaa = Ala or Ser
<220> FEATURE:
<221> NAME/KEY: MOD_RES
<222> LOCATION: (1116)
<223> OTHER INFORMATION: Xaa = Thr or Gln
<220> FEATURE:
<221> NAME/KEY: MOD_RES
<222> LOCATION: (1118)
<223> OTHER INFORMATION: Xaa = Gly or Asp
<220> FEATURE:
<221> NAME/KEY: MOD_RES
<222> LOCATION: (1119)
<223> OTHER INFORMATION: Xaa = Glu or Gly
<220> FEATURE:
<221> NAME/KEY: MOD_RES
<222> LOCATION: (1120)..(1127)
<223> OTHER INFORMATION: Xaa = any amino acid, Xaa at positions 1126 and
      1127 may be present or absent -continued <220> FEATURE:
<221> NAME/KEY: MOD_RES
<222> LOCATION: (1128)
<223> OTHER INFORMATION: Xaa = Pro or Ser
<220> FEATURE:
<221> NAME/KEY: MOD_RES
<222> LOCATION: (1129)..(1131)
<223> OTHER INFORMATION: Xaa = any amino acid
<220> FEATURE:
<221> NAME/KEY: MOD_RES
<222> LOCATION: (1133)..(1142)
<223> OTHER INFORMATION: Xaa = any amino acid, Xaa at positions
1139-1142 may be present or absent
<220> FEATURE:
<221> NAME/KEY: MOD_RES
<222> LOCATION: (1143)
<223> OTHER INFORMATION: Xaa = Met or Leu
<220> FEATURE:
<221> NAME/KEY: MOD_RES
<222> LOCATION: (1145)..(1148)
<223> OTHER INFORMATION: Xaa = any amino acid
<220> FEATURE:
<221> NAME/KEY: MOD_RES
<222> LOCATION: (1150)..(1151)
<223> OTHER INFORMATION: Xaa = any amino acid
<220> FEATURE:
<221> NAME/KEY: MOD_RES
<222> LOCATION: (1153)..(1155)
<223> OTHER INFORMATION: Xaa = any amino acid
<220> FEATURE:
<221> NAME/KEY: MOD_RES
<222> LOCATION: (1156)
<223> OTHER INFORMATION: Xaa = Arg or Lys
<220> FEATURE:
<221> NAME/KEY: MOD_RES
<222> LOCATION: (1158)..(1162)
<223> OTHER INFORMATION: Xaa = any amino acid
<220> FEATURE:
<221> NAME/KEY: MOD_RES
<222> LOCATION: (1163)
<223> OTHER INFORMATION: Xaa = Val or Phe
<220> FEATURE:
<221> NAME/KEY: MOD_RES
<222> LOCATION: (1167)
<223> OTHER INFORMATION: Xaa = Leu or Ile
<220> FEATURE:
<221> NAME/KEY: MOD_RES
<222> LOCATION: (1169)..(1190)
<223> OTHER INFORMATION: Xaa = any amino acid, Xaa at positions
1169-1190 may be present or absent
<220> FEATURE:
<221> NAME/KEY: MOD_RES
<222> LOCATION: (1191)
<223> OTHER INFORMATION: Xaa = Leu or Val
<220> FEATURE:
<221> NAME/KEY: MOD_RES
<222> LOCATION: (1196)
<223> OTHER INFORMATION: Xaa = any amino acid
<220> FEATURE:
<221> NAME/KEY: MOD_RES
<222> LOCATION: (1197)
<223> OTHER INFORMATION: Xaa = Ser or Thr
<220> FEATURE:
<221> NAME/KEY: MOD_RES
<222> LOCATION: (1198)
<223> OTHER INFORMATION: Xaa = Ser or Arg
<220> FEATURE:
<221> NAME/KEY: MOD_RES
<222> LOCATION: (1199)..(1200)
<223> OTHER INFORMATION: Xaa = any amino acid
<220> FEATURE:
<221> NAME/KEY: MOD_RES
<222> LOCATION: (1203)..(1205)
<223> OTHER INFORMATION: Xaa = any amino acid
<220> FEATURE:
<221> NAME/KEY: MOD_RES
<222> LOCATION: (1206)
<223> OTHER INFORMATION: Xaa = Arg or Thr
<220> FEATURE:

-continued

<221> NAME/KEY: MOD_RES
<222> LOCATION: (1207)..(1209)
<223> OTHER INFORMATION: Xaa = any amino acid
<220> FEATURE:
<221> NAME/KEY: MOD_RES
<222> LOCATION: (1210)
<223> OTHER INFORMATION: Xaa = Trp or Lys
<220> FEATURE:
<221> NAME/KEY: MOD_RES
<222> LOCATION: (1211)
<223> OTHER INFORMATION: Xaa = any amino acid
<220> FEATURE:
<221> NAME/KEY: MOD_RES
<222> LOCATION: (1213)
<223> OTHER INFORMATION: Xaa = any amino acid
<220> FEATURE:
<221> NAME/KEY: MOD_RES
<222> LOCATION: (1214)
<223> OTHER INFORMATION: Xaa = Arg or Lys
<220> FEATURE:
<221> NAME/KEY: MOD_RES
<222> LOCATION: (1216)..(1219)
<223> OTHER INFORMATION: Xaa = any amino acid
<220> FEATURE:
<221> NAME/KEY: MOD_RES
<222> LOCATION: (1221)
<223> OTHER INFORMATION: Xaa = Thr or Ser
<220> FEATURE:
<221> NAME/KEY: MOD_RES
<222> LOCATION: (1222)
<223> OTHER INFORMATION: Xaa = Ser or Thr
<220> FEATURE:
<221> NAME/KEY: MOD_RES
<222> LOCATION: (1223)..(1224)
<223> OTHER INFORMATION: Xaa = any amino acid
<220> FEATURE:
<221> NAME/KEY: MOD_RES
<222> LOCATION: (1225)
<223> OTHER INFORMATION: Xaa = Ser or Thr
<220> FEATURE:
<221> NAME/KEY: MOD_RES
<222> LOCATION: (1227)
<223> OTHER INFORMATION: Xaa = Phe or Cys
<220> FEATURE:
<221> NAME/KEY: MOD_RES
<222> LOCATION: (1228)
<223> OTHER INFORMATION: Xaa = Arg or Lys
<220> FEATURE:
<221> NAME/KEY: MOD_RES
<222> LOCATION: (1229)
<223> OTHER INFORMATION: Xaa = Gly or Leu
<220> FEATURE:
<221> NAME/KEY: MOD_RES
<222> LOCATION: (1231)
<223> OTHER INFORMATION: Xaa = any amino acid
<220> FEATURE:
<221> NAME/KEY: MOD_RES
<222> LOCATION: (1232)
<223> OTHER INFORMATION: Xaa = Thr or Val
<220> FEATURE:
<221> NAME/KEY: MOD_RES
<222> LOCATION: (1233)..(1234)
<223> OTHER INFORMATION: Xaa = any amino acid
<220> FEATURE:
<221> NAME/KEY: MOD_RES
<222> LOCATION: (1236)..(1237)
<223> OTHER INFORMATION: Xaa = any amino acid
<220> FEATURE:
<221> NAME/KEY: MOD_RES
<222> LOCATION: (1238)
<223> OTHER INFORMATION: Xaa = Cys or Asn
<220> FEATURE:
<221> NAME/KEY: MOD_RES
<222> LOCATION: (1240)
<223> OTHER INFORMATION: Xaa = Trp or Gln
<220> FEATURE:
<221> NAME/KEY: MOD_RES
<222> LOCATION: (1241)
<223> OTHER INFORMATION: Xaa = any amino acid -continued
<220> FEATURE:
<221> NAME/KEY: MOD_RES
<222> LOCATION: (1243)
<223> OTHER INFORMATION: Xaa = Phe or Tyr
<220> FEATURE:
<221> NAME/KEY: MOD_RES
<222> LOCATION: (1244)
<223> OTHER INFORMATION: Xaa = Val or Leu
<220> FEATURE:
<221> NAME/KEY: MOD_RES
<222> LOCATION: (1246)
<223> OTHER INFORMATION: Xaa = Val or Leu
<220> FEATURE:
<221> NAME/KEY: MOD_RES
<222> LOCATION: (1248)
<223> OTHER INFORMATION: Xaa = any amino acid
<220> FEATURE:
<221> NAME/KEY: MOD_RES
<222> LOCATION: (1250)
<223> OTHER INFORMATION: Xaa = Glu or Asp
<220> FEATURE:
<221> NAME/KEY: MOD_RES
<222> LOCATION: (1251)..(1253)
<223> OTHER INFORMATION: Xaa = any amino acid
<220> FEATURE:
<221> NAME/KEY: MOD_RES
<222> LOCATION: (1254)
<223> OTHER INFORMATION: Xaa = Arg or Gly
<220> FEATURE:
<221> NAME/KEY: MOD_RES
<222> LOCATION: (1255)
<223> OTHER INFORMATION: Xaa = any amino acid
<220> FEATURE:
<221> NAME/KEY: MOD_RES
<222> LOCATION: (1257)
<223> OTHER INFORMATION: Xaa = Arg or Lys
<220> FEATURE:
<221> NAME/KEY: MOD_RES
<222> LOCATION: (1258)
<223> OTHER INFORMATION: Xaa = any amino acid
<220> FEATURE:
<221> NAME/KEY: MOD_RES
<222> LOCATION: (1260)..(1261)
<223> OTHER INFORMATION: Xaa = any amino acid
<220> FEATURE:
<221> NAME/KEY: MOD_RES
<222> LOCATION: (1262)
<223> OTHER INFORMATION: Xaa = Arg or His
<220> FEATURE:
<221> NAME/KEY: MOD_RES
<222> LOCATION: (1265)..(1266)
<223> OTHER INFORMATION: Xaa = any amino acid
<220> FEATURE:
<221> NAME/KEY: MOD_RES
<222> LOCATION: (1267)
<223> OTHER INFORMATION: Xaa = Ala or Val

<400> SEQUENCE: 74

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Lys Xaa Lys Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Leu Xaa Xaa Xaa Xaa
            100                 105                 110
```

-continued

```
Xaa Xaa Xaa Xaa Xaa Xaa Asp Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Lys Val Xaa Xaa Asp Xaa Xaa Thr Xaa Xaa Xaa
            180                 185                 190

Trp Xaa Xaa Leu Xaa Xaa Xaa Xaa Asp Xaa Xaa Xaa Xaa Xaa Xaa Xaa
        195                 200                 205

Xaa Xaa Glu Arg Xaa Xaa Phe Xaa Xaa Arg Xaa Xaa Xaa Phe Ile Xaa
    210                 215                 220

Arg Met Xaa Xaa Xaa Gln Gly Xaa Arg Xaa Phe Xaa Xaa Trp Lys Gly
225                 230                 235                 240

Ser Val Val Asp Ser Val Xaa Gly Val Phe Leu Thr Gln Asn Xaa Asp
                245                 250                 255

Xaa Xaa Ser Ser Xaa Ala Xaa Met Xaa Xaa Ala Xaa Xaa Phe Pro Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Ser Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
        515                 520                 525
```

-continued

```
Xaa Xaa Xaa Xaa Xaa Xaa Xaa Xaa Xaa Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Glu Xaa Xaa Xaa Xaa Xaa Xaa Xaa
    610                 615                 620

Xaa Xaa Xaa Xaa Xaa Xaa Xaa Xaa Xaa Xaa Xaa Thr Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa Xaa Xaa
    690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Trp Xaa Xaa Xaa Arg Xaa
                725                 730                 735

Xaa Xaa Xaa Xaa Glu Xaa Xaa Xaa Xaa Xaa Xaa Asp Xaa Xaa Xaa Xaa
            740                 745                 750

Xaa Xaa Xaa Arg Xaa Xaa Xaa Xaa Xaa Xaa Xaa Xaa Xaa Xaa Ile Xaa
        755                 760                 765

Xaa Arg Gly Xaa Xaa Xaa Xaa Leu Xaa Xaa Arg Ile Xaa Xaa Xaa Xaa
    770                 775                 780

Xaa Xaa Xaa Xaa Xaa Xaa Xaa Xaa Phe Leu Xaa Xaa Xaa Val Xaa Xaa
785                 790                 795                 800

Xaa Gly Xaa Ile Asp Leu Glu Trp Leu Arg Xaa Xaa Xaa Xaa Xaa Xaa
                805                 810                 815

Xaa Lys Xaa Xaa Leu Leu Xaa Xaa Xaa Gly Xaa Gly Leu Lys Ser Xaa
            820                 825                 830

Glu Cys Val Arg Leu Leu Xaa Leu Xaa Xaa Xaa Ala Phe Pro Val Asp
        835                 840                 845

Thr Asn Val Gly Arg Ile Xaa Val Arg Xaa Gly Xaa Val Pro Leu Xaa
    850                 855                 860

Pro Leu Pro Xaa Xaa Xaa Gln Xaa His Xaa Leu Xaa Xaa Tyr Pro Xaa
865                 870                 875                 880

Xaa Xaa Xaa Xaa Gln Lys Xaa Leu Trp Pro Arg Leu Cys Lys Leu Xaa
                885                 890                 895

Gln Xaa Thr Leu Tyr Glu Leu His Tyr Xaa Xaa Ile Thr Phe Gly Lys
            900                 905                 910

Xaa Xaa Phe Cys Thr Lys Xaa Xaa Pro Asn Cys Asn Ala Cys Pro Met
        915                 920                 925

Xaa Xaa Xaa Glu Cys Xaa Xaa Xaa Xaa Ser Ala Xaa Xaa Xaa Xaa Xaa
    930                 935                 940

Xaa Xaa Xaa Xaa Xaa Xaa Xaa Ser Xaa Xaa Xaa Xaa Leu Xaa Xaa Xaa
```

-continued

```
945                 950                 955                 960

Xaa Xaa Xaa Xaa Xaa Xaa Xaa Xaa Xaa Xaa Xaa Xaa Xaa Xaa Xaa Xaa
                965                 970                 975

Xaa Pro Xaa Xaa Glu Xaa Pro Xaa Xaa Pro Xaa Xaa Xaa Xaa Xaa Glu
            980                 985                 990

Xaa Xaa Xaa Xaa Xaa Xaa Xaa Xaa Xaa Xaa Xaa Xaa Xaa Xaa Xaa Xaa
        995                 1000                1005

Ile Glu Xaa Xaa Xaa Xaa Xaa Xaa Xaa Xaa Xaa Xaa Xaa Xaa Xaa Xaa
   1010                1015                1020

Xaa Xaa Xaa Xaa Xaa Xaa Xaa Xaa Xaa Xaa Xaa Pro Xaa Ile Xaa Xaa
1025                1030                1035                1040

Xaa Xaa Xaa Xaa Xaa Xaa Xaa Xaa Xaa Xaa Xaa Xaa Xaa Xaa Xaa Xaa
                1045                1050                1055

Xaa Xaa Xaa Xaa Xaa Leu Val Xaa Xaa Xaa Xaa Xaa Xaa Xaa Xaa Xaa
           1060                1065                1070

Pro Xaa Xaa Xaa Xaa Xaa Xaa Xaa Lys Xaa Xaa Xaa Xaa Leu Arg Thr
       1075                1080                1085

Glu His Xaa Val Xaa Xaa Leu Pro Asp Xaa His Xaa Xaa Leu Xaa Xaa
   1090                1095                1100

Xaa Asp Xaa Xaa Xaa Tyr Leu Leu Xaa Ile Trp Xaa Pro Xaa Xaa Xaa
1105                1110                1115                1120

Xaa Xaa Xaa Xaa Xaa Xaa Xaa Xaa Xaa Xaa Xaa Cys Xaa Xaa Xaa Xaa
                1125                1130                1135

Xaa Xaa Xaa Xaa Xaa Xaa Xaa Cys Xaa Xaa Xaa Xaa Cys Xaa Xaa Cys
           1140                1145                1150

Xaa Xaa Xaa Xaa Glu Xaa Xaa Xaa Xaa Xaa Xaa Arg Gly Thr Xaa Leu
       1155                1160                1165

Xaa Xaa Xaa Xaa Xaa Xaa Xaa Xaa Xaa Xaa Xaa Xaa Xaa Xaa Xaa Xaa
   1170                1175                1180

Xaa Xaa Xaa Xaa Xaa Xaa Xaa Phe Ala Asp His Xaa Xaa Xaa Xaa Xaa
1185                1190                1195                1200

Pro Ile Xaa Xaa Xaa Xaa Xaa Xaa Xaa Xaa Xaa Leu Xaa Xaa Arg Xaa
                1205                1210                1215

Xaa Xaa Xaa Gly Xaa Xaa Xaa Xaa Xaa Ile Xaa Xaa Xaa Leu Xaa Xaa
           1220                1225                1230

Xaa Xaa Ile Xaa Xaa Xaa Phe Xaa Xaa Gly Xaa Xaa Cys Xaa Arg Xaa
       1235                1240                1245

Phe Xaa Xaa Xaa Xaa Xaa Xaa Pro Xaa Xaa Leu Xaa Xaa Xaa Leu His
   1250                1255                1260

Xaa Xaa Xaa Ser Lys
1265


<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence:DMT
      conserved HhH-GPD motif

<400> SEQUENCE: 75

Asp Lys Ala Lys Asp Tyr Leu Leu Ser Ile Arg Gly Leu Gly Leu Lys
  1               5                  10                  15

Ser Val Glu Cys Val Arg Leu Leu Thr Leu His Asn Leu Ala Phe Pro
             20                  25                  30
```

-continued

Val Asp

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence:primer
      Xba-SKEN-7

<400> SEQUENCE: 76
cctctagagg aattgtcggc aaaatcgag 29

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence:primer SKB-8

<400> SEQUENCE: 77
ggagagacgg ttattgtcaa cc 22

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence:primer SKB-7

<400> SEQUENCE: 78
aaaagtctac aagggagaga gagt 24

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence:primer SKB-5

<400> SEQUENCE: 79
gtagatgtac atacgtacc 19

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence:primer SKEN-8

<400> SEQUENCE: 80
gcatcctcca acaagtaaca atccactc 28

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence:primer SKB-6

<400> SEQUENCE: 81
cactgagatt aattcttcag actcg 25

<210> SEQ ID NO 82
<211> LENGTH: 27
<212> TYPE: DNA

-continued

```
<213> ORGANISM: Artificial Sequence
<220> FEATURE:
<223> OTHER INFORMATION: Description of Artificial Sequence:primer SKEN-3.5

<400> SEQUENCE: 82

ctcaggcgag tcaatgccgg agaacac                                          27


<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence:primer
      SKEN-3

<400> SEQUENCE: 83

cgagggctga tccgggggat agatatttt                                        29


<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence:primer
      SKEN-2

<400> SEQUENCE: 84

cccccggatc agccctcgaa ttc                                              23


<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence:primer
      SKEN-1

<400> SEQUENCE: 85

cccctgtcta caaattcacc acctgg                                           26


<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence:primer
      SKEL-4

<400> SEQUENCE: 86

ctgacccaac tgcttctctt c                                                21


<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence:primer
      skes1.5

<400> SEQUENCE: 87

tcacctgttc tgaacagact gg                                               22


<210> SEQ ID NO 88
<211> LENGTH: 26
<212> TYPE: DNA
<213> ORGANISM: Artificial Sequence
<220> FEATURE:
```

-continued

<223> OTHER INFORMATION: Description of Artificial Sequence:primer
      SKES-1.4

<400> SEQUENCE: 88
cagcagacga gtccataatg ctctgc 26

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence:primer
      SKES-2.4

<400> SEQUENCE: 89
ggtttgcctt ccacgaccac c 21

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence:primer
      SKES-1

<400> SEQUENCE: 90
ggaagccacg caaagctgca actcagg 27

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence:primer
      SKES-2.45

<400> SEQUENCE: 91
gagttgcagc tttgcgtggc ttcc 24

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence:primer
      SKES2.5

<400> SEQUENCE: 92
ttcagactca gagtcacctt gc 22

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:primer
      SKES-2

<400> SEQUENCE: 93
accagcagcc ttgcttggcc 20

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence:primer -continued

SKES-3

<400> SEQUENCE: 94
catgccagag aagcagggct cc 22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence:primer
SKES3.5

<400> SEQUENCE: 95
cgatgatact gtctcttcga gc 22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence:primer
SKES-6

<400> SEQUENCE: 96
cctccgcctg ctcatgcctc ag 22

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence:primer
SKEN-4

<400> SEQUENCE: 97
gtccatcagg agaacttctg tgtcaggat 29

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence:primer
SKES-4

<400> SEQUENCE: 98
gggaacaagt gcaccatctc c 21

<210> SEQ ID NO 99
<211> LENGTH: 29
<212> TYPE: DNA
<213> ORGANISM: Artificial Sequence
<220> FEATURE:
<223> OTHER INFORMATION: Description of Artificial Sequence:primer
SKEN-6

<400> SEQUENCE: 99
gctctcatag ggaacaagtg caccatctc 29

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:primer
SKES-5

-continued

<400> SEQUENCE: 100
cgctcgcatg cacctggtac 20

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence:primer SKB-1

<400> SEQUENCE: 101
ggagggaatc gagcagctag ag 22

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence:primer SKB-2

<400> SEQUENCE: 102
gagcagctaa gggactgttc aaactc 26

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence:primer SKB-3

<400> SEQUENCE: 103
ccaggaatgg gattgtccgg 20

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence:primer
3'RACE-2

<400> SEQUENCE: 104
cttggacggc gcttgaggaa cc 22

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence:primer
3'RACE-1

<400> SEQUENCE: 105
gcctacaagc cagtgggata g 21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence:primer
cDNA-1

<400> SEQUENCE: 106
gccaaggact atctcttgag c 21

-continued

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:primer SKB-4

<400> SEQUENCE: 107
ggatggactc gagcactggg 20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence:primer
SKE2.2-4

<400> SEQUENCE: 108
agaggagagt gcagacactt tg 22

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence:primer
cDNA-3

<400> SEQUENCE: 109
gaggaccctg acgagatccc aac 23

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence:primer
cDNA-9

<400> SEQUENCE: 110
ccatgtgttc ccgtagagtc attcc 25

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence:primer
2.2+SKE-1

<400> SEQUENCE: 111
atggagctcc aagaaggtga catg 24

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence:primer
cDNA-5

<400> SEQUENCE: 112
cagaagtgtg gagggaaagc gtctggc 27

-continued

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence:primer
cDNA-4

<400> SEQUENCE: 113
ccctcagact gttacactca gaac 24

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence:primer
cDNA-2

<400> SEQUENCE: 114
cccgttgagc ggaaaacttc ctctcatggc 30

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence:primer
cDNA-7

<400> SEQUENCE: 115
ggaaaggatt cgtatgtgtc cgtgg 25

<210> SEQ ID NO 116
<211> LENGTH: 29
<212> TYPE: DNA
<213> ORGANISM: Artificial Sequence
<220> FEATURE:
<223> OTHER INFORMATION: Description of Artificial Sequence:primer
SKEN-5

<400> SEQUENCE: 116
gcaatgcgtt tgctttcttc cagtcatct 29

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence:primer
cDNA-6

<400> SEQUENCE: 117
gaggagagca gagaagcaat gcgtttgc 28

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence:primer
cDNA-8

<400> SEQUENCE: 118
gttagagaga aaataaataa ccc 23

<210> SEQ ID NO 119

-continued

```
<211> LENGTH: 22
<212> TYPE: DNA
<213> ORGANISM: Artificial Sequence
<220> FEATURE:
<223> OTHER INFORMATION: Description of Artificial Sequence: primer
      2.2+SKE-3

<400> SEQUENCE: 119

ccgtaaacaa caccggatac ac                                              22
```